US011690898B2

(12) United States Patent
Bunting et al.

(10) Patent No.: US 11,690,898 B2
(45) Date of Patent: Jul. 4, 2023

(54) ADENO-ASSOCIATED VIRUS FACTOR VIII VECTORS, ASSOCIATED VIRAL PARTICLES AND THERAPEUTIC FORMULATIONS COMPRISING THE SAME

(71) Applicant: BIOMARIN PHARMACEUTICAL INC., Novato, CA (US)

(72) Inventors: Stuart Bunting, Novato, CA (US); Peter Cameron Colosi, Novato, CA (US); Erno Pungor, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 817 days.

(21) Appl. No.: 16/675,841

(22) Filed: Nov. 6, 2019

(65) Prior Publication Data

US 2020/0061161 A1 Feb. 27, 2020

Related U.S. Application Data

(62) Division of application No. 15/274,046, filed on Sep. 23, 2016, now Pat. No. 10,512,675.

(60) Provisional application No. 62/365,544, filed on Jul. 22, 2016, provisional application No. 62/323,182, filed on Apr. 15, 2016, provisional application No. 62/232,242, filed on Sep. 24, 2015.

(51) Int. Cl.

| | |
|---|---|
| ***C12N 15/864*** | (2006.01) |
| ***A61K 38/37*** | (2006.01) |
| ***A61K 48/00*** | (2006.01) |
| ***A61K 47/10*** | (2017.01) |
| ***A61K 47/26*** | (2006.01) |
| ***A61K 39/12*** | (2006.01) |
| ***C07K 14/755*** | (2006.01) |
| ***A61K 47/02*** | (2006.01) |
| ***C12N 7/00*** | (2006.01) |
| ***G01N 33/68*** | (2006.01) |

(52) U.S. Cl.

CPC .............. *A61K 38/37* (2013.01); *A61K 39/12* (2013.01); *A61K 47/02* (2013.01); *A61K 47/10* (2013.01); *A61K 47/26* (2013.01); *A61K 48/0008* (2013.01); *A61K 48/0075* (2013.01); *C07K 14/755* (2013.01); *C12N 7/00* (2013.01); *G01N 33/6854* (2013.01); *C12N 2710/16044* (2013.01); *C12N 2750/14121* (2013.01); *C12N 2750/14141* (2013.01); *C12N 2750/14143* (2013.01); *G01N 2333/015* (2013.01)

(58) Field of Classification Search

None

See application file for complete search history.

(56) References Cited

U.S. PATENT DOCUMENTS

| | | | | |
|---|---|---|---|---|
| 4,745,051 | A | 5/1988 | Smith et al. | |
| 6,200,560 | B1 | 3/2001 | Couto et al. | |
| 6,204,059 | B1 | 3/2001 | Samulski et al. | |
| 6,221,349 | B1 | 4/2001 | Couto et al. | |
| 6,521,225 | B1 | 2/2003 | Srivastava et al. | |
| 7,351,577 | B2 | 4/2008 | Couto et al. | |
| 8,030,065 | B2 | 10/2011 | Gray | |
| 9,504,762 | B2 | 11/2016 | Colosi et al. | |
| 10,512,675 | B2 * | 12/2019 | Bunting | A61K 47/02 |
| 2003/0148506 | A1 | 8/2003 | Kotin et al. | |
| 2007/0042462 | A1 | 2/2007 | Hildinger | |
| 2009/0118184 | A1 | 5/2009 | Fay et al. | |
| 2011/0201088 | A1 | 8/2011 | Beall et al. | |
| 2015/0071883 | A1 | 3/2015 | Colosi | |
| 2015/0111955 | A1 | 4/2015 | High et al. | |
| 2019/0048362 | A1 | 2/2019 | Kyostio-Moore et al. | |
| 2019/0111157 | A1 | 4/2019 | Stanek et al. | |

FOREIGN PATENT DOCUMENTS

| | | | |
|---|---|---|---|
| EP | 127839 | A2 | 12/1984 |
| EP | 155476 | A1 | 9/1985 |
| RU | 2531493 | C2 | 10/2014 |
| WO | WO-99/61595 | A2 | 12/1999 |
| WO | WO-03/074714 | A1 | 9/2003 |
| WO | WO-2011/005968 | A1 | 1/2011 |
| WO | WO-2013/186563 | A2 | 12/2013 |
| WO | WO-2014/064277 | A1 | 5/2014 |
| WO | WO-2015/038625 | A1 | 3/2015 |

OTHER PUBLICATIONS

Gurda et al., Capsid antibodies to different adeno-associated virus serotypes bind common regions, J. Virol., 87(16):9111-24 (Aug. 2013).
Arruda et al., Novel approaches to hemophilia therapy: successes and challenges, Blood, pp. 2251-2256 (2017).
Boutin et al., Prevalence of serum IgG and neutralizing factors against adeno-associated virus (AAV) types 1,2, 5, 6, 8, and 9 in the healthy population: implications for gene therapy using AAV vectors, Hum. Gene Ther., 21(6):704-12 (2010).
Bunting et al., Human Factor VII Expression and Normalization of Bleeding Following AAV Gene Therapy in a Double Knockout Mouse Model of Hemophilia, Blood, 126:3239, pp. 1-2 (2015).
Canale et al., Effect of corticosteroids on factor 8 level, J. Pediatr., 71(6):878-80 (Dec. 1967).

(Continued)

*Primary Examiner* — Maria Marvich
(74) *Attorney, Agent, or Firm* — Marshall, Gerstein & Borun LLP

(57) ABSTRACT

The invention provides adeno-associated virus (AAV) Factor VIII (FVIII)-encoding/expressing vectors and virus, including AAV FVIII vectors with high expression activity and AAV FVIII vectors that express full-length or truncated functional FVIII protein. The invention also relates to methods of making the herein described AAV FVIII vectors, recombinant AAV FVIII virus particles comprising or expressing such vectors, associated pharmaceutical formulations comprising the same and therapeutic uses thereof.

6 Claims, 18 Drawing Sheets

Specification includes a Sequence Listing.

(56) References Cited

OTHER PUBLICATIONS

Chen et al., Enhanced factor VIII heavy chain for gene therapy of hemophilia A, Mol. Ther., 17(3):417-24 (Mar. 2009).
Chiorini et al., Cloning and characterization of adeno-associated virus type 5, J. Virol., 73(2):1309-19 (1999).
Chiorini et al., Cloning of adeno-associated virus type 4 (AAV4) and generation of recombinant AAV4 particles, J. Virol., 71(9):6823-33 (1997).
De Simone et al., Cis- and trans-acting elements responsible for the cell-specific expression of the human alpha 1-antitrypsin gene, EMBO J., 6(9):2759-66 (1987).
EU Clinical Trials Register, EudraCT No. 2014-003880-38, A Phase 1/2, Dose-Escalation Safety, Tolerability and Efficacy Study of BMN 270, an Adenovirus-Associated Virus Vector-Mediated Gene Transfer of Human Factor VIII in Patients with Severe Haemophilia A. Accessed From the Internet at: <https://www.clinicaltrialsregister.eu/ctrsearch/trial/2014-003880-38/GB> (Jun. 9, 2015).
Fumoto et al., Targeted gene therapy: importance of administration routes, Chapter 1, Intech, pp. 3-31 (2013).
GenBank Accession No. AF043303.1, Adeno-associated virus 2, complete genome, May 20, 2010.
GenBank Accession No. AF085716.1, Adeno-associated virus 5 DNA binding trs helicase (Rep22) and capsid protein (VP1) genes, complete cds, Feb. 9, 1999.
GenBank Accession No. J01901.1, Adeno-associated virus 2, complete genome, Apr. 27, 1993.
GenBank Accession No. U89790.1, Adeno-associated virus 4, complete genome (Aug. 21, 1997).
Ghosh et al., Expanding adeno-associated viral vector capacity: a tale of two vectors, Biotechnol. Genet. Eng. Rev., 24:165-77 (2007).
Hirsch et al., Little vector, big gene transduction: fragmented genome reassembly of adeno-associated virus, Mol. Ther., 18(1):6-8 (2010).
Kajigaya et al., Self-assembled B19 parvovirus capsids, produced in a baculovirus system, are antigenically and immunogenically similar to native virions, Proc. Natl. Acad. Sci. USA, 88(11):4646-50 (1991).
Kirnbauer et al., Virus-like particles of bovine papillomavirus type 4 in prophylactic and therapeutic immunization, Virology, 219(1):37-44 (1996).
Masat et al., Humoral immunity to AAV vectors in gene therapy: challenges and potential solutions, Discov. Med., 15(85):379-89 (2013).
McIntosh et al., Therapeutic levels of FVIII following a single peripheral vein administration of rAAV vector encoding a novel human factor VIII variant, Blood, 121(17):3335-44 (2013).
Mingozzi et al., Immune responses to AAV vectors: overcoming barriers to successful gene therapy, Blood, 122(1):23-36 (2013).
Nathwani et al., Adenovirus-associated virus vector-mediated gene transfer in hemophilia B, N. Engl. J. Med., 365(25):2357-65 (2011).
Ruffing et al., Assembly of viruslike particles by recombinant structural proteins of adeno-associated virus type 2 in insect cells, J. Virol., 66(12):6922-30 (1992).
Rutledge et al., Infectious clones and vectors derived from adeno-associated virus (AAV) serotypes other than AAV type 2, J. Virol., 72(1):309-19 (1998).
Samulski et al., Helper-free stocks of recombinant adeno-associated viruses: normal integration does not require viral gene expression, J. Virol., 63(9):3822-8 (1989).
Shanks et al., Are animal models predictive for humans? Philosophy, Ethics, and Humanities in Medicine, pp. 1-20 (2009).
Vlak et al., Functional studies on the p10 gene of Autographa californica nuclear polyhedrosis virus using a recombinant expressing a p10-beta-galactosidase fusion gene, J. Gen. Virol., 69(Pt. 4):765-76 (1988).
Wang et al., Adeno-associated virus type 2 DNA replication in vivo: mutation analyses of the D sequence in viral inverted terminal repeats, J. Virol., 71(4):3077-82 (1997).
Wang et al., Rescue and replication of adeno-associated virus type 2 as well as vector DNA sequences from recombinant plasmids containing deletions in the viral inverted terminal repeats: selective encapsidation of viral genomes in progeny virions, J. Virol., 70(3):1668-77 (1996).
Ward et al., Codon optimization of human factor VIII cDNAs leads to high-level expression, Blood, 117(3):798-807 (2011).
Wu et al., Mutational analysis of the adeno-associated virus type 2 (AAV2) capsid gene and construction of AAV2 vectors with altered tropism, J. Virol., 74(18):8635-47 (2000).
Yan et al., Inverted terminal repeat sequences are important for intermolecular recombination and circularization of adeno-associated virus genomes, J. Virol., 79(1):364-79 (2005).
Zhao et al., BPV1 E2 protein enhances packaging of full-length plasmid DNA in BPV1 pseudovirions, Virology, 272(2):382-93 (2000).
UK-MHRA, EU Clinical Trials Register, EudraCT#2014-003880-38, 2015, pp. 1-5.

* cited by examiner

Schematic of Proto 1

Schematic of Proto 1S

Schematic of Proto 4

Schematic of Proto 5

Schematic of Proto 6

Schematic of Proto 7

ADENO-ASSOCIATED VIRUS FACTOR VIII VECTORS, ASSOCIATED VIRAL PARTICLES AND THERAPEUTIC FORMULATIONS COMPRISING THE SAME

This application Is a divisional of U.S. patent application Ser. No. 15/274,046, filed Sep. 23, 2016, now U.S. Pat. No. 10,512,675, which is a national phase application of International Patent Application No. PCT/US16/53269, which claims priority benefit of U.S. Provisional Patent Application No. 62/232,242 filed Sep. 24, 2015, U.S. Provisional Patent Application No. 62/323,182, filed Apr. 15, 2016 and U.S. Provisional Application No. 62/365,544 filed Jul. 22, 2016, which are incorporated herein by reference in their entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII protein. The invention also relates to methods of making the herein described AAV FVIII vectors, recombinant AAV FVIII virus particles comprising or expressing such vectors, associated pharmaceutical formulations comprising the same and therapeutic uses thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., *New Engl. J. Med.* 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., *Blood* 117:798-807, 2011, and McIntosh et al., *Blood* 121:3335-3344, 2013).

While AAV vectors have been reported in the literature having AAV genomes of >5.0 kb, in many of these cases the 5' or 3' ends of the encoded genes appear to be truncated (see Hirsch et al., *Molec. Ther.* 18:6-8, 2010 and Ghosh et al., *Biotech. Genet. Engin. Rev.* 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein, and recombinant AAV virus particles comprising the same, useful in gene therapy approaches for the treatment of hemophilia A. As such, the present invention relates to AAV vectors that encode functionally active FVIII such that either the recombinant AAV virus encapsidates the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. This invention also relates to the production of AAV FVIII vectors having high FVIII expression activity. Finally, the present invention relates to pharmaceutical formulations comprising AAV Factor VIII vectors and/or recombinant Factor VIII AAV particles/viruses comprising any of the herein described AAV FVIII vectors, associated pharmaceutical formulations, and associated methods of administration for the treatment of hemophilia A in subjects suffering therefrom.

SUMMARY OF INVENTION

The present invention provides AAV vectors encoding functionally active FVIII (referred to herein as "AAV FVIII vectors"). The recombinant AAV vectors of the present invention include non-naturally occurring derivatives of the AAV virus into which nucleic acid sequences encoding a functional FVIII protein have been introduced. The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, functionally contributing in the blood coagulation cascade and/or reducing the time that it takes for blood to clot in a subject suffering from hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa. One example of a functionally active FVIII protein is a FVIII SQ protein as described in WO 2015/038625, herein incorporated by reference.

As used herein, an “AAV vector” refers to nucleic acids, either single-stranded or double-stranded, having an AAV 5' inverted terminal repeat (ITR) sequence and an AAV 3' ITR flanking a protein-coding sequence (preferably a functional Factor VIII-encoding sequence) operably linked to transcription regulatory elements that are heterologous to the AAV viral genome, i.e., one or more promoters and/or enhancers and, optionally, a polyadenylation sequence and/or one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term “inverted terminal repeat (ITR)” as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., *J. Virol.* 79(1):364-379 (2005) which is herein incorporated by reference in its entirety. ITR sequences that find use herein may be full length, wild-type AAV ITRs or fragments thereof that retain functional capability, or may be sequence variants of full-length, wild-type AAV ITRs that are capable of functioning in cis as origins of replication. AAV ITRs useful in the recombinant AAV FVIII vectors of the present invention may derive from any known AAV serotype and, in certain preferred embodiments, derive from the AAV2 or AAV5 serotype.

A “transcription regulatory element” refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term “liver specific transcription regulatory element” refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII protein having the B domain replaced by the 14 amino acid SQ sequence. The SQ sequence is disclosed in Ward et al., *Blood,* 117:798-807, 2011, McIntosh et al., *Blood* 121:3335-3344, 2013, WO 2013/186563 and WO 2015/038625. The FVIII coding region sequence may be a codon-optimized FVIII-encoding sequence (see, e.g., WO 2011/005968, published Jan. 13, 2011, WO 2015/038625, published Mar. 19, 2015, and McIntosh et al., *Blood* 121:3335-3344, 2013, which are incorporated herein by reference in their entirety). In a preferred embodiment, the nucleic acid encoding the functionally active human FVIII protein of the AAV vector or recombinant AAV virus particle consists of nucleotides 403 to 4776 of SEQ ID NO:1. This sequence is herein referred to as “FVIII-SQ”.

In a first aspect, the recombinant AAV vector of the invention comprises Proto 1, which is depicted schematically in FIG. 2A, and comprises the nucleic acid sequence set forth in SEQ ID NO:1.

In a second aspect, the recombinant AAV vector of the invention comprises Proto 1S, which is depicted schematically in FIG. 2B, and comprises the nucleic acid sequence set forth in SEQ ID NO:2.

In a third aspect, the recombinant AAV vector of the invention comprises Proto 2S, which is depicted schematically in FIG. 2C, and comprises the nucleic acid sequence set forth in SEQ ID NO:3.

In a fourth aspect, the recombinant AAV vector of the invention comprises Proto 3S, which is depicted schematically in FIG. 2D, and comprises the nucleic acid sequence set forth in SEQ ID NO:4.

In another embodiment, the recombinant AAV vector of the invention comprises a nucleic acid encoding functional FVIII lacking the entire B domain, including the SQ sequence, and the a3 domain, which is located just N-terminal to the light chain or C domain. The FVIII coding region sequence may be a codon-optimized sequence (see, e.g., WO 2011/005968, published Jan. 13, 2011, WO 2015/038625, published Mar. 19, 2015, and McIntosh et al., *Blood* 121:3335-3344, 2013).

In a first aspect, the recombinant AAV vector of the invention comprises Proto 4, which is depicted schematically in FIG. 3A, and comprises the nucleic acid sequence set forth in SEQ ID NO:5.

In a second aspect, the recombinant AAV vector of the invention comprises Proto 5, which is depicted schematically in FIG. 3B, and comprises the nucleic acid sequence set forth in SEQ ID NO:6.

In a third aspect, the recombinant AAV vector of the invention comprises Proto 6, which is depicted schematically in FIG. 3C, and comprises the nucleic acid sequence set forth in SEQ ID NO:7.

In a fourth aspect, the recombinant AAV vector of the invention comprises Proto 7, which is depicted schematically in FIG. 3D, and comprises the nucleic acid sequence set forth in SEQ ID NO:8.

In other embodiments, the recombinant AAV vector of the invention comprises a nucleic acid comprising an AAV2 5' inverted terminal repeat (ITR) (which may or may not be modified as known in the art), a liver-specific transcription regulatory region, a codon-optimized functionally active FVIII coding region, optionally one or more introns, a polyadenylation sequence, and an AAV2 3' ITR (which may or may not be modified as known in the art). In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding region encoding the FVIII-SQ variant. In another preferred embodiment, the liver specific transcription regulatory region comprises an al-microglobulin enhancer sequence and the 186 base human alpha anti-trypsin (AAT) proximal promoter.

In a first aspect, the recombinant AAV vector of the invention comprises Construct 100ATG comprising the nucleic acid sequence forth in SEQ ID NO:9.

In a second aspect, the recombinant AAV vector of the invention comprises Construct 100ATG bGH poly A comprising the nucleic acid sequence set forth in SEQ ID NO:10.

In a third aspect, the recombinant AAV vector of the invention comprises Construct 100ATG short bGH polyA sequence set forth in SEQ ID NO:11.

In a fourth aspect, the recombinant AAV vector of the invention comprises Construct 103ATG comprising the nucleic acid sequence forth in SEQ ID NO:12.

In a fifth aspect, the recombinant AAV vector of the invention comprises Construct 103ATG short bGH poly A comprising the nucleic acid sequence set forth in SEQ ID NO:13.

In a sixth aspect, the recombinant AAV vector of the invention comprises Construct 105ATG bGH poly A comprising the nucleic acid sequence set forth in SEQ ID NO:14.

In a seventh aspect, the recombinant AAV vector of the invention comprises Construct DC172ATG FVIII comprising the nucleic acid sequence set forth in SEQ ID NO:15.

In an eighth aspect, the recombinant AAV vector of the invention comprises Construct DC172ATG FVIII hAAT comprising the nucleic acid sequence set forth in SEQ ID NO:16.

In a ninth aspect, the recombinant AAV vector of the invention comprises Construct DC172 2×HCR ATG FVIII comprising the nucleic acid sequence set forth in SEQ ID NO:17.

In a tenth aspect, the recombinant AAV vector of the invention comprises Construct DC172 2×HCR ATG FVIII hAAT comprising the nucleic acid sequence set forth in SEQ ID NO:18.

In an eleventh aspect, the recombinant AAV vector of the invention comprises Construct 2× SerpinA hAAT ATG FVIII comprising the nucleic acid sequence set forth in SEQ ID NO:19.

In a twelfth aspect, the recombinant AAV vector of the invention comprises Construct 2× SerpinA hAAT ATG FVIII 2× μ-globulin enhancer comprising the nucleic acid sequence set forth in SEQ ID NO:20.

In a thirteenth aspect, the recombinant AAV vector of the invention Construct 100ATG short polyA 2× μ-globulin enhancer comprising the nucleic acid sequence set forth in SEQ ID NO:21.

In a fourteenth aspect, the recombinant AAV vector of the invention comprises Construct Factor VIII-BMN001 comprising the nucleic acid sequence set forth in SEQ ID NO:22.

In a fifteenth aspect, the recombinant AAV vector of the invention comprises Construct Factor VIII-BMN002 sequence set forth in SEQ ID NO:23.

In a sixteenth aspect, the recombinant AAV vector of the invention comprises Construct 99 comprising the nucleic acid sequence set forth in SEQ ID NO:24.

In a seventeenth aspect, the recombinant AAV vector of the invention comprises Construct 100 comprising the nucleic acid sequence set forth in SEQ ID NO:25.

In an eighteenth aspect, the recombinant AAV vector of the invention comprises Construct 100 reverse orientation comprising the nucleic acid sequence set forth in SEQ ID NO:26.

In a nineteenth aspect, the recombinant AAV vector of the invention Construct 100AT comprising the nucleic acid sequence set forth in SEQ ID NO:27.

In a twentieth aspect, the recombinant AAV vector of the invention Construct 100AT 2× MG comprising the nucleic acid sequence set forth in SEQ ID NO:28.

In a twenty-first aspect, the recombinant AAV vector of the invention comprises Construct 100AT 2×MG bGH polyA comprising the nucleic acid sequence set forth in SEQ ID NO:29.

In a twenty-second aspect, the recombinant AAV vector of the invention comprises Construct 100AT 2×MG (reverse) bGH polyA comprising the nucleic acid sequence set forth in SEQ ID NO:30.

In a twenty-third aspect, the recombinant AAV vector of the invention comprises Construct 100 bGH polyA comprising the nucleic acid sequence set forth in SEQ ID NO:31.

In a twenty-fourth aspect, the recombinant AAV vector of the invention comprises Construct 100-400 comprising the nucleic acid sequence set forth in SEQ ID NO:32.

In a twenty-fifth aspect, the recombinant AAV vector of the invention comprises Construct 101 comprising the nucleic acid sequence set forth in SEQ ID NO:33.

In a twenty-sixth aspect, the recombinant AAV vector of the invention comprises Construct 102 sequence comprising the nucleic acid sequence set forth in SEQ ID NO:34.

In a twenty-seventh aspect, the recombinant AAV vector of the invention comprises Construct 103 comprising the nucleic acid sequence set forth in SEQ ID NO:35.

In a twenty-ninth aspect, the recombinant AAV vector of the invention comprises Construct 103 reverse orientation comprising the nucleic acid sequence set forth in SEQ ID NO:36.

In a thirtieth aspect, the recombinant AAV vector of the invention comprises Construct 103AT comprising the nucleic acid sequence set forth in SEQ ID NO:37.

In a thirty-first aspect, the recombinant AAV vector of the invention comprises Construct 103AT 2×MG comprising the nucleic acid sequence set forth in SEQ ID NO:38.

In a thirty-second aspect, the recombinant AAV vector of the invention comprises Construct 103AT 2×MG bGH polyA comprising the nucleic acid sequence set forth in SEQ ID NO:39.

In a thirty-third aspect, the recombinant AAV vector of the invention comprises the Construct 103 bGH polyA comprising the nucleic acid sequence set forth in SEQ ID NO:40.

In a thirty-fourth aspect, the recombinant AAV vector of the invention comprises Construct 104 comprising the nucleic acid comprising the nucleic acid sequence set forth in SEQ ID NO:41.

In a thirty-fifth aspect, the recombinant AAV vector of the invention comprises Construct 105 comprising the nucleic acid sequence set forth in SEQ ID NO:42.

In a thirty-sixth aspect, the recombinant AAV vector of the invention comprises Construct 106 comprising the nucleic acid sequence set forth in SEQ ID NO:43.

In a thirty-seventh aspect, the recombinant AAV vector of the invention comprises Construct 106AT comprising the nucleic acid sequence set forth in SEQ ID NO:44.

In a thirty-eighth aspect, the recombinant AAV vector of the invention comprises p-100 ATGB, which comprises the nucleic acid sequence set forth in SEQ ID NO:45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation. The present invention is also directed to recombinant AAV virus particles comprising the herein described AAV FVIII vectors and their use for the treatment of hemophilia A.

The AAV vectors of the invention in single strand form are less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand form range from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particles comprising any of the AAV vectors of the invention. The methods comprise the steps of culturing a cell that has been transfected with any of the AAV vectors of the invention (in association with various AAV cap and rep genes) and recovering recombinant AAV FVIII virus particles from the supernatant of the transfected cell.

The cells of the invention useful for recombinant AAV production are any cell type susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NS0, SP2/0, PER.C6, Vero, RD, BHK, HT 1080, A549, Cos-7, ARPE-19 and MRC-5.

The invention also provides for a recombinant viral particle comprising any of the AAV vectors of the invention or any viral particle produced by the forgoing methods of the invention.

An "AAV virion" or "AAV viral particle" or "AAV vector particle" or "AAV virus" refers to a viral particle composed of at least one AAV capsid protein and an encapsidated polynucleotide AAV vector as described herein. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particles necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient a therapeutically effective amount of any of the AAV vectors of the invention, or a viral particle of the invention or a viral particle produced by a method of the invention.

In another embodiment, the invention provides for methods of increasing circulating FVIII protein levels in a subject in need thereof comprising administering to the subject any of the AAV vectors of the invention, or a viral particle of the invention or a viral particle produced by a method of the invention.

In another embodiment, the invention provides for methods for inducing the expression of FVIII protein in a subject in need thereof comprising administering to the subject any of the AAV vectors of the invention, or viral particles of the invention or a viral particle produced by a method of the invention.

In another embodiment, the invention provides for methods for increasing FVIII protein expression in a subject in need thereof comprising administering to the subject any of the AAV vectors of the invention, or viral particles of the invention or a viral particle produced by a method of the invention.

The invention also provides for any of the methods of the invention further comprising the step of determining the absence or presence of anti-AAV capsid antibodies in the serum of said subject after administration of said therapeutically effective amount of said recombinant AAV FVIII virus. In addition, the invention provides for any of the methods of the invention further comprising the step of administering an effective amount of a corticosteroid to said subject after a determination of the presence of anti-AAV capsid antibodies in the serum of said subject is made.

In a further embodiment, the invention provides for a use of any of the AAV vectors of the invention or recombinant AAV virus particles of the invention for preparation of a medicament for the treatment of hemophilia A. In one aspect, the medicament comprises an amount of AAV vector or recombinant AAV FVIII virus particle that expresses human FVIII in an amount effective to treat hemophilia A. The invention also provides for any of the uses of the invention wherein after administration of the medicament, the absence or presence of anti-AAV capsid antibodies in the serum of the subject is determined. If the subject is determined to have anti-AAV capsid antibodies in the serum, use of an effective amount of a corticosteroid for the preparation of a medicament for the administration to the subject having anti-AAV capsid antibodies in the serum.

In another embodiment, the invention provides for a composition comprising any of the AAV vectors or recombinant AAV virus particles of the invention for the treatment of hemophilia A. In one aspect, the composition comprises an amount of AAV vector or recombinant AAV virus particles that expresses human FVIII in an amount effective to treat hemophilia A. In addition, any of the compositions of the invention are administered with an effective amount of a corticosteroid in a subject determined to have anti-AAV capsid antibodies in the serum after administration of the composition.

In another embodiment, the AAV vectors of the invention are used to produce AAV viral particles that are useful for treating a patient suffering from hemophilia A.

In another embodiment, the invention provides for pharmaceutical formulations comprising recombinant FVIII-encoding AAV virus particles as described herein. More specifically, in certain aspects, the present invention is directed to pharmaceutical formulations that comprise a recombinant AAV FVIII-encoding virus, a buffering agent, an isotonicity agent, a bulking agent and a surfactant. In particularly preferred embodiments, the pharmaceutical formulations of the present invention comprise AAV5-FVIII-SQ, p-100 ATGB or any of the other herein described vectors and/or are stable during storage at ≤65° C. for at least 2 weeks. In yet other embodiments of the present invention, the pharmaceutical formulation comprises sodium phosphate, dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml. In a particularly preferred embodiment, the pharmaceutical formulation of the present invention comprises sodium phosphate, dibasic at a concentration of about 1.42 mg/ml, sodium phosphate monobasic monohydrate at a concentration of about 1.38 mg/ml, sodium chloride at a concentration of about 8.18 mg/ml, mannitol at a concentration of about 20 mg/ml, and poloxamer 188 at a concentration of about 2 mg/ml. The pharmaceutical formulations of the present invention may be in liquid form and may comprise the AAV FVIII virus particle at a concentration of from about 1E12 vg/ml to about 2E14 vg/ml, more preferably at a concentration of about 2E13 vg/ml. In one embodiment, the pharmaceutical formulations of the invention are useful for intravenous administration to a human suffering from hemophilia A.

The present invention is also directed to methods for treating a subject suffering from hemophilia A which comprise the step of administering to the subject a therapeutically effective amount of a recombinant AAV FVIII virus, which optionally may be formulated as described above. In a preferred embodiment, the subject suffering from hemophilia A is a human. In one embodiment, the recombinant AAV FVIII virus is AAV5-FVIII-SQ. In one embodiment, the step of administering is accomplished by intravenous (IV) administration. In certain aspects of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, the therapeutically effective amount of AAV FVIII virus administered to the subject is least 2E13 vg/kg of body weight, sometimes at least 6E13 vg/kg of body weight. In certain embodiments, in addition to administration of a therapeutically effective amount of AAV FVIII virus, the subject is treated either prophylactically, therapeutically, or both with a corticosteroid to prevent and/or treat any hepatotoxicity associated with administration of the AAV FVIII virus. In one embodiment, associated hepatotoxicity is measured by comparing baseline (i.e., pre-dosing with FVIII AAV) alanine transaminase (ALT) levels to post-treatment ALT levels, wherein an increase in ALT levels post-dosing is evidence of associated hepatotoxicity. Prophylactic corticosteroid treatment refers to the administration of a corticosteroid to prevent hepatotoxicity and/or to prevent an increase in measured ALT levels in the subject. Therapeutic corticosteroid treatment refers to the administration of a corticosteroid to reduce hepatotoxicity caused by administration of an AVV FVIII virus and/or to reduce an elevated ALT concentration in the bloodstream of the subject caused by administration of an AAV FVIII virus. In certain embodiments, prophylactic or therapeutic corticosteroid treatment may comprise administration of at least 5, 10, 15, 20, 25, 30, 35, 40, 45, 50, 55, 60, or more mg/day of the corticosteroid to the subject. In certain embodiments, prophylactic or therapeutic corticosteroid treatment of a subject may occur over a continuous period of at least about 3, 4, 5, 6, 7, 8, 9, 10 weeks, or more.

The present invention is also directed to a composition comprising a therapeutically effective amount of a recombinant AAV FVIII virus for use in treating a subject suffering from hemophilia A. In one embodiment, the AAV FVIII virus is AAV5-FVIII-SQ. In another embodiment, the AAV FVIII virus comprises the p-100 ATGB vector. The composition optionally may be formulated as described above. In certain embodiments, compositions comprising a therapeutically effective amount of AAV FVIII virus are administered with a composition comprising a prophylactic and/or therapeutic corticosteroid for use in preventing and/or treating any hepatotoxicity associated with administration of the AAV FVIII virus. The composition comprising a prophylactic or therapeutic corticosteroid treatment may comprise at least 5, 10, 15, 20, 25, 30, 35, 40, 45, 50, 55, 60, or more mg/day of the corticosteroid. In certain embodiments, compositions comprising a prophylactic or therapeutic corticosteroid may be administered over a continuous period of at least about 3, 4, 5, 6, 7, 8, 9, 10 weeks, or more.

The present invention is also directed to use of a therapeutically effective amount of recombinant AAV FVIII virus for the preparation of a medicament for the treatment of a subject suffering from hemophilia A. In certain embodiments, the AAVFVIII virus is AAV5-FVIII-SQ or a virus comprising the p-100 ATGB vector. The medicament optionally may be formulated as described above. In a preferred embodiment, the subject suffering from hemophilia A is a human. In one embodiment, the medicament is administered by intravenous (IV) administration. In one aspect of the present invention, administration of the medicament results in expression of at least about 5 IU/dl of Factor VIII protein in the bloodstream of the subject, preferably at least about 5 IU/dl of Factor VIII protein in the bloodstream of the subject 16 weeks or more after administration. In certain embodiments, the medicament also comprises a prophylactic and/or therapeutic corticosteroid for the prevention and/or treatment of any hepatotoxicity associated with administration of the AAV FVIII virus. The medicament comprising a prophylactic or therapeutic corticosteroid treatment may comprise at least 5, 10, 15, 20, 25, 30, 35, 40, 45, 50, 55, 60, or more mg/day of the corticosteroid. In certain embodiments, the medicament comprising a prophylactic or therapeutic corticosteroid may be administered over a continuous period of at least about 3, 4, 5, 6, 7, 8, 9, 10 weeks, or more.

The present invention is also directed to methods for reducing bleeding time during a bleeding episode in a subject suffering from hemophilia A which comprise the step of administering to the subject a therapeutically effective amount of a recombinant AAV FVIII virus as described herein, which optionally may be formulated as described above. In a preferred embodiment, the subject suffering from hemophilia A is a human. In one embodiment, the step of administering is accomplished by intravenous (IV) administration. In certain embodiments, the step of administering occurs at least about 3, 4, 5, 6, 7, 8, 9, 10, 15, 20, 25, 30, 35, 40, 45, 50 weeks, or more, prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of a therapeutically effective amount of AAV FVIII virus, the subject is treated either prophylactically, therapeutically, or both with a corticosteroid to prevent and/or treat any hepatotoxicity associated with administration of the AAV FVIII virus, as described above.

The present invention is also directed to a composition comprising a therapeutically effective amount of a recombinant AAV FVIII virus for use in reducing bleeding time of a bleeding episode in a subject suffering from hemophilia A. In one embodiment, the AAVFVIII virus is AAV5-FVIII-SQ. The composition optionally may be formulated as described above. In a preferred embodiment, the subject suffering from hemophilia A is a human. The composition may be administered prior to the bleeding episode. In one embodiment, the composition is administered by intravenous (IV) administration prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, compositions comprising a therapeutically effective amount of AAV FVIII virus for use in reducing bleeding time are administered with a composition comprising a prophylactic and/or therapeutic corticosteroid for use in preventing and/or treating any hepatotoxicity associated with administration of the AAV FVIII virus, as described above.

The invention also provides for any of the methods of reducing bleeding time further comprising the step of determining the absence or presence of anti-AAV capsid antibodies in the serum of said subject after administration of said therapeutically effective amount of said recombinant AAV FVIII virus. In addition, the invention provides for any of the methods of reducing bleeding time further comprising the step of administering an effective amount of a corticosteroid to said subject after a determination of the presence of anti-AAV capsid antibodies in the serum of said subject is made.

The present invention is also directed to use of a therapeutically effective amount of recombinant AAV FVIII virus for the preparation of a medicament for reducing bleeding time of a bleeding episode in a subject suffering from hemophilia A. In one embodiment, the AAVFVIII virus is AAV5-FVIII-SQ. The medicament optionally may be formulated as described above. In a preferred embodiment, the subject suffering from hemophilia A is a human. The medicament may be administered prior to the bleeding episode. In one embodiment, the medicament is administered by intravenous (IV) administration prior to the bleeding episode. In one aspect of the present invention, administration of the medicament results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, administration of the medicament results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, medicaments comprising a therapeutically effective amount of AAV FVIII virus for reducing bleeding time also comprise a prophylactic and/or therapeutic corticosteroid for preventing and/or treating any hepatotoxicity associated with administration of the AAV FVIII virus, as described above. In addition, any of the compositions of the invention for use in reducing bleeding time are administered with an effective amount of a corticosteroid in a subject determined to have anti-AAV capsid antibodies in the serum after administration of the composition.

The present invention is also directed to methods for inducing expression of a functional FVIII protein in a subject in need thereof which comprise the step of administering to the subject a recombinant AAV FVIII virus as described herein, which optionally may be formulated as described above, wherein such administration results in increased expression of functional FVIII protein or increased concentrations of functional FVIII protein in the bloodstream of the subject. In a preferred embodiment, the subject in need is a human. In one embodiment, the step of administering is accomplished by intravenous (IV) administration. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of an AAV FVIII virus, the subject is treated either prophylactically, therapeutically, or both with a corticosteroid to prevent and/or treat any hepatotoxicity associated with administration of the AAV FVIII virus, as described above. In addition, in any of the uses of the invention after administration of the medicament to reduce bleeding time, the absence or presence of anti-AAV capsid antibodies in the serum of the subject is determined. If the subject is determined to have anti-AAV capsid antibodies in the serum, use of an effective amount of a corticosteroid for the preparation of a medicament for the administration to the subject having anti-AAV capsid antibodies in the serum is contemplated.

The present invention is also directed to methods for increasing expression of FVIII protein in a subject in need thereof which comprise the step of administering to the subject a recombinant AAV FVIII virus as described herein, which optionally may be formulated as described above, wherein such administration results in increased expression of functional FVIII protein or increased concentrations of functional FVIII protein in the bloodstream of the subject. In a preferred embodiment, the subject in need is a human. In one embodiment, the step of administering is accomplished by intravenous (IV) administration. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of an AAV FVIII virus, the subject is treated either prophylactically, therapeutically, or both with a corticosteroid to prevent and/or treat any hepatotoxicity associated with administration of the AAV FVIII virus, as described above.

The present invention is also directed to a composition comprising a therapeutically effective amount of a recombinant AAV FVIII virus for use in increasing or inducing expression of FVIII protein in a subject in need thereof. In one embodiment, the AAVFVIII virus is AAV5-FVIII-SQ. The composition optionally may be formulated as described above. In a preferred embodiment, the subject in need is a human suffering from hemophilia A. The composition may be administered prior to the bleeding episode. In one embodiment, the composition is administered by intravenous (IV) administration prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, compositions comprising a therapeutically effective amount of AAV FVIII virus for use in increasing or inducing expression of FVIII protein are administered with a composition comprising a prophylactic and/or therapeutic corticosteroid for use in preventing and/or treating any hepatotoxicity associated with administration of the AAV FVIII virus, as described above.

The present invention is also directed to use of a therapeutically effective amount of recombinant AAV FVIII virus for the preparation of a medicament for increasing or inducing expression of FVIII protein in a subject in need. In one embodiment, the subject in need is a human suffering from hemophilia A. In one embodiment, the AAVFVIII virus is AAV5-FVIII-SQ. The medicament optionally may be formulated as described above. The medicament may be administered prior to the bleeding episode. In one embodiment, the medicament is administered by intravenous (IV) administration prior to the bleeding episode. In one aspect of the present invention, administration of the medicament results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, administration of the medicament results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, medicaments comprising a therapeutically effective amount of AAV FVIII virus for increasing or inducing expression of FVIII protein also comprise a prophylactic and/or therapeutic corticosteroid for preventing and/or treating any hepatotoxicity associated with administration of the AAV FVIII virus, as described above.

The present invention is also directed to a method of treating a subject suffering from hemophilia A comprising the steps of (i) determining the absence of anti-AAV capsid antibodies in the serum of said subject, and (ii) administering to said subject a therapeutically effective amount of a recombinant AAV FVIII virus.

The present invention is also directed to use of a therapeutically effective amount of a recombinant AAV FVIII virus for the preparation of a medicament for the treatment of a subject suffering from hemophilia A, wherein anti-AAV capsid antibodies are absent from the serum of the subject.

The present invention is also directed to a composition comprising a therapeutically effective amount of a recombinant AAV FVIII virus for use in treating a subject suffering from hemophilia A, wherein anti-AAV capsid antibodies are absent from the subject's serum.

The present invention is also directed to a method of treating a subject suffering from hemophilia A comprising the steps of (i) administering to said subject a therapeutically effective amount of a recombinant AAV FVIII virus, and (ii) after administration of said therapeutically effective amount of said recombinant AAV FVIII virus, determining the absence or presence of anti-AAV capsid antibodies in the serum of said subject. In one embodiment, the method further comprises the step of administering an effective amount of a corticosteroid to the subject after a determination of the presence of anti-AAV capsid antibodies in the serum of said subject is made.

The present invention is directed to use of a therapeutically effective amount of a recombinant AAV FVIII virus for the preparation of a medicament for the treatment of hemophilia A wherein after administration of the medicament, the absence or presence of anti-AAV capsid antibodies in the serum of the subject is determined. If the subject is determined to have anti-AAV capsid antibodies in the serum, use of an effective amount of a corticosteroid for the preparation of a medicament for administration to the subject having anti-AAV capsid antibodies in the serum. The present invention is also directed to a composition comprising an effective amount of recombinant AAV FVIII for treatment of hemophilia A, wherein this composition is administered with an effective amount of a corticosteroid in a subject determined to have anti-AAV capsid antibodies in the serum after administration of the composition.

Other embodiments of the present invention will be evident to one skilled in the art upon reading the present patent specification.

DETAILED DESCRIPTION

The present invention provides for AAV vectors encoding functionally active FVIII, e.g., completely packaged AAV FVIII vectors or AAV FVIII vectors with high expression activity. The recombinant AAV FVIII vectors of the invention have improved transgene expression, as well as improved AAV virus production yield and simplified purification. Introducing one or more introns into the FVIII protein-coding region enhances expression. Reconfiguring the number and positioning of enhancers also enhances expression.

Exemplary AAV FVIII Vector

Figure 1:
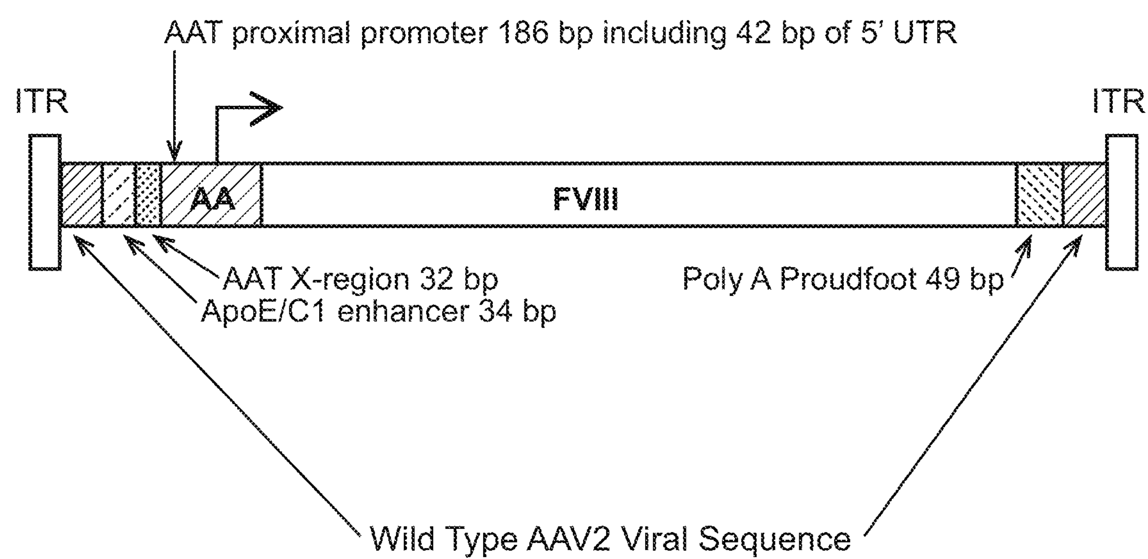
FIG. 1 provides a schematic of an exemplary FVIII-encoding recombinant AAV vector. From left to right, the vector comprises an AAV2 5' ITR sequence, wild-type AAV2 viral sequence, a 34 base human ApoE/C1 enhancer sequence, a 32 base human AAT promoter distal X region sequence, a 186 base human AAT promoter sequence that includes 42 bases of 5' UTR sequence, a codon-optimized human FVIII SQ sequence, a 49 base synthetic Proudfoot polyadenylation sequence, wild-type AAV2 viral sequence, and an AAV2 3'ITR sequence (see WO 2011/005968, published Jan. 13, 2011, which is incorporated herein by reference in its entirety, and McIntosh et al., *Blood* 121:3335-3344, 2013). This vector is 5081 bases in length.

The exemplary recombinant AAV FVIII vector shown in FIG. 1, which is described in detail in WO 2011/005968, published Jan. 13, 2011, which is incorporated herein by reference in its entirety, and McIntosh et al., *Blood* 121: 3335-3344, 2013, is an oversized, i.e., greater than 5.0 kb, AAV FVIII vector. As shown in FIG. 1, this AAV FVIII vector comprises, from left to right, the AAV serotype 2 (AAV2) 5' ITR, wild-type AAV2-derived viral sequence, a 34 base human apolipoprotein E (ApoE)/C1 enhancer element, a 32 base human alpha anti-trypsin (AAT) promoter distal X region, a 186 base human AAT (hAAT) promoter, including 42 bases of 5' untranslated region (UTR) sequence, a codon-optimized human FVIII sequence in which the FVIII B domain is replaced with the 14 amino acid SQ sequence, a 49 bases synthetic Proudfoot polyadenylation sequence, wild-type AAV2-derived viral sequence, and the AAV2 3' ITR. This vector is 5081 bases in length and, as shown in WO 2011/005968, expresses functionally active FVIII both in vitro and in vivo.

Proto 1, Proto 1S, Proto 2S and Proto 3S Vectors

To avoid problems associated with over-sized AAV vectors and/or to increase the expression of a FVIII transgene from AAV vectors, the present invention provides completely packaged, smaller, i.e., less than 5.0 kb, AAV vectors encoding a functional FVIII protein. The 4970 bp nucleotide sequence of the recombinant AAV Proto 1 construct is provided in SEQ ID NO:1.

To generate the recombinant AAV FVIII vector Proto 1, sequences that were determined to be unnecessary for production of functionally active FVIII were deleted from the vector shown in FIG. 1. As shown in Example 1, 111 bases of extraneous DNA were removed, including 53 bases of wild-type AAV2 viral sequence 3' to the AAV2 5' ITR, 46 bases of AAV2 viral sequence 5' to the AAV2 3' ITR, and 12 bases adjacent to the codon-optimized FVIII protein coding region. The codon-optimized FVIII SQ sequence of the vector shown in FIG. 1 was also replaced by a novel, codon-optimized FVIII SQ sequence referred to herein as "FVIII-SQ". The FVIII-SQ coding sequence (bases 403-4776 of SEQ ID NO:1) was then introduced into the Proto 1 vector. The resultant Proto 1 vector is 4970 bases in length and comprises, from left to right, a modified AAV serotype 2 (AAV2) 5' ITR, a 34 base human apolipoprotein E (ApoE)/C1 enhancer element, a 32 base human alpha anti-trypsin (AAT) promoter distal X region, a 186 base hAAT promoter, including 42 bases of 5' untranslated region (UTR) sequence, a novel codon-optimized human FVIII sequence in which the FVIII B domain is replaced with the 14 amino acid SQ sequence, a 49 bases synthetic Proudfoot polyadenylation sequence, and a modified AAV2 3' ITR. When designed, it was unknown whether the Proto 1 vector would be capable of expressing functional FVIII polypeptide, either in vitro or in vivo.

To generate the AAV vector Proto 1S, 10 bases at the 3' end of the AAV2 5' ITR, and 10 bases at the 5' end of the AAV2 3' ITR, were removed from the Proto 1 vector. The resultant Proto 1S vector is 4950 bases in length. The nucleotide sequence of sequence of Proto 1S is set forth in SEQ ID NO:2.

To generate the AAV vector Proto 2S, a synthetic 100 base intron was inserted between exons 1 and 2 of the FVIII-SQ sequence in the Proto 1S vector. The 34 base ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO:3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO:4.

Proto 4, Proto S, Proto 6 and Proto 7 Vectors

In an attempt to further reduce the size of the AAV FVIII vectors and/or increase the expression of the FVIII transgene from the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO:5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO:6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO:7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO:8.

Additional Recombinant AAV FVIII Vectors with Improved Promoter/Enhancer Sequences Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the μ-globulin enhancer or fragments thereof, the human alpha 1 antitrypsin promoter (hAAT) or fragments thereof, Serpin A enhancer or fragments thereof, the LP1 promoter enhancer or fragments thereof or macroglobulin enhancer or fragment thereof. These constructs comprise a polyadenylation sequence such as the bGH poly A sequence or the synthetic rabbit β-globin poly A sequence. In some embodiment, the constructs comprise an intron or fragments of an intron such as a hAAT intron or a human β-globin intron. In some embodiments, the recombinant AAV FVIII vectors comprise the novel codon-optimized FVIII-SQ coding sequence.

Figure 4A:
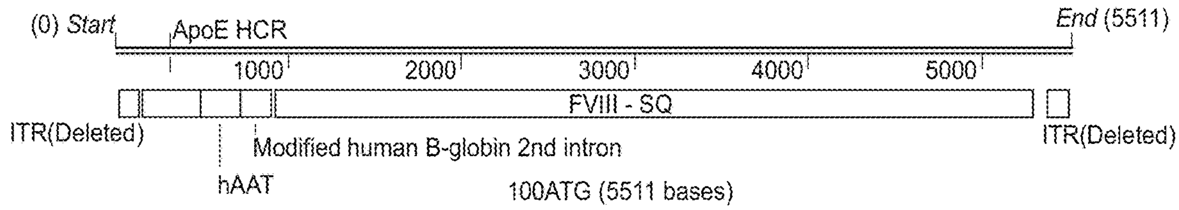
FIG. 4A-FIG. 4JJ provide schematic representations of certain recombinant AAV FVIII vectors of the present invention. (A) Construct 100ATG, (B) Construct 100ATG bGH polyA, (C) Construct 100ATG short bGH poly A, (D) Construct 103ATG, (E) Construct 103ATG short bGH poly A, (F) Construct 105ATG bGH polyA, (G) Construct DC172ATG FVIII, (H) Construct DC172ATG FVIII hAAT, (I) Construct DC172 2×HCR ATG FVIII, (J) Construct DC172 2×HCR ATG FVIII hAAT, (K) Construct 2× SerpinA hAAT ATG FVIII, (L) Construct 2× SerpinA hAAT ATG FVIII 2× μ-globulin enhancer, (M) Construct 100ATG short bGH poly A 2× μ-globulin enhancer, (N) Construct Factor VIII-BMN001, (O) Construct Factor VIII-BMN002, (P) Construct 99, (Q) Construct 100, (R) Construct 100 reverse orientation, (S) Construct 100AT, (T) Construct 100AT 2×MG, (U) Construct 100AT 2×MG bGH polyA, (V) Construct 100AT 2×MG (reverse) bGH poly A, (W) Construct 100 bGH poly A, (X) Construct 100-400, (Y) Construct 101, (Z) Construct 102, (AA) Construct 103, (BB) Construct 103 reverse orientation, (CC) Construct 103AT, (DD) Construct 103AT 2×MG, (EE) Construct 103AT 2×MG bGH poly A, (FF) Construct 103 bGH poly A, (GG) Construct 104, (HH) Construct 105, (II) Construct 106 and (JJ) Construct 106AT.

Construct 100ATG (FIG. 4A) is 5511 bases in length. The nucleotide sequence of this construct is set forth in SEQ ID NO:9 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5352 are a synthetic rabbit 3-globin poly A and bases 5367-5511 are a 3' AAV2 ITR.

Figure 4B:
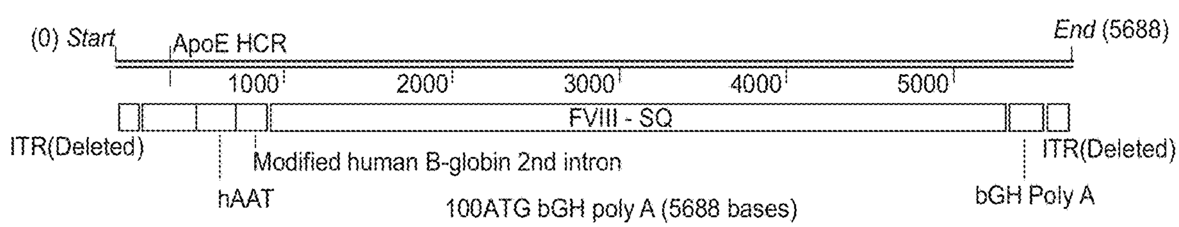

Construct 100ATG bGH poly A (FIG. 4B) is 5688 bases in length. The nucleotide sequence of this construct is set forth in SEQ ID NO:10 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5529 are a bGH poly A and bases 5544-5688 are a 3' AAV2 ITR.

Figure 4C:
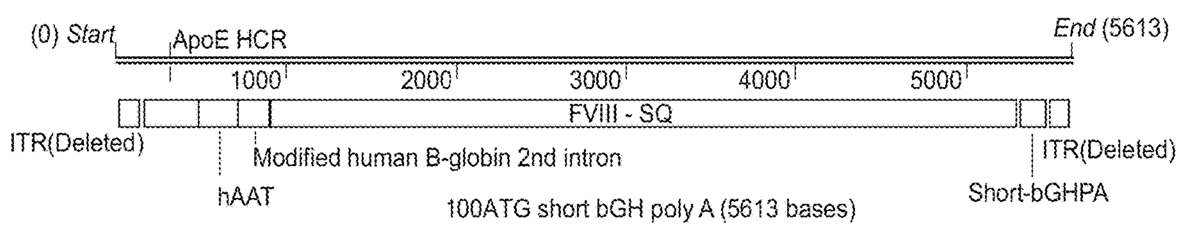

Construct 100ATG short bGH poly A (FIG. 4C) is 5613 bases in length. The nucleotide sequence of this construct is set forth in SEQ ID NO:11 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5454 are a short bGH poly A and bases 5469-5613 are a 3' AAV2 ITR.

Figure 4D:
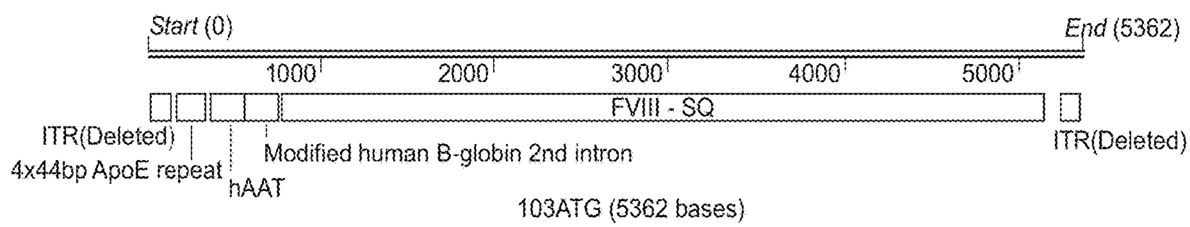

Construct 103ATG (FIG. 4D) is 5362 bases in length. The nucleotide sequence of this construct is set forth in SEQ ID NO:12 in which bases 1-145 are a 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are FVIII-SQ, bases 5156-5203 are a synthetic rabbit β-globin poly A and bases 5218-5362 are a 3' AAV2 ITR.

Figure 4E:
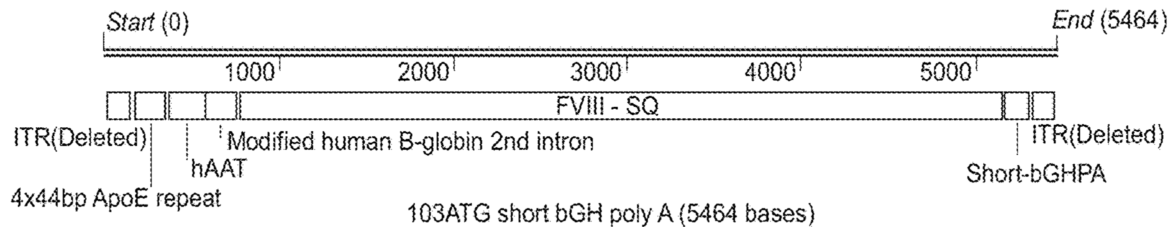

Construct 103ATG short bGH poly A (FIG. 4E) is 5464 bases in length. The nucleotide sequence of this construct is set forth in SEQ ID NO:13 in which bases 1-145 are a 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are FVIII-SQ, bases 5156-5305 are a bGH short poly A and bases 5320-5464 are a 3' AAV2 ITR.

Figure 4F:
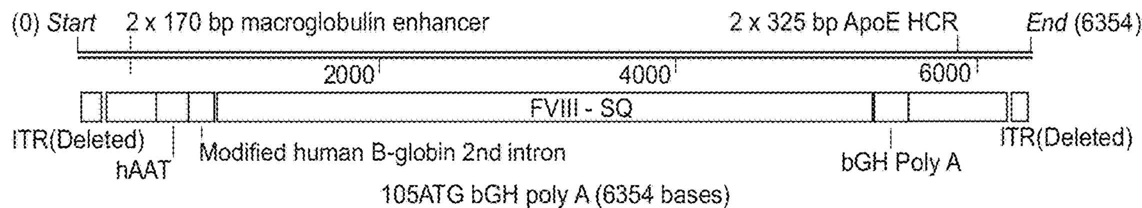

Construct 105ATG bGH polyA (FIG. 4F) is 6354 bases in length. The nucleotide sequence of this construct is set forth in SEQ ID NO:14 in which bases 1-145 are a 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are FVIII-SQ, bases 5315-5539 are a bGH poly A, bases 5546-6195 are two copies (2×) of a 325 bp ApoE HCR and bases 6210-6354 are a 3' AAV2 ITR.

Figure 4G:
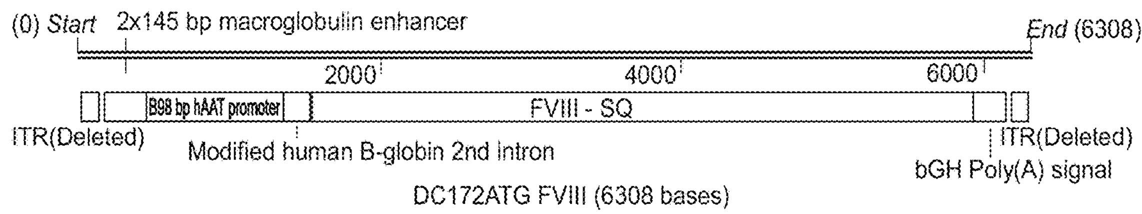

Construct DC172ATG FVIII (FIG. 4G) is 6308 bases in length. The nucleotide sequence of this construct is set forth in SEQ ID NO:15 in which bases 1-145 area 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are FVIII-SQ, bases 5926-6149 are a bGH poly A and bases 6164-6308 are a 3' AAV2 ITR.

Figure 4H:
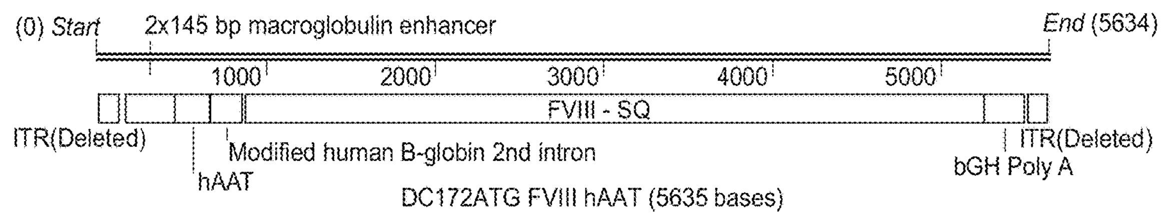

Construct DC172ATG FVIII hAAT (FIG. 4H) is 5635 bases in length, This construct is set forth as SEQ ID NO:16 in which bases 1-145 area 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are FVIII-SQ, bases 5253-5476 are a bGH poly A and bases 5490-5635 are a 3' AAV2 ITR.

Figure 4I:
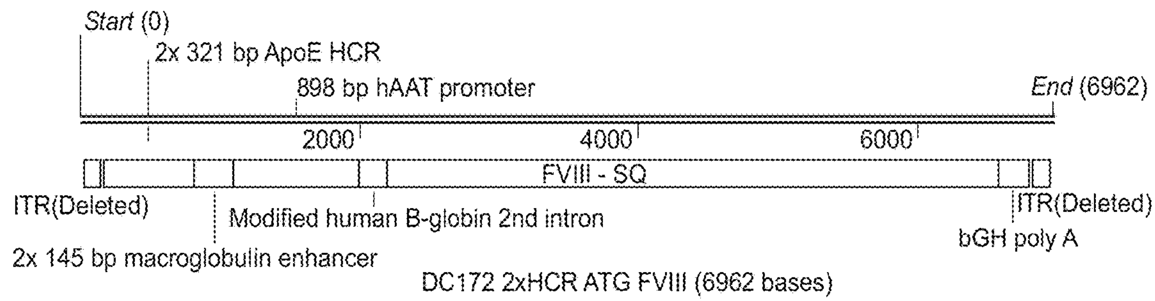

Construct DC172 2×HCR ATG FVIII (FIG. 4I) is 6962 bases in length. The nucleotide sequence of this construct is set forth in SEQ ID NO:17 in which bases 1-145 are a 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are FVIII-SQ, bases 6580-6803 are a bGH poly A and bases 6818-6962 are a 3' AAV2 ITR.

Figure 4J:
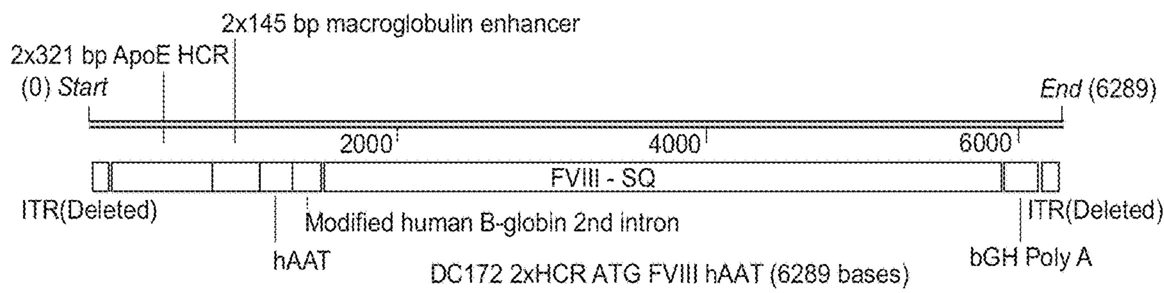

Construct DC172 2×HCR ATG FVIII hAAT (FIG. 4J) is 6289 bases in length. The nucleotide sequence of this construct is set forth in SEQ ID NO:18 in which bases 1-145 area 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are FVIII-SQ, bases 5907-6130 are a bGH poly A and bases 6245-6289 are a 3' AAV2 ITR.

Figure 4K:
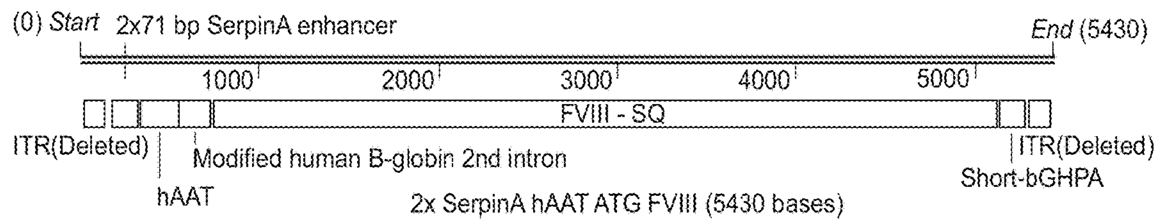

Construct 2× SerpinA hAAT ATG FVIII (FIG. 4K) is 5430 bases in length. The nucleotide sequence of this construct is set forth in SEQ ID NO:19 in which bases 1-145 are a 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are FVIII-SQ, bases 5122-5271 are a short bGH poly A, and bases 5286-5430 are a 3'AAV2 ITR.

Figure 4L:
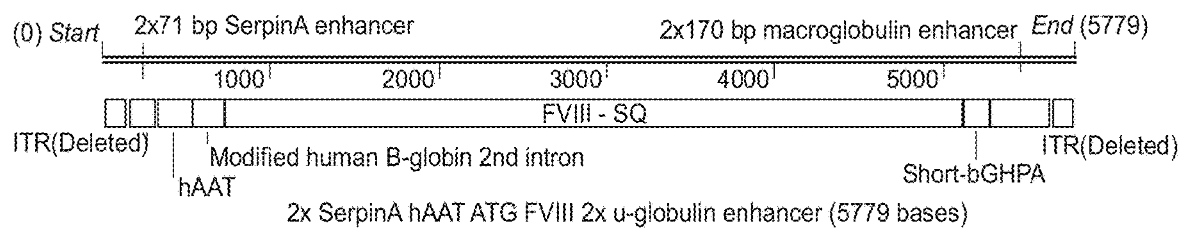

Construct 2× SerpinA hAAT ATG FVIII 2× μ-globulin enhancer (FIG. 4L) is 5779 bases in length. The nucleotide sequence of this construct is set forth in SEQ ID NO:20 in which bases 1-145 are a 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are FVIII-SQ, bases 5122-5271 are a short bGH poly A, bases 5279-5618 are two copies (2×) of a 170 bp μ-globulin enhancer and bases 5635-5779 are a 3' AAV2 ITR.

Figure 4M:
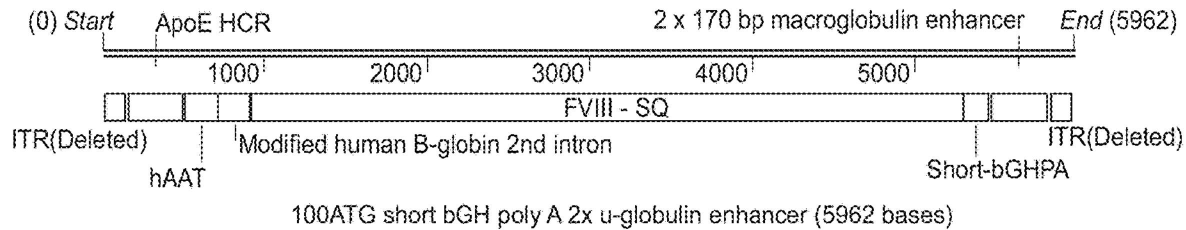

Construct 100ATG short bGH poly A 2× μ-globulin enhancer (FIG. 4M) is 5962 bases in length. The nucleotide sequence of this construct is set forth in SEQ ID NO:21 in which bases 1-145 are a 5' AAV2 ITR, bases 160-502 are an ApoE HCR, bases 509-726 are a hAAT promoter, bases 727-910 are a modified human β-globin $2^{nd}$ intron, bases 923-5296 are FVIII-SQ, bases 5305-5454 are a short bGH poly A, bases 5462-5801 are two copies (2×) of a 170 bp microglobulin enhancer and bases 5818-5962 are a 3' AAV2 ITR.

Figure 4N:
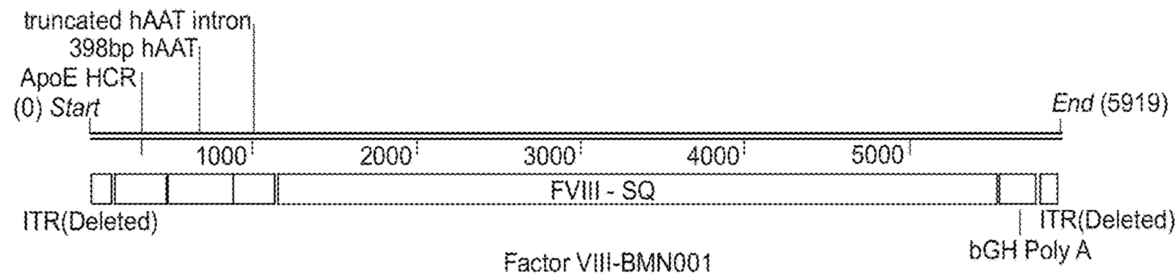

Construct Factor VIII-BMN001 (FIG. 4N) is 5919 bases in length. The nucleotide sequence of this construct is set forth in SEQ ID NO:22 in which bases 1-145 are a 5' AAV2 ITR, bases 160-480 are an ApoE HCR, bases 487-884 are a 398 bp hAAT promoter, bases 885-1145 are a truncated hAAT intron, bases 1155-5528 are FVIII-SQ, bases 5537-5760 are a bGH poly A and bases 5775-5919 are a 3' AAV2 ITR.

Figure 4O:
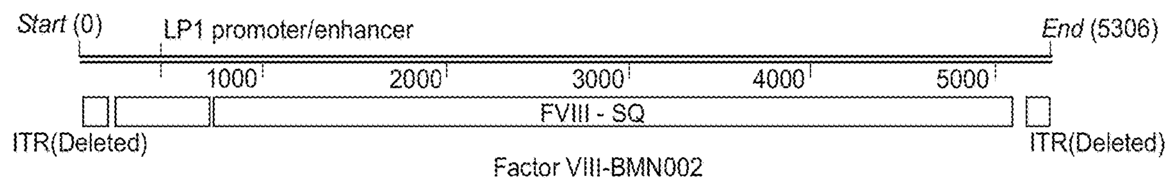

Construct Factor VIII-BMN002 (FIG. 4O) is 5306 bases in length. The nucleotide sequence of this construct is set forth in SEQ ID NO:23 in which bases 1-145 are a 5' AAV2 ITR, bases 175-705 are an LP1 promoter/enhancer, bases 718-5091 are FVIII-SQ, bases 5100-5147 are a synthetic rabbit β-globin poly A and bases 5162-5306 are a 3' AAV2 ITR.

Figure 4P:
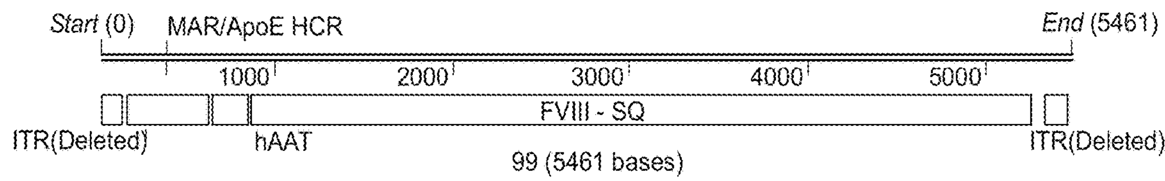

Construct 99 (FIG. 4P) is 5461 bases in length. The nucleotide sequence of this construct is set forth in SEQ ID NO:24 in which bases 1-145 are a 5' AAV2 ITR, bases 169-627 are an ApoE HCR/MAR, bases 634-866 are a hAAT promoter, bases 873-5246 are FVIII-SQ, bases 5255-5302 are a synthetic rabbit β-globin poly A and bases 5317-5461 are a 3' AAV2 ITR.

Figure 4Q:
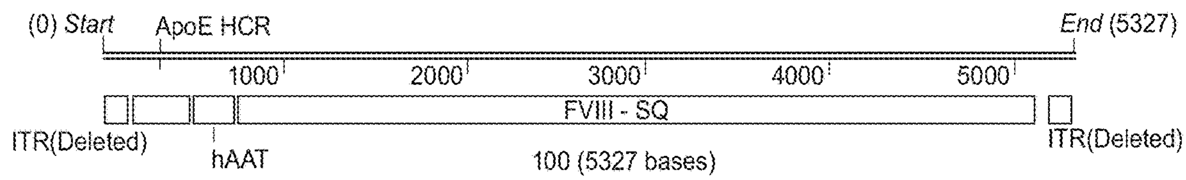

Construct 100 (FIG. 4Q) is 5327 bases in length. The nucleotide sequence of this construct is set forth in SEQ ID NO:25 in which bases 1-145 are a 5' AAV2 ITR, bases 169-493 are an ApoE HCR, bases 509-726 are a hAAT promoter, bases 739-5112 are FVIII-SQ, bases 5121-5168 are a synthetic rabbit β-globin poly A and bases 5183-5327 are a 3' AAV2 ITR.

Figure 4R:
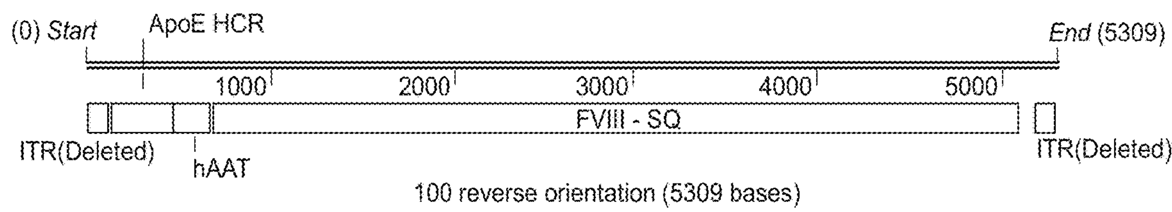

Construct 100 reverse orientation (FIG. 4R) is 5309 bases in length. The nucleotide sequence of this construct is set forth in SEQ ID NO:26 in which bases 1-145 are a 5' AAV2 ITR, bases 160-484 are an ApoE HCR in reverse orientation, bases 491-708 are a hAAT promoter, bases 721-5094 are FVIII-SQ, bases 5103-5150 are a synthetic rabbit β-globin poly A and bases 5165-5309 are a 3' AAV2 ITR.

Figure 4S:
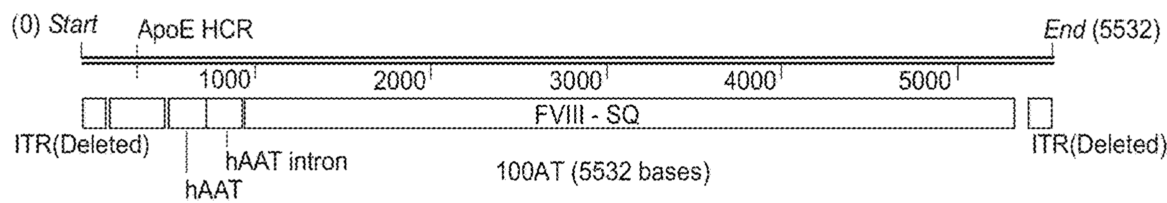

Construct 100AT (FIG. 4S) is 5532 bases in length. The nucleotide sequence of this construct is set forth in SEQ ID NO:27 in which bases 1-145 are a 5' AAV2 ITR, bases 169-493 are an ApoE HCR, bases 509-726 are a hAAT promoter, bases 727-931 are a hAAT intron, bases 944-5317 are FVIII-SQ, bases 5326-5373 are a synthetic rabbit β-globin poly A and bases 5388-5532 are a 3' AAV2 ITR.

Figure 4T:
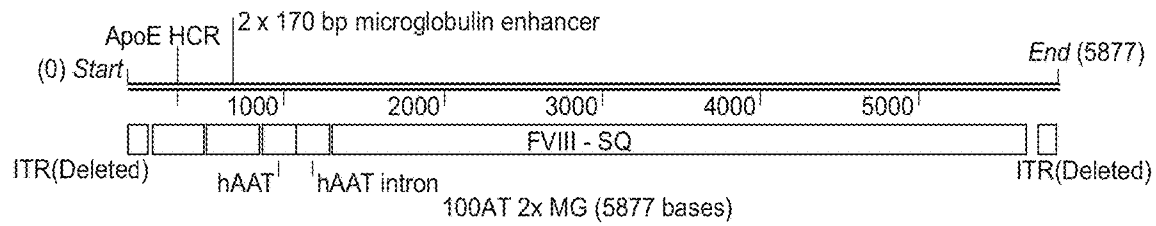

Construct 100AT 2×MG (FIG. 4T) is 5877 bases in length. The nucleotide sequence of this construct is set forth in SEQ ID NO:28 in which bases 1-145 are a 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are FVIII-SQ, bases 5671-5718 are a synthetic rabbit β-globin poly A and bases 5733-5877 are a 3' AAV2 ITR.

Figure 4U:
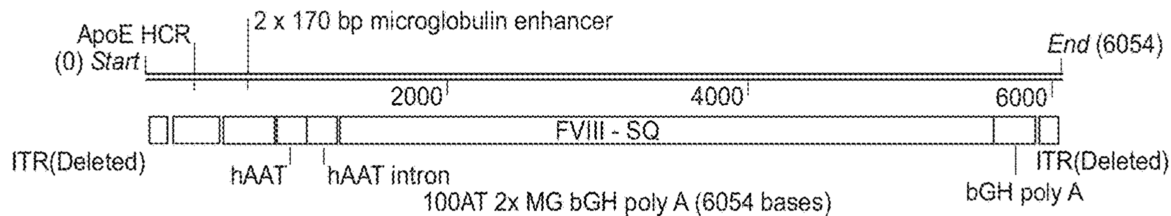

Construct 100AT 2×MG bGH poly A (FIG. 4U) is 6054 bases in length. The nucleotide sequence of this construct is set forth in SEQ ID NO:29 in which bases 1-145 are a 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are FVIII-SQ, bases 5671-5895 are a bGH poly A and bases 5910-6054 are a 3' AAV2 ITR.

Figure 4V:
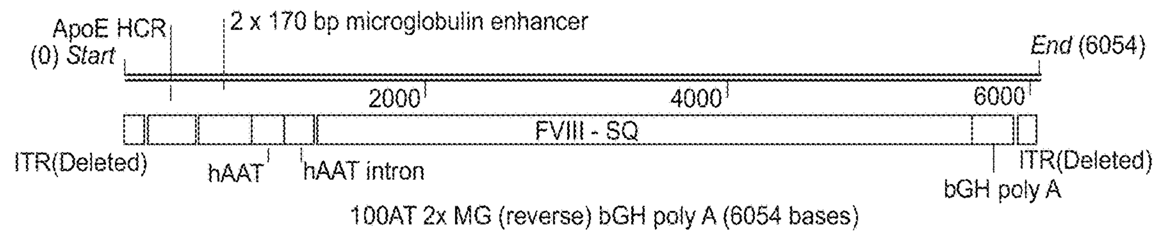

Construct 100AT 2×MG (reverse) bGH poly A (FIG. 4V) is 6054 bases in length. The nucleotide sequence of this construct is set forth in SEQ ID NO:30 in which bases 1-145 are a 5' AAV2 ITR, bases 169-493 are an ApoE HCR, bases 508-847 are two copies (2×) of a 170 bp μ-globulin enhancer in reverse orientation, bases 854-1071 are a hAAT promoter, bases 1072-1276 are a hAAT intron, bases 1289-5662 are FVIII-SQ, bases 5671-5895 are a bGH poly A and bases 5910-6054 are a 3' AAV2 ITR.

Figure 4W:
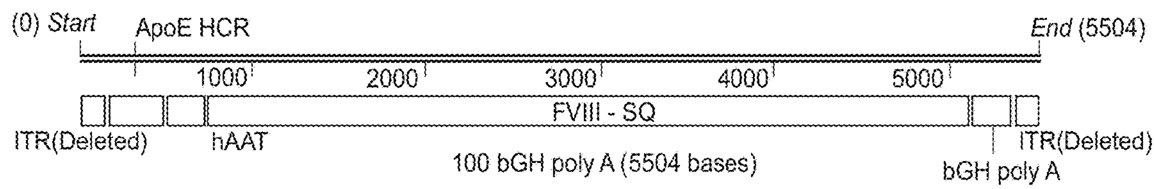

Construct 100 bGH poly A (FIG. 4W) is 5504 bases in length. The nucleotide sequence of this construct is set forth in SEQ ID NO:31 in which bases 1-145 are a 5' AAV2 ITR, bases 169-493 are an ApoE HCR, bases 509-726 are a hAAT promoter, bases 739-5112 are FVIII-SQ, base pairs 5121-5345 are a bGH poly A and bases 5360-5504 are a 3' AAV2 ITR.

Figure 4X:
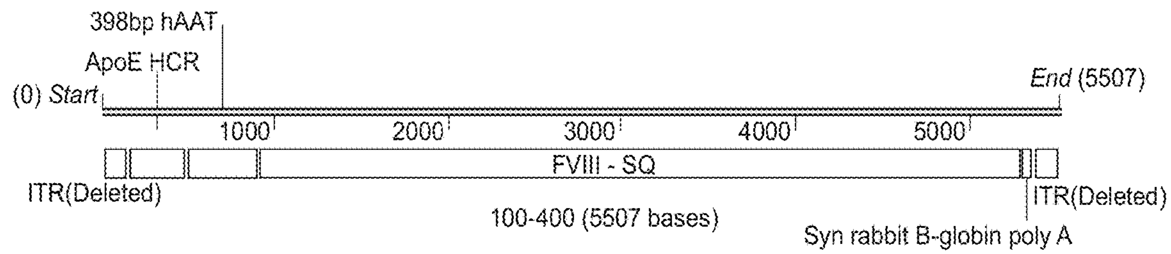

Construct 100-400 (FIG. 4X) is 5507 bases in length. The nucleotide sequence of this construct is set forth in SEQ ID NO:32 in which bases 1-145 are a 5' AAV2 ITR, bases 169-493 are an ApoE HCR, bases 512-906 are a 398 bp hAAT promoter, bases 919-5292 are FVIII-SQ, bases 5301-5348 are a synthetic rabbit β-globin poly A and bases 5363-5507 are a 3' AAV2 ITR.

Figure 4Y:
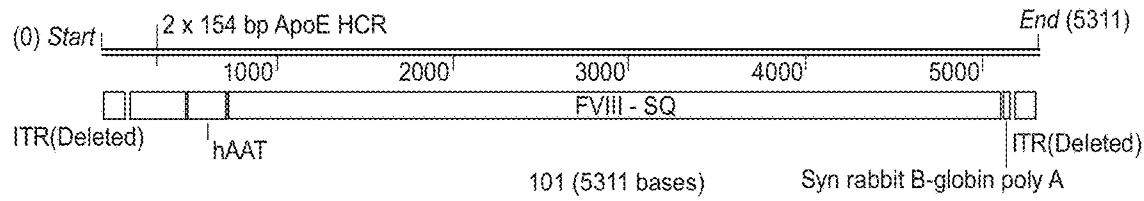

Construct 101 (FIG. 4Y) is 5311 base in length. The nucleotide sequence of this construct is set forth in SEQ ID NO:33 in which bases 1-145 are a 5' AAV2 ITR, bases 170-477 are two copies (2×) of a 154 bp ApoE HCR, bases 493-710 are a hAAT promoter, bases 723-5096 are FVIII-SQ, bases 5105-5152 are a synthetic rabbit β-globin poly A and bases 5167-5311 are a 3' AAV2 ITR.

Figure 4Z:
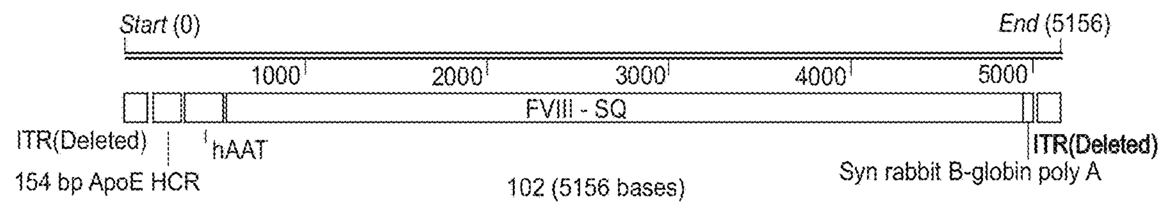
Figure 4A:
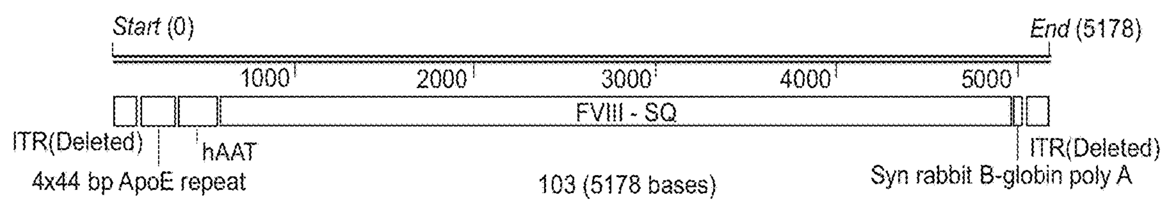
Figure 4B:
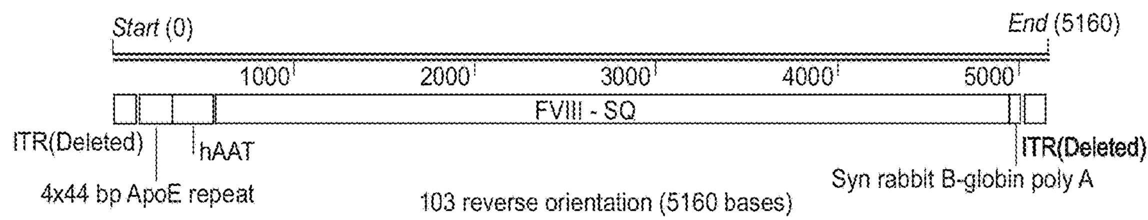
Figure 4C:
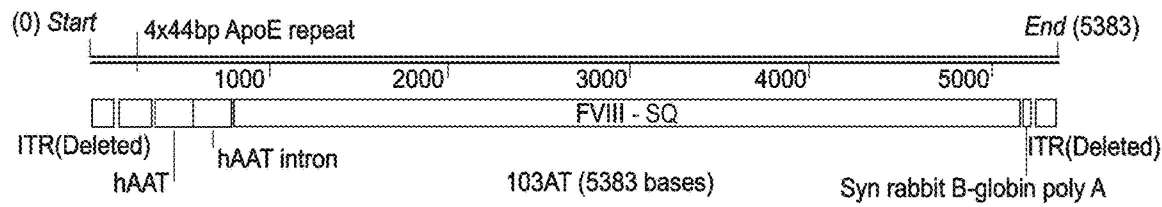
Figure 4D:
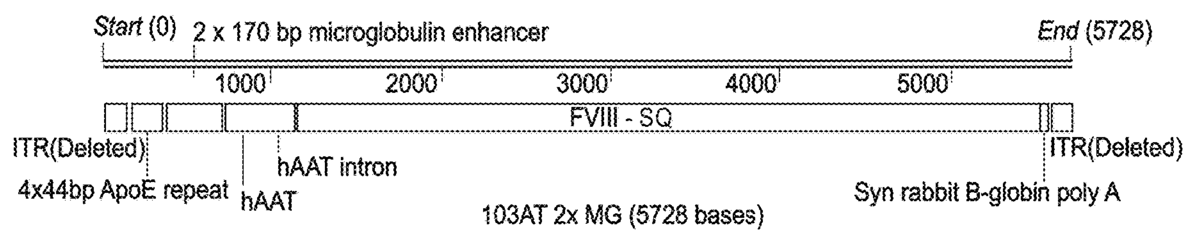
Figure 4E:
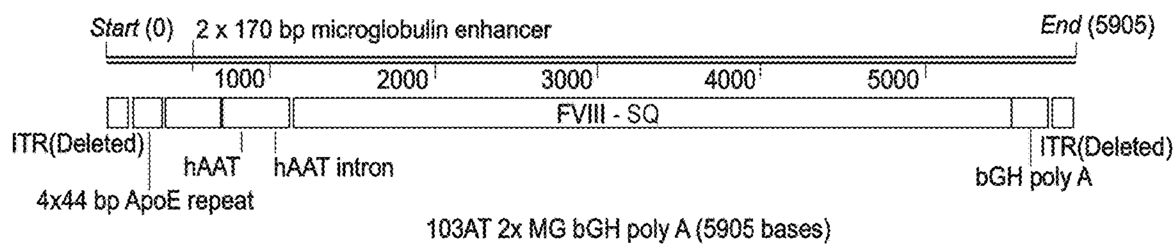
Figure 4F:
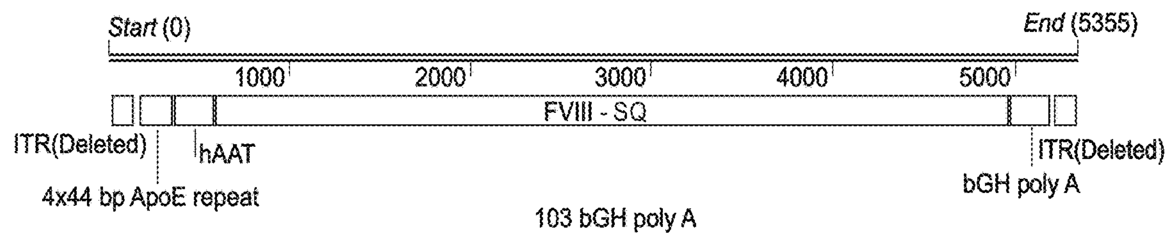
Figure 4G:
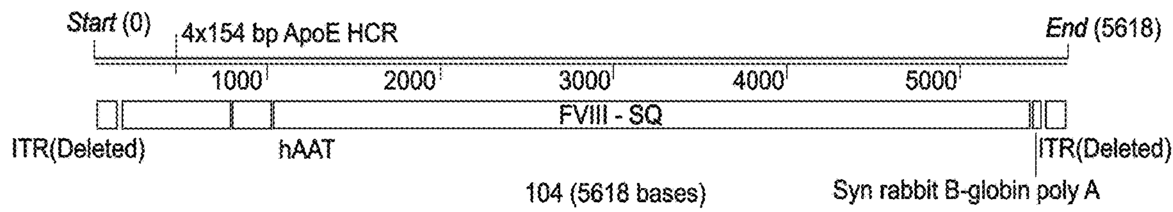
Figure 4H:
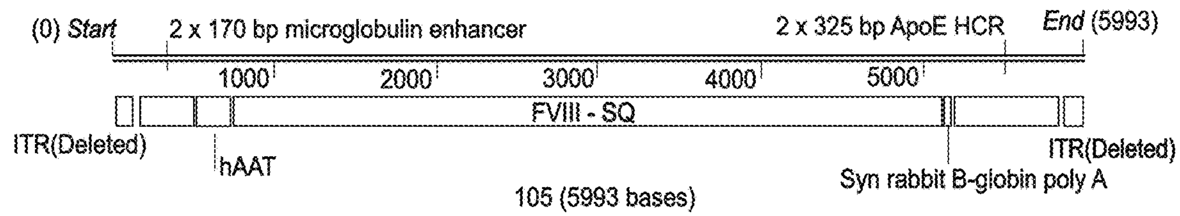
Figure 4I:
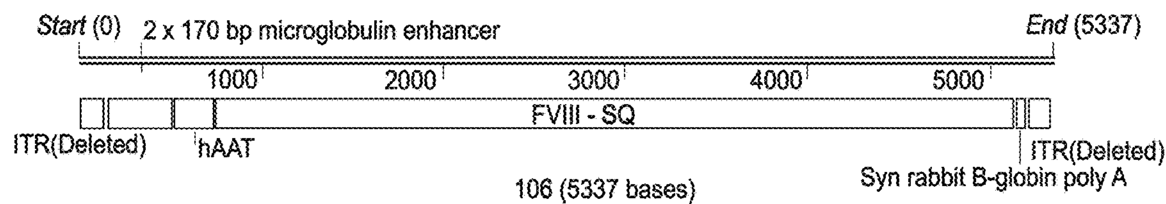
Figure 4J:
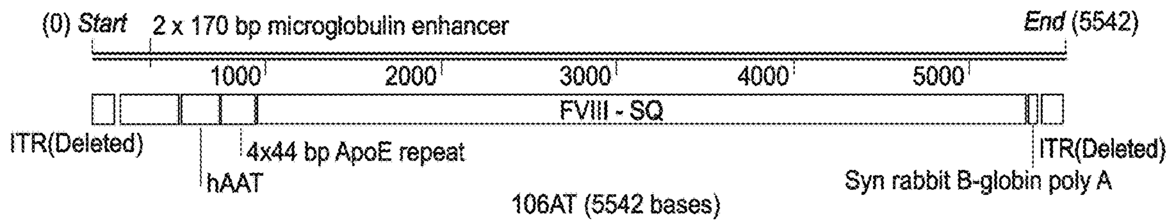

Construct 102 (FIG. 4Z) is 5156 bases in length. The nucleotide sequence of this construct is set forth in SEQ ID NO:34 in which bases 1-145 are a 5' AAV2 ITR, bases 169-322 are a 154 bp ApoE HCR, bases 338-555 are a hAAT promoter, bases 568-4941 are FVIII-SQ, bases 4950-4997 are a synthetic rabbit β-globin poly A and bases 5012-5156 are a 3' AAV2 ITR.

Construct 103 (FIG. 4AA) is 5178 bases in length. The nucleotide sequence of this construct is set forth in SEQ ID NO:35 in which bases 1-145 are a 5' AAV2 ITR, bases 169-344 are four copies (4×) of a 44 bp ApoE HCR, bases 360-577 are a hAAT promoter, bases 590-4963 are FVIII-SQ, bases 4972-5019 are a synthetic rabbit β-globin poly A and bases 5034-5178 are a 3' AAV2 ITR.

Construct 103 reverse orientation (FIG. 4BB) is 5160 bases in length. The nucleotide sequence of this construct is set forth in SEQ ID NO:36 in which bases 1-145 are a 5'

AAV2 ITR, bases 160-335 are four copies (4×) of a 44 bp ApoE HCR in reverse orientation, bases 342-559 are a hAAT promoter, bases 572-4945 are FVIII-SQ, bases 4954-5001 are a synthetic rabbit β-globin poly A and bases 5016-5160 are a 3' AAV2 ITR.

Construct 103AT (FIG. 4CC) is 5383 bases in length. The nucleotide sequence of this construct is set forth in SEQ ID NO:37 in which bases 1-145 are a 5' AAV2 ITR, bases 169-344 are four copies (4×) of a 44 bp ApoE HCR, bases 360-577 are a hAAT promoter, bases 578-782 are a hAAT intron, bases 795-4374 are FVIII-SQ, bases 5177-5224 are a synthetic rabbit β-globin poly A and bases 5239-5383 are a 3' AAV2 ITR.

Construct 103AT 2×MG (FIG. 4DD) is 5728 bases in length. The nucleotide sequence of this construct is set forth in SEQ ID NO:38 in which bases 1-145 are a 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are FVIII-SQ, bases 5522-5569 are a synthetic rabbit β-globin poly A and bases 5584-5728 are a 3' AAV2 ITR.

Construct 103AT 2×MG bGH poly A (FIG. 4EE) is 5905 bases in length. The nucleotide sequence of this construct is set forth in SEQ ID NO:39 in which bases 1-145 are a 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are FVIII-SQ, bases 5522-5746 are a synthetic rabbit β-globin poly A and bases 5761-5905 are a 5' AAV2 ITR.

Construct 103 bGH poly A (FIG. 4FF) is 5355 bases in length. The nucleotide sequence of this construct is set forth in SEQ ID NO:40 in which bases 1-145 are a 5' AAV2 ITR, bases 169-344 are four copies (4×) of a 44 bp ApoE HCR, bases 360-577 are a hAAT promoter, bases 590-4963 are FVIII-SQ, bases 4972-5196 are a synthetic rabbit β-globin poly A and bases 5211-5355 are a 3' AAV2 ITR.

Construct 104 (FIG. 4GG) is 5618 bases in length. The nucleotide sequence of this construct is set forth in SEQ ID NO:41 in which bases 1-145 are a 5' AAV2 ITR, bases 169-784 are four copies (4×) of a 154 bp ApoE HCR, bases 800-1017 are a hAAT promoter, bases 1030-5403 are FVIII-SQ, bases 5412-5459 are a synthetic rabbit β-globin poly A and bases 5474-5618 are a 3' AAV2 ITR.

Construct 105 (FIG. 4HH) is 5993 bases in length. The nucleotide sequence of this construct is set forth in SEQ ID NO:42 in which bases 1-145 are a 5' AAV2 ITR, bases 173-512 are two copies (2×) of a 170 bp μ-globulin enhancer, bases 519-736 are a hAAT promoter, bases 749-5122 are FVIII-SQ, bases 5131-5178 are a synthetic rabbit β-globin poly A, bases 5185-5834 are two copies (2×) of an ApoE HCR and bases 5849-5993 are a 3' AAV2 ITR.

Construct 106 (FIG. 411) is 5337 bases in length. The nucleotide sequence of this construct is set forth in SEQ ID NO:43 in which bases 1-145 are a 5' AAV2 ITR, bases 173-512 are two copies (2×) of a 170 bp μ-globulin enhancer, bases 519-736 are a hAAT promoter, bases 749-5122 are FVIII-SQ, bases 5131-5178 are a synthetic rabbit β-globin poly A and bases 5193-5337 are a 3' AAV2 ITR.

Construct 106AT (FIG. 4JJ) is 5542 bases in length. The nucleotide sequence of this construct is set forth in SEQ ID NO:44 in which bases 1-145 are a 5' AAV2 ITR, bases 173-512 are two copies (2×) of a 170 bp μ-globulin enhancer, bases 519-736 are a hAAT promoter, bases 737-941 are a hAAT intron, bases 954-5327 are FVIII-SQ, bases 5336-5383 are a synthetic rabbit β-globin poly A and bases 5398-5542 are a 3' AAV2 ITR.

Construct p-100 ATGB is 5640 bases in length. The nucleotide sequence of this construct is set forth in SEQ ID NO:45 and comprises a 5' AAV2 ITR, an ApoE HCR, a hAAT promoter, a modified human β-globin 2nd intron, an FVIII-SQ encoding sequence, a bGH poly A sequence and a 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989*, Handbook of Parvoviruses*, Vol. 1, pp. 169-228, and Berns, 1990*, Virology*, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of *Parvoviruses and Human Disease*, J. R. Pattison, ed.; and Rose, *Comprehensive Virology* 3:1-61 (1974)). For example, all AAV serotypes apparently exhibit very similar replication properties mediated by homologous rep genes; and all bear three related capsid proteins. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs) and operably linked to one or more expression control elements. Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap genes in accordance with the present invention encode Cap proteins which are capable of packaging AAV vectors in the presence of rep and adeno helper function and are capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chiorini et al., *J. Vir.* 71: 6823-33(1997); Srivastava et al., *J. Vir.* 45:555-64 (1983); Chiorini et al., *J. Vir.* 73:1309-1319 (1999); Rutledge et al., *J. Vir.* 72:309-319 (1998); and Wu et al., *J. Vir.* 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter. The ITRs employed in the vectors of the present invention may correspond to the same serotype as the associated cap genes, or may differ. In a particularly preferred embodiment, the ITRs employed in the vectors of the present invention correspond to an AAV2 serotype and the cap genes correspond to an AAV5 serotype.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. *A Manual of Methods for Baculovirus Vectors and Insect Culture Procedures*, Texas Agricultural Experimental Station Bull. No. 7555, College Station, Tex.; Luckow. 1991. In Prokop et al., *Cloning and Expression of Heterologous Genes in Insect Cells with Baculovirus Vectors' Recombinant DNA Technology and Applications,* 97-152; King, L. A. and R. D. Possee, 1992, *The baculovirus expression system*, Chapman and Hall, United Kingdom; O'Reilly, D. R., L. K. Miller, *V. A. Luckow,* 1992, *Baculovirus Expression Vectors: A Laboratory Manual*, New York; W.H. Freeman and Richardson, C. D., 1995, *Baculovirus Expression Protocols, Methods in Molecular Biology*, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, *METHODS IN MOLECULAR BIOLOGY*, ed. Richard, Humana Press, N J (1995); O'Reilly et al., *BACULOVIRUS EXPRESSION VECTORS, A LABORATORY MANUAL*, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kirnbauer et al., *Vir.* 219:37-44 (1996); Zhao et al., *Vir.* 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No.

4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene which may or may not correspond to the same serotype as the cap genes. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be produced using any invertebrate cell type which allows for production of AAV or biologic products and which can be maintained in culture. For example, the insect cell line used can be from *Spodoptera frugiperda*, such as SF9, SF21, SF900+, *drosophila* cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm-NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in HEK293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the representative vector shown in FIG. 1, and preferably 1.5-fold, 2-fold, 3-fold, 4-fold, or 5-fold or more expression and/or activity as compared to the vector shown in FIG. 1.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the vector shown in FIG. 1.

Pharmaceutical Formulations

In other embodiments, the present invention is directed to pharmaceutical formulations of FVIII AAV vectors/virions useful for administration to subjects suffering from hemophilia A. In certain aspects, the pharmaceutical formulations of the present invention are liquid formulations that comprise recombinant AAV FVIII virions produced from the vectors disclosed herein, wherein the concentration of recombinant AAV FVIII virions in the formulation may vary widely. In certain embodiments, the concentration of recombinant AAV FVIII virion in the formulation may range from 1E12 vg/ml to 2E14 vg/ml. In a particularly preferred embodiment, the concentration of recombinant AAV FVIII virion in the formulation is about 2E13 vg/ml. In another preferred embodiment, the recombinant AAV FVIII virion present in the formulation is AAV5-FVIII-SQ derived from encapsidation of the Proto 1 vector shown schematically in FIG. 2A in an AAV5 capsid.

In other aspects, the AAV FVIII pharmaceutical formulation of the invention comprises one or more pharmaceutically acceptable excipients to provide the formulation with advantageous properties for storage and/or administration to subjects for the treatment of hemophilia A. In certain embodiments, the pharmaceutical formulations of the present invention are capable of being stored at ≤65° C. for a period of at least 2 weeks, preferably at least 4 weeks, more preferably at least 6 weeks and yet more preferably at least about 8 weeks, without detectable change in stability. In this regard, the term "stable" means that the recombinant AAV FVIII virus present in the formulation essentially retains its physical stability, chemical stability and/or biological activity during storage. In certain embodiments of the present invention, the recombinant AAV FVIII virus present in the pharmaceutical formulation retains at least about 80% of its biological activity in a human patient during storage for a determined period of time at −65° C., more preferably at least about 85%, 90%, 95%, 98% or 99% of its biological activity in a human patient.

In certain aspects, the formulation comprising recombinant AAV FVIII virions further comprises one or more buffering agents. For example, in various aspects, the formulation of the present invention comprises sodium phosphate dibasic at a concentration of about 0.1 mg/ml to about 3 mg/ml, about 0.5 mg/ml to about 2.5 mg/ml, about 1 mg/ml to about 2 mg/ml, or about 1.4 mg/ml to about 1.6 mg/ml. In a particularly preferred embodiment, the AAV FVIII formulation of the present invention comprises about 1.42 mg/ml of sodium phosphate, dibasic (dried). Another buffering agent that may find use in the recombinant AAV FVIII formulations of the present invention is sodium phosphate, monobasic monohydrate which, in some embodiments, finds use at a concentration of from about 0.1 mg/ml to about 3 mg/ml, about 0.5 mg/ml to about 2.5 mg/ml, about 1 mg/ml to about 2 mg/ml, or about 1.3 mg/ml to about 1.5 mg/ml. In a particularly preferred embodiment, the AAV FVIII formulation of the present invention comprises about 1.38 mg/ml of sodium phosphate, monobasic monohydrate. In a yet more particularly preferred embodiment of the present invention, the recombinant AAV FVIII formulation of the present invention comprises about 1.42 mg/ml of sodium phosphate, dibasic and about 1.38 mg/ml of sodium phosphate, monobasic monohydrate.

In another aspect, the recombinant AAV FVIII formulation of the present invention may comprise one or more isotonicity agents, such as sodium chloride, preferably at a concentration of about 1 mg/ml to about 20 mg/ml, for example, about 1 mg/ml to about 10 mg/ml, about 5 mg/ml to about 15 mg/ml, or about 8 mg/ml to about 20 mg/ml. In a particularly preferred embodiment, the formulation of the present invention comprises about 8.18 mg/ml sodium chloride. Other buffering agents and isotonicity agents known in the art are suitable and may be routinely employed for use in the formulations of the present disclosure.

In another aspect, the recombinant AAV FVIII formulations of the present invention may comprise one or more bulking agents. Exemplary bulking agents include without limitation mannitol, sucrose, dextran, lactose, trehalose, and povidone (PVP K24). In certain preferred embodiments, the formulations of the present invention comprise mannitol, which may be present in an amount from about 5 mg/ml to about 40 mg/ml, or from about 10 mg/ml to about 30 mg/ml, or from about 15 mg/ml to about 25 mg/ml. In a particularly preferred embodiment, mannitol is present at a concentration of about 20 mg/ml.

In yet another aspect, the recombinant AAV FVIII formulations of the present invention may comprise one or more surfactants, which may be non-ionic surfactants. Exemplary surfactants include ionic surfactants, non-ionic surfactants, and combinations thereof. For example, the surfactant can be, without limitation, TWEEN 80 (also known as polysorbate 80, or its chemical name polyoxyethylene sorbitan monooleate), sodium dodecylsulfate, sodium stearate, ammonium lauryl sulfate, TRITON AG 98 (Rhone-Poulenc), poloxamer 407, poloxamer 188 and the like, and combinations thereof. In a particularly preferred embodiment, the formulation of the present invention comprises poloxamer 188, which may be present at a concentration of from about 0.1 mg/ml to about 4 mg/ml, or from about 0.5 mg/ml to about 3 mg/ml, from about 1 mg/ml to about 3 mg/ml, about 1.5 mg/ml to about 2.5 mg/ml, or from about 1.8 mg/ml to about 2.2 mg/ml. In a particularly preferred embodiment, poloxamer 188 is present at a concentration of about 2.0 mg/ml.

In a particular preferred embodiment of the present invention, the pharmaceutical formulation of the present invention comprises AAV5-FVIII-SQ formulated in a liquid solution that comprises about 1.42 mg/ml of sodium phosphate, dibasic, about 1.38 mg/ml of sodium phosphate, monobasic monohydrate, about 8.18 mg/ml sodium chloride, about 20 mg/ml mannitol and about 2 mg/ml poloxamer 188.

The recombinant AAV FVIII virus-containing formulations of the present disclosure are stable and can be stored for extended periods of time without an unacceptable change in quality, potency, or purity. In one aspect, the formulation is stable at a temperature of about 5° C. (e.g., 2° C. to 8° C.) for at least 1 month, for example, at least 1 month, at least 3 months, at least 6 months, at least 12 months, at least 18 months, at least 24 months, or more. In another aspect, the formulation is stable at a temperature of less than or equal to about −20° C. for at least 6 months, for example, at least 6 months, at least 12 months, at least 18 months, at least 24 months, at least 36 months, or more. In another aspect, the formulation is stable at a temperature of less than or equal to about −40° C. for at least 6 months, for example, at least 6 months, at least 12 months, at least 18 months, at least 24 months, at least 36 months, or more. In another aspect, the formulation is stable at a temperature of less than or equal to about −60° C. for at least 6 months, for example, at least 6 months, at least 12 months, at least 18 months, at least 24 months, at least 36 months, or more.

Methods of Treatment

In certain embodiments, the present invention is directed to methods for treating a subject suffering from hemophilia A comprising administering to that subject a therapeutically effective amount of an AAV FVIII vector, recombinant AAV FVIII virus or a pharmaceutical composition comprising the same. In yet other embodiments, the present invention is directed to methods for reducing bleeding time during a bleeding episode in a subject suffering from hemophilia A comprising administering to that subject a therapeutically effective amount of an AAV FVIII vector, recombinant AAV FVIII virus or a pharmaceutical composition comprising the same. In this regard, a "therapeutically effective amount", in reference to the treatment of hemophilia A or for use in a method for reducing bleeding time during a bleeding episode in a subject suffering from hemophilia A, refers to an amount capable of invoking one or more of the following effects: (1) reduction, inhibition, or prevention, to some extent, of one or more of the physiological symptoms of hemophilia A including, for example, bruising, joint pain or swelling, prolonged headache, vomiting or fatigue, (2) improvement in the capability to clot blood, (3) reduction of overall bleeding time during a bleeding episode, (4) administration resulting in a measurable increase in the concentration or activity of functional FVIII protein in the plasma of a subject, and/or (5) relief, to some extent, of one or more symptoms associated with the disorder. A "therapeutically effective amount" of an AAV FVIII vector or virus or a pharmaceutical composition comprising the same for purposes of treatment as described herein may be determined empirically and in a routine manner. In certain embodiments, however, a "therapeutically effective amount" of recombinant AAV FVIII virus ranges from about 1E12 vg/kg body weight to about 1E14 vg/kg body weight, preferably from about 6E12 vg/kg body weight to about 6E13 vg/kg body weight. In a particularly preferred embodiment, a therapeutically effective amount of recombinant AAV FVIII virus is about 2E13 vg/kg body weight. In another particularly preferred embodiment, a therapeutically effective amount of recombinant AAV FVIII virus is about 6E13 vg/kg body weight.

Recombinant AAV FVIII vectors/virus of the present invention may be administered to a subject, preferably a mammalian subject, more preferably a human subject, through a variety of known administration techniques. In a preferred embodiment, the recombinant AAV FVIII gene therapy virus is administered by intravenous injection either as a single bolus or over a prolonged time period, which may be at least about 1, 5, 10, 15, 30, 45, 60, 75, 90, 120, 150, 180, 210 or 240 minutes, or more. In a particularly preferred embodiment of the present invention, the recombinant AAV FVIII virus administered is AAV5-FVIII-SQ.

Administration of a recombinant AAV FVIII vector/virus, or pharmaceutical formulation comprising the same, of the present invention preferably results in an increase in functional FVIII protein activity in the plasma of the subject of at least 1, 2, 3, 4, 5, 6, 7, 8, 9, 10, 11, 12, 13, 14, 15, or more IU/dl as compared to the amount of functional FVIII protein activity present in the plasma in the subject prior to administration. In certain embodiments, administration of a recombinant AAV FVIII vector/virus, or pharmaceutical formulation comprising the same, of the present invention results in the expression of at least about 1, 2, 3, 4, 5, 6, 7, 8, 9, 10 or more IU/dl of functional FVIII protein activity in the plasma of the subject. In this regard, the term "IU" or "international unit" in regards to FVIII activity is a well understood and accepted term, wherein 1 IU of FVIII activity is equivalent to the quantity of FVIII in one ml of normal human plasma. FVIII activity in the plasma may be quantitatively determined by a number of well-known and accepted assays including, for example, the activated partial thromboplastin time (APPT) method (see, e.g., Miletich J P: *Activated partial thromboplastin time*. In Williams Hematology. Fifth edition. Edited by E Beutler, M A Lichtman, B A Coller, T J Kipps. New York, McGraw-Hill, 1995, pp L85-86, Greaves and Preston, *Approach to the bleeding patient*. In Hemostasis and Thrombosis: Basic Principles and Clinical Practice. Fourth edition. Edited by R W Colman, J Hirsh, V J Marder, et al. Philadelphia, JB Lippincott Co, 2001, pp 1197-1234 and Olson et al, *Arch. Pathol. Lab. Med.* 122: 782-798 (1998)) or chromogenic FXa assay (Harris et al., Thromb. Res. 128(6):125-129 (2011)).

In other embodiments of the present invention, bleeding time in a subject may be measured by well-known and accepted techniques including, for example, the Ivy method (see, e.g., Ivy et al., *Surg. Gynec. Obstet.* 60:781 (1935) and Ivy et al., *J Lab. Clin. Med.* 26:1812 (1941)) or the Duke method (see, e.g., Duke et al., *JAMA* 55:1185 (1910)). A "bleeding episode" in a subject refers to an injury that results in bleeding in the subject, either externally or internally, and generally comprises the time period from injury to formation of a blood clot.

Administration of an AAV FVIII virus of the present invention may, in some cases, result in an observable degree of hepatotoxicity. Hepatotoxicity may be measured by a variety of well-known and routinely used techniques for example, measuring concentrations of certain liver-associated enzyme(s) (e.g., alanine transaminase, ALT) in the bloodstream of a subject both prior to AAV FVIII administration (i.e., baseline) and after AAV FVIII administration. An observable increase in ALT concentration after AAV FVIII administration (as compared to prior to administration) is indicative of drug-induced hepatotoxicity. In certain embodiments of the present invention, in addition to administration of a therapeutically effective amount of AAV FVIII virus, the subject may be treated either prophylactically, therapeutically, or both with a corticosteroid to prevent and/or treat any hepatotoxicity associated with administration of the AAV FVIII virus. "Prophylactic" corticosteroid treatment refers to the administration of a corticosteroid to prevent hepatotoxicity and/or to prevent an increase in measured ALT levels in the subject. "Therapeutic" corticosteroid treatment refers to the administration of a corticosteroid to reduce hepatotoxicity caused by administration of an AVV FVIII virus and/or to reduce an elevated ALT concentration in the bloodstream of the subject caused by administration of an AAV FVIII virus. In certain embodiments, prophylactic or therapeutic corticosteroid treatment may comprise administration of at least 5, 10, 15, 20, 25, 30, 35, 40, 45, 50, 55, 60, or more mg/day of the corticosteroid to the subject. In certain embodiments, prophylactic or therapeutic corticosteroid treatment of a subject may occur over a continuous period of at least about 3, 4, 5, 6, 7, 8, 9, 10 weeks, or more. Corticosteroids that find use in the methods described herein include any known or routinely-employed corticosteroid including, for example, dexamethasone, prednisone, fludrocortisone, hydrocortisone, and the like.

Detection of Anti-AAV Antibodies

To maximize the likelihood of successful liver transduction with systemic AAV-mediated Factor VIII gene transfer, prior to administration of an AAV vector in a therapeutic regimen to a human patient as described above, the prospective patient may be assessed for the presence of anti-AAV capsid antibodies that are capable of blocking cell transduction or otherwise reduce the overall efficiency of the therapeutic regimen. Such antibodies may be present in the serum of the prospective patient and may be directed against an AAV capsid of any serotype. In one embodiment, the serotype against which pre-existing antibodies are directed is AAV5.

Methods to detect pre-existing AAV immunity are well known and routinely employed in the art and include cell-based in vitro transduction inhibition (TI) assays, in vivo (e.g., in mice) TI assays, and ELISA-based detection of total anti-capsid antibodies (TAb) (see, e.g., Masat et al., *Discov. Med.* 15:379-389 (2013) and Boutin et al., *Hum. Gene Ther.* 21:704-712 (2010)). TI assays may employ host cells into which an AAV-inducible reporter vector has been previously introduced. The reporter vector may comprise an inducible reporter gene such as GFP, etc. whose expression is induced upon transduction of the host cell by an AAV virus. Anti-AAV capsid antibodies present in human serum that are capable of preventing/reducing host cell transduction would thereby reduce overall expression of the reporter gene in the system. Therefore, such assays may be employed to detect the presence of anti-AAV capsid antibodies in human serum that are capable of preventing/reducing cell transduction by the therapeutic FVIII AAV virus.

TAb assays to detect anti-AAV capsid antibodies may employ solid-phase-bound AAV capsid as a "capture agent" over which human serum is passed, thereby allowing anti-capsid antibodies present in the serum to bind to the solid-phase-bound capsid "capture agent". Once washed to remove non-specific binding, a "detection agent" may be employed to detect the presence of anti-capsid antibodies bound to the capture agent. The detection agent may be an antibody, an AAV capsid, or the like, and may be detectably-labeled to aid in detection and quantitation of bound anti-capsid antibody. In one embodiment, the detection agent is labeled with ruthenium or a ruthenium-complex that may be detected using electrochemiluminescence techniques and equipment.

The same above-described methodology may be employed to assess and detect the generation of an anti-AAV capsid immune response in a patient previously treated with a therapeutic AAV virus of interest. As such, not only may these techniques be employed to assess the presence of anti-AAV capsid antibodies prior to treatment with a therapeutic FVIII AAV virus, they may also be employed to assess and measure the induction of an immune response against the administered therapeutic FVIII AAV virus after administration. As such, the present invention contemplates methods that combine techniques for detecting anti-AAV capsid antibodies in human serum and administration of a therapeutic FVIII AAV virus for the treatment of hemophilia A, wherein the techniques for detecting anti-AAV capsid antibodies in human serum may be performed either prior to or after administration of the therapeutic FVIII AAV virus.

Other aspects and advantages of the present invention will be understood upon consideration of the following illustrative examples.

EXAMPLES

Example 1

Generation of Proto 1, Proto 1S, Proto 2S and Proto 3S Vectors

The recombinant AAV FVIII vector schematically shown in FIG. 1, which is described in detail in WO 2011/005968, published Jan. 13, 2011, which is incorporated herein by reference in its entirety, and McIntosh et al., *Blood* 121: 3335-3344, 2013, is an oversized, i.e., greater than 5.0 kb, AAV vector. As shown in FIG. 1, this vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3' ITR. This vector is 5081 bases in length.

To obtain a vector that is smaller than the FVIII vector shown in FIG. 1, DNA sequences believed by the inventors herein to be unnecessary for FVIII expression and/or activity, or for AAV virion production, were removed from the original vector sequence. Extraneous DNA sequence was removed, including 53 bases of AAV2 viral sequence 3' to the AAV2 5' ITR, 46 bases of AAV2 viral sequence 5' to the AAV2 3' ITR, and 11 bases adjacent to the codon-optimized FVIII SQ coding region. A novel codon-optimized, B-domain-deleted FVIII-encoding sequence possessing an SQ linker was also produced and introduced into new recombinant AAV FVIII vectors. Certain sequence changes were made to the AAV2 5' and 3' ITRs. The resultant Proto 1 vector, which is 4970 bases in length, is shown in schematic form in FIG. 2A, and the complete nucleotide sequence is set forth in SEQ ID NO:1. The inventors herein have demonstrated that Proto 1 produced infectious recombinant AAV virus and encodes a functional Factor VIII polypeptide.

Sequences adjacent to the hairpin loop in the AAV2 ITR may also be dispensable in recombinant AAV vectors (see Srivastava et al., U.S. Pat. No. 6,521,225; Wang et al., *J. Virol.* 70:1668-1677, 1996; and Wang et al., *J. Virol.* 71:3077-3082, 1997). To further reduce the size of the Proto 1 vector, 10 bases of AAV2 sequence was removed directly 3' to the hairpin loop in the AAV2 5' ITR and 10 bases of AAV2 sequence was removed directly 5' to the hairpin loop in the AAV2 3' ITR. The resultant Proto 1S vector, which is 4950 bases in length, is shown in schematic form in FIG. 2B, and the sequence is set forth in SEQ ID NO:2.

In an effort to increase the expression of the FVIII SQ variant in the Proto 1S vector, a 100 base synthetic intron was inserted between exons 1 and 2 in the codon-optimized FVIII sequence. It is known that insertion of an intron possibly can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in U.S. Pat. No. 8,030,065 (FIX expression) and in WO 2011/005968 (FVIII expression), both of which are incorporated herein by reference in their entirety. The 32 base human AAT promoter distal X region, described in Di Simone et al., *EMBO J.* 6:2759-2766, 1987, is located within a regulatory domain that enhances expression of a heterologous promoter.

In another attempt to further increase the expression of the FVIII SQ variant in the Proto is vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 1S. The resultant Proto 2S vector, which is 4983 bases in length, is shown in schematic form in FIG. 2C, and the sequence set forth in SEQ ID NO:3.

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO:4.

The Proto 1, Proto 15, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
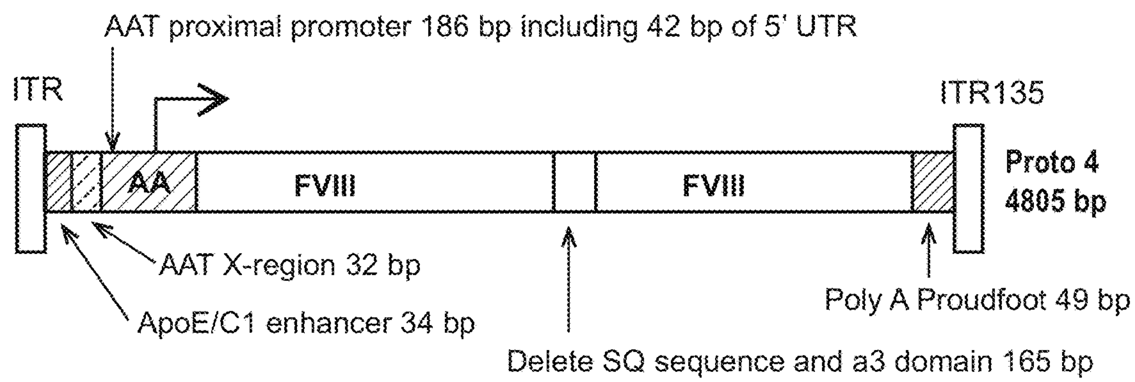
FIG. 3A-FIG. 3D provide schematic representations of certain recombinant AAV FVIII vectors of the present invention. (A) Proto 4, (B) Proto 5, (C) Proto 6 and (D) Proto 7.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO:5.

Figure 3B:
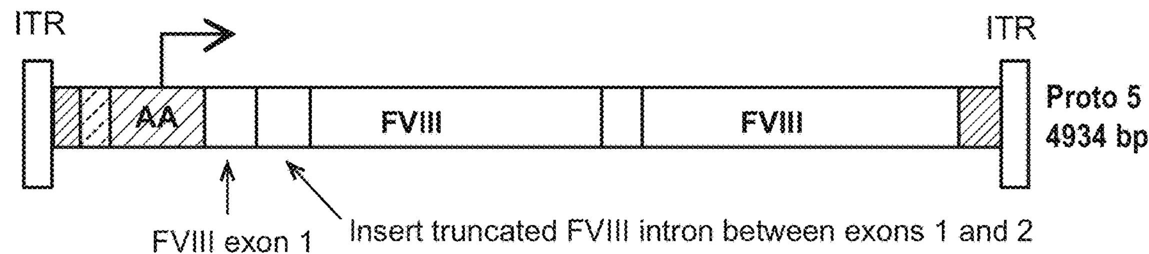

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO:6.

Figure 3C:
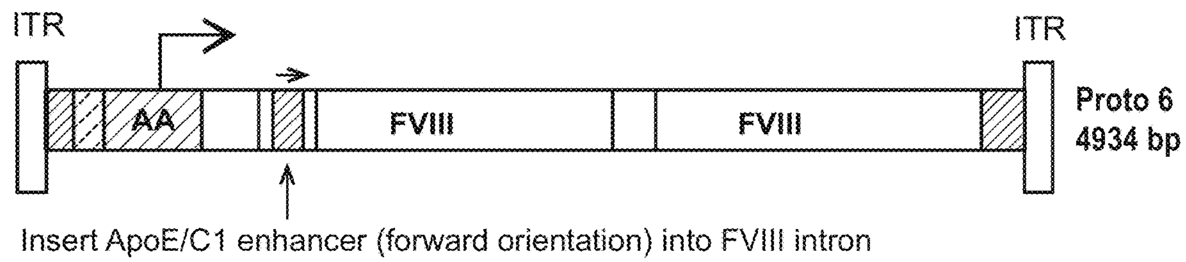

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO:7.

Figure 3D:
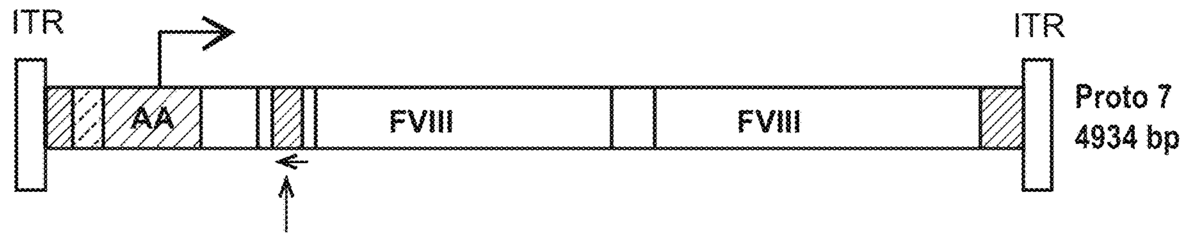

The resultant Proto 7 vector, which is 4934 bases in length and has the intronic ApoE/C1 enhancer in the reverse orientation, is shown in schematic form in FIG. 3D, and the sequence is set forth in SEQ ID NO:8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the recombinant AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays

A preliminary in vitro assay is performed to compare the FVIII expression and activity from the AAV FVIII vectors of the present invention with that from the FVIII-expressing vector shown in FIG. 1. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the FVIII vector of FIG. 1, demonstrating that the Proto 1, Proto 1S and Proto 2S vectors were capable of expressing functional Factor VIII protein.

Production of AAV FVIII Virions in 293 Cells and Baculovirus-Infected Insect Cells To demonstrate that the recombinant AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5' ITR (sense strand) or 3' ITR (anti-sense strand).

Alternatively, a PCR assay is used to determine whether the AAV FVIII vectors nucleic acids have complete ends, i.e., terminate at the 5' end of the hairpin loop in the AAV2 5' ITR (sense strand) or 3' ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, administered intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional recombinant AAV vectors with strong promoters that increase expression of functional FVIII, constructs were generated with modified enhancer and/or promoter sequences. In some embodiments, the constructs comprised shortened versions of the ApoE or the μ-globulin enhancers. These constructs were generated using standard DNA cloning techniques and the sequences thereof are shown in SEQ ID NOS:9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described above. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1\times10^6$ cells/well in a 6-well plate (or $6\times10^6$ cells in a 10-cm plate or $1.7\times10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30~45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of Baculovirus (P1)

Sf9 cells were grown to approximately $4\times10^6$ cells/mL and diluted to approximately $2\times10^6$ cells/mL with fresh medium in shaking flasks. An amount of the Sf9 cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV Using P1 Recombinant Baculoviruses

Sf9 cells were grown to about $1\times10^7$ cells/mL and diluted to about $5\times10^6$ cells/mL. An amount of the diluted Sf9 cells were infected with Bac-vector (5Moi) and Bac-helper (15Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding/Purification Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV virions which comprise a codon-optimized SQ FVIII-encoding gene sequence were generated using baculovirus and 293 cells using the FVIII vector of FIG. 1, Proto 1, Proto 1S, Proto 2S and Proto 3S constructs. The packaging limits are about 4800 bp for baculovirus and about 4950 bp for 293 cells.

Figure 5:
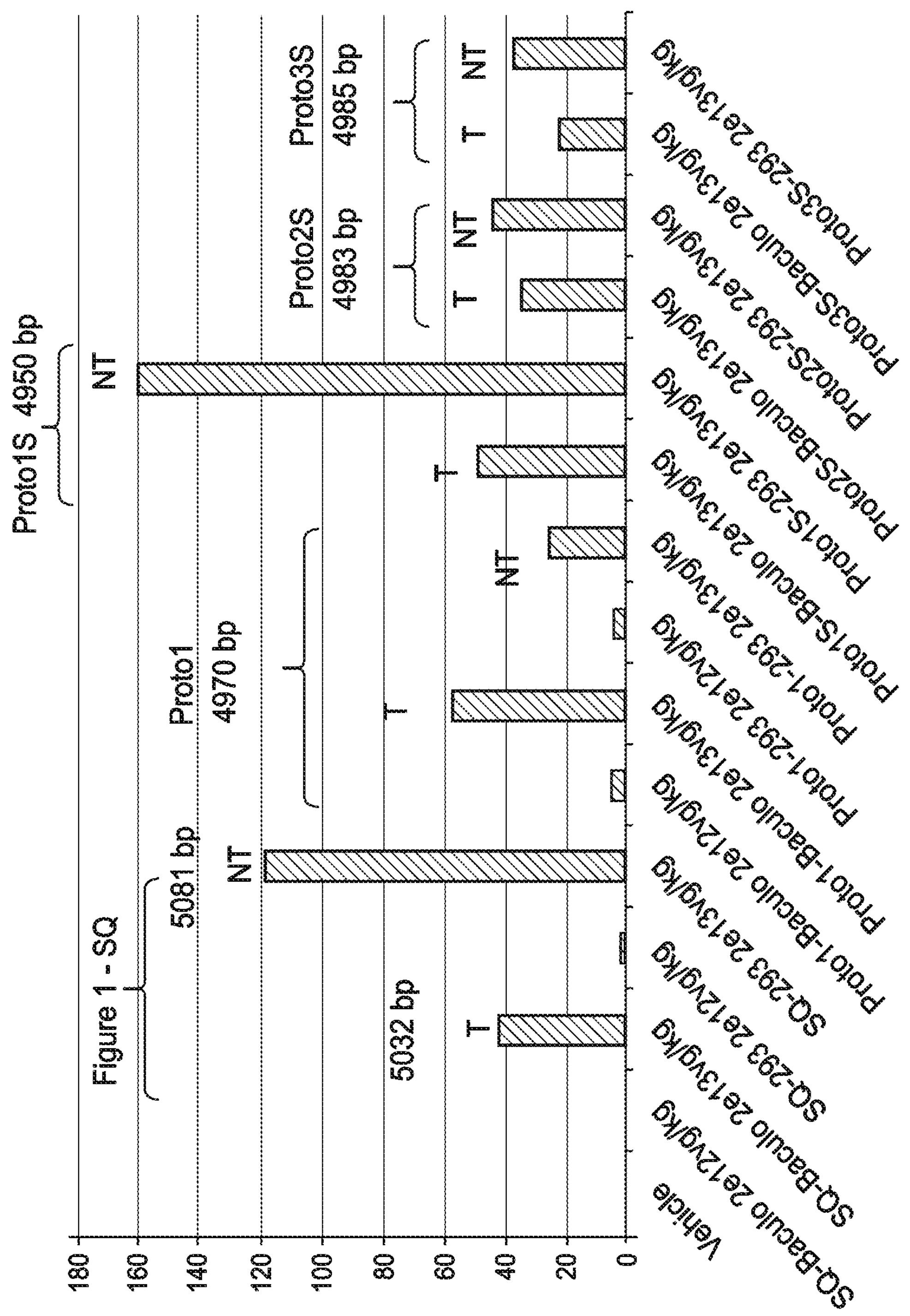
FIG. 5 provides the results of the evaluation of the recombinant AAV FVIII Proto constructs in Rag2 mice, and demonstrates that the Proto viral constructs transduce FVIII similarly to the vector shown in FIG. 1, wherein the y-axis represents ng/ml of FVIII protein determined by ELISA analysis.

As shown in FIG. 5, all constructs tested with truncated (T) or non-truncated (NT) genomes are capable of inducing FVIII expression. Expression of FVIII from Proto 1 was similar to the FVIII construct of FIG. 1 when these AAV were made by the baculovirus system. Inclusion of the intron in Proto 2S and Proto 3S did not result in improved FVIII expression as compared to Proto 1. The FVIII vector of FIG. 1 containing the AAV flanking sequences made in 293 cells were more potent than the same vector lacking the AAV sequence made in baculovirus. As a result, additional enhancers were added to Proto 1, e.g. Constructs 101, 102, 102 and 104, in an attempt to increase potency and associated FVIII expression.

Example 6

Expression and Activity of AAV FVIII Vectors with Improved Promoters/Enhancer Sequences The expression and activity of additional recombinant AAV FVIII vectors were tested using a hydrodynamic injection protocol. Hydrodynamic delivery is a rapid method to screen the efficiency of various recombinant AAV FVIII vectors in vivo. Specifically, AAV FVIII plasmid DNA was generated as described above and then diluted in TransIT-QR Hydrodynamic Delivery Solution. The plasmid DNA was injected into the tail vein of 5-6 week old C57Bl/6 mice (18-25 g) at a volume determined by (mouse weight (g)/10) =0.1 ml delivery solution). The injection time was less than 5 seconds. Plasma from each mouse was then collected 48 hours after injection and the amount of FVIII protein expressed was measured using an ELISA assay. The amount of FVIII in the plasma of the injected mouse was measured using an ELISA test and recombinant FVIII (Xyntha SQ equivalents) was used as a standard for comparison.

Figure 6:
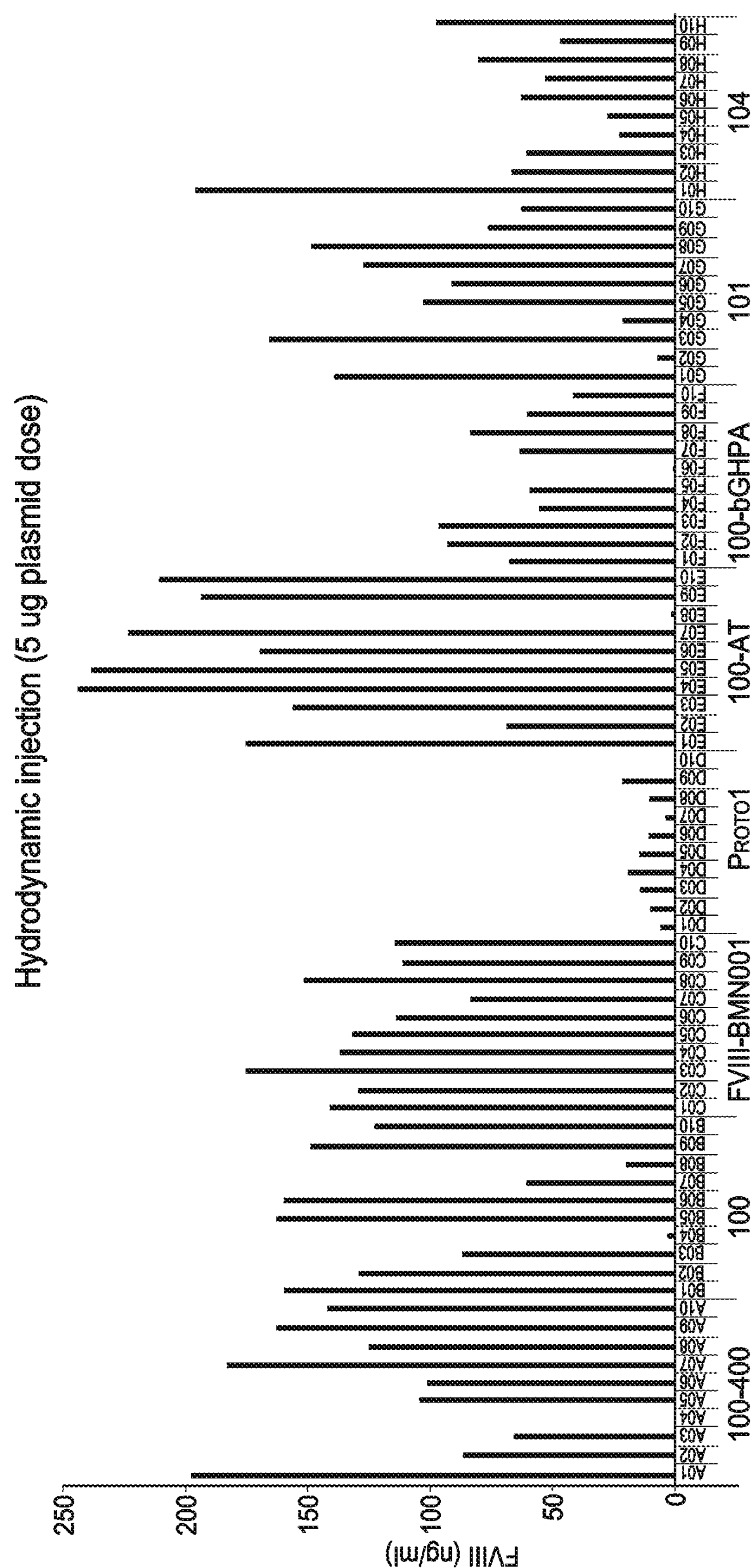
FIG. 6 demonstrates that various recombinant AAV FVIII constructs of the present invention induce in vivo expression of FVIII protein as measured in a mouse tail vein hydrodynamic injection assay.

To investigate FVIII expression, certain recombinant AAV FVIII constructs of the present invention were tested in the hydrodynamic injection protocol to measure their ability to result in expression of functional FVIII protein in vivo. As shown in FIG. 6, all constructs tested at a 5 μg of plasmid dose produced functional FVIII at varying levels of efficiency.

Figure 7:
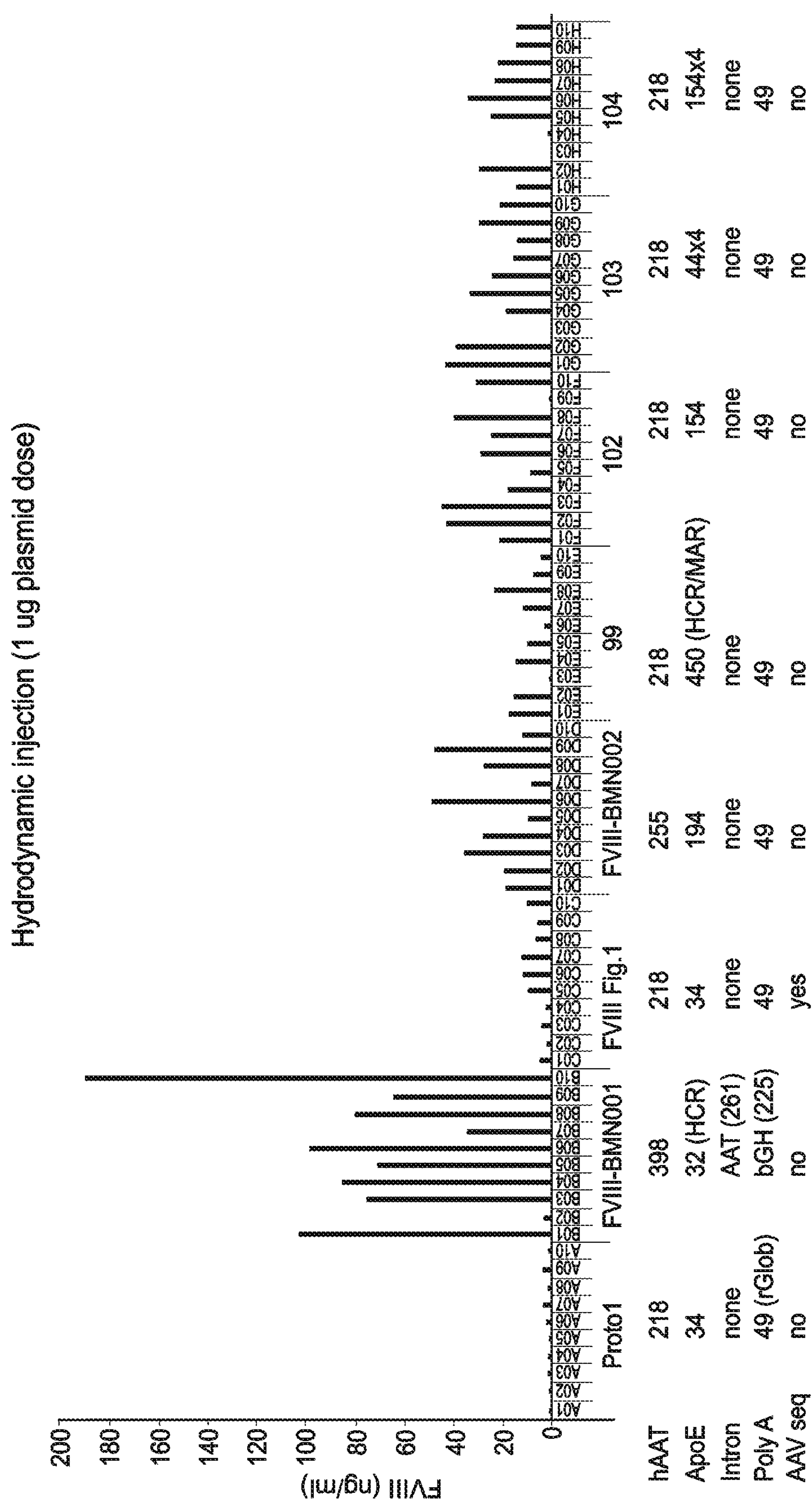
FIG. 7 demonstrates that various recombinant AAV FVIII constructs of the present invention induce in vivo expression of FVIII protein as measured in a mouse tail vein hydrodynamic injection assay.
Figure 8:
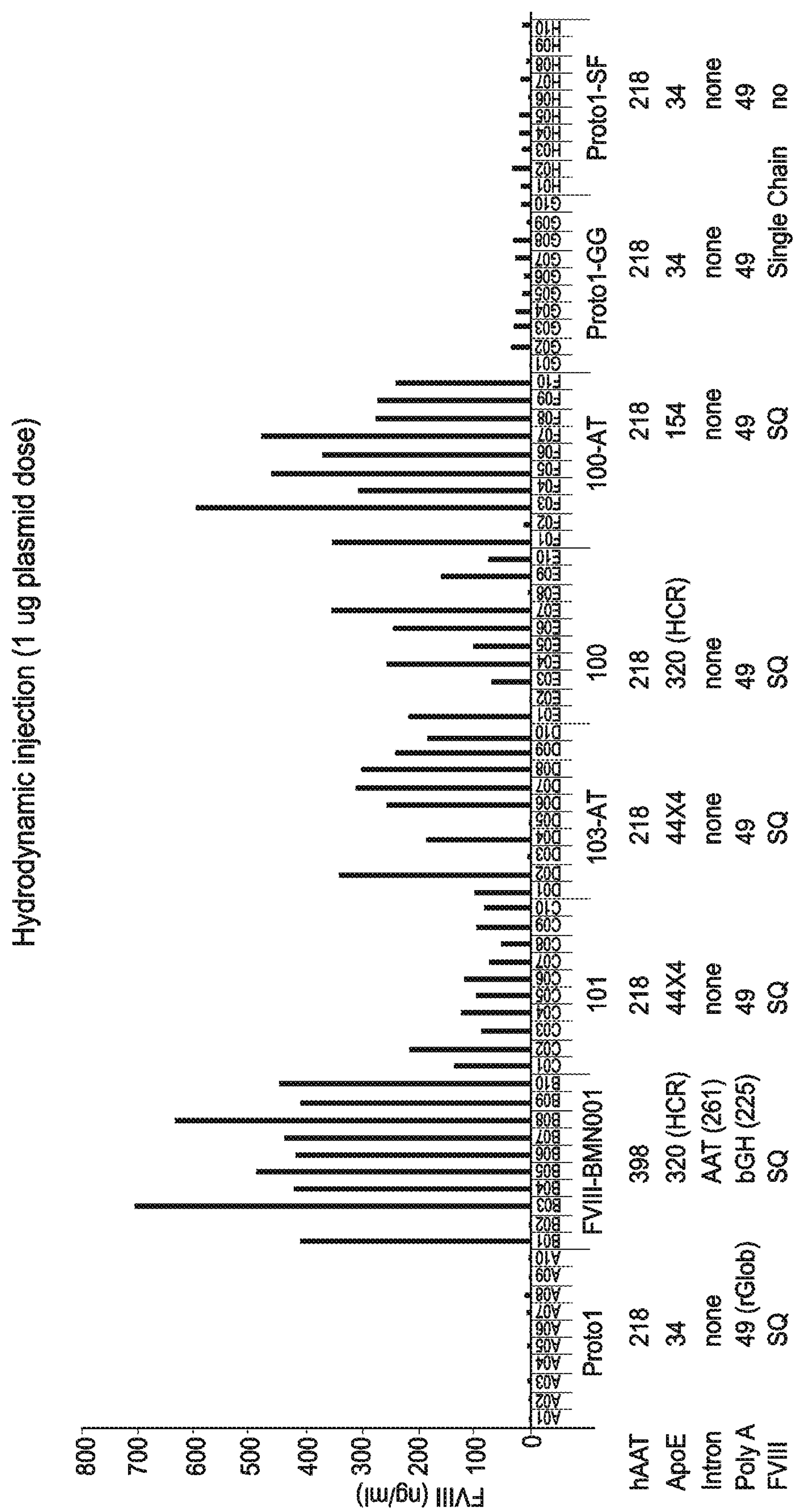
FIG. 8 demonstrates that various recombinant AAV FVIII constructs of the present invention induce in vivo expression of FVIII protein as measured in a mouse tail vein hydrodynamic injection assay.

FIGS. 7 and 8 provide data for hydrodynamic injection for a dose of 1 μg of plasmid of various recombinant AAV FVIII constructs of the present invention. As shown in FIGS. 7 and 8, injection of the various constructs tested all resulted in the in vivo expression of FVIII protein with varying levels of efficiency.

Example 7

Analysis of AAV Virus Comprising p-100 ATGB Vector

AAV virus comprising the FVIII-SQ-encoding vector p-100 ATGB shown herein as SEQ ID NO:45 ("AAV5-p100ATGB-FVIII") were produced and evaluated for the ability to express functional FVIII-SQ protein in Rag2 mice as described in Example 5 above. More specifically, Rag2 mice were administered a single dose of either AAV5-FVIII-SQ virus or AAV5-p100ATGB-FVIII virus at a dose of either 6E12 vg/kg, 2E13 vg.kg or 6E13 vg/kg and FVIII protein concentrations were subsequently determined in the bloodstream of the mice. The results of these analyses demonstrated that administration of the AAV5-p100ATGB-FVIII virus produced approximately a 3-fold higher level of circulating functional FVIII protein than did the AAV5-FVIII-SQ virus at the two lower doses tested. The observed difference in expression was somewhat attenuated at the highest dose tested, although even at the highest dose tested, the AAV5-p100ATGB-FVIII virus produced a higher level of circulating functional FVIII protein than did the AAV5-FVIII-SQ virus. These results demonstrate that the AAV5-p100ATGB-FVIII virus effectively transduces liver cells in vivo and provides for expression of high levels of functional FVIII protein.

Example 8

Studies of a Specific Recombinant FVIII AAV Vector/Virus for Hemophilia A

Hemophilia A (HA) is an X-linked recessive bleeding disorder that affects approximately 1 in 5,000 males. It is caused by deficiency in the activity of coagulation factor VIII (FVIII), an essential cofactor in the intrinsic coagulation cascade. This disorder can be either inherited, due to a new mutation or an acquired immunologic process, leading to insufficient quantities of FVIII or a dysfunctional FVIII, but all are characterized by a defective coagulation process. The clinical phenotype of HA patients is largely governed by the level of residual expression. Severe HA is classified as FVIII activity less than 1% of wild type (<1 IU/dL), moderate disease comprises 1-5% of wild type activity (1 IU/dl-5 IU/dl) and the mild form is 5-40% activity (5 IU/dl-40 IU/dl). The clinical manifestations of severe HA remain frequent spontaneous bleeding episodes, predominantly in joints and soft tissues, with a substantially increased risk of death from hemorrhage when the brain is involved.

Treatment of severe HA presently consists of intravenous injection of plasma-derived or recombinant FVIII protein (rhFVIII) concentrates, both as prophylaxis 2-3 times per week, and at the time of a bleed, to prevent or control bleeding episodes, respectively. The half-life for rhFVIII (under 24 hours for most approved products) necessitates frequent infusions, and although a major advance in the treatment of HA, it remains common for severe HA patients to continue to have multiple bleeding events on treatment (mean of 1 to 7 episodes/year with prophylaxis up to 30 to 50 for on demand treatment). The consequence of multiple bleeding events is the development of an underlying pathology that contributes to debilitating multiple-joint arthropathy and substantially increased risk of death. Chemical modification (e.g. direct conjugation of polyethylene glycol (PEG) polymers) and bioengineering of FVIII (e.g. FVIII-Fc fusion proteins) improve half-life by approximately 50%, and thus, show promise in reduced dosing and maintaining activity levels above 1% trough. However, these longer acting FVIIIs remain dependent on multiple infusions to maintain critical levels of FVIII activity in severe HA patients. There is therefore a strong unmet need for a fully preventive treatment of HA to give patients a FVIII level compatible with a normal and hemorrhage-free life.

Gene therapy offers the potential of disease-modifying therapy by continuous endogenous production of active FVIII following a single intravenous administration of a vector with the appropriate gene sequence. Hemophilia A is well suited for a gene replacement approach because clinical manifestations are attributable to the lack of a single gene product (FVIII) that circulates in minute amounts (200 ng/ml) in the plasma. Tightly regulated control of gene expression is not essential, and modest increases in the level of FVIII (any increase of the plasma level by 2 ng/ml induces an increase in activity of 1%) can ameliorate the severe form of the disease. Thus, relatively small changes in endogenous FVIII activity results in clinically relevant improvements in disease phenotype. Finally, the response to gene transduction can be assessed using validated quantitative rather than qualitative endpoints that are easily assayed using established laboratory techniques.

Several different gene transfer strategies for FVIII replacement have been evaluated, but adeno-associated viral (AAV) vectors show the greatest promise. They have an excellent and well-defined safety profile, and can direct long term transgene expression with tropism for specific tissues such as the liver (for serotypes 2, 5 and 8, among others). Indeed, an ongoing gene therapy clinical trial for a related disorder, hemophilia B, has established that stable (>36 months) expression of human factor IX at levels that are sufficient for conversion of their bleeding phenotype from severe to moderate or mild is achievable following a single peripheral vein administration of recombinant FIX AAV-8 vector. Several participants in this trial have been able to discontinue factor prophylaxis without suffering spontaneous hemorrhages, even when they undertook activities that previously resulted in bleeding. Thus, gene therapy treatment has resulted in a substantial improvement in their quality of life.

Additional Preclinical Studies

The recombinant FVIII-SQ-encoding vector Protol (shown herein in FIG. 2A and SEQ ID NO:1) was used to produce recombinant AAV5 FVIII-SQ-encoding virus using a baculovirus/SP9-based expression system as described above. The virus generated (herein referred to as "AAV5-FVIII-SQ") was purified and formulated for pre-clinical animal studies in Dulbecco's phosphate buffered saline (DPBS) containing 0.001% Poloxamer 188.

The AAV5-FVIII-SQ nonclinical program was designed to elucidate the transduction, relative expression and activity of the FVIII-SQ protein and the overall safety profile of the AAV5 capsid and FVIII-SQ transgene product components of AAV5-FVIII-SQ to support a single IV administration of the recombinant virus in human patients. The nonclinical profile of AAV5-FVIII-SQ was assessed across one in vitro study and ten single dose studies in mice, normal wild type (WT), Rag2−/−(B6.129S6-Rag2tm1Fwa N12) and Factor VIII−/− (B6; 129S-F8tm1Kaz/J) crossed with Rag2−/− mouse (Rag2−/−×FVIII−/−), and cynomolgus and rhesus monkeys.

Pharmacodynamics (PD) assessment demonstrated that AAV5-FVIII-SQ gene therapy results in (i) plasma expression of the correctly sized FVIII-SQ (light and heavy chains) compared to ReFacto® (rhFVIII-SQ; marketed as ReFacto® in the EU and Xyntha® in the US) in mice, (ii) administration of AAV5-FVIII-SQ corrected the coagulopathy in a mouse model of hemophilia A, in a dose dependent fashion, similar to exogenously administered ReFacto® and (iii) the proposed clinical route of administration via IV infusion is likely to be similar to or better than bolus administration when plasma FVIII-SQ protein and activity or corresponding liver RNA and DNA levels are compared in mice.

The transient FVIII-SQ expression in non-human primates is suspected to be species-specific and not expected to occur in the clinic, as was seen in other clinical studies that have achieved stable transgene expression in human patients. Immunogenicity will be closely monitored in the clinic and the relationship to protein expression will be evaluated.

The overall nonclinical program considered the potential for toxicity due to AAV5-FVIII-SQ and its major components, AAV5 capsid and the transgene product, FVIII-SQ. FVIII-SQ has the same amino acid sequence as the marketed recombinant factor replacement treatment, ReFacto®. The design of the toxicology program was intended to characterize the toxicological profile of AAV5-FVIII-SQ including the identification of target organs, relative plasma FVIII-SQ protein and relative activity, immunogenicity and liver DNA genomes and RNA. One GLP single-dose study in normal CD-1 mice with a 4- and 13-week follow up period was conducted with AAV5-FVIII-SQ. PD studies in Rag2−/−×

FVIII−/− mice and normal monkeys included additional toxicity parameters of histology and clinical pathology.

The nonclinical safety profile of AAV5-FVIII-SQ included expected observations of immunogenicity: (i) detection of anti-AAV5 antibodies in the plasma of all AAV5 vector treated immuno-competent animals (CD1 mouse and monkeys) and (ii) detection of anti-FVIII-SQ antibodies in immune-competent animals was observed in one mouse and several monkeys that did not correlate with FVIII expression or activity but may be a contributor in slight APTT prolongation in four monkeys given 6E12 or 6E13 vg/kg AAV5-FVIII-SQ. Antibody levels were not determined in the Rag2−/− derived mice because they lack mature B and T lymphocytes, and are incapable of generating antibody responses. However interspecies cross reactivity of anti-FVIII-SQ antibody with monkey FVIII was not assessed, precluding firm conclusions regarding the impact of antibody on coagulation. Non-dose dependent minimal to mild kidney inflammation was observed in Rag2−/−×FVIII−/− mice after 8-weeks with no corresponding changes in kidney clinical chemistry parameters indicating kidney dysfunction. Kidney findings were not observed in CD-1 mice after 13-weeks suggesting a strain specific response to a heterologous protein. No AAV5-FVIII-SQ-related changes in liver clinical chemistry was observed in monkey that would indicate liver dysfunction or cytotoxicity. One unscheduled euthanasia in rhesus monkey given 6E12 vg/kg on Day 14 due to body weight loss throughout the acclimation and study period, and morbidity was deemed not related to AAV5-FVIII-SQ due to persistent body weight loss and on-going colon findings. No other AAV5-FVIII-SQ-related findings, including changes in liver clinical chemistry parameters were noted in monkeys, cynomolgus or rhesus, given AAV5-FVIII-SQ.

No specific findings were associated with the FVIII-SQ transgene product other than expected immunogenicity. Because the FVIII-SQ transgene product has a final sequence that is the same as the marketed enzyme treatment, ReFacto®, no unique FVIII-specific target organs toxicity were identified.

No unique AAV5 capsid related toxicities, in addition to expected immunogenicity, were observed in the nonclinical program. Immunogenicity of the AAV capsid will be monitored in the nonclinical and clinical programs.

Both normal and disease model mice and a limited number of monkeys were utilized to establish proof of concept, evaluate potential species scaling and dose response in order to select the FIH dose of 6E12 vg/kg. The starting dose took into consideration the overall data from the pre-clinical studies conducted in mice (normal and disease model, Rag2−/−×FVIII−/−) and monkey. A detectable pharmacological response based on activity was observed at 6E12 vg/kg in mice and two species of monkeys. No consistent interspecies scaling was noted between the mouse and cynomolgus and rhesus monkeys that could ascertain a more precise dose recommendation. A 10-fold safety margin was based on a NOAEL of 6E13 vg/kg AAV5-F VIII-SQ in the GLP 13-week study in normal mouse at the highest dose administered. No AAV5-FVIII-SQ-related changes in clinical observations or chemistry was observed in the monkey at doses up to 6E13 vg/kg, a 10-fold safety margin after 8-weeks. Overall, no AAV5-FVIII-SQ-related findings, except expected formation of anti-AAV5 antibodies in all animals and limited formation of low titers of anti-FVIII-SQ antibodies in immune-competent animals were observed at the highest administered doses of 6E13 vg/kg in the normal mouse and monkey, respectively.

One in vitro and nine in vivo studies were conducted to evaluate the primary pharmacodynamics (PD) of AAV5-FVIII-SQ (six non-GLP mouse studies and three non-GLP monkey studies). All studies were single dose and used the intravenous (IV) route of administration. The proposed clinical route of administration is IV infusion up to 60 minutes. The majority of animals in this program were administered AAV5-FVIII-SQ via IV bolus injection, so an evaluation of the duration of administration (IV bolus versus infusion for 30 minutes) on FVIII-SQ expression was evaluated one mouse study. Two dose response studies in mouse given 2E10 to 2E14 vg/kg AAV5-FVIII-SQ established the PD relationship of FVIII-SQ protein and activity plasma concentrations including DNA and RNA expression in the liver after 8-weeks. One mouse study supported the selection of the baculovirus-infected cell line for manufacturing. One mouse study assessed plasma FVIII protein and activity along with liver DNA and RNA over 4- and 13-weeks. One mouse study evaluated bleeding time as a functional assessment of coagulation. Two monkey studies supported the selection of the vector AAV5 and the baculovirus-infected cell line for manufacturing. A third monkey study compared the PD effect of AAV5-FVIII-SQ in cynomolgus and rhesus monkey.

The PD endpoints (plasma FVIII-SQ protein and activity, liver DNA vector genomes and RNA transcription copies) were evaluated in the mouse and monkey studies. Liver DNA vector genomes and RNA transcription copies were assessed to confirm liver transduction by AAV5-FVIII-SQ. Plasma FVIII-SQ protein and activity were used as biomarkers of liver expression of the FVIII-SQ transgene. Several toxicity endpoints were combined into one mouse study (histology) and three monkey studies (clinical pathology) to assess dose relationship across the two species.

Pharmacodynamic Assessment of AAV5-FVIII-SQ in Rag2−/−×FVIII−/− Mice

The objective of this study was to evaluate the primary PD of AAV5-FVIII-SQ over 4- and 13-weeks following a single IV administration in male Rag2−/−×FVIII−/− mice given 6E12 or 6E13 vg/kg AAV5-FVIII-SQ. PD endpoints included plasma FVIII-SQ protein and activity levels and presence of liver FVIII-SQ RNA and DNA. Sixty male Rag2−/−×FVIII−/− mice were 8-weeks of age at study initiation. Animals were randomly assigned to six groups (10/group) and were given a single IV injection via the tail vein of either vehicle, 6E12 or 6E13 vg/kg AAV5-FVIII-SQ.

Appropriate monoclonal antibodies were coated onto plates overnight at a final concentration of 2 μg/ml, GMA8023 for FVIII heavy chain, and GMA8001 for FVIII light chain. The following day, wells were blocked with green diluent, and mouse plasma samples (50 ul) from Group 4 and Group 6, or normal mouse plasma samples spiked with Xyntha® (500 ng/ml), were diluted with equal volume of green diluent and 100 μl mixture was added to individual wells for enrichment of FVIII heavy or light chains. Enriched plasma samples were resolved by denaturing reducing polyacrylamide gels and transferred to nitrocellulose membrane for western analysis. FVIII heavy chain was detected by sequential incubation with biotin conjugated anti-FVIII polyclonal (SAFC-APBIO, 0.5 μg/ml) and Streptavidin conjugated alkaline phosphatase (0.25 μg/ml). FVIII-SQ light chain was detected by sequential incubation with anti-FVIII monoclonal (GMA8025, 1.0 μg/ml) and Donkey anti-mouse conjugated alkaline phosphatase (0.25

μg/ml). Membranes were developed using colorimetric precipitating alkaline phosphatase substrate (WesternBlue) and imaged.

The assessment of molecular weight of AAV transgene-derived FVIII-SQ heavy and light chains of serum from animals given 6E13 vg/kg AAV5-FVIII-SQ by western blot established that that the expressed plasma FVIII-SQ heavy and light chains were of similar molecular size as rhFVIII-SQ protein. This indicates that despite a potentially truncated genome, expression of the both the heavy and light chain of FVIII-SQ was the correct size. Efficient and functional expression of dysferlin and hemophilia A factor VIII from vectors with such truncated genomes have been demonstrated previously. The molecular weight of both chains of plasma FVIII-SQ protein were the correct size and the corresponding mice had FVIII-SQ activity.

IV Bolus and Infusion Study in Rag2−/− Mice

The objective of this study was to compare the effect of a single IV bolus or 30-minute IV infusion of 6.0E12 and 2.0E13 vg/kg on FVIII-SQ DNA and RNA in liver tissue and plasma FVIII-SQ protein and activity levels in Rag2−/− mice at 5 weeks post-dose. Sixty male Rag2−/− mice were approximately 8-weeks old at study initiation. Animals were randomly distributed into 6 groups (10 animals/group). Groups 1-3 and 4-6 were administered a single IV bolus or 30-minute IV infusion (vehicle, 6.0E12, or 2.0E13 vg/kg AAV5-FVIII-SQ) via the tail vein, respectively.

In animals given 6.0E12 vg/kg AAV5-FVIII-SQ, hFVIII-SQ vector genomes/liver cell were 5.06E-2 and 3.50E-2 in the IV infusion and slow bolus group, respectively. FVIII-SQ expression copies/μg RNA in the liver were 3.76E4 and 1.87E4 in the IV infusion and bolus groups, respectively. In animals given 2.0E13vg/kg AAV5-FVIII-SQ, DNA values were 0.342 vector genomes/cell for the infusion group and 0.316 vector genomes/cell for the bolus group. FVIII-SQ expression copies/μg RNA in the liver were 2.35E5 for the infusion group and 1.53E5 for the bolus group.

In animals given 6.0E12 vg/kg AAV5-FVIII-SQ (low dose) there was little difference in liver RNA and DNA levels or plasma FVIII-SQ protein and activity when administered IV either by bolus or 30-minute infusion. In animals given 2.0E13 vg/kg AAV5-FVIII-SQ, administration by IV infusion over 30 minutes resulted in roughly twice the FVIII-SQ protein and activity in plasma, while liver RNA and DNA levels remained similar. Based on these data, the proposed clinical administration of AAV5-FVIII-SQ via IV infusion is likely to be similar to or better than bolus administration.

Bleeding Time Evaluation in Rag2−/−×FVIII−/− Mice

The objective this study was to evaluate the functional coagulation endpoint of bleeding time 8 weeks after a single dose of AAV5-FVIII-SQ in male Rag2−/−×FVIII−/− mice, compared to wild-type mice (C57BL/6J). Additionally, the changes in bleeding time 8 weeks after AAV5-FVIII-SQ treatment were compared to results achieved in Rag2−/−×FVIII−/− mice treated with ReFacto®. One hundred male Rag2−/−×FVIII−/− mice and twenty male age-matched 057BL/6J mice were approximately 8 weeks old at study initiation. Animals were randomly distributed into four groups (20 animals/dose) and administered a single IV injection of AAV5-FVIII-SQ via the tail vein (C57BL/6J: vehicle; Rag2−/−×FVIII−/−: vehicle, 2.0E13 or 1E14 vg/kg AAV5-FVIII-SQ).

Rag2−/−×FVIII−/− animals given ReFacto® had dose related decrease in bleeding time and volume. In Rag2−/−×FVIII−/− animals given 50 U/kg of ReFacto® a mean blood loss of 0.49±0.30 g and a mean bleeding time of 18.1±9.39 min was observed. Rag2−/−×FVIII−/− mice given 200 U/kg of ReFacto® had a mean blood loss and bleeding time of 0.134±0.19 g and 4.29±6.16 min.

Plasma levels of ReFacto® and FVIII-SQ were similar in mice given 50 U/kg ReFacto® and 2E13 vg/kg AAV5-FVIII-SQ, respectively.

Administration of AAV5-FVIII-SQ to Rag2−/−×FVIII−/− mice resulted in a dose dependent reduction in blood loss volume and bleeding time at 8 weeks post-dose. A dose dependent reduction in blood volume loss and bleeding time was observed at 8-weeks, postdose. In animals given 1E14 vg/kg AAV5-FVIII-SQ blood loss and bleeding time was corrected to wild-type levels, comparable to the correction achieved with ReFacto® treatment. Administration of AAV5-FVIII-SQ can correct the coagulopathy in the mouse model of hemophilia A, in a dose dependent fashion, similar to exogenously administered ReFacto®.

Dose Response in Rag2−/−×FVIII−/− Mice

In Rag2−/−×FVIII−/− mice given 2E11 through 2E12 vg/kg AAV5-FVIII-SQ, no plasma FVIII-SQ protein or activity levels were detected.

In the present study, sixty male Rag2−/−×FVIII−/− mice were approximately 8 weeks old at study initiation. Animals were randomly distributed into six groups (10 animals/dose) and administered a single IV injection of AAV5-FVIII-SQ via the tail vein (vehicle, 2E12, 6E12, 2E13, 6E13 and 2E14 vg/kg AAV5-FVIII-SQ).

FVIII-SQ plasma protein levels were generally dose related in animals given ≥1.5E12 vg/kg AAV5-FVIII-SQ. FVIII-SQ protein levels were below the level of quantitation in animals given ≤1.7E11 vg/kg AAV5-FVIII-SQ. PD activity generally increased with dose and was correlated with activity. In animals given ≤1.8E13 vg/kg AAV5-FVIII-SQ, inter-animal variability was observed and only a subset of animals had detectable levels of plasma FVIII-SQ and activity.

Consistent with the FVIII-SQ protein and activity levels, vector genome copies and expression copies (RNA) were observed in animals given ≥1.5E12 vg/kg AAV5-FVIII-SQ. Vector genome DNA copies and expression copies RNA/μg RNA generally increased with dose.

FVIII-SQ plasma protein levels, activity levels and vector genome and RNA levels were generally dose related in Rag2−/−×FVIII−/− animals given >1.5E12 vg/kg AAV5-FVIII-SQ. In a subset of animals given 1.5E12 (two animals) or 1.8E13 vg/kg AAV5-FVIII-SQ (eight of ten animals), doses which bracket the proposed FIH clinical dose of 6.0E12 vg/kg AAV5-FVIII-SQ, activity ranged from 2.8 through 66.4% of normal. This indicates that PD activity in the clinic may be achieved at the 6.0E12 dose level because the resulting plasma FVIII-SQ protein and activity levels will likely give a more consistent response in animals.

Capsid Selection in Cynomolgus Monkeys

The objective of this study was to assess the relative activity of two capsids (AAV5.2 FVIII-SQ and AAV8.2 FVIII-SQ, i.e., AAV5 and AAV8 capsid protein, respectively, and AAV2 ITRs) with FVIII-SQ transgenes over 8 weeks when given as a single IV bolus to cynomolgous monkey. Eight male cynomolgus monkeys were 2.8 to 4.1 years old and weighed between 2.6 and 3.6 kg at the time of study initiation. All animals were prescreened for anti-AAV5 or anti-AAV8 transduction inhibition activities in comparison to immune-depleted cynomolgus monkey serum. Animals were assigned to four groups and were given either 2.0E12 or 2.0E13 vg/kg of AAV5.2-hFVIII-SQ or AAV8.2-hFVIII-SQ as a single slow bolus intravenous administration (0.5 and 5.0 mL/kg, respectively).

Administration of a single injection of AAV5.2 hFVIII-SQ and AAV8.2 hFVIII-SQ resulted in detectable levels of plasma FVIII-SQ protein levels that was well tolerated in cynomolgus monkeys given 2.0E13 vector/kg. No AAV5-FVIII-SQ related changes in liver clinical chemistry was observed, indicating no liver dysfunction was observed. The AAV5 capsid was selected for continued development.

Single Dose IV Study in Cynomolgus Monkeys

The objective of this study was to assess the relative activity of AAV5-FVIII-SQ of two manufacturing lots produced in two cell lines (Baculovirus infected sf9 insect and human 293 cells) over 8 weeks when given as a single IV administration to cynomolgous monkey. Eight naive male monkeys were 3.9 to 4.3 years of age and weighed 2.8 to 4.3 kg at treatment initiation. All animals were prescreened for anti-AAV5 antibodies and AAV5 transduction inhibition activities prior to assignment to the study. Each monkey (2/dose group) received a single slow bolus IV injection (2E13 and 6E13 vg/kg AAV5-FVIII-SQ) and was observed for eight weeks.

Relative plasma FVIII-SQ protein levels were assessed over 8-weeks. Possible AAV5-FVIII-SQ-related APTT prolongation was observed in animals with anti-FVIII antibody formation. This is a known potential immunogenicity outcome for exogenous factor replacement. No AAV5-FVIII-SQ-related changes in liver clinical chemistry was observed, indicating no liver dysfunction was observed. Plasma FVIII-SQ levels increased over three to six weeks but declined thereafter.

All animals given AAV5-FVIII-SQ expressed levels of FVIII-SQ in the plasma after Week 2 post administration. In general, FVIII-SQ levels increased over time and then decreased by Week 8. Peak levels of plasma FVIII-SQ ranged from 4.8 ng to 67.4 ng FVIII-SQ/ml.

Single Dose IV Study in Cynomolgus and Rhesus Monkeys

In cynomolgus and rhesus monkey given 6E12 and 2E13 vg/kg AAV5-FVIII-SQ, relative expression of FVIII-SQ was assessed over 6 weeks. No AAV5-FVIII-SQ-related changes in liver clinical chemistry were observed, indicating no liver dysfunction. Plasma FVIII-SQ protein levels were greater in cynomolgus monkey compared to rhesus. Plasma FVIII-SQ levels increased over four to five weeks but declined thereafter. Liver vector genome DNA was detected in all animals given AAV5-FVIII-SQ, which implied that levels of AAV5-FVIII-SQ transduction occurred in all animals. Liver FVIII-SQ RNA copies were observed in animals that expressed plasma FVIII-SQ protein. No AAV5-FVIII-SQ-related changes in liver clinical chemistry was observed in surviving monkeys, indicating no liver dysfunction was observed.

Conclusions

Overall in multiple Rag2−/−×FVIII−/− mouse studies, plasma FVIII-SQ protein and % of normal human activity appear generally proportional with dose; similarly for DNA and RNA in liver. FVIII-SQ activity and protein levels generally increased with time after a single dose of AAV5-FVIII-SQ in mouse, while RNA increased in the liver with time. Plasma FVIII-SQ protein expression and activity tended to correlate in these studies. There was high inter-animal and inter-study variability in animals given ≤6E12 vg/kg AAV5-FVIII-SQ as evidenced by plasma FVIII-SQ levels and activity. Consistent expression of plasma FVIII-SQ protein levels was observed in animals given ≥6E12 vg/kg AAV5-FVIII-SQ.

In the limited number of monkeys given 2E12 to 6E13 vg/kg AAV5-FVIII-SQ, plasma FVIII-SQ levels were detected in animals given ≥6E12 vg/mL with no detectable plasma levels observed in animals given 2E12 vg/kg.

In studies conducted in cynomolgus monkeys, expression of FVIII-SQ peaked between 3 and 5 weeks post dosing, and declined toward study end to levels that were in some cases below the limit of detection. In some instances, anti-FVIII antibodies were detected in animals prior to, or following peak FVIII-SQ levels in the plasma. However, antibody was not detected in all animals with diminished expression of FVIII-SQ, suggesting other potential mechanisms are inhibiting expression, such as cytotoxic T-Lymphocyte (CTL) mediated clearance of transduced cells, or possibly other non-specified inhibitors of expression. The transient FVIII-SQ expression in non-human primates is suspected to be species-specific and not expected to occur in the clinic.

A single IV bolus of AAV5-FVIII-SQ in the monkey resulted in measurable FVIII-SQ protein levels in plasma at the proposed clinical starting dose 6E12 vg/kg and up to 6E13 vg/kg AAV5-FVIII-SQ; administration of AAV5-FVIII-SQ in the mouse has resulted in plasma FVIII-SQ protein and activity levels consistently observed in studies over a comparable dose range. The proposed starting dose of a Phase 1/2 human clinical trial, 6E12 vg/kg AAV5-FVIII-SQ, was selected based on a 10-fold safety factor that also had a detectable plasma FVIII-SQ protein and activity level in both monkey and mice reducing the possibility of a sub-therapeutic outcome.

Figure 2A:
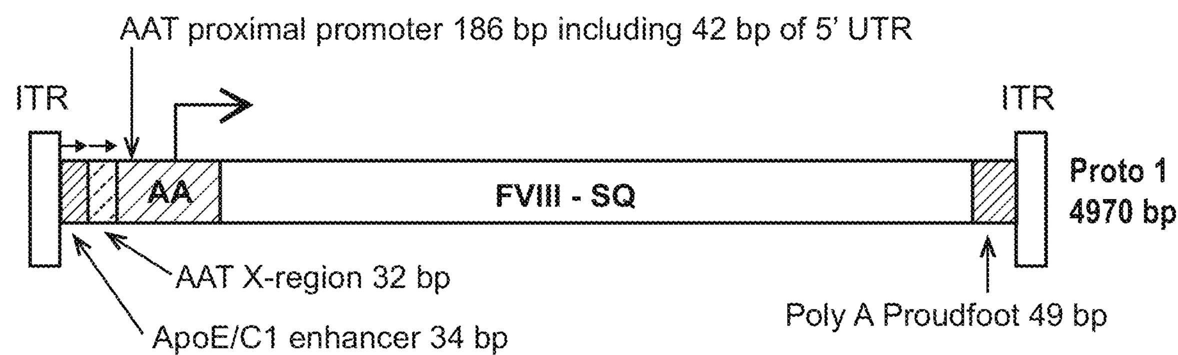
FIG. 2A-FIG. 2D provide schematic representations of certain recombinant AAV FVIII vectors of the present invention. (A) Proto 1, (B) Proto 1S, (C) Proto 2S and (D) Proto 3 S.
Figure 2B:
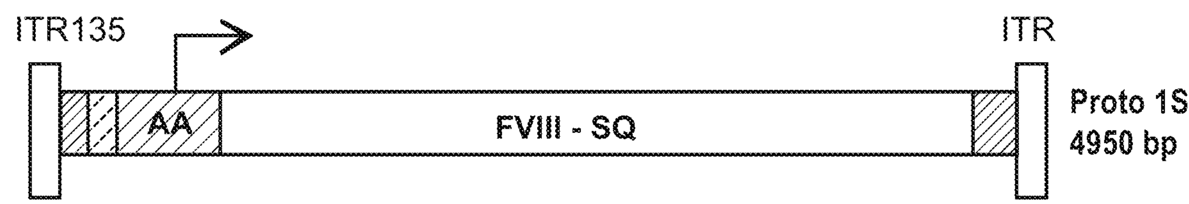
Figure 2C:
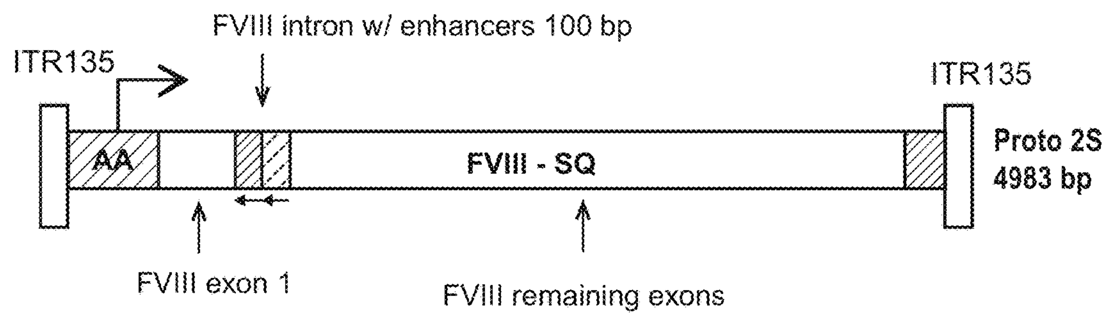
Figure 2D:
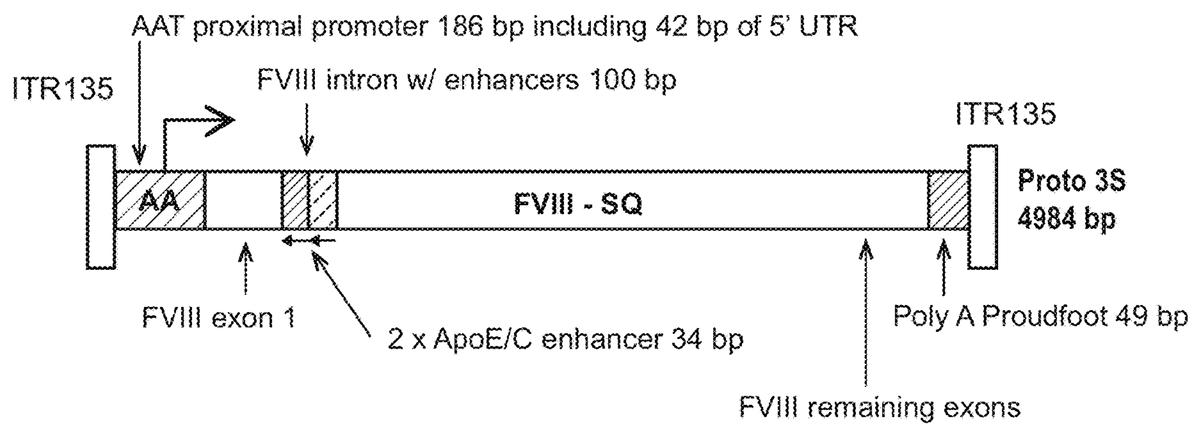

Dose Escalation Safety, Tolerability and Efficacy Study of AAV5-FVIII-SQ in Human Patients with Severe Hemophilia a In the present study, recombinant FVIII AAV virions comprising the Protol FVIII-SQ vector of FIG. 2A (SEQ ID NO:1) will be delivered to human patients by single intravenous dose. The study is designed to achieve stable, potentially life-long expression of active hFVIII in the plasma, synthesized from vector-transduced liver tissue. This clinical study is a first-in-human study designed to assess the relationship of vector dose to the augmentation of residual FVIII activity, and whether these levels are sufficient to alter the clinical phenotype. The relationship of dose to safety will be correlated to the activity of hFVIII in patients with severe HA.

The primary objectives of this study are (i) to assess the safety of a single intravenous administration of a recombinant AAV encoding human FVIII-SQ and (ii) to determine the dose of recombinant AAV encoding FVIII-SQ required to achieve expression of FVIII at or above 5% of normal activity (>5 IU/dL) at 16 weeks after infusion. The kinetics, duration and magnitude of AAV-mediated FVIII activity in individuals with hemophilia A will be determined and correlated to an appropriate dose.

Secondary objectives of this study are (i) to describe the immune response to the FVIII transgene and/or AAV capsid proteins following systemic administration of the recombinant FVIII AAV virus, (ii) to assess the impact of FVIII AAV dosing on the frequency of FVIII replacement therapy during the study and (iii) to assess the impact of dosing on the number of bleeding episodes requiring treatment during the study.

The recombinant FVIII-SQ-encoding vector Protol (shown herein in FIG. 2A and SEQ ID NO:1) was used to produce recombinant AAV5-FVIII-SQ virus using a baculovirus/519-based expression system. The AAV5-FVIII-SQ process consists of batch cell culture, harvest, purification, and formulation, resulting in formulated bulk drug substance (FBDS). The FBDS is filtered through tandem 0.2 μm sterilizing filters and collected into sterile bioprocess collection bags prior to filling. AAV5-FVIII-SQ is then aseptically prepared by filling 1.1 ml of the sterile FBDS into 2 ml cryovials and closed with sterile caps. The filled vials are then visually inspected prior to labeling, packaging and freezing at ≤−65° C.

Clinical AAV5-FVIII-SQ Liquid Formulation

As the AAV5-FVIII-SQ liquid formulation described above and employed for the non-/pre-clinical studies exhibited significant adsorption of the recombinant AAV to glass and plastic surfaces, work was conducted herein to develop a novel AAV5-FVIII-SQ formulation with advantageous properties for use in human clinical studies. Purified AAV5-FVIII-SQ was formulated for human clinical studies as follows.

Purified recombinant AAV5-FVIII-SQ virus was formulated at various concentrations in a liquid formulation useful for IV administration to human patients comprising 1.38 mg/ml sodium phosphate, monobasic monohydrate, 1.42 mg/ml sodium phosphate, dibasic (dried), 8.18 mg/ml sodium chloride, 20 mg/ml mannitol and 2.0 mg/ml Poloxamer 188 (Pluronic F-68), pH 7.4. In one embodiment, the concentration of recombinant AAV5-FVIII-SQ virus in the above described formulation was 2E13 vg/ml. The resulting liquid formulation is a sterile clear/colorless to pale yellow solution useful for IV infusion and, as compared to the formulation employed for the non-/pre-clinical studies described above, reduced viral adsorptive losses to binding to glass and plastic to acceptable levels. This liquid formulation proved to be stable for extended periods during storage at ≤−65° C. and is employed for the human clinical studies described below.

Human Clinical Study Design

Participants in this first-in-man, dose-escalation study with severe hemophilia A will be enrolled sequentially into one of up to three cohorts according to dose level, (i) 6E12 vector genomes [vg] per kilogram of body weight, given as a single intravenous dose (iv), (ii) 2E13 vg per kilogram, iv, or (iii) 6E13 vg per kilogram, iv, followed by a 16 week post-infusion follow-up period during which safety and efficacy assessments will be taken. After the primary endpoint analysis at 16 weeks, safety and efficacy will then be assessed for approximately 5 years.

Patients will be enrolled sequentially every 3 weeks or more between cohorts. Dose escalation may occur after a single patient has been safely dosed if the resulting FVIII activity at Week 3 is <5 IU/dL. Three weeks is expected to be the time the expression will be close to the maximum. This escalation paradigm is intended to minimize the patient numbers exposed to sub-therapeutic doses.

The starting dose was based on the expression and safety of FVIII observed in nonclinical studies of mice and monkeys. The starting dose has a significant safety margin (10-fold) from no observed adverse effect level (NOAEL) in non-human primates.

Approximately three weeks after an injection, the decision to escalate to the next dose level will be made based on the review of safety parameters and FVIII activity. If the FVIII activity is ≥5 IU/dL, then the other patients of the dose group will be enrolled without waiting for 3 weeks between patients.

Patient 1 will be dosed by intravenous perfusion with 6E12 vector genomes [vg] per kilogram of body weight. If the activity level does not reach ≥5 IU/dL at 21 days, then a higher dose (2E13 vg per kilogram) will be used for the next patient.

If the activity level does not reach ≥5 IU/dL after Patient 2, then the highest dose (6E13 vg per kilogram) will be used for the next patient.

For each dose, if the activity level reaches 5 IU/dL and if no safety issue is found, then up to four patients will receive this dose. If at any time activity levels reach 10 IU/dL or higher, no further dose escalation will take place, but additional patients will then be dosed at this dose level for a total of 6 patients per dose.

Frequent monitoring of liver enzymes will be performed on all patients in the trial. Baseline (i.e., prior to FVIII vector administration) alanine transaminase (ALT) concentrations will be determined and post-administration ALT elevations of 1.5-fold or greater will trigger therapeutic corticosteroid use. Patients may also be treated prophylactically (i.e., prior to FVIII vector administration) with corticosteroids to protect against hepatotoxicity.

Results—Patient One

Patient One was dosed by single intravenous perfusion with 6E12 vector genomes [vg] of AAV5-FVIII-SQ per kilogram of body weight as described above. At the time of dosing, Patient One had a circulating blood Factor VIII level of ≤0.5 IU/dl. Seven days after dosing, Patient One's circulating blood Factor VIII level had increased to 5.4 IU/dl and had further increased to 19.2 IU/dl 14 days post-dosing. At 21 days post-dosing, however, Patient One's circulating Factor VIII level had decreased to ≤0.5 IU/dl and held consistently at that level thereafter.

Results—Patient Two

As the Factor VIII activity level of Patient One was not at least 5 IU/dl on day 21 post-dosing, Patient Two was escalated to a dose by single intravenous perfusion of 2E13 vector genomes [vg] of AAV5-FVIII-SQ per kilogram of body weight as described above. At the time of dosing, Patient Two had a circulating blood Factor VIII level of ≤0.1 IU/dl. Twenty-one days after dosing, Patient Two's circulating blood Factor VIII level had increased to 0.7 IU/dl, 2.1 IU/dl at 10 weeks post-dosing, 2.4 IU/dl at 12 weeks post-dosing, 1.9 IU/dl at 16 weeks post-dosing and 2.4 IU/dl at 28 weeks post-dosing, the latter representing an at least 24-fold increase as compared to pre-dosing levels. ALT levels measured in Patient Two did not increase to 1.5-fold or greater above baseline at any point during the 28 week observation period and, as such, no corticosteroid treatment was initiated.

Results—Patient Three

Patient Three was escalated to a dose by single intravenous perfusion of 6E13 vector genomes [vg] of AAV5-FVIII-SQ per kilogram of body weight as described above. At the time of dosing, Patient Three had a circulating blood Factor VIII level of <1.0 UL/dl. Twenty-one days after dosing, Patient Three's circulating blood Factor VIII level had increased to 3.1 IU/dl, 20.8 IU/dl at 10 weeks post-dosing, 34.7 IU/dl at 12 weeks post-dosing, 56.6 IU/dl at 16 weeks post-dosing and 89.3 IU/dl at 28 weeks post-dosing, well above the concentration of Factor VIII required for satisfactory blood coagulation in humans and decrease in bleeding time during a bleeding event in the patient.

As ALT levels in Patient Three were observed to increase 1.5-fold above baseline after FVIII vector administration, the subject was treated therapeutically with corticosteroid at concentrations ranging from 5 mg/day to 60 mg/day over the continued period of observation. Therapeutic corticosteroid treatment reduced hepatotoxicity-related ALT concentration to acceptable levels without concomitant decrease in Factor VIII levels or any associated serious adverse events.

Results—Patient Four

Patient Four was dosed by single intravenous perfusion of 6E13 vector genomes [vg] of AAV5-FVIII-SQ per kilogram of body weight as described above. At the time of dosing, Patient Four had a circulating blood Factor VIII level of <1.0 UL/dl. Twenty-one days after dosing, Patient Four's circulating blood Factor VIII level had increased to 5.6 IU/dl, 67.8 IU/dl at 10 weeks post-dosing, 89 IU/dl at 12 weeks post-dosing, >170 IU/dl at 16 weeks post-dosing and 219.2 IU/dl at 20 weeks post-dosing, well above the concentration of Factor VIII required for satisfactory blood coagulation in humans and decrease in bleeding time during a bleeding event in the patient.

Patient Four was treated prophylactically with corticosteroid at concentrations ranging from 5 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Five

Patient Five was dosed by single intravenous perfusion of 6E13 vector genomes [vg] of AAV5-FVIII-SQ per kilogram of body weight as described above. At the time of dosing, Patient Five had a circulating blood Factor VIII level of <1.0 UL/dl. Twenty-one days after dosing, Patient Five's circulating blood Factor VIII level had increased to 2.2 IU/dl, 24.4 IU/dl at 10 weeks post-dosing, 59.4 IU/dl at 12 weeks post-dosing, 126.5 IU/dl at 16 weeks post-dosing and 271.2 IU/dl at 19 weeks post-dosing, well above the concentration of Factor VIII required for satisfactory blood coagulation in humans and decrease in bleeding time during a bleeding event in the patient.

Patient Five was treated both prophylactically and therapeutically with corticosteroid at concentrations ranging from 5 mg/day to 40 mg/day over the continued period of observation. Prophylactic and therapeutic corticosteroid treatment maintained hepatotoxicity-related ALT concentrations at acceptable levels without concomitant decrease in Factor VIII levels or any associated serious adverse events.

Results—Patient Six

Patient Six was dosed by single intravenous perfusion of 6E13 vector genomes [vg] of AAV5-FVIII-SQ per kilogram of body weight as described above. At the time of dosing, Patient Six had a circulating blood Factor VIII level of <1.0 UL/dl. Twenty-one days after dosing, Patient Six's circulating blood Factor VIII level was <1.0 IU/dl, 6.2 IU/dl at 10 weeks post-dosing, 19.6 IU/dl at 12 weeks post-dosing, 13 IU/dl at 16 weeks post-dosing and 13 IU/dl at 19 weeks post-dosing, well above the concentration of Factor VIII required for satisfactory blood coagulation in humans and decrease in bleeding time during a bleeding event in the patient.

Patient Six was treated therapeutically with corticosteroid at concentrations ranging from 5 mg/day to 60 mg/day over the continued period of observation. Therapeutic corticosteroid treatment maintained hepatotoxicity-related ALT concentrations at acceptable levels without concomitant decrease in Factor VIII levels or any associated serious adverse events.

Results—Patient Seven

Patient Seven was dosed by single intravenous perfusion of 6E13 vector genomes [vg] of AAV5-FVIII-SQ per kilogram of body weight as described above. At the time of dosing, Patient Seven had a circulating blood Factor VIII level of <1.0 UL/dl. Twenty-one days after dosing, Patient Seven's circulating blood Factor VIII level had increased to 10.4 IU/dl, 56.4 IU/dl at 10 weeks post-dosing, 58 IU/dl at 12 weeks post-dosing, 93.1 IU/dl at 16 weeks post-dosing and 135.8 IU/dl at 18 weeks post-dosing, well above the concentration of Factor VIII required for satisfactory blood coagulation in humans and decrease in bleeding time during a bleeding event in the patient.

Patient Seven was treated prophylactically with corticosteroid at concentrations ranging from 5 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Eight

Patient Eight was dosed by single intravenous perfusion of 6E13 vector genomes [vg] of AAV5-FVIII-SQ per kilogram of body weight as described above. At the time of dosing, Patient Eight had a circulating blood Factor VIII level of <1.0 UL/dl. Twenty-one days after dosing, Patient Eight's circulating blood Factor VIII level had increased to 5.1 IU/dl, 35.2 IU/dl at 10 weeks post-dosing, 42.7 IU/dl at 12 weeks post-dosing, 49.7 IU/dl at 16 weeks post-dosing and 68.8 IU/dl at 17 weeks post-dosing, well above the concentration of Factor VIII required for satisfactory blood coagulation in humans and decrease in bleeding time during a bleeding event in the patient.

Patient Eight was treated prophylactically with corticosteroid at concentrations ranging from 10 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Nine

Patient Nine was dosed by single intravenous perfusion of 6E13 vector genomes [vg] of AAV5-FVIII-SQ per kilogram of body weight as described above. At the time of dosing, Patient Nine had a circulating blood Factor VIII level of <1.0 UL/dl. Twelve weeks after dosing, Patient Nine's circulating blood Factor VIII level had increased to 78.7 IU/dl, well above the concentration of Factor VIII required for satisfactory blood coagulation in humans and decrease in bleeding time during a bleeding event in the patient.

Patient Nine was treated therapeutically with corticosteroid at concentrations ranging from 10 mg/day to 40 mg/day over the continued period of observation. Therapeutic corticosteroid treatment maintained hepatotoxicity-related ALT concentrations at acceptable levels without concomitant decrease in Factor VIII levels or any associated serious adverse events.

Summary

The results presented in this Example 8 demonstrate that successful therapy of hemophilia A in human patients can be achieved using the compositions and methods of the present invention. More specifically, demonstrated herein is that treatment of humans suffering from hemophilia A with at least 2E13 vector genomes [vg] of AAV5-FVIII-SQ per kilogram of body weight results in stable FVIII activity of ≥2 IU/dl over at least 26 weeks post-dosing and that treatment of humans suffering from hemophilia A with at least 6E13 vector genomes [vg] of AAV5-FVIII-SQ per kilogram of body weight results in high, sustained FVIII activity of >10 IU/dl in all patients treated. Moreover, the data provided herein demonstrates that treatment with AAV5-FVIII-SQ is well-tolerated and results in no clinically-relevant sustained rises in ALT levels or other markers of hepatotoxicity. Prophylactic and/or therapeutic corticosteroid treatment of patients is capable of maintaining hepatotoxicity-related ALT concentrations at acceptable levels without concomitant decrease in Factor VIII levels or any associated serious adverse events. Finally, initial data demonstrates that patients treated either prophylactically or therapeutically with corticosteroids can be successfully tapered off steroid treatment with no adverse impact on FVIII expression or ALT concentration levels.

What is claimed:

1. A pharmaceutical formulation comprising a recombinant AAV FVIII virus, sodium phosphate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml.

2. The pharmaceutical formulation of claim 1, wherein the recombinant AAV FVIII virus is AAV5-FVIII-SQ.

3. The pharmaceutical formulation of claim 1 which comprises said AAV FVIII virus at a concentration of from about 1E12 vg/ml to about 2E14 vg/ml or from about 6E12 vg/kg to about 6E13 vg/kg of the recombinant AAV FVIII virus.

4. The pharmaceutical formulation of claim 3 which comprises said AAV FVIII virus at a concentration of about 2E13 vg/ml.

5. The pharmaceutical formulation of claim 1 which is liquid.

6. The pharmaceutical formulation of claim 1, wherein the formulation is formulated for IV administration.

* * * * *

SEQUENCE LISTING

```
<160> NUMBER OF SEQ ID NOS: 44

<210> SEQ ID NO 1
<211> LENGTH: 4970
<212> TYPE: DNA
<213> ORGANISM: Adeno-Associated Virus

<400> SEQUENCE: 1

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgtttg ctgcttgcaa tgtttgccca ttttagggtg    180

gacacaggac gctgtggttt ctgagccagg gggcgactca gatcccagcc agtggactta    240

gcccctgttt gctcctccga taactggggt gaccttggtt aatattcacc agcagcctcc    300

cccgttgccc ctctggatcc actgcttaaa tacggacgag gacagggccc tgtctcctca    360

gcttcaggca ccaccactga cctgggacag tgaatcgcca ccatgcagat tgagctgagc    420

acctgcttct tcctgtgcct gctgaggttc tgcttctctg ccaccaggag atactacctg    480

ggggctgtgg agctgagctg ggactacatg cagtctgacc tgggggagct gcctgtggat    540

gccaggttcc cccccagagt gcccaagagc ttccccttca acacctctgt ggtgtacaag    600

aagaccctgt ttgtggagtt cactgaccac ctgttcaaca ttgccaagcc caggcccccc    660

tggatgggcc tgctgggccc caccatccag gctgaggtgt atgacactgt ggtgatcacc    720

ctgaagaaca tggccagcca ccctgtgagc ctgcatgctg tgggggtgag ctactggaag    780

gcctctgagg gggctgagta tgatgaccag accagccaga gggagaagga ggatgacaag    840

gtgttccctg ggggcagcca cacctatgtg tggcaggtgc tgaaggagaa tggccccatg    900

gcctctgacc ccctgtgcct gacctacagc tacctgagcc atgtggacct ggtgaaggac    960

ctgaactctg gcctgattgg ggccctgctg gtgtgcaggg agggcagcct ggccaaggag   1020

aagacccaga ccctgcacaa gttcatcctg ctgtttgctg tgtttgatga gggcaagagc   1080

tggcactctg aaaccaagaa cagcctgatg caggacaggg atgctgcctc tgccagggcc   1140

tggcccaaga tgcacactgt gaatggctat gtgaacagga gcctgcctgg cctgattggc   1200

tgccacagga agtctgtgta ctggcatgtg attggcatgg gcaccacccc tgaggtgcac   1260

agcatcttcc tggagggcca caccttcctg gtcaggaacc acaggcaggc cagcctggag   1320

atcagcccca tcaccttcct gactgcccag accctgctga tggacctggg ccagttcctg   1380

ctgttctgcc acatcagcag ccaccagcat gatggcatgg aggcctatgt gaaggtggac   1440

agctgccctg aggagcccca gctgaggatg aagaacaatg aggaggctga ggactatgat   1500

gatgacctga ctgactctga gatggatgtg gtgaggtttg atgatgacaa cagccccagc   1560

ttcatccaga tcaggtctgt ggccaagaag caccccaaga cctgggtgca ctacattgct   1620

gctgaggagg aggactggga ctatgccccc ctggtgctgg cccctgatga caggagctac   1680

aagagccagt acctgaacaa tggcccccag aggattggca ggaagtacaa gaaggtcagg   1740

ttcatggcct acactgatga aaccttcaag accagggagg ccatccagca tgagtctggc   1800

atcctgggcc ccctgctgta tggggaggtg ggggacaccc tgctgatcat cttcaagaac   1860

caggccagca ggccctacaa catctacccc catggcatca ctgatgtgag gcccctgtac   1920
```

```
agcaggaggc tgcccaaggg ggtgaagcac ctgaaggact tccccatcct gcctggggag   1980
atcttcaagt acaagtggac tgtgactgtg gaggatggcc ccaccaagtc tgaccccagg   2040
tgcctgacca gatactacag cagctttgtg aacatggaga gggacctggc ctctggcctg   2100
attggccccc tgctgatctg ctacaaggag tctgtggacc agaggggcaa ccagatcatg   2160
tctgacaaga ggaatgtgat cctgttctct gtgtttgatg agaacaggag ctggtacctg   2220
actgagaaca tccagaggtt cctgcccaac cctgctgggg tgcagctgga ggaccctgag   2280
ttccaggcca gcaacatcat gcacagcatc aatggctatg tgtttgacag cctgcagctg   2340
tctgtgtgcc tgcatgaggt ggcctactgg tacatcctga gcattggggc ccagactgac   2400
ttcctgtctg tgttcttctc tggctacacc ttcaagcaca agatggtgta tgaggacacc   2460
ctgaccctgt tccccttctc tggggagact gtgttcatga gcatggagaa ccctggcctg   2520
tggattctgg gctgccacaa ctctgacttc aggaacaggg gcatgactgc cctgctgaaa   2580
gtctccagct gtgacaagaa cactggggac tactatgagg acagctatga ggacatctct   2640
gcctacctgc tgagcaagaa caatgccatt gagcccagga gcttcagcca gaacccccca   2700
gtgctgaaga ggcaccagag ggagatcacc aggaccaccc tgcagtctga ccaggaggag   2760
attgactatg atgacaccat ctctgtggag atgaagaagg aggactttga catctacgac   2820
gaggacgaga accagagccc caggagcttc cagaagaaga ccaggcacta cttcattgct   2880
gctgtggaga ggctgtggga ctatggcatg agcagcagcc cccatgtgct gaggaacagg   2940
gcccagtctg gctctgtgcc ccagttcaag aaggtggtgt tccaggagtt cactgatggc   3000
agcttcaccc agcccctgta cagaggggag ctgaatgagc acctgggcct gctgggcccc   3060
tacatcaggg ctgaggtgga ggacaacatc atggtgacct tcaggaacca ggccagcagg   3120
ccctacagct tctacagcag cctgatcagc tatgaggagg accagaggca gggggctgag   3180
cccaggaaga actttgtgaa gcccaatgaa accaagacct acttctggaa ggtgcagcac   3240
cacatggccc ccaccaagga tgagtttgac tgcaaggcct gggcctactt ctctgatgtg   3300
gacctggaga aggatgtgca ctctggcctg attggccccc tgctggtgtg ccacaccaac   3360
accctgaacc ctgcccatgg caggcaggtg actgtgcagg agtttgccct gttcttcacc   3420
atctttgatg aaaccaagag ctggtacttc actgagaaca tggagaggaa ctgcagggcc   3480
ccctgcaaca tccagatgga ggaccccacc ttcaaggaga actacaggtt ccatgccatc   3540
aatggctaca tcatggacac cctgcctggc ctggtgatgg cccaggacca gaggatcagg   3600
tggtacctgc tgagcatggg cagcaatgag aacatccaca gcatccactt ctctggccat   3660
gtgttcactg tgaggaagaa ggaggagtac aagatggccc tgtacaacct gtaccctggg   3720
gtgtttgaga ctgtggagat gctgcccagc aaggctggca tctggagggt ggagtgcctg   3780
attggggagc acctgcatgc tggcatgagc accctgttcc tggtgtacag caacaagtgc   3840
cagacccccc tgggcatggc ctctggccac atcagggact tccagatcac tgcctctggc   3900
cagtatggcc agtgggcccc caagctggcc aggctgcact actctggcag catcaatgcc   3960
tggagcacca aggagccctt cagctggatc aaggtggacc tgctggcccc catgatcatc   4020
catggcatca agacccaggg ggccaggcag aagttcagca gcctgtacat cagccagttc   4080
atcatcatgt acagcctgga tggcaagaag tggcagacct acaggggcaa cagcactggc   4140
accctgatgg tgttctttgg caatgtggac agctctggca tcaagcacaa catcttcaac   4200
ccccccatca ttgccagata catcaggctg caccccaccc actacagcat caggagcacc   4260
```

```
ctgaggatgg agctgatggg ctgtgacctg aacagctgca gcatgcccct gggcatggag   4320
agcaaggcca tctctgatgc ccagatcact gccagcagct acttcaccaa catgtttgcc   4380
acctggagcc ccagcaaggc caggctgcac ctgcagggca ggagcaatgc ctggaggccc   4440
caggtcaaca accccaagga gtggctgcag gtggacttcc agaagaccat gaaggtgact   4500
ggggtgacca cccagggggt gaagagcctg ctgaccagca tgtatgtgaa ggagttcctg   4560
atcagcagca gccaggatgg ccaccagtgg accctgttct tccagaatgg caaggtgaag   4620
gtgttccagg gcaaccagga cagcttcacc cctgtggtga acagcctgga cccccccctg   4680
ctgaccagat acctgaggat tcacccccag agctgggtgc accagattgc cctgaggatg   4740
gaggtgctgg gctgtgaggc ccaggacctg tactgaaata aaagatcttt attttcatta   4800
gatctgtgtg ttggtttttt gtgtgaggaa cccctagtga tggagttggc cactccctct   4860
ctgcgcgctc gctcgctcac tgaggccggg cgaccaaagg tcgcccgacg cccgggcttt   4920
gcccgggcgg cctcagtgag cgagcgagcg cgcagagagg gagtggccaa              4970
```

<210> SEQ ID NO 2
<211> LENGTH: 4950
<212> TYPE: DNA
<213> ORGANISM: Adeno-Associated Virus

<400> SEQUENCE: 2

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactgtttg ctgcttgcaa tgtttgccca ttttagggtg gacacaggac    180
gctgtggttt ctgagccagg gggcgactca gatcccagcc agtggactta gcccctgttt    240
gctcctccga taactggggt gaccttggtt aatattcacc agcagcctcc cccgttgccc    300
ctctggatcc actgcttaaa tacggacgag gacagggccc tgtctcctca gcttcaggca    360
ccaccactga cctgggacag tgaatcgcca ccatgcagat tgagctgagc acctgcttct    420
tcctgtgcct gctgaggttc tgcttctctg ccaccaggag atactacctg gggctgtgg     480
agctgagctg ggactacatg cagtctgacc tgggggagct gcctgtggat gccaggttcc    540
cccccagagt gcccaagagc ttccccttca acacctctgt ggtgtacaag aagaccctgt    600
ttgtggagtt cactgaccac ctgttcaaca ttgccaagcc caggcccccc tggatgggcc    660
tgctgggccc caccatccag gctgaggtgt atgacactgt ggtgatcacc ctgaagaaca    720
tggccagcca ccctgtgagc ctgcatgctg tgggggtgag ctactggaag gcctctgagg    780
gggctgagta tgatgaccag accagccaga gggagaagga ggatgacaag gtgttccctg    840
ggggcagcca cacctatgtg tggcaggtgc tgaaggagaa tggccccatg gcctctgacc    900
ccctgtgcct gacctacagc tacctgagcc atgtggacct ggtgaaggac ctgaactctg    960
gcctgattgg ggccctgctg gtgtgcaggg agggcagcct ggccaaggag aagacccaga   1020
ccctgcacaa gttcatcctg ctgtttgctg tgtttgatga gggcaagagc tggcactctg   1080
aaaccaagaa cagcctgatg caggacaggg atgctgcctc tgccagggcc tggcccaaga   1140
tgcacactgt gaatggctat gtgaacagga gcctgcctgg cctgattggc tgccacagga   1200
agtctgtgta ctggcatgtg attggcatgg gcaccacccc tgaggtgcac agcatcttcc   1260
tggagggcca caccttcctg gtcaggaacc acaggcaggc cagcctggag atcagcccca   1320
tcaccttcct gactgcccag accctgctga tggacctggg ccagttcctg ctgttctgcc   1380
acatcagcag ccaccagcat gatggcatgg aggcctatgt gaaggtggac agctgccctg   1440
```

```
aggagcccca gctgaggatg aagaacaatg aggaggctga ggactatgat gatgacctga   1500
ctgactctga gatggatgtg gtgaggtttg atgatgacaa cagccccagc ttcatccaga   1560
tcaggtctgt ggccaagaag caccccaaga cctgggtgca ctacattgct gctgaggagg   1620
aggactggga ctatgccccc ctggtgctgg cccctgatga caggagctac aagagccagt   1680
acctgaacaa tggcccccag aggattggca ggaagtacaa gaaggtcagg ttcatggcct   1740
acactgatga aaccttcaag accagggagg ccatccagca tgagtctggc atcctgggcc   1800
ccctgctgta tggggaggtg gggacaccc tgctgatcat cttcaagaac caggccagca   1860
ggccctacaa catctacccc catggcatca ctgatgtgag gcccctgtac agcaggaggc   1920
tgcccaaggg ggtgaagcac ctgaaggact tccccatcct gcctggggag atcttcaagt   1980
acaagtggac tgtgactgtg gaggatggcc ccaccaagtc tgaccccagg tgcctgacca   2040
gatactacag cagctttgtg aacatggaga gggacctggc ctctggcctg attggccccc   2100
tgctgatctg ctacaaggag tctgtggacc agaggggcaa ccagatcatg tctgacaaga   2160
ggaatgtgat cctgttctct gtgtttgatg agaacaggag ctggtacctg actgagaaca   2220
tccagaggtt cctgcccaac cctgctgggg tgcagctgga ggaccctgag ttccaggcca   2280
gcaacatcat gcacagcatc aatggctatg tgtttgacag cctgcagctg tctgtgtgcc   2340
tgcatgaggt ggcctactgg tacatcctga gcattggggc ccagactgac ttcctgtctg   2400
tgttcttctc tggctacacc ttcaagcaca agatggtgta tgaggacacc ctgaccctgt   2460
tccccttctc tggggagact gtgttcatga gcatggagaa ccctggcctg tggattctgg   2520
gctgccacaa ctctgacttc aggaacaggg gcatgactgc cctgctgaaa gtctccagct   2580
gtgacaagaa cactggggac tactatgagg acagctatga ggacatctct gcctacctgc   2640
tgagcaagaa caatgccatt gagcccagga gcttcagcca gaacccccca gtgctgaaga   2700
ggcaccagag ggagatcacc aggaccaccc tgcagtctga ccaggaggag attgactatg   2760
atgacaccat ctctgtggag atgaagaagg aggactttga catctacgac gaggacgaga   2820
accagagccc caggagcttc cagaagaaga ccaggcacta cttcattgct gctgtggaga   2880
ggctgtggga ctatggcatg agcagcagcc cccatgtgct gaggaacagg gcccagtctg   2940
gctctgtgcc ccagttcaag aaggtggtgt tccaggagtt cactgatggc agcttcaccc   3000
agcccctgta cagaggggag ctgaatgagc acctgggcct gctgggcccc tacatcaggg   3060
ctgaggtgga ggacaacatc atggtgacct tcaggaacca ggccagcagg ccctacagct   3120
tctacagcag cctgatcagc tatgaggagg accagaggca gggggctgag cccaggaaga   3180
actttgtgaa gcccaatgaa accaagacct acttctggaa ggtgcagcac cacatggccc   3240
ccaccaagga tgagtttgac tgcaaggcct gggcctactt ctctgatgtg gacctggaga   3300
aggatgtgca ctctggcctg attggccccc tgctggtgtg ccacaccaac accctgaacc   3360
ctgcccatgg caggcaggtg actgtgcagg agtttgccct gttcttcacc atctttgatg   3420
aaaccaagag ctggtacttc actgagaaca tggagaggaa ctgcagggcc ccctgcaaca   3480
tccagatgga ggaccccacc ttcaaggaga actacaggtt ccatgccatc aatggctaca   3540
tcatggacac cctgcctggc ctggtgatgg cccaggacca gaggatcagg tggtacctgc   3600
tgagcatggg cagcaatgag aacatccaca gcatccactt ctctggccat gtgttcactg   3660
tgaggaagaa ggaggagtac aagatggccc tgtacaacct gtaccctggg gtgtttgaga   3720
ctgtggagat gctgcccagc aaggctggca tctggagggt ggagtgcctg attggggagc   3780
```

```
acctgcatgc tggcatgagc accctgttcc tggtgtacag caacaagtgc cagaccccc   3840
tgggcatggc ctctggccac atcagggact tccagatcac tgcctctggc cagtatggcc   3900
agtgggcccc caagctggcc aggctgcact actctggcag catcaatgcc tggagcacca   3960
aggagccctt cagctggatc aaggtggacc tgctggcccc catgatcatc catggcatca   4020
agacccaggg ggccaggcag aagttcagca gcctgtacat cagccagttc atcatcatgt   4080
acagcctgga tggcaagaag tggcagacct acaggggcaa cagcactggc accctgatgg   4140
tgttctttgg caatgtggac agctctggca tcaagcacaa catcttcaac ccccccatca   4200
ttgccagata catcaggctg caccccaccc actacagcat caggagcacc ctgaggatgg   4260
agctgatggg ctgtgacctg aacagctgca gcatgcccct gggcatggag agcaaggcca   4320
tctctgatgc ccagatcact gccagcagct acttcaccaa catgtttgcc acctggagcc   4380
ccagcaaggc caggctgcac ctgcagggca ggagcaatgc ctggaggccc caggtcaaca   4440
accccaagga gtggctgcag gtggacttcc agaagaccat gaaggtgact ggggtgacca   4500
cccagggggt gaagagcctg ctgaccagca tgtatgtgaa ggagttcctg atcagcagca   4560
gccaggatgg ccaccagtgg accctgttct tccagaatgg caaggtgaag gtgttccagg   4620
gcaaccagga cagcttcacc cctgtggtga acagcctgga cccccccctg ctgaccagat   4680
acctgaggat tcacccccag agctgggtgc accagattgc cctgaggatg gaggtgctgg   4740
gctgtgaggc ccaggacctg tactgaaata aaagatcttt attttcatta gatctgtgtg   4800
ttggtttttt gtgtgagtga tggagttggc cactccctct ctgcgcgctc gctcgctcac   4860
tgaggccggg cgaccaaagg tcgcccgacg cccgggcttt gcccgggcgg cctcagtgag   4920
cgagcgagcg cgcagagagg gagtggccaa                                    4950
```

<210> SEQ ID NO 3
<211> LENGTH: 4983
<212> TYPE: DNA
<213> ORGANISM: Adeno-Associated Virus

<400> SEQUENCE: 3

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctcccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac aacctggctc agaaaccaca gcgtcctgtg    540
tccattctaa tttttccttt cttcacgcag atttcctcct agagtgccaa aatcttttcc    600
attcaacacc tcagtcgtgt acaaaaagac tctgtttgta gaattcacgg atcacctttt    660
caacatcgct aagcccaggc cccctggat gggcctgctg ggccccacca tccaggctga    720
ggtgtatgac actgtggtga tcaccctgaa gaacatggcc agccaccctg tgagcctgca    780
tgctgtgggg gtgagctact ggaaggcctc tgagggggct gagtatgatg accagaccag    840
ccagagggag aaggaggatg acaaggtgtt ccctgggggc agccacacct atgtgtggca    900
ggtgctgaag gagaatggcc ccatggcctc tgaccccctg tgcctgacct acagctacct    960
```

```
gagccatgtg gacctggtga aggacctgaa ctctggcctg attggggccc tgctggtgtg   1020
cagggagggc agcctggcca aggagaagac ccagaccctg cacaagttca tcctgctgtt   1080
tgctgtgttt gatgagggca agagctggca ctctgaaacc aagaacagcc tgatgcagga   1140
cagggatgct gcctctgcca gggcctggcc caagatgcac actgtgaatg gctatgtgaa   1200
caggagcctg cctggcctga ttggctgcca caggaagtct gtgtactggc atgtgattgg   1260
catgggcacc acccctgagg tgcacagcat cttcctggag ggccacacct tcctggtcag   1320
gaaccacagg caggccagcc tggagatcag ccccatcacc ttcctgactg cccagaccct   1380
gctgatggac ctgggccagt tcctgctgtt ctgccacatc agcagccacc agcatgatgg   1440
catggaggcc tatgtgaagg tggacagctg ccctgaggag ccccagctga ggatgaagaa   1500
caatgaggag gctgaggact atgatgatga cctgactgac tctgagatgg atgtggtgag   1560
gtttgatgat gacaacagcc ccagcttcat ccagatcagg tctgtggcca agaagcaccc   1620
caagacctgg gtgcactaca ttgctgctga ggaggaggac tgggactatg ccccccctggt   1680
gctggcccct gatgacagga gctacaagag ccagtacctg aacaatggcc cccagaggat   1740
tggcaggaag tacaagaagg tcaggttcat ggcctacact gatgaaacct tcaagaccag   1800
ggaggccatc cagcatgagt ctggcatcct gggccccctg ctgtatgggg aggtggggga   1860
caccctgctg atcatcttca agaaccaggc cagcaggccc tacaacatct acccccatgg   1920
catcactgat gtgaggcccc tgtacagcag gaggctgccc aagggggtga agcacctgaa   1980
ggacttcccc atcctgcctg ggagatcttt caagtacaag tggactgtga ctgtggagga   2040
tggccccacc aagtctgacc ccaggtgcct gaccagatac tacagcagct ttgtgaacat   2100
ggagagggac ctggcctctg gcctgattgg cccccctgctg atctgctaca aggagtctgt   2160
ggaccagagg ggcaaccaga tcatgtctga caagaggaat gtgatcctgt tctctgtgtt   2220
tgatgagaac aggagctggt acctgactga gaacatccag aggttcctgc ccaaccctgc   2280
tggggtgcag ctggaggacc ctgagttcca ggccagcaac atcatgcaca gcatcaatgg   2340
ctatgtgttt gacagcctgc agctgtctgt gtgcctgcat gaggtggcct actggtacat   2400
cctgagcatt ggggcccaga ctgacttcct gtctgtgttc ttctctggct acaccttcaa   2460
gcacaagatg gtgtatgagg acaccctgac cctgttcccc ttctctgggg agactgtgtt   2520
catgagcatg gagaaccctg gcctgtggat tctgggctgc cacaactctg acttcaggaa   2580
caggggcatg actgccctgc tgaaagtctc cagctgtgac aagaacactg gggactacta   2640
tgaggacagc tatgaggaca tctctgccta cctgctgagc aagaacaatg ccattgagcc   2700
caggagcttc agccagaacc ccccagtgct gaagaggcac cagagggaga tcaccaggac   2760
caccctgcag tctgaccagg aggagattga ctatgatgac accatctctg tggagatgaa   2820
gaaggaggac tttgacatct acgacgagga cgagaaccag agccccagga gcttccagaa   2880
gaagaccagg cactacttca ttgctgctgt ggagaggctg tgggactatg gcatgagcag   2940
cagcccccat gtgctgagga acagggccca gtctggctct gtgccccagt tcaagaaggt   3000
ggtgttccag gagttcactg atggcagctt cacccagccc ctgtacagag gggagctgaa   3060
tgagcacctg ggcctgctgg gcccctacat cagggctgag gtggaggaca acatcatggt   3120
gaccttcagg aaccaggcca gcaggcccta cagcttctac agcagcctga tcagctatga   3180
ggaggaccag aggcaggggg ctgagcccag gaagaacttt gtgaagccca atgaaaccaa   3240
gacctacttc tggaaggtgc agcaccacat ggcccccacc aaggatgagt ttgactgcaa   3300
```

```
ggcctgggcc tacttctctg atgtggacct ggagaaggat gtgcactctg gcctgattgg   3360
cccccctgctg gtgtgccaca ccaacaccct gaaccctgcc catggcaggc aggtgactgt   3420
gcaggagttt gccctgttct tcaccatctt tgatgaaacc aagagctggt acttcactga   3480
gaacatggag aggaactgca gggccccctg caacatccag atggaggacc ccaccttcaa   3540
ggagaactac aggttccatg ccatcaatgg ctacatcatg gacaccctgc ctggcctggt   3600
gatggcccag gaccagagga tcaggtggta cctgctgagc atgggcagca atgagaacat   3660
ccacagcatc cacttctctg gccatgtgtt cactgtgagg aagaaggagg agtacaagat   3720
ggccctgtac aacctgtacc ctggggtgtt tgagactgtg gagatgctgc ccagcaaggc   3780
tggcatctgg agggtggagt gcctgattgg ggagcacctg catgctggca tgagcaccct   3840
gttcctggtg tacagcaaca agtgccagac cccccctgggc atggcctctg gccacatcag   3900
ggacttccag atcactgcct ctggccagta tggccagtgg gcccccaagc tggccaggct   3960
gcactactct ggcagcatca atgcctggag caccaaggag cccttcagct ggatcaaggt   4020
ggacctgctg gcccccatga tcatccatgg catcaagacc caggggggcca ggcagaagtt   4080
cagcagcctg tacatcagcc agttcatcat catgtacagc ctggatggca agaagtggca   4140
gacctacagg ggcaacagca ctggcaccct gatggtgttc tttggcaatg tggacagctc   4200
tggcatcaag cacaacatct tcaacccccc catcattgcc agatacatca ggctgcaccc   4260
cacccactac agcatcagga gcaccctgag gatggagctg atgggctgtg acctgaacag   4320
ctgcagcatg cccctgggca tggagagcaa ggccatctct gatgcccaga tcactgccag   4380
cagctacttc accaacatgt ttgccacctg gagccccagc aaggccaggc tgcacctgca   4440
gggcaggagc aatgcctgga ggccccaggt caacaacccc aaggagtggc tgcaggtgga   4500
cttccagaag accatgaagg tgactggggt gaccacccag ggggtgaaga gcctgctgac   4560
cagcatgtat gtgaaggagt tcctgatcag cagcagccag gatggccacc agtggaccct   4620
gttcttccag aatggcaagg tgaaggtgtt ccagggcaac caggacagct tcacccctgt   4680
ggtgaacagc ctggaccccc ccctgctgac cagatacctg aggattcacc cccagagctg   4740
ggtgcaccag attgccctga ggatggaggt gctgggctgt gaggcccagg acctgtacta   4800
ataaaagatc tttattttca ttagatctgt gtgttggttt tttgtgtgag tgatggagtt   4860
ggccactccc tctctgcgcg ctcgctcgct cactgaggcc gggcgaccaa aggtcgcccg   4920
acgcccgggc tttgcccggg cggcctcagt gagcgagcga gcgcgcagag agggagtggc   4980
caa                                                                 4983
```

<210> SEQ ID NO 4
<211> LENGTH: 4984
<212> TYPE: DNA
<213> ORGANISM: Adeno-Associated Virus

<400> SEQUENCE: 4

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctcccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
```

```
tcatgggact atatgcaaag tgatctcggt gagctgcctg tggacgcaag gtaaatgccc    480
taaaatgggc aaacattgca agcagcaaac accctaaaat gggcaaacat tgcaagcagc    540
aaacattcta atttttcctt tcttcacgca gatttcctcc tagagtgcca aaatcttttc    600
cattcaacac ctcagtcgtg tacaaaaaga ctctgtttgt agaattcacg gatcaccttt    660
tcaacatcgc taagcccagg ccccccctgga tgggcctgct gggccccacc atccaggctg    720
aggtgtatga cactgtggtg atcaccctga agaacatggc cagccaccct gtgagcctgc    780
atgctgtggg ggtgagctac tggaaggcct ctgaggggggc tgagtatgat gaccagacca    840
gccagaggga gaaggaggat gacaaggtgt tccctggggg cagccacacc tatgtgtggc    900
aggtgctgaa ggagaatggc cccatggcct ctgacccccct gtgcctgacc tacagctacc    960
tgagccatgt ggacctggtg aaggacctga actctggcct gattggggcc ctgctggtgt   1020
gcagggaggg cagcctggcc aaggagaaga cccagaccct gcacaagttc atcctgctgt   1080
ttgctgtgtt tgatgagggc aagagctggc actctgaaac caagaacagc ctgatgcagg   1140
acagggatgc tgcctctgcc agggcctggc ccaagatgca cactgtgaat ggctatgtga   1200
acaggagcct gcctggcctg attggctgcc acaggaagtc tgtgtactgg catgtgattg   1260
gcatgggcac caccccctgag gtgcacagca tcttcctgga gggccacacc ttcctggtca   1320
ggaaccacag gcaggccagc ctggagatca gccccatcac cttcctgact gcccagaccc   1380
tgctgatgga cctgggccag ttcctgctgt tctgccacat cagcagccac cagcatgatg   1440
gcatggaggc ctatgtgaag gtggacagct gccctgagga gccccagctg aggatgaaga   1500
acaatgagga ggctgaggac tatgatgatg acctgactga ctctgagatg gatgtggtga   1560
ggtttgatga tgacaacagc cccagcttca tccagatcag gtctgtggcc aagaagcacc   1620
ccaagacctg ggtgcactac attgctgctg aggaggagga ctgggactat gccccccctgg   1680
tgctggcccc tgatgacagg agctacaaga gccagtacct gaacaatggc ccccagagga   1740
ttggcaggaa gtacaagaag gtcaggttca tggcctacac tgatgaaacc ttcaagacca   1800
gggaggccat ccagcatgag tctggcatcc tgggccccct gctgtatggg gaggtggggg   1860
acaccctgct gatcatcttc aagaaccagg ccagcaggcc ctacaacatc taccccccatg   1920
gcatcactga tgtgaggccc ctgtacagca ggaggctgcc caagggggtg aagcacctga   1980
aggacttccc catcctgcct ggggagatct tcaagtacaa gtggactgtg actgtggagg   2040
atggccccac caagtctgac cccaggtgcc tgaccagata ctacagcagc tttgtgaaca   2100
tggagaggga cctggcctct ggcctgattg gcccccctgct gatctgctac aaggagtctg   2160
tggaccagag gggcaaccag atcatgtctg acaagaggaa tgtgatcctg ttctctgtgt   2220
ttgatgagaa caggagctgg tacctgactg agaacatcca gaggttcctg cccaaccctg   2280
ctggggtgca gctggaggac cctgagttcc aggccagcaa catcatgcac agcatcaatg   2340
gctatgtgtt tgacagcctg cagctgtctg tgtgcctgca tgaggtggcc tactggtaca   2400
tcctgagcat tggggcccag actgacttcc tgtctgtgtt cttctctggc tacaccttca   2460
agcacaagat ggtgtatgag gacaccctga ccctgttccc cttctctggg gagactgtgt   2520
tcatgagcat ggagaaccct ggcctgtgga ttctgggctg ccacaactct gacttcagga   2580
acaggggcat gactgccctg ctgaaagtct ccagctgtga caagaacact ggggactact   2640
atgaggacag ctatgaggac atctctgcct acctgctgag caagaacaat gccattgagc   2700
ccaggagctt cagccagaac cccccagtgc tgaagaggca ccagagggag atcaccagga   2760
```

```
ccaccctgca gtctgaccag gaggagattg actatgatga caccatctct gtggagatga   2820
agaaggagga ctttgacatc tacgacgagg acgagaacca gagccccagg agcttccaga   2880
agaagaccag gcactacttc attgctgctg tggagaggct gtgggactat ggcatgagca   2940
gcagccccca tgtgctgagg aacagggccc agtctggctc tgtgccccag ttcaagaagg   3000
tggtgttcca ggagttcact gatggcagct tcacccagcc cctgtacaga ggggagctga   3060
atgagcacct gggcctgctg ggcccctaca tcagggctga ggtggaggac aacatcatgg   3120
tgaccttcag gaaccaggcc agcaggccct acagcttcta cagcagcctg atcagctatg   3180
aggaggacca gaggcagggg gctgagccca ggaagaactt tgtgaagccc aatgaaacca   3240
agacctactt ctggaaggtg cagcaccaca tggcccccac caaggatgag tttgactgca   3300
aggcctgggc ctacttctct gatgtggacc tggagaagga tgtgcactct ggcctgattg   3360
gcccccctgct ggtgtgccac accaacaccc tgaaccctgc ccatggcagg caggtgactg   3420
tgcaggagtt tgccctgttc ttcaccatct ttgatgaaac caagagctgg tacttcactg   3480
agaacatgga gaggaactgc agggcccccct gcaacatcca gatggaggac cccaccttca   3540
aggagaacta caggttccat gccatcaatg gctacatcat ggacaccctg cctggcctgg   3600
tgatggccca ggaccagagg atcaggtggt acctgctgag catgggcagc aatgagaaca   3660
tccacagcat ccacttctct ggccatgtgt tcactgtgag gaagaaggag gagtacaaga   3720
tggccctgta caacctgtac cctggggtgt ttgagactgt ggagatgctg cccagcaagg   3780
ctggcatctg gagggtggag tgcctgattg gggagcacct gcatgctggc atgagcaccc   3840
tgttcctggt gtacagcaac aagtgccaga ccccccctgggg catggcctct ggccacatca   3900
gggacttcca gatcactgcc tctggccagt atggccagtg ggcccccaag ctggccaggc   3960
tgcactactc tggcagcatc aatgcctgga gcaccaagga gcccttcagc tggatcaagg   4020
tggacctgct ggcccccatg atcatccatg gcatcaagac ccaggggggcc aggcagaagt   4080
tcagcagcct gtacatcagc cagttcatca tcatgtacag cctggatggc aagaagtggc   4140
agacctacag gggcaacagc actggcaccc tgatggtgtt ctttggcaat gtggacagct   4200
ctggcatcaa gcacaacatc ttcaaccccc ccatcattgc cagatacatc aggctgcacc   4260
ccacccacta cagcatcagg agcaccctga ggatggagct gatgggctgt gacctgaaca   4320
gctgcagcat gcccctgggc atggagagca aggccatctc tgatgcccag atcactgcca   4380
gcagctactt caccaacatg tttgccacct ggagccccag caaggccagg ctgcacctgc   4440
agggcaggag caatgcctgg aggccccagg tcaacaaccc caaggagtgg ctgcaggtgg   4500
acttccagaa gaccatgaag gtgactgggg tgaccaccca gggggtgaag agcctgctga   4560
ccagcatgta tgtgaaggag ttcctgatca gcagcagcca ggatggccac cagtggaccc   4620
tgttcttcca gaatggcaag gtgaaggtgt tccagggcaa ccaggacagc ttcacccctg   4680
tggtgaacag cctggacccc cccctgctga ccagatacct gaggattcac ccccagagct   4740
gggtgcacca gattgccctg aggatggagg tgctgggctg tgaggcccag gacctgtact   4800
aataaaagat ctttattttc attagatctg tgtgttggtt ttttgtgtga gtgatggagt   4860
tggccactcc ctctctgcgc gctcgctcgc tcactgaggc cgggcgacca aaggtcgccc   4920
gacgcccggg ctttgcccgg gcggcctcag tgagcgagcg agcgcgcaga gagggagtgg   4980
ccaa                                                               4984
```

<210> SEQ ID NO 5
<211> LENGTH: 4805

<212> TYPE: DNA
<213> ORGANISM: Adeno-Associated Virus

<400> SEQUENCE: 5

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240
gcccctgttt gctcctccga taactggggt gaccttggtt aatattcacc agcagcctcc     300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgaggttc tgcttctctg ccaccaggag atactacctg     480
ggggctgtgg agctgagctg ggactacatg cagtctgacc tgggggagct gcctgtggat     540
gccaggttcc cccccagagt gcccaagagc ttccccttca acacctctgt ggtgtacaag     600
aagaccctgt ttgtggagtt cactgaccac ctgttcaaca ttgccaagcc caggcccccc     660
tggatgggcc tgctgggccc caccatccag gctgaggtgt atgacactgt ggtgatcacc     720
ctgaagaaca tggccagcca ccctgtgagc ctgcatgctg tgggggtgag ctactggaag     780
gcctctgagg gggctgagta tgatgaccag accagccaga gggagaagga ggatgacaag     840
gtgttccctg gggggcagcca cacctatgtg tggcaggtgc tgaaggagaa tggccccatg     900
gcctctgacc ccctgtgcct gacctacagc tacctgagcc atgtggacct ggtgaaggac     960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga agtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggatg aagaacaatg aggaggctga ggactatgat    1500
gatgacctga ctgactctga gatggatgtg gtgaggtttg atgatgacaa cagccccagc    1560
ttcatccaga tcaggtctgt ggccaagaag caccccaaga cctgggtgca ctacattgct    1620
gctgaggagg aggactggga ctatgccccc ctggtgctgg cccctgatga caggagctac    1680
aagagccagt acctgaacaa tggcccccag aggattggca ggaagtacaa gaaggtcagg    1740
ttcatggcct acactgatga aaccttcaag accagggagg ccatccagca tgagtctggc    1800
atcctgggcc ccctgctgta tggggaggtg ggggacaccc tgctgatcat cttcaagaac    1860
caggccagca ggccctacaa catctacccc catggcatca ctgatgtgag gcccctgtac    1920
agcaggaggc tgcccaaggg ggtgaagcac ctgaaggact tccccatcct gcctggggag    1980
atcttcaagt acaagtggac tgtgactgtg gaggatggcc ccaccaagtc tgaccccagg    2040
tgcctgacca gatactacag cagctttgtg aacatggaga gggacctggc ctctggcctg    2100
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
```

```
actgagaaca tccagaggtt cctgcccaac cctgctgggg tgcagctgga ggaccctgag   2280
ttccaggcca gcaacatcat gcacagcatc aatggctatg tgtttgacag cctgcagctg   2340
tctgtgtgcc tgcatgaggt ggcctactgg tacatcctga gcattggggc ccagactgac   2400
ttcctgtctg tgttcttctc tggctacacc ttcaagcaca agatggtgta tgaggacacc   2460
ctgaccctgt tccccttctc tggggagact gtgttcatga gcatggagaa ccctggcctg   2520
tggattctgg gctgccacaa ctctgacttc aggaacaggg gcatgactgc cctgctgaaa   2580
gtctccagct gtgacaagaa cactggggac tactatgagg acagctatga ggacatctct   2640
gcctacctgc tgagcaagaa caatgccatt gagcccagga gcttccagaa gaagaccagg   2700
cactacttca ttgctgctgt ggagaggctg tgggactatg gcatgagcag cagcccccat   2760
gtgctgagga acagggccca gtctggctct gtgccccagt tcaagaaggt ggtgttccag   2820
gagttcactg atggcagctt cacccagccc ctgtacagag gggagctgaa tgagcacctg   2880
ggcctgctgg gcccctacat cagggctgag gtggaggaca acatcatggt gaccttcagg   2940
aaccaggcca gcaggcccta cagcttctac agcagcctga tcagctatga ggaggaccag   3000
aggcaggggg ctgagcccag gaagaacttt gtgaagccca atgaaaccaa gacctacttc   3060
tggaaggtgc agcaccacat ggcccccacc aaggatgagt ttgactgcaa ggcctgggcc   3120
tacttctctg atgtggacct ggagaaggat gtgcactctg gcctgattgg cccccctgctg  3180
gtgtgccaca ccaacaccct gaaccctgcc catggcaggc aggtgactgt gcaggagttt   3240
gccctgttct tcaccatctt tgatgaaacc aagagctggt acttcactga gaacatggag   3300
aggaactgca gggcccccctg caacatccag atggaggacc ccaccttcaa ggagaactac  3360
aggttccatg ccatcaatgg ctacatcatg gacaccctgc ctggcctggt gatggcccag   3420
gaccagagga tcaggtggta cctgctgagc atgggcagca atgagaacat ccacagcatc   3480
cacttctctg gccatgtgtt cactgtgagg aagaaggagg agtacaagat ggccctgtac   3540
aacctgtacc ctggggtgtt tgagactgtg gagatgctgc ccagcaaggc tggcatctgg   3600
agggtggagt gcctgattgg ggagcacctg catgctggca tgagcaccct gttcctggtg   3660
tacagcaaca agtgccagac ccccctgggc atggcctctg gccacatcag ggacttccag   3720
atcactgcct ctggccagta tggccagtgg gcccccaagc tggccaggct gcactactct   3780
ggcagcatca atgcctggag caccaaggag cccttcagct ggatcaaggt ggacctgctg   3840
gcccccatga tcatccatgg catcaagacc caggggggcca ggcagaagtt cagcagcctg  3900
tacatcagcc agttcatcat catgtacagc ctggatggca agaagtggca gacctacagg   3960
ggcaacagca ctggcaccct gatggtgttc tttggcaatg tggacagctc tggcatcaag   4020
cacaacatct tcaacccccc catcattgcc agatacatca ggctgcaccc cacccactac   4080
agcatcagga gcaccctgag gatggagctg atgggctgtg acctgaacag ctgcagcatg   4140
cccctgggca tggagagcaa ggccatctct gatgcccaga tcactgccag cagctacttc   4200
accaacatgt ttgccacctg gagccccagc aaggccaggc tgcacctgca gggcaggagc   4260
aatgcctgga ggccccaggt caacaacccc aaggagtggc tgcaggtgga cttccagaag   4320
accatgaagg tgactggggt gaccacccag ggggtgaaga gcctgctgac cagcatgtat   4380
gtgaaggagt tcctgatcag cagcagccag gatggccacc agtggaccct gttcttccag   4440
aatggcaagg tgaaggtgtt ccagggcaac caggacagct tcacccctgt ggtgaacagc   4500
ctggaccccc ccctgctgac cagatacctg aggattcacc cccagagctg ggtgcaccag   4560
attgccctga ggatggaggt gctgggctgt gaggcccagg acctgtactg aaataaaaga   4620
```

```
tctttatttt cattagatct gtgtgttggt tttttgtgtg aggaacccct agtgatggag   4680

ttggccactc cctctctgcg cgctcgctcg ctcactgagg ccgggcgacc aaaggtcgcc   4740

cgacgcccgg gctttgcccg ggcggcctca gtgagcgagc gagcgcgcag agagggagtg   4800

gccaa                                                               4805


<210> SEQ ID NO 6
<211> LENGTH: 4934
<212> TYPE: DNA
<213> ORGANISM: Adeno-Associated Virus

<400> SEQUENCE: 6

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgtttg ctgcttgcaa tgtttgccca ttttagggtg    180

gacacaggac gctgtggttt ctgagccagg gggcgactca gatcccagcc agtggactta    240

gcccctgttt gctcctccga taactggggt gaccttggtt aatattcacc agcagcctcc    300

cccgttgccc ctctggatcc actgcttaaa tacggacgag gacagggccc tgtctcctca    360

gcttcaggca ccaccactga cctgggacag tgaatcgcca ccatgcagat tgagctgagc    420

acctgcttct tcctgtgcct gctgagattc tgctttagtg ccaccagaag atactacctg    480

ggtgcagtgg aactgtcatg ggactatatg caaagtgatc tcggtgagct gcctgtggac    540

gcaaggtaaa ggcatgtcct gtagggtctg atcggggcca ggattgtggg gatgtaagtc    600

tgcttggagg aaggtgcaga catcgggtta ggatggttgt gatgctattc tgactttttc    660

ctttcttcac gcagatttcc tcctagagtg ccaaaatctt ttccattcaa cacctcagtc    720

gtgtacaaaa agactctgtt tgtagaattc acggatcacc ttttcaacat cgctaagccc    780

aggccccccct ggatgggcct gctgggcccc accatccagg ctgaggtgta tgacactgtg   840

gtgatcaccc tgaagaacat ggccagccac cctgtgagcc tgcatgctgt gggggtgagc    900

tactggaagg cctctgaggg ggctgagtat gatgaccaga ccagccagag ggagaaggag    960

gatgacaagg tgttccctgg gggcagccac acctatgtgt ggcaggtgct gaaggagaat   1020

ggccccatgg cctctgaccc cctgtgcctg acctacagct acctgagcca tgtggacctg   1080

gtgaaggacc tgaactctgg cctgattggg gccctgctgg tgtgcaggga gggcagcctg   1140

gccaaggaga agacccagac cctgcacaag ttcatcctgc tgtttgctgt gtttgatgag   1200

ggcaagagct ggcactctga aaccaagaac agcctgatgc aggacaggga tgctgcctct   1260

gccagggcct ggcccaagat gcacactgtg aatggctatg tgaacaggag cctgcctggc   1320

ctgattggct gccacaggaa gtctgtgtac tggcatgtga ttggcatggg caccacccct   1380

gaggtgcaca gcatcttcct ggagggccac accttcctgg tcaggaacca caggcaggcc   1440

agcctggaga tcagccccat caccttcctg actgcccaga ccctgctgat ggacctgggc   1500

cagttcctgc tgttctgcca catcagcagc caccagcatg atggcatgga ggcctatgtg   1560

aaggtggaca gctgccctga ggagccccag ctgaggatga agaacaatga ggaggctgag   1620

gactatgatg atgacctgac tgactctgag atggatgtgg tgaggtttga tgatgacaac   1680

agccccagct tcatccagat caggtctgtg gccaagaagc accccaagac ctgggtgcac   1740

tacattgctg ctgaggagga ggactgggac tatgcccccc tggtgctggc ccctgatgac   1800

aggagctaca agagccagta cctgaacaat ggcccccaga ggattggcag gaagtacaag   1860
```

```
aaggtcaggt tcatggccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctaccccc atggcatcac tgatgtgagg   2040
cccctgtaca gcaggaggct gcccaagggg gtgaagcacc tgaaggactt ccccatcctg   2100
cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggcccccct gctgatctgc tacaaggagt ctgtggacca gaggggcaac   2280
cagatcatgt ctgacaagag gaatgtgatc ctgttctctg tgtttgatga gaacaggagc   2340
tggtacctga ctgagaacat ccagaggttc ctgcccaacc ctgctggggt gcagctggag   2400
gaccctgagt tccaggccag caacatcatg cacagcatca atggctatgt gtttgacagc   2460
ctgcagctgt ctgtgtgcct gcatgaggtg gcctactggt acatcctgag cattggggcc   2520
cagactgact tcctgtctgt gttcttctct ggctacacct tcaagcacaa gatggtgtat   2580
gaggacaccc tgaccctgtt ccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg gagaggctgt gggactatgg catgagcagc   2880
agcccccatg tgctgaggaa cagggcccag tctggctctg tgccccagtt caagaaggtg   2940
gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggccctac agcttctaca gcagcctgat cagctatgag   3120
gaggaccaga ggcagggggc tgagcccagg aagaactttg tgaagcccaa tgaaaccaag   3180
acctacttct ggaaggtgca gcaccacatg gcccccacca aggatgagtt tgactgcaag   3240
gcctgggcct acttctctga tgtggacctg gagaaggatg tgcactctgg cctgattggc   3300
cccctgctgg tgtgccacac caacaccctg aaccctgccc atggcaggca ggtgactgtg   3360
caggagtttg ccctgttctt caccatcttt gatgaaacca agagctggta cttcactgag   3420
aacatggaga ggaactgcag ggccccctgc aacatccaga tggaggaccc caccttcaag   3480
gagaactaca ggttccatgc catcaatggc tacatcatgg acaccctgcc tggcctggtg   3540
atggcccagg accagaggat caggtggtac ctgctgagca tgggcagcaa tgagaacatc   3600
cacagcatcc acttctctgg ccatgtgttc actgtgagga agaaggagga gtacaagatg   3660
gccctgtaca acctgtaccc tggggtgttt gagactgtgg agatgctgcc cagcaaggct   3720
ggcatctgga gggtggagtg cctgattggg gagcacctgc atgctggcat gagcaccctg   3780
ttcctggtgt acagcaacaa gtgccagacc cccctgggca tggcctctgg ccacatcagg   3840
gacttccaga tcactgcctc tggccagtat ggccagtggg cccccaagct ggccaggctg   3900
cactactctg gcagcatcaa tgcctggagc accaaggagc ccttcagctg gatcaaggtg   3960
gacctgctgg cccccatgat catccatggc atcaagaccc agggggccag gcagaagttc   4020
agcagcctgt acatcagcca gttcatcatc atgtacagcc tggatggcaa gaagtggcag   4080
acctacaggg gcaacagcac tggcaccctg atggtgttct ttggcaatgt ggacagctct   4140
ggcatcaagc acaacatctt caaccccccc atcattgcca gatacatcag gctgcacccc   4200
acccactaca gcatcaggag caccctgagg atggagctga tgggctgtga cctgaacagc   4260
```

```
tgcagcatgc ccctgggcat ggagagcaag gccatctctg atgcccagat cactgccagc   4320
agctacttca ccaacatgtt tgccacctgg agccccagca aggccaggct gcacctgcag   4380
ggcaggagca atgcctggag gccccaggtc aacaacccca aggagtggct gcaggtggac   4440
ttccagaaga ccatgaaggt gactggggtg accacccagg gggtgaagag cctgctgacc   4500
agcatgtatg tgaaggagtt cctgatcagc agcagccagg atggccacca gtggaccctg   4560
ttcttccaga atggcaaggt gaaggtgttc cagggcaacc aggacagctt caccccctgtg   4620
gtgaacagcc tggacccccc cctgctgacc agatacctga ggattcaccc ccagagctgg   4680
gtgcaccaga ttgccctgag gatggaggtg ctgggctgtg aggcccagga cctgtactga   4740
aataaaagat ctttattttc attagatctg tgtgttggtt ttttgtgtga ggaaccccta   4800
gtgatggagt tggccactcc ctctctgcgc gctcgctcgc tcactgaggc cgggcgacca   4860
aaggtcgccc gacgcccggg ctttgcccgg gcggcctcag tgagcgagcg agcgcgcaga   4920
gagggagtgg ccaa                                                     4934
```

<210> SEQ ID NO 7
<211> LENGTH: 4934
<212> TYPE: DNA
<213> ORGANISM: Adeno-Associated Virus

<400> SEQUENCE: 7

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggctgtttgc tgcttgcaat gtttgcccat tttagggggg gatgtaagtc    600
tgcttggagg aaggtgcaga catcgggtta ggatggttgt gatgctattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggccccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg   1080
gtgaaggacc tgaactctgg cctgattggg gccctgctgg tgtgcaggga gggcagcctg   1140
gccaaggaga agacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccacccct   1380
```

```
gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagccccag ctgaggatga agaacaatga ggaggctgag   1620
gactatgatg atgacctgac tgactctgag atggatgtgg tgaggtttga tgatgacaac   1680
agccccagct tcatccagat caggtctgtg gccaagaagc accccaagac ctgggtgcac   1740
tacattgctg ctgaggagga ggactgggac tatgcccccc tggtgctggc ccctgatgac   1800
aggagctaca agagccagta cctgaacaat ggcccccaga ggattggcag gaagtacaag   1860
aaggtcaggt tcatggccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctaccccc atggcatcac tgatgtgagg   2040
cccctgtaca gcaggaggct gcccaagggg gtgaagcacc tgaaggactt ccccatcctg   2100
cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggcccccct gctgatctgc tacaaggagt ctgtggacca gaggggcaac   2280
cagatcatgt ctgacaagag gaatgtgatc ctgttctctg tgtttgatga gaacaggagc   2340
tggtacctga ctgagaacat ccagaggttc ctgcccaacc ctgctggggt gcagctggag   2400
gaccctgagt tccaggccag caacatcatg cacagcatca atggctatgt gtttgacagc   2460
ctgcagctgt ctgtgtgcct gcatgaggtg gcctactggt acatcctgag cattggggcc   2520
cagactgact tcctgtctgt gttcttctct ggctacacct tcaagcacaa gatggtgtat   2580
gaggacaccc tgaccctgtt ccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg gagaggctgt gggactatgg catgagcagc   2880
agcccccatg tgctgaggaa cagggcccag tctggctctg tgccccagtt caagaaggtg   2940
gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggccctac agcttctaca gcagcctgat cagctatgag   3120
gaggaccaga ggcagggggc tgagcccagg aagaactttg tgaagcccaa tgaaaccaag   3180
acctacttct ggaaggtgca gcaccacatg gcccccacca aggatgagtt tgactgcaag   3240
gcctgggcct acttctctga tgtggacctg gagaaggatg tgcactctgg cctgattggc   3300
cccctgctgg tgtgccacac caacaccctg aaccctgccc atggcaggca ggtgactgtg   3360
caggagtttg ccctgttctt caccatcttt gatgaaacca agagctggta cttcactgag   3420
aacatggaga ggaactgcag ggcccccctgc aacatccaga tggaggaccc caccttcaag   3480
gagaactaca ggttccatgc catcaatggc tacatcatgg acaccctgcc tggcctggtg   3540
atggcccagg accagaggat caggtggtac ctgctgagca tgggcagcaa tgagaacatc   3600
cacagcatcc acttctctgg ccatgtgttc actgtgagga agaaggagga gtacaagatg   3660
gccctgtaca acctgtaccc tggggtgttt gagactgtgg agatgctgcc cagcaaggct   3720
ggcatctgga gggtggagtg cctgattggg gagcacctgc atgctggcat gagcaccctg   3780
```

```
ttcctggtgt acagcaacaa gtgccagacc cccctgggca tggcctctgg ccacatcagg   3840
gacttccaga tcactgcctc tggccagtat ggccagtggg cccccaagct ggccaggctg   3900
cactactctg gcagcatcaa tgcctggagc accaaggagc ccttcagctg gatcaaggtg   3960
gacctgctgg cccccatgat catccatggc atcaagaccc agggggccag gcagaagttc   4020
agcagcctgt acatcagcca gttcatcatc atgtacagcc tggatggcaa gaagtggcag   4080
acctacaggg gcaacagcac tggcaccctg atggtgttct ttggcaatgt ggacagctct   4140
ggcatcaagc acaacatctt caaccccccc atcattgcca gatacatcag gctgcacccc   4200
acccactaca gcatcaggag caccctgagg atggagctga tgggctgtga cctgaacagc   4260
tgcagcatgc ccctgggcat ggagagcaag gccatctctg atgcccagat cactgccagc   4320
agctacttca ccaacatgtt tgccacctgg agccccagca aggccaggct gcacctgcag   4380
ggcaggagca atgcctggag gccccaggtc aacaacccca aggagtggct gcaggtggac   4440
ttccagaaga ccatgaaggt gactggggtg accacccagg gggtgaagag cctgctgacc   4500
agcatgtatg tgaaggagtt cctgatcagc agcagccagg atggccacca gtggaccctg   4560
ttcttccaga atggcaaggt gaaggtgttc cagggcaacc aggacagctt cacccctgtg   4620
gtgaacagcc tggacccccc cctgctgacc agatacctga ggattcaccc ccagagctgg   4680
gtgcaccaga ttgccctgag gatggaggtg ctgggctgtg aggcccagga cctgtactga   4740
aataaaagat ctttattttc attagatctg tgtgttggtt ttttgtgtga ggaaccccta   4800
gtgatggagt tggccactcc ctctctgcgc gctcgctcgc tcactgaggc cgggcgacca   4860
aaggtcgccc gacgcccggg ctttgcccgg gcggcctcag tgagcgagcg agcgcgcaga   4920
gagggagtgg ccaa                                                     4934
```

<210> SEQ ID NO 8
<211> LENGTH: 4934
<212> TYPE: DNA
<213> ORGANISM: Adeno-Associated Virus

<400> SEQUENCE: 8

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggcatgtcct gtagggtctg atcggggcca ggattgtggg gatgtaagtc    600
tgcttggagg aagccctaaa atgggcaaac attgcaagca gcaaacattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
```

```
tactggaagg cctctgaggg ggctgagtat gatgaccaga ccagccagag ggagaaggag     960
gatgacaagg tgttccctgg gggcagccac acctatgtgt ggcaggtgct gaaggagaat    1020
ggccccatgg cctctgaccc cctgtgcctg acctacagct acctgagcca tgtggacctg    1080
gtgaaggacc tgaactctgg cctgattggg gccctgctgg tgtgcaggga gggcagcctg    1140
gccaaggaga agacccagac cctgcacaag ttcatcctgc tgtttgctgt gtttgatgag    1200
ggcaagagct ggcactctga aaccaagaac agcctgatgc aggacaggga tgctgcctct    1260
gccagggcct ggcccaagat gcacactgtg aatggctatg tgaacaggag cctgcctggc    1320
ctgattggct gccacaggaa gtctgtgtac tggcatgtga ttggcatggg caccacccct    1380
gaggtgcaca gcatcttcct ggagggccac accttcctgg tcaggaacca caggcaggcc    1440
agcctggaga tcagccccat caccttcctg actgcccaga ccctgctgat ggacctgggc    1500
cagttcctgc tgttctgcca catcagcagc caccagcatg atggcatgga ggcctatgtg    1560
aaggtggaca gctgccctga ggagccccag ctgaggatga agaacaatga ggaggctgag    1620
gactatgatg atgacctgac tgactctgag atggatgtgg tgaggtttga tgatgacaac    1680
agccccagct tcatccagat caggtctgtg gccaagaagc accccaagac ctgggtgcac    1740
tacattgctg ctgaggagga ggactgggac tatgcccccc tggtgctggc ccctgatgac    1800
aggagctaca agagccagta cctgaacaat ggcccccaga ggattggcag gaagtacaag    1860
aaggtcaggt tcatggccta cactgatgaa accttcaaga ccagggaggc catccagcat    1920
gagtctggca tcctgggccc cctgctgtat ggggaggtgg gggacaccct gctgatcatc    1980
ttcaagaacc aggccagcag gccctacaac atctaccccc atggcatcac tgatgtgagg    2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggcccccct gctgatctgc tacaaggagt ctgtggacca gaggggcaac    2280
cagatcatgt ctgacaagag gaatgtgatc ctgttctctg tgtttgatga gaacaggagc    2340
tggtacctga ctgagaacat ccagaggttc ctgcccaacc ctgctggggt gcagctggag    2400
gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg gagaggctgt gggactatgg catgagcagc    2880
agcccccatg tgctgaggaa cagggcccag tctggctctg tgccccagtt caagaaggtg    2940
gtgttccagg agttcactga tggcagcttc acccagcccc tgtacagagg ggagctgaat    3000
gagcacctgg gcctgctggg cccctacatc agggctgagg tggaggacaa catcatggtg    3060
accttcagga accaggccag caggccctac agcttctaca gcagcctgat cagctatgag    3120
gaggaccaga ggcagggggc tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg gagaaggatg tgcactctgg cctgattggc    3300
```

cccctgctgg tgtgccacac caacaccctg aaccctgccc atggcaggca ggtgactgtg 3360
caggagtttg ccctgttctt caccatcttt gatgaaacca agagctggta cttcactgag 3420
aacatggaga ggaactgcag gcccccctgc aacatccaga tggaggaccc caccttcaag 3480
gagaactaca ggttccatgc catcaatggc tacatcatgg acaccctgcc tggcctggtg 3540
atggcccagg accagaggat caggtggtac ctgctgagca tgggcagcaa tgagaacatc 3600
cacagcatcc acttctctgg ccatgtgttc actgtgagga agaaggagga gtacaagatg 3660
gccctgtaca acctgtaccc tggggtgttt gagactgtgg agatgctgcc cagcaaggct 3720
ggcatctgga gggtggagtg cctgattggg gagcacctgc atgctggcat gagcaccctg 3780
ttcctggtgt acagcaacaa gtgccagacc cccctgggca tggcctctgg ccacatcagg 3840
gacttccaga tcactgcctc tggccagtat ggccagtggg cccccaagct ggccaggctg 3900
cactactctg gcagcatcaa tgcctggagc accaaggagc ccttcagctg gatcaaggtg 3960
gacctgctgg cccccatgat catccatggc atcaagaccc agggggccag gcagaagttc 4020
agcagcctgt acatcagcca gttcatcatc atgtacagcc tggatggcaa gaagtggcag 4080
acctacaggg gcaacagcac tggcaccctg atggtgttct ttggcaatgt ggacagctct 4140
ggcatcaagc acaacatctt caaccccccc atcattgcca gatacatcag gctgcacccc 4200
acccactaca gcatcaggag caccctgagg atggagctga tgggctgtga cctgaacagc 4260
tgcagcatgc ccctgggcat ggagagcaag gccatctctg atgcccagat cactgccagc 4320
agctacttca ccaacatgtt tgccacctgg agccccagca aggccaggct gcacctgcag 4380
ggcaggagca atgcctggag gccccaggtc aacaacccca aggagtggct gcaggtggac 4440
ttccagaaga ccatgaaggt gactggggtg accacccagg gggtgaagag cctgctgacc 4500
agcatgtatg tgaaggagtt cctgatcagc agcagccagg atggccacca gtggaccctg 4560
ttcttccaga atggcaaggt gaaggtgttc cagggcaacc aggacagctt cacccctgtg 4620
gtgaacagcc tggacccccc cctgctgacc agatacctga ggattcaccc ccagagctgg 4680
gtgcaccaga ttgccctgag gatggaggtg ctgggctgtg aggcccagga cctgtactga 4740
aataaaagat ctttattttc attagatctg tgtgttggtt ttttgtgtga ggaaccccta 4800
gtgatggagt tggccactcc ctctctgcgc gctcgctcgc tcactgaggc cgggcgacca 4860
aaggtcgccc gacgcccggg ctttgcccgg gcggcctcag tgagcgagcg agcgcgcaga 4920
gagggagtgg ccaa 4934

<210> SEQ ID NO 9
<211> LENGTH: 5511
<212> TYPE: DNA
<213> ORGANISM: Adeno-Associated Virus 2

<400> SEQUENCE: 9
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgaccc ctctcacact 180
acctaaacca cgccaggaca acctctgctc ctctccaccg aaattccaag ggtcgagtg 240 gatgttggag gtggcatggg cccagagagg tctctgacct ctgccccagc tccaaggtca 300
gcaggcaggg agggctgtgt gtttgctgtt tgctgcttgc aatgtttgcc cattttaggg 360
acatgagtag gctgaagttt gttcagtgtg gacttcagag gcagcacaca aacagctgct 420

```
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg gggctgtgg  agctgagctg   1020
ggactacatg cagtctgacc tgggggagct gcctgtggat gccaggttcc cccccagagt   1080
gcccaagagc ttccccttca acacctctgt ggtgtacaag aagaccctgt ttgtggagtt   1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg gggcagcca    1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
```

-continued

```
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaacccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac ccccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
```

```
cagcttcacc cctgtggtga acagcctgga cccccccctg ctgaccagat acctgaggat   5220

tcacccccag agctgggtgc accagattgc cctgaggatg gaggtgctgg gctgtgaggc   5280

ccaggacctg tactgacctc gaggaataaa ggaaatttat tttcattgca atagtgtgtt   5340

ggtttttttgt gtcacgtggc ggccgcagga acccctagtg atggagttgg ccactccctc   5400

tctgcgcgct cgctcgctca ctgaggccgg gcgaccaaag gtcgcccgac gcccgggctt   5460

tgcccgggcg gcctcagtga gcgagcgagc gcgcagagag ggagtggcca a            5511
```

<210> SEQ ID NO 10
<211> LENGTH: 5688
<212> TYPE: DNA
<213> ORGANISM: Adeno-Associated Virus 2

<400> SEQUENCE: 10

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg     240

gatgttggag gtggcatggg cccagagagg tctctgacct ctgccccagc tccaaggtca    300

gcaggcaggg agggctgtgt gtttgctgtt tgctgcttgc aatgtttgcc cattttaggg    360

acatgagtag gctgaagttt gttcagtgtg gacttcagag gcagcacaca aacagctgct    420

ggaggatggg aactgagggg ttggaagggg gcagggtgag cccagaaact cctgtgtgcc    480

tctgagcctg cagacgcgaa acgtcgactg gacacaggac gctgtggttt ctgagccagg    540

gggcgactca gatcccagcc agtggactta gcccctgttt gctcctccga taactggggt    600

gaccttggtt aatattcacc agcagcctcc cccgttgccc ctctggatcc actgcttaaa    660

tacggacgag gacagggccc tgtctcctca gcttcaggca ccaccactga cctgggacag    720

tgaatcgtaa gtactagcag ctacaatcca gctaccattc tgcttttatt ttatggttgg    780

gataaggctg gattattctg agtccaagct aggccctttt gctaatcatg ttcatacctc    840

ttatcttcct cccacagctc ctgggcaacg tgctggtctg tgtgctggcc catcactttg    900

gcaaagaatt gcgatcgcca ccatgcagat tgagctgagc acctgcttct tcctgtgcct    960

gctgaggttc tgcttctctg ccaccaggag atactacctg gggctgtgg agctgagctg    1020

ggactacatg cagtctgacc tgggggagct gcctgtggat gccaggttcc cccccagagt   1080

gcccaagagc ttccccttca acacctctgt ggtgtacaag aagaccctgt ttgtggagtt   1140

cactgaccac ctgttcaaca ttgccaagcc caggcccccc tggatgggcc tgctgggccc   1200

caccatccag gctgaggtgt atgacactgt ggtgatcacc ctgaagaaca tggccagcca   1260

ccctgtgagc ctgcatgctg tgggggtgag ctactggaag gcctctgagg gggctgagta   1320

tgatgaccag accagccaga gggagaagga ggatgacaag gtgttccctg ggggcagcca   1380

cacctatgtg tggcaggtgc tgaaggagaa tggccccatg gcctctgacc ccctgtgcct   1440

gacctacagc tacctgagcc atgtggacct ggtgaaggac ctgaactctg gcctgattgg   1500

ggccctgctg gtgtgcaggg agggcagcct ggccaaggag aagacccaga ccctgcacaa   1560

gttcatcctg ctgtttgctg tgtttgatga gggcaagagc tggcactctg aaaccaagaa   1620

cagcctgatg caggacaggg atgctgcctc tgccagggcc tggcccaaga tgcacactgt   1680

gaatggctat gtgaacagga gcctgcctgg cctgattggc tgccacagga agtctgtgta   1740

ctggcatgtg attggcatgg gcaccacccc tgaggtgcac agcatcttcc tggagggcca   1800
```

```
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg gggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tcccctttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaacccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
```

```
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac ccccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga ccccccccctg ctgaccagat acctgaggat   5220
tcacccccag agctgggtgc accagattgc cctgaggatg gaggtgctgg gctgtgaggc   5280
ccaggacctg tactgacctc gaggtgtgcc ttctagttgc cagccatctg ttgtttgccc   5340
ctcccccgtg ccttccttga ccctggaagg tgccactccc actgtccttt cctaataaaa   5400
tgaggaaatt gcatcgcatt gtctgagtag gtgtcattct attctggggg gtggggtggg   5460
gcaggacagc aagggggagg attgggaaga caatagcagg catgctgggg atgcggtggg   5520
ctctatgggc acgtggcggc cgcaggaacc cctagtgatg gagttggcca ctccctctct   5580
gcgcgctcgc tcgctcactg aggccgggcg accaaaggtc gcccgacgcc cgggctttgc   5640
ccgggcggcc tcagtgagcg agcgagcgcg cagagaggga gtggccaa                 5688
```

<210> SEQ ID NO 11
<211> LENGTH: 5613
<212> TYPE: DNA
<213> ORGANISM: Adeno-Associated Virus 2

<400> SEQUENCE: 11

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
```

```
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgctttttatt tttatggttgg    780
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg gggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt ttgtggagtt   1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg gggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg gggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
```

```
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaaccccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac ccccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga cccccccctg ctgaccagat acctgaggat   5220
tcacccccag agctgggtgc accagattgc cctgaggatg gaggtgctgg gctgtgaggc   5280
ccaggacctg tactgacctc gaggcactgt cctttcctaa taaaatgagg aaattgcatc   5340
```

```
gcattgtctg agtaggtgtc attctattct ggggggtggg gtggggcagg acagcaaggg   5400

ggaggattgg gaagacaata gcaggcatgc tggggatgcg gtgggctcta tgggcacgtg   5460

gcggccgcag gaacccctag tgatggagtt ggccactccc tctctgcgcg ctcgctcgct   5520

cactgaggcc gggcgaccaa aggtcgcccg acgcccgggc tttgcccggg cggcctcagt   5580

gagcgagcga gcgcgcagag agggagtggc caa                                5613
```

<210> SEQ ID NO 12
<211> LENGTH: 5362
<212> TYPE: DNA
<213> ORGANISM: Adeno-Associated Virus 2

<400> SEQUENCE: 12

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactg tttgctgttt    180

gctgcttgca atgtttgccc attttaggga catgtttgct gtttgctgct tgcaatgttt    240

gcccatttta gggacatgtt tgctgtttgc tgcttgcaat gtttgcccat tttagggaca    300

tgtttgctgt ttgctgcttg caatgtttgc ccattttagg gacaacgcga aacgtcgact    360

ggacacagga cgctgtggtt tctgagccag ggggcgactc agatcccagc cagtggactt    420

agcccctgtt tgctcctccg ataactgggg tgaccttggt taatattcac cagcagcctc    480

ccccgttgcc cctctggatc cactgcttaa atacggacga ggacagggcc ctgtctcctc    540

agcttcaggc accaccactg acctgggaca gtgaatcgta agtactagca gctacaatcc    600

agctaccatt ctgcttttat tttatggttg ggataaggct ggattattct gagtccaagc    660

taggcccttt tgctaatcat gttcatacct cttatcttcc tcccacagct cctgggcaac    720

gtgctggtct gtgtgctggc ccatcacttt ggcaaagaat tgcgatcgcc accatgcaga    780

ttgagctgag cacctgcttc ttcctgtgcc tgctgaggtt ctgcttctct gccaccagga    840

gatactacct gggggctgtg gagctgagct gggactacat gcagtctgac ctgggggagc    900

tgcctgtgga tgccaggttc ccccccagag tgcccaagag cttccccttc aacacctctg    960

tggtgtacaa gaagaccctg tttgtggagt tcactgacca cctgttcaac attgccaagc   1020

ccaggccccc ctggatgggc ctgctgggcc ccaccatcca ggctgaggtg tatgacactg   1080

tggtgatcac cctgaagaac atggccagcc accctgtgag cctgcatgct gtgggggtga   1140

gctactggaa ggcctctgag ggggctgagt atgatgacca gaccagccag agggagaagg   1200

aggatgacaa ggtgttccct gggggcagcc acacctatgt gtggcaggtg ctgaaggaga   1260

atggccccat ggcctctgac cccctgtgcc tgacctacag ctacctgagc catgtggacc   1320

tggtgaagga cctgaactct ggcctgattg gggccctgct ggtgtgcagg gagggcagcc   1380

tggccaagga gaagacccag accctgcaca agttcatcct gctgtttgct gtgtttgatg   1440

agggcaagag ctggcactct gaaaccaaga acagcctgat gcaggacagg gatgctgcct   1500

ctgccagggc ctggcccaag atgcacactg tgaatggcta tgtgaacagg agcctgcctg   1560

gcctgattgg ctgccacagg aagtctgtgt actggcatgt gattggcatg ggcaccaccc   1620

ctgaggtgca cagcatcttc ctggagggcc acaccttcct ggtcaggaac cacaggcagg   1680

ccagcctgga gatcagcccc atcaccttcc tgactgccca gaccctgctg atggacctgg   1740

gccagttcct gctgttctgc cacatcagca gccaccagca tgatggcatg gaggcctatg   1800
```

-continued

```
tgaaggtgga cagctgccct gaggagcccc agctgaggat gaagaacaat gaggaggctg   1860
aggactatga tgatgacctg actgactctg agatggatgt ggtgaggttt gatgatgaca   1920
acagccccag cttcatccag atcaggtctg tggccaagaa gcaccccaag acctgggtgc   1980
actacattgc tgctgaggag gaggactggg actatgcccc cctggtgctg gcccctgatg   2040
acaggagcta caagagccag tacctgaaca atggccccca gaggattggc aggaagtaca   2100
agaaggtcag gttcatggcc tacactgatg aaaccttcaa gaccagggag gccatccagc   2160
atgagtctgg catcctgggc cccctgctgt atggggaggt gggggacacc ctgctgatca   2220
tcttcaagaa ccaggccagc aggccctaca acatctaccc ccatggcatc actgatgtga   2280
ggcccctgta cagcaggagg ctgcccaagg gggtgaagca cctgaaggac ttccccatcc   2340
tgcctgggga gatcttcaag tacaagtgga ctgtgactgt ggaggatggc cccaccaagt   2400
ctgaccccag gtgcctgacc agatactaca gcagctttgt gaacatggag agggacctgg   2460
cctctggcct gattggcccc ctgctgatct gctacaagga gtctgtggac cagaggggca   2520
accagatcat gtctgacaag aggaatgtga tcctgttctc tgtgtttgat gagaacagga   2580
gctggtacct gactgagaac atccagaggt tcctgcccaa ccctgctggg gtgcagctgg   2640
aggaccctga gttccaggcc agcaacatca tgcacagcat caatggctat gtgtttgaca   2700
gcctgcagct gtctgtgtgc ctgcatgagg tggcctactg gtacatcctg agcattgggg   2760
cccagactga cttcctgtct gtgttcttct ctggctacac cttcaagcac aagatggtgt   2820
atgaggacac cctgaccctg ttccccttct ctggggagac tgtgttcatg agcatggaga   2880
accctggcct gtggattctg ggctgccaca actctgactt caggaacagg ggcatgactg   2940
ccctgctgaa agtctccagc tgtgacaaga acactgggga ctactatgag gacagctatg   3000
aggacatctc tgcctacctg ctgagcaaga acaatgccat tgagcccagg agcttcagcc   3060
agaacccccc agtgctgaag aggcaccaga gggagatcac caggaccacc ctgcagtctg   3120
accaggagga gattgactat gatgacacca tctctgtgga gatgaagaag gaggactttg   3180
acatctacga cgaggacgag aaccagagcc ccaggagctt ccagaagaag accaggcact   3240
acttcattgc tgctgtggag aggctgtggg actatggcat gagcagcagc ccccatgtgc   3300
tgaggaacag ggcccagtct ggctctgtgc cccagttcaa gaaggtggtg ttccaggagt   3360
tcactgatgg cagcttcacc cagcccctgt acagagggga gctgaatgag cacctgggcc   3420
tgctgggccc ctacatcagg gctgaggtgg aggacaacat catggtgacc ttcaggaacc   3480
aggccagcag gccctacagc ttctacagca gcctgatcag ctatgaggag gaccagaggc   3540
aggggggctga gcccaggaag aactttgtga agcccaatga aaccaagacc tacttctgga   3600
aggtgcagca ccacatggcc cccaccaagg atgagtttga ctgcaaggcc tgggcctact   3660
tctctgatgt ggacctggag aaggatgtgc actctggcct gattggcccc ctgctggtgt   3720
gccacaccaa caccctgaac cctgcccatg gcaggcaggt gactgtgcag gagtttgccc   3780
tgttcttcac catctttgat gaaaccaaga gctggtactt cactgagaac atggagagga   3840
actgcagggc cccctgcaac atccagatgg aggaccccac cttcaaggag aactacaggt   3900
tccatgccat caatggctac atcatggaca ccctgcctgg cctggtgatg gcccaggacc   3960
agaggatcag gtggtacctg ctgagcatgg gcagcaatga gaacatccac agcatccact   4020
tctctggcca tgtgttcact gtgaggaaga aggaggagta caagatggcc ctgtacaacc   4080
tgtaccctgg ggtgtttgag actgtggaga tgctgcccag caaggctggc atctggaggg   4140
tggagtgcct gattggggag cacctgcatg ctggcatgag caccctgttc ctggtgtaca   4200
```

```
gcaacaagtg ccagaccccc ctgggcatgg cctctggcca catcagggac ttccagatca   4260

ctgcctctgg ccagtatggc cagtgggccc ccaagctggc caggctgcac tactctggca   4320

gcatcaatgc ctggagcacc aaggagccct tcagctggat caaggtggac ctgctggccc   4380

ccatgatcat ccatggcatc aagacccagg gggccaggca gaagttcagc agcctgtaca   4440

tcagccagtt catcatcatg tacagcctgg atggcaagaa gtggcagacc tacaggggca   4500

acagcactgg caccctgatg gtgttctttg gcaatgtgga cagctctggc atcaagcaca   4560

acatcttcaa cccccccatc attgccagat acatcaggct gcaccccacc cactacagca   4620

tcaggagcac cctgaggatg gagctgatgg gctgtgacct gaacagctgc agcatgcccc   4680

tgggcatgga gagcaaggcc atctctgatg cccagatcac tgccagcagc tacttcacca   4740

acatgtttgc cacctggagc cccagcaagg ccaggctgca cctgcagggc aggagcaatg   4800

cctggaggcc ccaggtcaac aaccccaagg agtggctgca ggtggacttc cagaagacca   4860

tgaaggtgac tggggtgacc acccaggggg tgaagagcct gctgaccagc atgtatgtga   4920

aggagttcct gatcagcagc agccaggatg gccaccagtg gaccctgttc ttccagaatg   4980

gcaaggtgaa ggtgttccag ggcaaccagg acagcttcac ccctgtggtg aacagcctgg   5040

accccccct gctgaccaga tacctgagga ttcaccccca gagctgggtg caccagattg   5100

ccctgaggat ggaggtgctg ggctgtgagg cccaggacct gtactgacct cgaggaataa   5160

aggaaattta ttttcattgc aatagtgtgt tggttttttg tgtcacgtgg cggccgcagg   5220

aacccctagt gatggagttg gccactccct ctctgcgcgc tcgctcgctc actgaggccg   5280

ggcgaccaaa ggtcgcccga cgcccgggct ttgcccgggc ggcctcagtg agcgagcgag   5340

cgcgcagaga gggagtggcc aa                                            5362
```

```
<210> SEQ ID NO 13
<211> LENGTH: 5464
<212> TYPE: DNA
<213> ORGANISM: Adeno-Associated Virus 2

<400> SEQUENCE: 13
```

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactg tttgctgttt    180

gctgcttgca atgtttgccc attttaggga catgtttgct gtttgctgct tgcaatgttt    240

gcccatttta gggacatgtt tgctgtttgc tgcttgcaat gtttgcccat tttagggaca    300

tgtttgctgt ttgctgcttg caatgtttgc ccattttagg gacaacgcga aacgtcgact    360

ggacacagga cgctgtggtt tctgagccag gggcgactc agatcccagc cagtggactt    420

agcccctgtt tgctcctccg ataactgggg tgaccttggt taatattcac cagcagcctc    480

ccccgttgcc cctctggatc cactgcttaa atacggacga ggacagggcc ctgtctcctc    540

agcttcaggc accaccactg acctgggaca gtgaatcgta agtactagca gctacaatcc    600

agctaccatt ctgcttttat tttatggttg ggataaggct ggattattct gagtccaagc    660

taggcccttt tgctaatcat gttcatacct cttatcttcc tcccacagct cctgggcaac    720

gtgctggtct gtgtgctggc ccatcacttt ggcaaagaat tgcgatcgcc accatgcaga    780

ttgagctgag cacctgcttc ttcctgtgcc tgctgaggtt ctgcttctct gccaccagga    840

gatactacct gggggctgtg gagctgagct gggactacat gcagtctgac ctgggggagc    900
```

-continued

```
tgcctgtgga tgccaggttc ccccccagag tgcccaagag cttccccttc aacacctctg    960
tggtgtacaa gaagaccctg tttgtggagt tcactgacca cctgttcaac attgccaagc   1020
ccaggccccc ctggatgggc ctgctgggcc ccaccatcca ggctgaggtg tatgacactg   1080
tggtgatcac cctgaagaac atggccagcc accctgtgag cctgcatgct gtgggggtga   1140
gctactggaa ggcctctgag ggggctgagt atgatgacca gaccagccag agggagaagg   1200
aggatgacaa ggtgttccct gggggcagcc acacctatgt gtggcaggtg ctgaaggaga   1260
atggccccat ggcctctgac cccctgtgcc tgacctacag ctacctgagc catgtggacc   1320
tggtgaagga cctgaactct ggcctgattg ggccctgct ggtgtgcagg gagggcagcc   1380
tggccaagga gaagacccag accctgcaca agttcatcct gctgtttgct gtgtttgatg   1440
agggcaagag ctggcactct gaaaccaaga acagcctgat gcaggacagg gatgctgcct   1500
ctgccagggc ctggcccaag atgcacactg tgaatggcta tgtgaacagg agcctgcctg   1560
gcctgattgg ctgccacagg aagtctgtgt actggcatgt gattggcatg ggcaccaccc   1620
ctgaggtgca cagcatcttc ctggagggcc acaccttcct ggtcaggaac cacaggcagg   1680
ccagcctgga gatcagcccc atcaccttcc tgactgccca gaccctgctg atggacctgg   1740
gccagttcct gctgttctgc cacatcagca gccaccagca tgatggcatg gaggcctatg   1800
tgaaggtgga cagctgccct gaggagcccc agctgaggat gaagaacaat gaggaggctg   1860
aggactatga tgatgacctg actgactctg agatggatgt ggtgaggttt gatgatgaca   1920
acagccccag cttcatccag atcaggtctg tggccaagaa gcaccccaag acctgggtgc   1980
actacattgc tgctgaggag gaggactggg actatgcccc cctggtgctg gcccctgatg   2040
acaggagcta caagagccag tacctgaaca atggccccca gaggattggc aggaagtaca   2100
agaaggtcag gttcatggcc tacactgatg aaaccttcaa gaccagggag gccatccagc   2160
atgagtctgg catcctgggc cccctgctgt atggggaggt gggggacacc ctgctgatca   2220
tcttcaagaa ccaggccagc aggccctaca acatctaccc ccatggcatc actgatgtga   2280
ggcccctgta cagcaggagg ctgcccaagg gggtgaagca cctgaaggac ttccccatcc   2340
tgcctgggga gatcttcaag tacaagtgga ctgtgactgt ggaggatggc cccaccaagt   2400
ctgaccccag gtgcctgacc agatactaca gcagctttgt gaacatggag agggacctgg   2460
cctctggcct gattggcccc ctgctgatct gctacaagga gtctgtggac cagaggggca   2520
accagatcat gtctgacaag aggaatgtga tcctgttctc tgtgtttgat gagaacagga   2580
gctggtacct gactgagaac atccagaggt tcctgcccaa ccctgctggg gtgcagctgg   2640
aggaccctga gttccaggcc agcaacatca tgcacagcat caatggctat gtgtttgaca   2700
gcctgcagct gtctgtgtgc ctgcatgagg tggcctactg gtacatcctg agcattgggg   2760
cccagactga cttcctgtct gtgttcttct ctggctacac cttcaagcac aagatggtgt   2820
atgaggacac cctgaccctg ttccccttct ctggggagac tgtgttcatg agcatggaga   2880
accctggcct gtggattctg ggctgccaca actctgactt caggaacagg ggcatgactg   2940
ccctgctgaa agtctccagc tgtgacaaga acactgggga ctactatgag gacagctatg   3000
aggacatctc tgcctacctg ctgagcaaga acaatgccat tgagcccagg agcttcagcc   3060
agaacccccc agtgctgaag aggcaccaga gggagatcac caggaccacc ctgcagtctg   3120
accaggagga gattgactat gatgacacca tctctgtgga gatgaagaag gaggactttg   3180
acatctacga cgaggacgag aaccagagcc ccaggagctt ccagaagaag accaggcact   3240
acttcattgc tgctgtggag aggctgtggg actatggcat gagcagcagc ccccatgtgc   3300
```

```
tgaggaacag ggcccagtct ggctctgtgc cccagttcaa gaaggtggtg ttccaggagt   3360
tcactgatgg cagcttcacc cagcccctgt acagagggga gctgaatgag cacctgggcc   3420
tgctgggccc ctacatcagg gctgaggtgg aggacaacat catggtgacc ttcaggaacc   3480
aggccagcag gccctacagc ttctacagca gcctgatcag ctatgaggag gaccagaggc   3540
agggggctga gcccaggaag aactttgtga agcccaatga aaccaagacc tacttctgga   3600
aggtgcagca ccacatggcc cccaccaagg atgagtttga ctgcaaggcc tgggcctact   3660
tctctgatgt ggacctggag aaggatgtgc actctggcct gattggcccc ctgctggtgt   3720
gccacaccaa caccctgaac cctgcccatg gcaggcaggt gactgtgcag gagtttgccc   3780
tgttcttcac catctttgat gaaaccaaga gctggtactt cactgagaac atggagagga   3840
actgcagggc cccctgcaac atccagatgg aggaccccac cttcaaggag aactacaggt   3900
tccatgccat caatggctac atcatggaca ccctgcctgg cctggtgatg gcccaggacc   3960
agaggatcag gtggtacctg ctgagcatgg gcagcaatga gaacatccac agcatccact   4020
tctctggcca tgtgttcact gtgaggaaga aggaggagta caagatggcc ctgtacaacc   4080
tgtaccctgg ggtgtttgag actgtggaga tgctgcccag caaggctggc atctggaggg   4140
tggagtgcct gattggggag cacctgcatg ctggcatgag caccctgttc ctggtgtaca   4200
gcaacaagtg ccagaccccc ctgggcatgg cctctggcca catcagggac ttccagatca   4260
ctgcctctgg ccagtatggc cagtgggccc ccaagctggc caggctgcac tactctggca   4320
gcatcaatgc ctggagcacc aaggagccct tcagctggat caaggtggac ctgctggccc   4380
ccatgatcat ccatggcatc aagacccagg gggccaggca gaagttcagc agcctgtaca   4440
tcagccagtt catcatcatg tacagcctgg atggcaagaa gtggcagacc tacaggggca   4500
acagcactgg caccctgatg gtgttctttg gcaatgtgga cagctctggc atcaagcaca   4560
acatcttcaa cccccccatc attgccagat acatcaggct gcaccccacc cactacagca   4620
tcaggagcac cctgaggatg gagctgatgg gctgtgacct gaacagctgc agcatgcccc   4680
tgggcatgga gagcaaggcc atctctgatg cccagatcac tgccagcagc tacttcacca   4740
acatgtttgc cacctggagc cccagcaagg ccaggctgca cctgcagggc aggagcaatg   4800
cctggaggcc ccaggtcaac aaccccaagg agtggctgca ggtggacttc cagaagacca   4860
tgaaggtgac tggggtgacc acccaggggg tgaagagcct gctgaccagc atgtatgtga   4920
aggagttcct gatcagcagc agccaggatg gccaccagtg gaccctgttc ttccagaatg   4980
gcaaggtgaa ggtgttccag ggcaaccagg acagcttcac ccctgtggtg aacagcctgg   5040
acccccccct gctgaccaga tacctgagga ttcaccccca gagctgggtg caccagattg   5100
ccctgaggat ggaggtgctg ggctgtgagg cccaggacct gtactgacct cgaggcactg   5160
tcctttccta ataaaatgag gaaattgcat cgcattgtct gagtaggtgt cattctattc   5220
tggggggtgg ggtggggcag gacagcaagg gggaggattg ggaagacaat agcaggcatg   5280
ctggggatgc ggtgggctct atgggcacgt ggcggccgca ggaaccccta gtgatggagt   5340
tggccactcc ctctctgcgc gctcgctcgc tcactgaggc cgggcgacca aaggtcgccc   5400
gacgcccggg ctttgcccgg gcggcctcag tgagcgagcg agcgcgcaga gagggagtgg   5460
ccaa                                                                5464
```

<210> SEQ ID NO 14
<211> LENGTH: 6354
<212> TYPE: DNA

<213> ORGANISM: Adeno-Associated Virus 2

<400> SEQUENCE: 14

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgtaa gtactagcag ctacaatcca gctaccattc tgcttttatt    780
ttatggttgg gataaggctg gattattctg agtccaagct aggccctttt gctaatcatg    840
ttcatacctc ttatcttcct cccacagctc ctgggcaacg tgctggtctg tgtgctggcc    900
catcactttg gcaaagaatt gcgatcgcca ccatgcagat tgagctgagc acctgcttct    960
tcctgtgcct gctgaggttc tgcttctctg ccaccaggag atactacctg ggggctgtgg   1020
agctgagctg ggactacatg cagtctgacc tgggggagct gcctgtggat gccaggttcc   1080
cccccagagt gcccaagagc ttccccttca acacctctgt ggtgtacaag aagaccctgt   1140
ttgtggagtt cactgaccac ctgttcaaca ttgccaagcc caggcccccc tggatgggcc   1200
tgctgggccc caccatccag gctgaggtgt atgacactgt ggtgatcacc ctgaagaaca   1260
tggccagcca ccctgtgagc ctgcatgctg tgggggtgag ctactggaag gcctctgagg   1320
gggctgagta tgatgaccag accagccaga gggagaagga ggatgacaag gtgttccctg   1380
ggggcagcca cacctatgtg tggcaggtgc tgaaggagaa tggccccatg gcctctgacc   1440
ccctgtgcct gacctacagc tacctgagcc atgtggacct ggtgaaggac ctgaactctg   1500
gcctgattgg ggccctgctg gtgtgcaggg agggcagcct ggccaaggag aagacccaga   1560
ccctgcacaa gttcatcctg ctgtttgctg tgtttgatga gggcaagagc tggcactctg   1620
aaaccaagaa cagcctgatg caggacaggg atgctgcctc tgccagggcc tggcccaaga   1680
tgcacactgt gaatggctat gtgaacagga gcctgcctgg cctgattggc tgccacagga   1740
agtctgtgta ctggcatgtg attggcatgg gcaccacccc tgaggtgcac agcatcttcc   1800
tggagggcca caccttcctg gtcaggaacc acaggcaggc cagcctggag atcagcccca   1860
tcaccttcct gactgcccag accctgctga tggacctggg ccagttcctg ctgttctgcc   1920
acatcagcag ccaccagcat gatggcatgg aggcctatgt gaaggtggac agctgccctg   1980
aggagcccca gctgaggatg aagaacaatg aggaggctga ggactatgat gatgacctga   2040
ctgactctga gatggatgtg gtgaggtttg atgatgacaa cagccccagc ttcatccaga   2100
tcaggtctgt ggccaagaag caccccaaga cctgggtgca ctacattgct gctgaggagg   2160
aggactggga ctatgccccc ctggtgctgg cccctgatga caggagctac aagagccagt   2220
acctgaacaa tggcccccag aggattggca ggaagtacaa gaaggtcagg ttcatggcct   2280
```

```
acactgatga aaccttcaag accagggagg ccatccagca tgagtctggc atcctgggcc   2340
ccctgctgta tggggaggtg gggacaccc tgctgatcat cttcaagaac caggccagca   2400
ggccctacaa catctacccc catggcatca ctgatgtgag gcccctgtac agcaggaggc   2460
tgcccaaggg ggtgaagcac ctgaaggact tccccatcct gcctggggag atcttcaagt   2520
acaagtggac tgtgactgtg gaggatggcc ccaccaagtc tgaccccagg tgcctgacca   2580
gatactacag cagctttgtg aacatggaga gggacctggc ctctggcctg attggccccc   2640
tgctgatctg ctacaaggag tctgtggacc agaggggcaa ccagatcatg tctgacaaga   2700
ggaatgtgat cctgttctct gtgtttgatg agaacaggag ctggtacctg actgagaaca   2760
tccagaggtt cctgcccaac cctgctgggg tgcagctgga ggaccctgag ttccaggcca   2820
gcaacatcat gcacagcatc aatggctatg tgtttgacag cctgcagctg tctgtgtgcc   2880
tgcatgaggt ggcctactgg tacatcctga gcattggggc ccagactgac ttcctgtctg   2940
tgttcttctc tggctacacc ttcaagcaca agatggtgta tgaggacacc ctgaccctgt   3000
tccccttctc tggggagact gtgttcatga gcatggagaa ccctggcctg tggattctgg   3060
gctgccacaa ctctgacttc aggaacaggg gcatgactgc cctgctgaaa gtctccagct   3120
gtgacaagaa cactggggac tactatgagg acagctatga ggacatctct gcctacctgc   3180
tgagcaagaa caatgccatt gagcccagga gcttcagcca gaaccccccca gtgctgaaga   3240
ggcaccagag ggagatcacc aggaccaccc tgcagtctga ccaggaggag attgactatg   3300
atgacaccat ctctgtggag atgaagaagg aggactttga catctacgac gaggacgaga   3360
accagagccc caggagcttc cagaagaaga ccaggcacta cttcattgct gctgtggaga   3420
ggctgtggga ctatggcatg agcagcagcc cccatgtgct gaggaacagg gcccagtctg   3480
gctctgtgcc ccagttcaag aaggtggtgt tccaggagtt cactgatggc agcttcaccc   3540
agcccctgta cagaggggag ctgaatgagc acctgggcct gctgggcccc tacatcaggg   3600
ctgaggtgga ggacaacatc atggtgacct tcaggaacca ggccagcagg ccctacagct   3660
tctacagcag cctgatcagc tatgaggagg accagaggca gggggctgag cccaggaaga   3720
actttgtgaa gcccaatgaa accaagacct acttctggaa ggtgcagcac cacatggccc   3780
ccaccaagga tgagtttgac tgcaaggcct gggcctactt ctctgatgtg gacctggaga   3840
aggatgtgca ctctggcctg attggccccc tgctggtgtg ccacaccaac accctgaacc   3900
ctgcccatgg caggcaggtg actgtgcagg agtttgccct gttcttcacc atctttgatg   3960
aaaccaagag ctggtacttc actgagaaca tggagaggaa ctgcagggcc ccctgcaaca   4020
tccagatgga ggaccccacc ttcaaggaga actacaggtt ccatgccatc aatggctaca   4080
tcatggacac cctgcctggc ctggtgatgg cccaggacca gaggatcagg tggtacctgc   4140
tgagcatggg cagcaatgag aacatccaca gcatccactt ctctggccat gtgttcactg   4200
tgaggaagaa ggaggagtac aagatggccc tgtacaacct gtaccctggg gtgtttgaga   4260
ctgtggagat gctgcccagc aaggctggca tctggagggt ggagtgcctg attggggagc   4320
acctgcatgc tggcatgagc accctgttcc tggtgtacag caacaagtgc cagaccccccc   4380
tgggcatggc ctctggccac atcagggact tccagatcac tgcctctggc cagtatggcc   4440
agtgggcccc caagctggcc aggctgcact actctggcag catcaatgcc tggagcacca   4500
aggagccctt cagctggatc aaggtggacc tgctggcccc catgatcatc catggcatca   4560
agacccaggg ggccaggcag aagttcagca gcctgtacat cagccagttc atcatcatgt   4620
```

```
acagcctgga tggcaagaag tggcagacct acaggggcaa cagcactggc accctgatgg   4680
tgttctttgg caatgtggac agctctggca tcaagcacaa catcttcaac ccccccatca   4740
ttgccagata catcaggctg caccccaccc actacagcat caggagcacc ctgaggatgg   4800
agctgatggg ctgtgacctg aacagctgca gcatgcccct gggcatggag agcaaggcca   4860
tctctgatgc ccagatcact gccagcagct acttcaccaa catgtttgcc acctggagcc   4920
ccagcaaggc caggctgcac ctgcagggca ggagcaatgc ctggaggccc caggtcaaca   4980
accccaagga gtggctgcag gtggacttcc agaagaccat gaaggtgact ggggtgacca   5040
cccagggggt gaagagcctg ctgaccagca tgtatgtgaa ggagttcctg atcagcagca   5100
gccaggatgg ccaccagtgg accctgttct tccagaatgg caaggtgaag gtgttccagg   5160
gcaaccagga cagcttcacc cctgtggtga acagcctgga cccccccctg ctgaccagat   5220
acctgaggat tcacccccag agctgggtgc accagattgc cctgaggatg gaggtgctgg   5280
gctgtgaggc ccaggacctg tactgacctc gaggtgtgcc ttctagttgc cagccatctg   5340
ttgtttgccc ctcccccgtg ccttccttga ccctggaagg tgccactccc actgtccttt   5400
cctaataaaa tgaggaaatt gcatcgcatt gtctgagtag gtgtcattct attctggggg   5460
gtggggtggg gcaggacagc aagggggagg attgggaaga caatagcagg catgctgggg   5520
atgcggtggg ctctatgggc acgtgccctc tcacactacc taaaccacgc caggacaacc   5580
tctgctcctc tccaccgaaa ttccaagggg tcgagtggat gttggaggtg gcatgggccc   5640
agagaggtct ctgacctctg ccccagctcc aaggtcagca ggcagggagg gctgtgtgtt   5700
tgctgtttgc tgcttgcaat gtttgcccat tttagggaca tgagtaggct gaagtttgtt   5760
cagtgtggac ttcagaggca gcacacaaac agctgctgga ggatgggaac tgaggggttg   5820
gaagggggca gggtgagccc agaaactcct gtgtgcctct gagcctgcag ccctctcaca   5880
ctacctaaac cacgccagga caacctctgc tcctctccac cgaaattcca aggggtcgag   5940
tggatgttgg aggtggcatg ggcccagaga ggtctctgac ctctgcccca gctccaaggt   6000
cagcaggcag ggagggctgt gtgtttgctg tttgctgctt gcaatgtttg cccattttag   6060
ggacatgagt aggctgaagt ttgttcagtg tggacttcag aggcagcaca caaacagctg   6120
ctggaggatg ggaactgagg ggttggaagg gggcagggtg agcccagaaa ctcctgtgtg   6180
cctctgagcc tgcagcacgt ggcggccgca ggaaccccta gtgatggagt tggccactcc   6240
ctctctgcgc gctcgctcgc tcactgaggc cgggcgacca aaggtcgccc gacgcccggg   6300
ctttgcccgg gcggcctcag tgagcgagcg agcgcgcaga gagggagtgg ccaa         6354
```

<210> SEQ ID NO 15
<211> LENGTH: 6308
<212> TYPE: DNA
<213> ORGANISM: Adeno-Associated Virus 2

<400> SEQUENCE: 15

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttaattttta aaaagcagtc    180
aaaagtccaa gtggcccttg gcagcattta ctctctctgt ttgctctggt taataatctc    240
aggagcacaa acattcctgg aggcaggaga agaaatcaac atcctggact tatcctctgg    300
gcctgttaat ttttaaaaag cagtcaaaag tccaagtggc ccttggcagc atttactctc    360
tctgtttgct ctggttaata atctcaggag cacaaacatt cctggaggca ggagaagaaa    420
```

```
tcaacatcct ggacttatcc tctgggccta ggcctgaggc tggtcaaaat tgaacctcct    480
cctgctctga gcagcctggg gggcagacta agcagagggc tgtgcagacc cacataaaga    540
gcctactgtg tgccaggcac ttcacccgag gcacttcaca agcatgcttg ggaatgaaac    600
ttccaactct ttgggatgca ggtgaaacag ttcctggttc agagaggtga agcggcctgc    660
ctgaggcagc acagctcttc tttacagatg tgcttcccca cctctaccct gtctcacggc    720
cccccatgcc agcctgacgg ttgtgtctgc ctcagtcatg ctccattttt ccatcgggac    780
catcaagagg gtgtttgtgt ctaaggctga ctgggtaact ttggatgagc ggtctctccg    840
ctctgagcct gtttcctcat ctgtcaaatg ggctctaacc cactctgatc tcccagggcg    900
gcagtaagtc ttcagcatca ggcattttgg ggtgactcag taaatggtag atcttgctac    960
cagtggaaca gccactaagg attctgcagt gagagcagag ggccagctaa gtggtactct   1020
cccagagact gtctgactca cgccaccccc tccaccttgg acacaggacg ctgtggtttc   1080
tgagccaggt acaatgactc ctttcggtaa gtgcagtgga agctgtacac tgcccaggca   1140
aagcgtccgg gcagcgtagg cgggcgactc agatcccagc cagtggactt agcccctgtt   1200
tgctcctccg ataactgggg tgaccttggt taatattcac cagcagcctc ccccgttgcc   1260
cctctggatc cactgcttaa atacggacga ggacagggcc ctgtctcctc agcttcaggc   1320
accaccactg acctgggaca gtgaatcgta agtactagca gctacaatcc agctaccatt   1380
ctgcttttat tttatggttg ggataaggct ggattattct gagtccaagc taggcccttt   1440
tgctaatcat gttcatacct cttatcttcc tcccacagct cctgggcaac gtgctggtct   1500
gtgtgctggc ccatcacttt ggcaaagaat tgcgatcgcc accatgcaga ttgagctgag   1560
cacctgcttc ttcctgtgcc tgctgaggtt ctgcttctct gccaccagga gatactacct   1620
gggggctgtg gagctgagct gggactacat gcagtctgac ctgggggagc tgcctgtgga   1680
tgccaggttc ccccccagag tgcccaagag cttccccttc aacacctctg tggtgtacaa   1740
gaagaccctg tttgtggagt tcactgacca cctgttcaac attgccaagc ccaggccccc   1800
ctggatgggc ctgctgggcc ccaccatcca ggctgaggtg tatgacactg tggtgatcac   1860
cctgaagaac atggccagcc accctgtgag cctgcatgct gtgggggtga gctactggaa   1920
ggcctctgag gggggctgagt atgatgacca gaccagccag agggagaagg aggatgacaa   1980
ggtgttccct gggggcagcc acacctatgt gtggcaggtg ctgaaggaga atggccccat   2040
ggcctctgac cccctgtgcc tgacctacag ctacctgagc catgtggacc tggtgaagga   2100
cctgaactct ggcctgattg gggccctgct ggtgtgcagg gagggcagcc tggccaagga   2160
gaagacccag accctgcaca agttcatcct gctgtttgct gtgtttgatg agggcaagag   2220
ctggcactct gaaaccaaga acagcctgat gcaggacagg gatgctgcct ctgccagggc   2280
ctggcccaag atgcacactg tgaatggcta tgtgaacagg agcctgcctg gcctgattgg   2340
ctgccacagg aagtctgtgt actggcatgt gattggcatg ggcaccaccc ctgaggtgca   2400
cagcatcttc ctggagggcc acaccttcct ggtcaggaac cacaggcagg ccagcctgga   2460
gatcagcccc atcaccttcc tgactgccca gaccctgctg atggacctgg gccagttcct   2520
gctgttctgc cacatcagca gccaccagca tgatggcatg gaggcctatg tgaaggtgga   2580
cagctgccct gaggagcccc agctgaggat gaagaacaat gaggaggctg aggactatga   2640
tgatgacctg actgactctg agatggatgt ggtgaggttt gatgatgaca acagccccag   2700
cttcatccag atcaggtctg tggccaagaa gcaccccaag acctgggtgc actacattgc   2760
```

```
tgctgaggag gaggactggg actatgcccc cctggtgctg gcccctgatg acaggagcta   2820
caagagccag tacctgaaca atggccccca gaggattggc aggaagtaca agaaggtcag   2880
gttcatggcc tacactgatg aaaccttcaa gaccagggag gccatccagc atgagtctgg   2940
catcctgggc cccctgctgt atggggaggt gggggacacc ctgctgatca tcttcaagaa   3000
ccaggccagc aggccctaca acatctaccc ccatggcatc actgatgtga ggcccctgta   3060
cagcaggagg ctgcccaagg gggtgaagca cctgaaggac ttccccatcc tgcctgggga   3120
gatcttcaag tacaagtgga ctgtgactgt ggaggatggc cccaccaagt ctgaccccag   3180
gtgcctgacc agatactaca gcagctttgt gaacatggag agggacctgg cctctggcct   3240
gattggcccc ctgctgatct gctacaagga gtctgtggac cagaggggca accagatcat   3300
gtctgacaag aggaatgtga tcctgttctc tgtgtttgat gagaacagga gctggtacct   3360
gactgagaac atccagaggt tcctgcccaa ccctgctggg gtgcagctgg aggaccctga   3420
gttccaggcc agcaacatca tgcacagcat caatggctat gtgtttgaca gcctgcagct   3480
gtctgtgtgc ctgcatgagg tggcctactg gtacatcctg agcattgggg cccagactga   3540
cttcctgtct gtgttcttct ctggctacac cttcaagcac aagatggtgt atgaggacac   3600
cctgaccctg ttccccttct ctggggagac tgtgttcatg agcatggaga accctggcct   3660
gtggattctg ggctgccaca actctgactt caggaacagg ggcatgactg ccctgctgaa   3720
agtctccagc tgtgacaaga acactgggga ctactatgag gacagctatg aggacatctc   3780
tgcctacctg ctgagcaaga acaatgccat tgagcccagg agcttcagcc agaacccccc   3840
agtgctgaag aggcaccaga gggagatcac caggaccacc ctgcagtctg accaggagga   3900
gattgactat gatgacacca tctctgtgga gatgaagaag gaggactttg acatctacga   3960
cgaggacgag aaccagagcc ccaggagctt ccagaagaag accaggcact acttcattgc   4020
tgctgtggag aggctgtggg actatggcat gagcagcagc cccccatgtgc tgaggaacag   4080
ggcccagtct ggctctgtgc cccagttcaa gaaggtggtg ttccaggagt tcactgatgg   4140
cagcttcacc cagcccctgt acagagggga gctgaatgag cacctgggcc tgctgggccc   4200
ctacatcagg gctgaggtgg aggacaacat catggtgacc ttcaggaacc aggccagcag   4260
gccctacagc ttctacagca gcctgatcag ctatgaggag gaccagaggc aggggggctga   4320
gcccaggaag aactttgtga agcccaatga aaccaagacc tacttctgga aggtgcagca   4380
ccacatggcc cccaccaagg atgagtttga ctgcaaggcc tgggcctact tctctgatgt   4440
ggacctggag aaggatgtgc actctggcct gattggcccc ctgctggtgt gccacaccaa   4500
caccctgaac cctgcccatg gcaggcaggt gactgtgcag gagtttgccc tgttcttcac   4560
catctttgat gaaaccaaga gctggtactt cactgagaac atggagagga actgcagggc   4620
cccctgcaac atccagatgg aggaccccac cttcaaggag aactacaggt tccatgccat   4680
caatggctac atcatggaca ccctgcctgg cctggtgatg gcccaggacc agaggatcag   4740
gtggtacctg ctgagcatgg gcagcaatga gaacatccac agcatccact tctctggcca   4800
tgtgttcact gtgaggaaga aggaggagta caagatggcc ctgtacaacc tgtaccctgg   4860
ggtgtttgag actgtggaga tgctgcccag caaggctggc atctggaggg tggagtgcct   4920
gattggggag cacctgcatg ctggcatgag caccctgttc ctggtgtaca gcaacaagtg   4980
ccagaccccc ctgggcatgg cctctggcca catcagggac ttccagatca ctgcctctgg   5040
ccagtatggc cagtgggccc ccaagctggc caggctgcac tactctggca gcatcaatgc   5100
ctggagcacc aaggagccct tcagctggat caaggtggac ctgctggccc ccatgatcat   5160
```

```
ccatggcatc aagacccagg gggccaggca gaagttcagc agcctgtaca tcagccagtt   5220

catcatcatg tacagcctgg atggcaagaa gtggcagacc tacaggggca acagcactgg   5280

caccctgatg gtgttctttg gcaatgtgga cagctctggc atcaagcaca acatcttcaa   5340

cccccccatc attgccagat acatcaggct gcaccccacc cactacagca tcaggagcac   5400

cctgaggatg gagctgatgg gctgtgacct gaacagctgc agcatgcccc tgggcatgga   5460

gagcaaggcc atctctgatg cccagatcac tgccagcagc tacttcacca acatgtttgc   5520

cacctggagc cccagcaagg ccaggctgca cctgcagggc aggagcaatg cctggaggcc   5580

ccaggtcaac aaccccaagg agtggctgca ggtggacttc cagaagacca tgaaggtgac   5640

tggggtgacc acccaggggg tgaagagcct gctgaccagc atgtatgtga aggagttcct   5700

gatcagcagc agccaggatg gccaccagtg gaccctgttc ttccagaatg gcaaggtgaa   5760

ggtgttccag ggcaaccagg acagcttcac ccctgtggtg aacagcctgg acccccccct   5820

gctgaccaga tacctgagga ttcaccccca gagctgggtg caccagattg ccctgaggat   5880

ggaggtgctg ggctgtgagg cccaggacct gtactgacct cgagctgtgc cttctagttg   5940

ccagccatct gttgtttgcc cctcccccgt gccttccttg accctggaag gtgccactcc   6000

cactgtcctt tcctaataaa atgaggaaat tgcatcgcat tgtctgagta ggtgtcattc   6060

tattctgggg ggtggggtgg ggcaggacag caagggggag gattgggaag acaatagcag   6120

gcatgctggg gatgcggtgg gctctatgga ccggtgcggc cgcaggaacc cctagtgatg   6180

gagttggcca ctccctctct gcgcgctcgc tcgctcactg aggccgggcg accaaaggtc   6240

gcccgacgcc cgggctttgc ccgggcggcc tcagtgagcg agcgagcgcg cagagaggga   6300

gtggccaa                                                             6308
```

```
<210> SEQ ID NO 16
<211> LENGTH: 5635
<212> TYPE: DNA
<213> ORGANISM: Adeno-Associate Virus 2

<400> SEQUENCE: 16

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttaattttta aaaagcagtc    180

aaaagtccaa gtggcccttg gcagcattta ctctctctgt ttgctctggt taataatctc    240

aggagcacaa acattcctgg aggcaggaga agaaatcaac atcctggact tatcctctgg    300

gcctgttaat ttttaaaaag cagtcaaaag tccaagtggc ccttggcagc atttactctc    360

tctgtttgct ctggttaata atctcaggag cacaaacatt cctggaggca ggagaagaaa    420

tcaacatcct ggacttatcc tctgggccta gtcgactgga cacaggacgc tgtggtttct    480

gagccagggg gcgactcaga tcccagccag tggacttagc ccctgtttgc tcctccgata    540

actggggtga ccttggttaa tattcaccag cagcctcccc cgttgcccct ctggatccac    600

tgcttaaata cggacgagga cagggccctg tctcctcagc ttcaggcacc accactgacc    660

tgggacagtg aatcgtaagt actagcagct acaatccagc taccattctg cttttatttt    720

atggttggga taaggctgga ttattctgag tccaagctag gcccttttgc taatcatgtt    780

catacctctt atcttcctcc cacagctcct gggcaacgtg ctggtctgtg tgctggccca    840

tcactttggc aaagaattgc gatcgccacc atgcagattg agctgagcac ctgcttcttc    900
```

```
ctgtgcctgc tgaggttctg cttctctgcc accaggagat actacctggg ggctgtggag    960
ctgagctggg actacatgca gtctgacctg gggggagctgc ctgtggatgc caggttcccc   1020
cccagagtgc ccaagagctt cccccttcaac acctctgtgg tgtacaagaa gaccctgttt   1080
gtggagttca ctgaccacct gttcaacatt gccaagccca ggccccctg gatgggcctg   1140
ctgggcccca ccatccaggc tgaggtgtat gacactgtgg tgatcaccct gaagaacatg   1200
gccagccacc ctgtgagcct gcatgctgtg gggtgagct actggaaggc ctctgagggg   1260
gctgagtatg atgaccagac cagccagagg gagaaggagg atgacaaggt gttccctggg   1320
ggcagccaca cctatgtgtg gcaggtgctg aaggagaatg gccccatggc ctctgacccc   1380
ctgtgcctga cctacagcta cctgagccat gtggacctgg tgaaggacct gaactctggc   1440
ctgattgggg ccctgctggt gtgcagggag ggcagcctgg ccaaggagaa gacccagacc   1500
ctgcacaagt tcatcctgct gtttgctgtg tttgatgagg gcaagagctg gcactctgaa   1560
accaagaaca gcctgatgca ggacagggat gctgcctctg ccagggcctg gcccaagatg   1620
cacactgtga atggctatgt gaacaggagc ctgcctggcc tgattggctg ccacaggaag   1680
tctgtgtact ggcatgtgat tggcatgggc accacccctg aggtgcacag catcttcctg   1740
gagggccaca ccttcctggt caggaaccac aggcaggcca gcctggagat cagccccatc   1800
accttcctga ctgcccagac cctgctgatg gacctgggcc agttcctgct gttctgccac   1860
atcagcagcc accagcatga tggcatggag gcctatgtga aggtggacag ctgccctgag   1920
gagccccagc tgaggatgaa gaacaatgag gaggctgagg actatgatga tgacctgact   1980
gactctgaga tggatgtggt gaggtttgat gatgacaaca gccccagctt catccagatc   2040
aggtctgtgg ccaagaagca ccccaagacc tgggtgcact acattgctgc tgaggaggag   2100
gactgggact atgcccccct ggtgctggcc cctgatgaca ggagctacaa gagccagtac   2160
ctgaacaatg gcccccagag gattggcagg aagtacaaga aggtcaggtt catggcctac   2220
actgatgaaa ccttcaagac cagggaggcc atccagcatg agtctggcat cctgggcccc   2280
ctgctgtatg gggaggtggg ggacaccctg ctgatcatct tcaagaacca ggccagcagg   2340
ccctacaaca tctaccccca tggcatcact gatgtgaggc ccctgtacag caggaggctg   2400
cccaaggggg tgaagcacct gaaggacttc cccatcctgc ctggggagat cttcaagtac   2460
aagtggactg tgactgtgga ggatggcccc accaagtctg accccaggtg cctgaccaga   2520
tactacagca gctttgtgaa catggagagg gacctggcct ctggcctgat tggcccctg   2580
ctgatctgct acaaggagtc tgtggaccag aggggcaacc agatcatgtc tgacaagagg   2640
aatgtgatcc tgttctctgt gtttgatgag aacaggagct ggtacctgac tgagaacatc   2700
cagaggttcc tgcccaaccc tgctggggtg cagctggagg accctgagtt ccaggccagc   2760
aacatcatgc acagcatcaa tggctatgtg tttgacagcc tgcagctgtc tgtgtgcctg   2820
catgaggtgg cctactggta catcctgagc attggggccc agactgactt cctgtctgtg   2880
ttcttctctg gctacacctt caagcacaag atggtgtatg aggacaccct gaccctgttc   2940
cccttctctg gggagactgt gttcatgagc atggagaacc ctggcctgtg gattctgggc   3000
tgccacaact ctgacttcag gaacaggggc atgactgccc tgctgaaagt ctccagctgt   3060
gacaagaaca ctggggacta ctatgaggac agctatgagg acatctctgc ctacctgctg   3120
agcaagaaca atgccattga gcccaggagc ttcagccaga accccccagt gctgaagagg   3180
caccagaggg agatcaccag gaccaccctg cagtctgacc aggaggagat tgactatgat   3240
gacaccatct ctgtggagat gaagaaggag gactttgaca tctacgacga ggacgagaac   3300
```

```
cagagcccca ggagcttcca gaagaagacc aggcactact tcattgctgc tgtggagagg   3360
ctgtgggact atggcatgag cagcagcccc catgtgctga ggaacagggc ccagtctggc   3420
tctgtgcccc agttcaagaa ggtggtgttc caggagttca ctgatggcag cttcacccag   3480
cccctgtaca gaggggagct gaatgagcac ctgggcctgc tgggccccta catcagggct   3540
gaggtggagg acaacatcat ggtgaccttc aggaaccagg ccagcaggcc ctacagcttc   3600
tacagcagcc tgatcagcta tgaggaggac cagaggcagg gggctgagcc caggaagaac   3660
tttgtgaagc ccaatgaaac caagacctac ttctggaagg tgcagcacca catggccccc   3720
accaaggatg agtttgactg caaggcctgg gcctacttct ctgatgtgga cctggagaag   3780
gatgtgcact ctggcctgat tggcccccctg ctggtgtgcc acaccaacac cctgaaccct   3840
gcccatggca ggcaggtgac tgtgcaggag tttgccctgt tcttcaccat ctttgatgaa   3900
accaagagct ggtacttcac tgagaacatg gagaggaact gcagggcccc ctgcaacatc   3960
cagatggagg accccacctt caaggagaac tacaggttcc atgccatcaa tggctacatc   4020
atggacaccc tgcctggcct ggtgatggcc caggaccaga ggatcaggtg gtacctgctg   4080
agcatgggca gcaatgagaa catccacagc atccacttct ctggccatgt gttcactgtg   4140
aggaagaagg aggagtacaa gatggccctg tacaacctgt accctggggt gtttgagact   4200
gtggagatgc tgcccagcaa ggctggcatc tggagggtgg agtgcctgat tggggagcac   4260
ctgcatgctg gcatgagcac cctgttcctg gtgtacagca acaagtgcca gacccccctg   4320
ggcatggcct ctggccacat cagggacttc cagatcactg cctctggcca gtatggccag   4380
tgggccccca agctggccag gctgcactac tctggcagca tcaatgcctg gagcaccaag   4440
gagcccttca gctggatcaa ggtggacctg ctggccccca tgatcatcca tggcatcaag   4500
acccaggggg ccaggcagaa gttcagcagc ctgtacatca gccagttcat catcatgtac   4560
agcctggatg gcaagaagtg gcagacctac aggggcaaca gcactggcac cctgatggtg   4620
ttctttggca atgtggacag ctctggcatc aagcacaaca tcttcaaccc ccccatcatt   4680
gccagataca tcaggctgca ccccacccac tacagcatca ggagcaccct gaggatggag   4740
ctgatgggct gtgacctgaa cagctgcagc atgcccctgg gcatggagag caaggccatc   4800
tctgatgccc agatcactgc cagcagctac ttcaccaaca tgtttgccac ctggagcccc   4860
agcaaggcca ggctgcacct gcagggcagg agcaatgcct ggaggcccca ggtcaacaac   4920
cccaaggagt ggctgcaggt ggacttccag aagaccatga aggtgactgg ggtgaccacc   4980
caggggggtga agagcctgct gaccagcatg tatgtgaagg agttcctgat cagcagcagc   5040
caggatggcc accagtggac cctgttcttc cagaatggca aggtgaaggt gttccagggc   5100
aaccaggaca gcttcacccc tgtggtgaac agcctggacc ccccccctgct gaccagatac   5160
ctgaggattc acccccagag ctgggtgcac cagattgccc tgaggatgga ggtgctgggc   5220
tgtgaggccc aggacctgta ctgacctcga gctgtgcctt ctagttgcca gccatctgtt   5280
gtttgcccct cccccgtgcc ttccttgacc ctggaaggtg ccactcccac tgtcctttcc   5340
taataaaatg aggaaattgc atcgcattgt ctgagtaggt gtcattctat tctggggggt   5400
ggggtggggc aggacagcaa gggggaggat tgggaagaca atagcaggca tgctggggat   5460
gcggtgggct ctatggaccg gtgcggccgc aggaacccct agtgatggag ttggccactc   5520
cctctctgcg cgctcgctcg ctcactgagg ccgggcgacc aaaggtcgcc cgacgcccgg   5580
gctttgcccg ggcggcctca gtgagcgagc gagcgcgcag agagggagtg gccaa        5635
```

<210> SEQ ID NO 17
<211> LENGTH: 6962
<212> TYPE: DNA
<213> ORGANISM: Adeno-Associated Virus 2

<400> SEQUENCE: 17
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgta ggctcagagg cacacaggag 180
tttctgggct caccctgccc ccttccaacc cctcagttcc catcctccag cagctgtttg 240
tgtgctgcct ctgaagtcca cactgaacaa acttcagcct actcatgtcc ctaaaatggg 300
caaacattgc aagcagcaaa cagcaaacac acagccctcc ctgcctgctg accttggagc 360
tggggcagag gtcagagacc tctctgggcc catgccacct ccaacatcca ctcgacccct 420
tggaatttcg gtggagagga gcagaggttg tcctggcgtg gtttaggtag tgtgagaggg 480
gtcgacaggc tcagaggcac acaggagttt ctgggctcac cctgccccct tccaacccct 540
cagttcccat cctccagcag ctgtttgtgt gctgcctctg aagtccacac tgaacaaact 600
tcagcctact catgtcccta aaatgggcaa acattgcaag cagcaaacag caaacacaca 660
gccctccctg cctgctgacc ttggagctgg ggcagaggtc agagacctct ctgggcccat 720
gccacctcca acatccactc gaccccttgg aatttcggtg gagaggagca gaggttgtcc 780
tggcgtggtt taggtagtgt gagaggggtc gacgttaatt tttaaaaagc agtcaaaagt 840
ccaagtggcc cttggcagca tttactctct ctgtttgctc tggttaataa tctcaggagc 900
acaaacattc ctggaggcag gagaagaaat caacatcctg gacttatcct ctgggcctgt 960
taatttttaa aaagcagtca aaagtccaag tggcccttgg cagcatttac tctctctgtt 1020
tgctctggtt aataatctca ggagcacaaa cattcctgga ggcaggagaa gaaatcaaca 1080
tcctggactt atcctctggg cctaggcctg aggctggtca aaattgaacc tcctcctgct 1140
ctgagcagcc tgggggggcag actaagcaga gggctgtgca gacccacata aagagcctac 1200
tgtgtgccag gcacttcacc cgaggcactt cacaagcatg cttgggaatg aaacttccaa 1260
ctctttggga tgcaggtgaa acagttcctg gttcagagag gtgaagcggc ctgcctgagg 1320
cagcacagct cttctttaca gatgtgcttc cccacctcta ccctgtctca cggcccccca 1380
tgccagcctg acggttgtgt ctgcctcagt catgctccat tttccatcgg gaccatcaa 1440 gagggtgttt gtgtctaagg ctgactgggt aactttggat gagcggtctc tccgctctga 1500
gcctgtttcc tcatctgtca aatgggctct aacccactct gatctcccag ggcggcagta 1560
agtcttcagc atcaggcatt ttggggtgac tcagtaaatg gtagatcttg ctaccagtgg 1620
aacagccact aaggattctg cagtgagagc agagggccag ctaagtggta ctctcccaga 1680
gactgtctga ctcacgccac cccctccacc ttggacacag gacgctgtgg tttctgagcc 1740
aggtacaatg actcctttcg gtaagtgcag tggaagctgt acactgccca ggcaaagcgt 1800
ccgggcagcg taggcgggcg actcagatcc cagccagtgg acttagcccc tgtttgctcc 1860
tccgataact ggggtgacct tggttaatat tcaccagcag cctcccccgt tgcccctctg 1920
gatccactgc ttaaatacgg acgaggacag ggccctgtct cctcagcttc aggcaccacc 1980
actgacctgg gacagtgaat cgtaagtact agcagctaca atccagctac cattctgctt 2040
ttattttatg gttgggataa ggctggatta ttctgagtcc aagctaggcc cttttgctaa 2100
tcatgttcat acctcttatc ttcctcccac agctcctggg caacgtgctg gtctgtgtgc 2160

```
tggcccatca ctttggcaaa gaattgcgat cgccaccatg cagattgagc tgagcacctg   2220
cttcttcctg tgcctgctga ggttctgctt ctctgccacc aggagatact acctgggggc   2280
tgtggagctg agctgggact acatgcagtc tgacctgggg gagctgcctg tggatgccag   2340
gttccccccc agagtgccca agagcttccc cttcaacacc tctgtggtgt acaagaagac   2400
cctgtttgtg gagttcactg accacctgtt caacattgcc aagcccaggc ccccctggat   2460
gggcctgctg ggccccacca tccaggctga ggtgtatgac actgtggtga tcaccctgaa   2520
gaacatggcc agccaccctg tgagcctgca tgctgtgggg gtgagctact ggaaggcctc   2580
tgagggggct gagtatgatg accagaccag ccagagggag aaggaggatg acaaggtgtt   2640
ccctgggggc agccacacct atgtgtggca ggtgctgaag gagaatggcc ccatggcctc   2700
tgacccccctg tgcctgacct acagctacct gagccatgtg gacctggtga aggacctgaa   2760
ctctggcctg attggggccc tgctggtgtg cagggagggc agcctggcca aggagaagac   2820
ccagaccctg cacaagttca tcctgctgtt tgctgtgttt gatgagggca agagctggca   2880
ctctgaaacc aagaacagcc tgatgcagga cagggatgct gcctctgcca gggcctggcc   2940
caagatgcac actgtgaatg gctatgtgaa caggagcctg cctggcctga ttggctgcca   3000
caggaagtct gtgtactggc atgtgattgg catgggcacc acccctgagg tgcacagcat   3060
cttcctggag ggccacacct tcctggtcag gaaccacagg caggccagcc tggagatcag   3120
ccccatcacc ttcctgactg cccagaccct gctgatggac ctgggccagt tcctgctgtt   3180
ctgccacatc agcagccacc agcatgatgg catggaggcc tatgtgaagg tggacagctg   3240
ccctgaggag ccccagctga ggatgaagaa caatgaggag gctgaggact atgatgatga   3300
cctgactgac tctgagatgg atgtggtgag gtttgatgat gacaacagcc ccagcttcat   3360
ccagatcagg tctgtggcca agaagcaccc caagacctgg gtgcactaca ttgctgctga   3420
ggaggaggac tgggactatg ccccccctggt gctggcccct gatgacagga gctacaagag   3480
ccagtacctg aacaatggcc cccagaggat tggcaggaag tacaagaagg tcaggttcat   3540
ggcctacact gatgaaacct tcaagaccag ggaggccatc cagcatgagt ctggcatcct   3600
gggcccccctg ctgtatgggg aggtggggga caccctgctg atcatcttca agaaccaggc   3660
cagcaggccc tacaacatct acccccatgg catcactgat gtgaggcccc tgtacagcag   3720
gaggctgccc aagggggtga agcacctgaa ggacttcccc atcctgcctg gggagatctt   3780
caagtacaag tggactgtga ctgtggagga tggccccacc aagtctgacc ccaggtgcct   3840
gaccagatac tacagcagct ttgtgaacat ggagagggac ctggcctctg gcctgattgg   3900
cccccctgctg atctgctaca aggagtctgt ggaccagagg ggcaaccaga tcatgtctga   3960
caagaggaat gtgatcctgt tctctgtgtt tgatgagaac aggagctggt acctgactga   4020
gaacatccag aggttcctgc ccaaccctgc tggggtgcag ctggaggacc ctgagttcca   4080
ggccagcaac atcatgcaca gcatcaatgg ctatgtgttt gacagcctgc agctgtctgt   4140
gtgcctgcat gaggtggcct actggtacat cctgagcatt ggggcccaga ctgacttcct   4200
gtctgtgttc ttctctggct acaccttcaa gcacaagatg gtgtatgagg acaccctgac   4260
cctgttcccc ttctctgggg agactgtgtt catgagcatg gagaaccctg gcctgtggat   4320
tctgggctgc cacaactctg acttcaggaa caggggcatg actgccctgc tgaaagtctc   4380
cagctgtgac aagaacactg gggactacta tgaggacagc tatgaggaca tctctgccta   4440
cctgctgagc aagaacaatg ccattgagcc caggagcttc agccagaacc ccccagtgct   4500
```

```
gaagaggcac cagagggaga tcaccaggac caccctgcag tctgaccagg aggagattga   4560
ctatgatgac accatctctg tggagatgaa gaaggaggac tttgacatct acgacgagga   4620
cgagaaccag agccccagga gcttccagaa gaagaccagg cactacttca ttgctgctgt   4680
ggagaggctg tgggactatg gcatgagcag cagcccccat gtgctgagga acagggccca   4740
gtctggctct gtgccccagt tcaagaaggt ggtgttccag gagttcactg atggcagctt   4800
cacccagccc ctgtacagag gggagctgaa tgagcacctg ggcctgctgg gcccctacat   4860
cagggctgag gtggaggaca acatcatggt gaccttcagg aaccaggcca gcaggcccta   4920
cagcttctac agcagcctga tcagctatga ggaggaccag aggcaggggg ctgagcccag   4980
gaagaacttt gtgaagccca atgaaaccaa gacctacttc tggaaggtgc agcaccacat   5040
ggcccccacc aaggatgagt ttgactgcaa ggcctgggcc tacttctctg atgtggacct   5100
ggagaaggat gtgcactctg gcctgattgg cccccctgctg gtgtgccaca ccaacaccct   5160
gaaccctgcc catggcaggc aggtgactgt gcaggagttt gccctgttct tcaccatctt   5220
tgatgaaacc aagagctggt acttcactga gaacatggag aggaactgca gggcccccctg   5280
caacatccag atggaggacc ccaccttcaa ggagaactac aggttccatg ccatcaatgg   5340
ctacatcatg gacaccctgc ctggcctggt gatggcccag gaccagagga tcaggtggta   5400
cctgctgagc atgggcagca atgagaacat ccacagcatc cacttctctg gccatgtgtt   5460
cactgtgagg aagaaggagg agtacaagat ggccctgtac aacctgtacc ctggggtgtt   5520
tgagactgtg gagatgctgc ccagcaaggc tggcatctgg agggtggagt gcctgattgg   5580
ggagcacctg catgctggca tgagcaccct gttcctggtg tacagcaaca agtgccagac   5640
cccccctgggc atggcctctg gccacatcag ggacttccag atcactgcct ctggccagta   5700
tggccagtgg gcccccaagc tggccaggct gcactactct ggcagcatca atgcctggag   5760
caccaaggag cccttcagct ggatcaaggt ggacctgctg gcccccatga tcatccatgg   5820
catcaagacc caggggggcca ggcagaagtt cagcagcctg tacatcagcc agttcatcat   5880
catgtacagc ctggatggca agaagtggca gacctacagg ggcaacagca ctggcaccct   5940
gatggtgttc tttggcaatg tggacagctc tggcatcaag cacaacatct tcaaccccccc   6000
catcattgcc agatacatca ggctgcaccc cacccactac agcatcagga gcaccctgag   6060
gatggagctg atgggctgtg acctgaacag ctgcagcatg cccctgggca tggagagcaa   6120
ggccatctct gatgcccaga tcactgccag cagctacttc accaacatgt ttgccacctg   6180
gagccccagc aaggccaggc tgcacctgca gggcaggagc aatgcctgga ggccccaggt   6240
caacaacccc aaggagtggc tgcaggtgga cttccagaag accatgaagg tgactggggt   6300
gaccacccag ggggtgaaga gcctgctgac cagcatgtat gtgaaggagt tcctgatcag   6360
cagcagccag gatggccacc agtggaccct gttcttccag aatggcaagg tgaaggtgtt   6420
ccagggcaac caggacagct tcacccctgt ggtgaacagc ctggaccccc ccctgctgac   6480
cagatacctg aggattcacc cccagagctg ggtgcaccag attgccctga ggatggaggt   6540
gctgggctgt gaggcccagg acctgtactg acctcgagct gtgccttcta gttgccagcc   6600
atctgttgtt tgcccctccc ccgtgccttc cttgaccctg gaaggtgcca ctcccactgt   6660
cctttcctaa taaaatgagg aaattgcatc gcattgtctg agtaggtgtc attctattct   6720
ggggggtggg gtggggcagg acagcaaggg ggaggattgg gaagacaata gcaggcatgc   6780
tggggatgcg gtgggctcta tggaccggtg cggccgcagg aacccctagt gatggagttg   6840
```

gccactccct ctctgcgcgc tcgctcgctc actgaggccg ggcgaccaaa ggtcgcccga 6900
cgcccgggct ttgcccgggc ggcctcagtg agcgagcgag cgcgcagaga gggagtggcc 6960
aa 6962

<210> SEQ ID NO 18
<211> LENGTH: 6289
<212> TYPE: DNA
<213> ORGANISM: Adeno-Associated Virus 2

<400> SEQUENCE: 18
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgta ggctcagagg cacacaggag 180
tttctgggct caccctgccc ccttccaacc cctcagttcc catcctccag cagctgtttg 240
tgtgctgcct ctgaagtcca cactgaacaa acttcagcct actcatgtcc ctaaaatggg 300
caaacattgc aagcagcaaa cagcaaacac acagccctcc ctgcctgctg accttggagc 360
tggggcagag gtcagagacc tctctgggcc catgccacct ccaacatcca ctcgacccct 420
tggaatttcg gtggagagga gcagaggttg tcctggcgtg gtttaggtag tgtgagaggg 480
gtcgacaggc tcagaggcac acaggagttt ctgggctcac cctgccccct tccaacccct 540
cagttcccat cctccagcag ctgtttgtgt gctgcctctg aagtccacac tgaacaaact 600
tcagcctact catgtcccta aaatgggcaa acattgcaag cagcaaacag caaacacaca 660
gccctccctg cctgctgacc ttggagctgg ggcagaggtc agagacctct ctgggcccat 720
gccacctcca acatccactc gaccccttgg aatttcggtg gagaggagca gaggttgtcc 780
tggcgtggtt taggtagtgt gagaggggtc gacgttaatt tttaaaaagc agtcaaaagt 840
ccaagtggcc cttggcagca tttactctct ctgtttgctc tggttaataa tctcaggagc 900
acaaacattc ctggaggcag gagaagaaat caacatcctg gacttatcct ctgggcctgt 960
taatttttaa aaagcagtca aaagtccaag tggcccttgg cagcatttac tctctctgtt 1020
tgctctggtt aataatctca ggagcacaaa cattcctgga ggcaggagaa gaaatcaaca 1080
tcctggactt atcctctggg cctagtcgac tggacacagg acgctgtggt ttctgagcca 1140
gggggcgact cagatcccag ccagtggact tagcccctgt ttgctcctcc gataactggg 1200
gtgaccttgg ttaatattca ccagcagcct cccccgttgc ccctctggat ccactgctta 1260
aatacggacg aggacagggc cctgtctcct cagcttcagg caccaccact gacctgggac 1320
agtgaatcgt aagtactagc agctacaatc cagctaccat tctgctttta ttttatggtt 1380
gggataaggc tggattattc tgagtccaag ctaggccctt ttgctaatca tgttcatacc 1440
tcttatcttc ctcccacagc tcctgggcaa cgtgctggtc tgtgtgctgg cccatcactt 1500
tggcaaagaa ttgcgatcgc caccatgcag attgagctga gcacctgctt cttcctgtgc 1560
ctgctgaggt tctgcttctc tgccaccagg agatactacc tgggggctgt ggagctgagc 1620
tgggactaca tgcagtctga cctgggggag ctgcctgtgg atgccaggtt cccccccaga 1680
gtgcccaaga gcttcccctt caacacctct gtggtgtaca agaagaccct gtttgtggag 1740
ttcactgacc acctgttcaa cattgccaag cccaggcccc cctggatggg cctgctgggc 1800
cccaccatcc aggctgaggt gtatgacact gtggtgatca ccctgaagaa catggccagc 1860
caccctgtga gcctgcatgc tgtgggggtg agctactgga aggcctctga gggggctgag 1920

-continued

```
tatgatgacc agaccagcca gagggagaag gaggatgaca aggtgttccc tgggggcagc   1980
cacacctatg tgtggcaggt gctgaaggag aatggcccca tggcctctga ccccctgtgc   2040
ctgacctaca gctacctgag ccatgtggac ctggtgaagg acctgaactc tggcctgatt   2100
ggggccctgc tggtgtgcag ggagggcagc ctggccaagg agaagaccca gaccctgcac   2160
aagttcatcc tgctgtttgc tgtgtttgat gagggcaaga gctggcactc tgaaaccaag   2220
aacagcctga tgcaggacag ggatgctgcc tctgccaggg cctggcccaa gatgcacact   2280
gtgaatggct atgtgaacag gagcctgcct ggcctgattg gctgccacag gaagtctgtg   2340
tactggcatg tgattggcat gggcaccacc cctgaggtgc acagcatctt cctggagggc   2400
cacaccttcc tggtcaggaa ccacaggcag gccagcctgg agatcagccc catcaccttc   2460
ctgactgccc agaccctgct gatggacctg ggccagttcc tgctgttctg ccacatcagc   2520
agccaccagc atgatggcat ggaggcctat gtgaaggtgg acagctgccc tgaggagccc   2580
cagctgagga tgaagaacaa tgaggaggct gaggactatg atgatgacct gactgactct   2640
gagatggatg tggtgaggtt tgatgatgac aacagcccca gcttcatcca gatcaggtct   2700
gtggccaaga agcaccccaa gacctgggtg cactacattg ctgctgagga ggaggactgg   2760
gactatgccc ccctggtgct ggcccctgat gacaggagct acaagagcca gtacctgaac   2820
aatggccccc agaggattgg caggaagtac aagaaggtca ggttcatggc ctacactgat   2880
gaaaccttca agaccaggga ggccatccag catgagtctg gcatcctggg ccccctgctg   2940
tatggggagg tgggggacac cctgctgatc atcttcaaga accaggccag caggccctac   3000
aacatctacc cccatggcat cactgatgtg aggcccctgt acagcaggag gctgcccaag   3060
gggggtgaagc acctgaagga cttccccatc ctgcctgggg agatcttcaa gtacaagtgg   3120
actgtgactg tggaggatgg ccccaccaag tctgacccca ggtgcctgac cagatactac   3180
agcagctttg tgaacatgga gagggacctg gcctctggcc tgattggccc cctgctgatc   3240
tgctacaagg agtctgtgga ccagaggggc aaccagatca tgtctgacaa gaggaatgtg   3300
atcctgttct ctgtgtttga tgagaacagg agctggtacc tgactgagaa catccagagg   3360
ttcctgccca accctgctgg ggtgcagctg gaggaccctg agttccaggc cagcaacatc   3420
atgcacagca tcaatggcta tgtgtttgac agcctgcagc tgtctgtgtg cctgcatgag   3480
gtggcctact ggtacatcct gagcattggg gcccagactg acttcctgtc tgtgttcttc   3540
tctggctaca ccttcaagca caagatggtg tatgaggaca ccctgaccct gttccccttc   3600
tctggggaga ctgtgttcat gagcatggag aaccctggcc tgtggattct gggctgccac   3660
aactctgact tcaggaacag gggcatgact gccctgctga aagtctccag ctgtgacaag   3720
aacactgggg actactatga ggacagctat gaggacatct ctgcctacct gctgagcaag   3780
aacaatgcca ttgagcccag gagcttcagc cagaaccccc cagtgctgaa gaggcaccag   3840
agggagatca ccaggaccac cctgcagtct gaccaggagg agattgacta tgatgacacc   3900
atctctgtgg agatgaagaa ggaggacttt gacatctacg acgaggacga gaaccagagc   3960
cccaggagct tccagaagaa gaccaggcac tacttcattg ctgctgtgga gaggctgtgg   4020
gactatggca tgagcagcag cccccatgtg ctgaggaaca gggcccagtc tggctctgtg   4080
ccccagttca agaaggtggt gttccaggag ttcactgatg gcagcttcac ccagcccctg   4140
tacagagggg agctgaatga gcacctgggc ctgctgggcc cctacatcag ggctgaggtg   4200
gaggacaaca tcatggtgac cttcaggaac caggccagca ggccctacag cttctacagc   4260
agcctgatca gctatgagga ggaccagagg caggggggctg agcccaggaa gaactttgtg   4320
```

```
aagcccaatg aaaccaagac ctacttctgg aaggtgcagc accacatggc ccccaccaag   4380

gatgagtttg actgcaaggc ctgggcctac ttctctgatg tggacctgga gaaggatgtg   4440

cactctggcc tgattggccc cctgctggtg tgccacacca acaccctgaa ccctgcccat   4500

ggcaggcagg tgactgtgca ggagtttgcc ctgttcttca ccatctttga tgaaaccaag   4560

agctggtact tcactgagaa catggagagg aactgcaggg ccccctgcaa catccagatg   4620

gaggacccca ccttcaagga gaactacagg ttccatgcca tcaatggcta catcatggac   4680

accctgcctg gcctggtgat ggcccaggac cagaggatca ggtggtacct gctgagcatg   4740

ggcagcaatg agaacatcca cagcatccac ttctctggcc atgtgttcac tgtgaggaag   4800

aaggaggagt acaagatggc cctgtacaac ctgtaccctg ggtgtttgga gactgtggag   4860

atgctgccca gcaaggctgg catctggagg gtggagtgcc tgattgggga gcacctgcat   4920

gctggcatga gcaccctgtt cctggtgtac agcaacaagt gccagacccc cctgggcatg   4980

gcctctggcc acatcaggga cttccagatc actgcctctg gccagtatgg ccagtgggcc   5040

cccaagctgg ccaggctgca ctactctggc agcatcaatg cctggagcac caaggagccc   5100

ttcagctgga tcaaggtgga cctgctggcc cccatgatca tccatggcat caagacccag   5160

ggggccaggc agaagttcag cagcctgtac atcagccagt tcatcatcat gtacagcctg   5220

gatggcaaga agtggcagac ctacaggggc aacagcactg gcaccctgat ggtgttcttt   5280

ggcaatgtgg acagctctgg catcaagcac aacatcttca acccccccat cattgccaga   5340

tacatcaggc tgcaccccac ccactacagc atcaggagca ccctgaggat ggagctgatg   5400

ggctgtgacc tgaacagctg cagcatgccc ctgggcatgg agagcaaggc catctctgat   5460

gcccagatca ctgccagcag ctacttcacc aacatgtttg ccacctggag ccccagcaag   5520

gccaggctgc acctgcaggg caggagcaat gcctggaggc cccaggtcaa caaccccaag   5580

gagtggctgc aggtggactt ccagaagacc atgaaggtga ctggggtgac cacccagggg   5640

gtgaagagcc tgctgaccag catgtatgtg aaggagttcc tgatcagcag cagccaggat   5700

ggccaccagt ggaccctgtt cttccagaat ggcaaggtga aggtgttcca gggcaaccag   5760

gacagcttca cccctgtggt gaacagcctg gacccccccc tgctgaccag atacctgagg   5820

attcaccccc agagctgggt gcaccagatt gccctgagga tggaggtgct gggctgtgag   5880

gcccaggacc tgtactgacc tcgagctgtg ccttctagtt gccagccatc tgttgtttgc   5940

ccctcccccg tgccttcctt gaccctggaa ggtgccactc ccactgtcct ttcctaataa   6000

aatgaggaaa ttgcatcgca ttgtctgagt aggtgtcatt ctattctggg gggtggggtg   6060

gggcaggaca gcaaggggga ggattgggaa gacaatagca ggcatgctgg ggatgcggtg   6120

ggctctatgg accggtgcgg ccgcaggaac ccctagtgat ggagttggcc actccctctc   6180

tgcgcgctcg ctcgctcact gaggccgggc gaccaaaggt cgcccgacgc ccgggctttg   6240

cccgggcggc ctcagtgagc gagcgagcgc gcagagaggg agtggccaa               6289
```

<210> SEQ ID NO 19
<211> LENGTH: 5430
<212> TYPE: DNA
<213> ORGANISM: Adeno-Associated Virus 2

<400> SEQUENCE: 19

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120
```

```
gccaactcca tcactagggg ttcctgcggc cgcacgcgtg ttttcgacgt ggacttagcc    180
cctgtttgct cctccgataa ctggggtgac cttggttaat attcaccagc agcctccccg    240
tggacttagc ccctgtttgc tcctccgata actggggtga ccttggttaa tattcaccag    300
cagcctcccc acgcgaaacg tcgactggac acaggacgct gtggtttctg agccaggggg    360
cgactcagat cccagccagt ggacttagcc cctgtttgct cctccgataa ctggggtgac    420
cttggttaat attcaccagc agcctccccc gttgcccctc tggatccact gcttaaatac    480
ggacgaggac agggccctgt ctcctcagct tcaggcacca ccactgacct gggacagtga    540
atcgtaagta ctagcagcta caatccagct accattctgc ttttatttta tggttgggat    600
aaggctggat tattctgagt ccaagctagg cccttttgct aatcatgttc atacctctta    660
tcttcctccc acagctcctg ggcaacgtgc tggtctgtgt gctggcccat cactttggca    720
aagaattgcg atcgccacca tgcagattga gctgagcacc tgcttcttcc tgtgcctgct    780
gaggttctgc ttctctgcca ccaggagata ctacctgggg gctgtggagc tgagctggga    840
ctacatgcag tctgacctgg gggagctgcc tgtggatgcc aggttccccc ccagagtgcc    900
caagagcttc cccttcaaca cctctgtggt gtacaagaag accctgtttg tggagttcac    960
tgaccacctg ttcaacattg ccaagcccag gccccccctgg atgggcctgc tgggccccac   1020
catccaggct gaggtgtatg acactgtggt gatcaccctg aagaacatgg ccagccaccc   1080
tgtgagcctg catgctgtgg gggtgagcta ctggaaggcc tctgaggggg ctgagtatga   1140
tgaccagacc agccagaggg agaaggagga tgacaaggtg ttccctgggg gcagccacac   1200
ctatgtgtgg caggtgctga aggagaatgg ccccatggcc tctgaccccc tgtgcctgac   1260
ctacagctac ctgagccatg tggacctggt gaaggacctg aactctggcc tgattggggc   1320
cctgctggtg tgcagggagg gcagcctggc caaggagaag acccagaccc tgcacaagtt   1380
catcctgctg tttgctgtgt ttgatgaggg caagagctgg cactctgaaa ccaagaacag   1440
cctgatgcag gacagggatg ctgcctctgc cagggcctgg cccaagatgc acactgtgaa   1500
tggctatgtg aacaggagcc tgcctggcct gattggctgc cacaggaagt ctgtgtactg   1560
gcatgtgatt ggcatgggca ccacccctga ggtgcacagc atcttcctgg agggccacac   1620
cttcctggtc aggaaccaca ggcaggccag cctggagatc agccccatca ccttcctgac   1680
tgcccagacc ctgctgatgg acctgggcca gttcctgctg ttctgccaca tcagcagcca   1740
ccagcatgat ggcatggagg cctatgtgaa ggtggacagc tgccctgagg agccccagct   1800
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgccccccctg gtgctggccc ctgatgacag gagctacaag agccagtacc tgaacaatgg   2040
cccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc ccaagggggt   2280
gaagcacctg aaggacttcc ccatcctgcc tggggagatc ttcaagtaca agtggactgt   2340
gactgtggag gatggcccca ccaagtctga ccccaggtgc ctgaccagat actacagcag   2400
ctttgtgaac atggagaggg acctggcctc tggcctgatt ggcccccctgc tgatctgcta   2460
caaggagtct gtggaccaga ggggcaacca gatcatgtct gacaagagga atgtgatcct   2520
```

```
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
ctacaccttc aagcacaaga tggtgtatga ggacaccctg accctgttcc ccttctctgg   2820
ggagactgtg ttcatgagca tggagaaccc tggcctgtgg attctgggct gccacaactc   2880
tgacttcagg aacaggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact ttgtgaagcc   3540
caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggcccccctgc tggtgtgcca caccaacacc ctgaaccctg cccatggcag   3720
gcaggtgact gtgcaggagt ttgccctgtt cttcaccatc tttgatgaaa ccaagagctg   3780
gtacttcact gagaacatgg agaggaactg cagggccccc tgcaacatcc agatggagga   3840
ccccaccttc aaggagaact acaggttcca tgccatcaat ggctacatca tggacaccct   3900
gcctggcctg gtgatggccc aggaccagag gatcaggtgg tacctgctga gcatgggcag   3960
caatgagaac atccacagca tccacttctc tggccatgtg ttcactgtga ggaagaagga   4020
ggagtacaag atggccctgt acaacctgta ccctggggtg tttgagactg tggagatgct   4080
gcccagcaag gctggcatct ggagggtgga gtgcctgatt ggggagcacc tgcatgctgg   4140
catgagcacc ctgttcctgg tgtacagcaa caagtgccag accccccctgg gcatggcctc   4200
tggccacatc agggacttcc agatcactgc ctctggccag tatggccagt gggcccccaa   4260
gctggccagg ctgcactact ctggcagcat caatgcctgg agcaccaagg agcccttcag   4320
ctggatcaag gtggacctgc tggcccccat gatcatccat ggcatcaaga cccagggggc   4380
caggcagaag ttcagcagcc tgtacatcag ccagttcatc atcatgtaca gcctggatgg   4440
caagaagtgg cagacctaca ggggcaacag cactggcacc ctgatggtgt tctttggcaa   4500
tgtggacagc tctggcatca agcacaacat cttcaacccc cccatcattg ccagatacat   4560
caggctgcac cccacccact acagcatcag gagcaccctg aggatggagc tgatgggctg   4620
tgacctgaac agctgcagca tgcccctggg catggagagc aaggccatct ctgatgccca   4680
gatcactgcc agcagctact tcaccaacat gtttgccacc tggagcccca gcaaggccag   4740
gctgcacctg cagggcagga gcaatgcctg gaggccccag gtcaacaacc ccaaggagtg   4800
gctgcaggtg gacttccaga agaccatgaa ggtgactggg gtgaccaccc agggggtgaa   4860
```

```
gagcctgctg accagcatgt atgtgaagga gttcctgatc agcagcagcc aggatggcca   4920

ccagtggacc ctgttcttcc agaatggcaa ggtgaaggtg ttccagggca accaggacag   4980

cttcacccct gtggtgaaca gcctggaccc ccccctgctg accagatacc tgaggattca   5040

cccccagagc tgggtgcacc agattgccct gaggatggag gtgctgggct gtgaggccca   5100

ggacctgtac tgacctcgag gcactgtcct ttcctaataa aatgaggaaa ttgcatcgca   5160

ttgtctgagt aggtgtcatt ctattctggg gggtggggtg gggcaggaca gcaaggggga   5220

ggattgggaa gacaatagca ggcatgctgg ggatgcggtg ggctctatgg gcacgtggcg   5280

gccgcaggaa cccctagtga tggagttggc cactccctct ctgcgcgctc gctcgctcac   5340

tgaggccggg cgaccaaagg tcgcccgacg cccgggcttt gcccgggcgg cctcagtgag   5400

cgagcgagcg cgcagagagg gagtggccaa                                 5430
```

```
<210> SEQ ID NO 20
<211> LENGTH: 5779
<212> TYPE: DNA
<213> ORGANISM: Adeno-Associated Virus 2

<400> SEQUENCE: 20

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgacgt ggacttagcc    180

cctgtttgct cctccgataa ctggggtgac cttggttaat attcaccagc agcctccccg    240

tggacttagc ccctgtttgc tcctccgata actggggtga ccttggttaa tattcaccag    300

cagcctcccc acgcgaaacg tcgactggac acaggacgct gtggtttctg agccaggggg    360

cgactcagat cccagccagt ggacttagcc cctgtttgct cctccgataa ctggggtgac    420

cttggttaat attcaccagc agcctccccc gttgcccctc tggatccact gcttaaatac    480

ggacgaggac agggccctgt ctcctcagct tcaggcacca ccactgacct gggacagtga    540

atcgtaagta ctagcagcta caatccagct accattctgc ttttatttta tggttgggat    600

aaggctggat tattctgagt ccaagctagg cccttttgct aatcatgttc atacctctta    660

tcttcctccc acagctcctg ggcaacgtgc tggtctgtgt gctggcccat cactttggca    720

aagaattgcg atcgccacca tgcagattga gctgagcacc tgcttcttcc tgtgcctgct    780

gaggttctgc ttctctgcca ccaggagata ctacctgggg gctgtggagc tgagctggga    840

ctacatgcag tctgacctgg gggagctgcc tgtggatgcc aggttccccc ccagagtgcc    900

caagagcttc cccttcaaca cctctgtggt gtacaagaag accctgtttg tggagttcac    960

tgaccacctg ttcaacattg ccaagcccag gcccccctgg atgggcctgc tgggccccac   1020

catccaggct gaggtgtatg acactgtggt gatcaccctg aagaacatgg ccagccaccc   1080

tgtgagcctg catgctgtgg gggtgagcta ctggaaggcc tctgaggggg ctgagtatga   1140

tgaccagacc agccagaggg agaaggagga tgacaaggtg ttccctgggg gcagccacac   1200

ctatgtgtgg caggtgctga aggagaatgg ccccatggcc tctgaccccc tgtgcctgac   1260

ctacagctac ctgagccatg tggacctggt gaaggacctg aactctggcc tgattggggc   1320

cctgctggtg tgcagggagg gcagcctggc caaggagaag acccagaccc tgcacaagtt   1380

catcctgctg tttgctgtgt ttgatgaggg caagagctgg cactctgaaa ccaagaacag   1440

cctgatgcag gacagggatg ctgcctctgc cagggcctgg cccaagatgc acactgtgaa   1500

tggctatgtg aacaggagcc tgcctggcct gattggctgc cacaggaagt ctgtgtactg   1560
```

```
gcatgtgatt ggcatgggca ccacccctga ggtgcacagc atcttcctgg agggccacac   1620
cttcctggtc aggaaccaca ggcaggccag cctggagatc agccccatca ccttcctgac   1680
tgcccagacc ctgctgatgg acctgggcca gttcctgctg ttctgccaca tcagcagcca   1740
ccagcatgat ggcatggagg cctatgtgaa ggtggacagc tgccctgagg agccccagct   1800
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgccccccctg gtgctggccc ctgatgacag gagctacaag agccagtacc tgaacaatgg   2040
cccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc ccaagggggt   2280
gaagcacctg aaggacttcc ccatcctgcc tggggagatc ttcaagtaca agtggactgt   2340
gactgtggag gatggcccca ccaagtctga ccccaggtgc ctgaccagat actacagcag   2400
ctttgtgaac atggagaggg acctggcctc tggcctgatt ggcccccctgc tgatctgcta   2460
caaggagtct gtggaccaga ggggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
ctacaccttc aagcacaaga tggtgtatga ggacaccctg accctgttcc ccttctctgg   2820
ggagactgtg ttcatgagca tggagaaccc tggcctgtgg attctgggct gccacaactc   2880
tgacttcagg aacaggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact ttgtgaagcc   3540
caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggcccccctgc tggtgtgcca caccaacacc ctgaaccctg cccatggcag   3720
gcaggtgact gtgcaggagt ttgccctgtt cttcaccatc tttgatgaaa ccaagagctg   3780
gtacttcact gagaacatgg agaggaactg cagggccccc tgcaacatcc agatggagga   3840
ccccaccttc aaggagaact acaggttcca tgccatcaat ggctacatca tggacaccct   3900
```

```
gcctggcctg gtgatggccc aggaccagag gatcaggtgg tacctgctga gcatgggcag   3960
caatgagaac atccacagca tccacttctc tggccatgtg ttcactgtga ggaagaagga   4020
ggagtacaag atggccctgt acaacctgta ccctggggtg tttgagactg tggagatgct   4080
gcccagcaag gctggcatct ggagggtgga gtgcctgatt ggggagcacc tgcatgctgg   4140
catgagcacc ctgttcctgg tgtacagcaa caagtgccag accccccctgg gcatggcctc  4200
tggccacatc agggacttcc agatcactgc ctctggccag tatggccagt gggcccccaa   4260
gctggccagg ctgcactact ctggcagcat caatgcctgg agcaccaagg agcccttcag   4320
ctggatcaag gtggacctgc tggcccccat gatcatccat ggcatcaaga cccagggggc   4380
caggcagaag ttcagcagcc tgtacatcag ccagttcatc atcatgtaca gcctggatgg   4440
caagaagtgg cagacctaca ggggcaacag cactggcacc ctgatggtgt tctttggcaa   4500
tgtggacagc tctggcatca agcacaacat cttcaacccc cccatcattg ccagatacat   4560
caggctgcac ccccacccact acagcatcag gagcaccctg aggatggagc tgatgggctg  4620
tgacctgaac agctgcagca tgcccctggg catggagagc aaggccatct ctgatgccca   4680
gatcactgcc agcagctact tcaccaacat gtttgccacc tggagcccca gcaaggccag   4740
gctgcacctg cagggcagga gcaatgcctg gaggccccag gtcaacaacc ccaaggagtg   4800
gctgcaggtg gacttccaga agaccatgaa ggtgactggg gtgaccaccc agggggtgaa   4860
gagcctgctg accagcatgt atgtgaagga gttcctgatc agcagcagcc aggatggcca   4920
ccagtggacc ctgttcttcc agaatggcaa ggtgaaggtg ttccagggca accaggacag   4980
cttcacccct gtggtgaaca gcctggaccc ccccctgctg accagatacc tgaggattca   5040
cccccagagc tgggtgcacc agattgccct gaggatggag gtgctgggct gtgaggccca   5100
ggacctgtac tgacctcgag gcactgtcct ttcctaataa aatgaggaaa ttgcatcgca   5160
ttgtctgagt aggtgtcatt ctattctggg gggtggggtg gggcaggaca gcaaggggga   5220
ggattgggaa gacaatagca ggcatgctgg ggatgcggtg ggctctatgg gcactcgaca   5280
ggttaatttt taaaaagcag tcaaaagtcc aagtggccct tggcagcatt tactctctct   5340
gtttgctctg gttaataatc tcaggagcac aaacattcct ggaggcagga gaagaaatca   5400
acatcctgga cttatcctct gggcctctcc ccacccccag gagaggctca ggttaatttt   5460
taaaaagcag tcaaaagtcc aagtggccct tggcagcatt tactctctct gtttgctctg   5520
gttaataatc tcaggagcac aaacattcct ggaggcagga gaagaaatca acatcctgga   5580
cttatcctct gggcctctcc ccacccccag gagaggctgt cgagtggcgg ccgcaggaac   5640
ccctagtgat ggagttggcc actccctctc tgcgcgctcg ctcgctcact gaggccgggc   5700
gaccaaaggt cgcccgacgc ccgggctttg cccgggcggc ctcagtgagc gagcgagcgc   5760
gcagagaggg agtggccaa                                                5779
```

<210> SEQ ID NO 21
<211> LENGTH: 5962
<212> TYPE: DNA
<213> ORGANISM: Adeno-Associated Virus 2

<400> SEQUENCE: 21

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg    240
```

```
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg gggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt ttgtggagtt   1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg gggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg gggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
```

```
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaacccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac ccccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
```

```
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga cccccccctg ctgaccagat acctgaggat   5220
tcacccccag agctgggtgc accagattgc cctgaggatg gaggtgctgg gctgtgaggc   5280
ccaggacctg tactgacctc gaggcactgt cctttcctaa taaaatgagg aaattgcatc   5340
gcattgtctg agtaggtgtc attctattct ggggggtggg gtggggcagg acagcaaggg   5400
ggaggattgg gaagacaata gcaggcatgc tggggatgcg gtgggctcta tgggcactcg   5460
acaggttaat ttttaaaaag cagtcaaaag tccaagtggc ccttggcagc atttactctc   5520
tctgtttgct ctggttaata atctcaggag cacaaacatt cctggaggca ggagaagaaa   5580
tcaacatcct ggacttatcc tctgggcctc tccccacccc caggagaggc tcaggttaat   5640
ttttaaaaag cagtcaaaag tccaagtggc ccttggcagc atttactctc tctgtttgct   5700
ctggttaata atctcaggag cacaaacatt cctggaggca ggagaagaaa tcaacatcct   5760
ggacttatcc tctgggcctc tccccacccc caggagaggc tgtcgagtgg cggccgcagg   5820
aacccctagt gatggagttg gccactccct ctctgcgcgc tcgctcgctc actgaggccg   5880
ggcgaccaaa ggtcgcccga cgcccgggct ttgcccgggc ggcctcagtg agcgagcgag   5940
cgcgcagaga gggagtggcc aa                                            5962
```

<210> SEQ ID NO 22
<211> LENGTH: 5919
<212> TYPE: DNA
<213> ORGANISM: Adeno-Associated Virus 2

<400> SEQUENCE: 22

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgta ggctcagagg cacacaggag    180
tttctgggct caccctgccc ccttccaacc cctcagttcc catcctccag cagctgtttg    240
tgtgctgcct ctgaagtcca cactgaacaa acttcagcct actcatgtcc ctaaaatggg    300
caaacattgc aagcagcaaa cagcaaacac acagccctcc ctgcctgctg accttggagc    360
tggggcagag gtcagagacc tctctgggcc catgccacct ccaacatcca ctcgacccct    420
tggaatttcg gtggagagga gcagaggttg tcctggcgtg gtttaggtag tgtgagaggg    480
gtcgacgatc ttgctaccag tggaacagcc actaaggatt ctgcagtgag agcagagggc    540
cagctaagtg gtactctccc agagactgtc tgactcacgc cacccccctcc accttggaca    600
caggacgctg tggtttctga gccaggtaca atgactcctt tcggtaagtg cagtggaagc    660
tgtacactgc ccaggcaaag cgtccgggca gcgtaggcgg gcgactcaga tcccagccag    720
tggacttagc ccctgtttgc tcctccgata actggggtga ccttggttaa tattcaccag    780
cagcctcccc cgttgcccct ctggatccac tgcttaaata cggacgagga cagggccctg    840
tctcctcagc ttcaggcacc accactgacc tgggacagtg aatcgtaagt atgcctttca    900
ctgcgagagg ttctggagag gcttctgagc tccccatggc ccaggcaggc agcaggtctg    960
gggcaggagg ggggttgtgg agtgggtatc cgcctgctga ggtgcagggc agatcatcat   1020
gtgccttgac tcggggcctg gcccccccat ctctgtcttg caggacaatt gccgtcttct   1080
```

```
gtctcgtggg gcatcctcct gctggcaggc ctgtgctgcc tggtccctgt ctccctggct   1140
gaggaccggc caccatgcag attgagctga gcacctgctt cttcctgtgc ctgctgaggt   1200
tctgcttctc tgccaccagg agatactacc tgggggctgt ggagctgagc tgggactaca   1260
tgcagtctga cctgggggag ctgcctgtgg atgccaggtt cccccccaga gtgcccaaga   1320
gcttcccctt caacacctct gtggtgtaca agaagaccct gtttgtggag ttcactgacc   1380
acctgttcaa cattgccaag cccaggcccc cctggatggg cctgctgggc cccaccatcc   1440
aggctgaggt gtatgacact gtggtgatca ccctgaagaa catggccagc caccctgtga   1500
gcctgcatgc tgtgggggtg agctactgga aggcctctga gggggctgag tatgatgacc   1560
agaccagcca gagggagaag gaggatgaca aggtgttccc tgggggcagc cacacctatg   1620
tgtggcaggt gctgaaggag aatggcccca tggcctctga cccccctgtgc ctgacctaca   1680
gctacctgag ccatgtggac ctggtgaagg acctgaactc tggcctgatt ggggccctgc   1740
tggtgtgcag ggagggcagc ctggccaagg agaagaccca gaccctgcac aagttcatcc   1800
tgctgtttgc tgtgtttgat gagggcaaga gctggcactc tgaaaccaag aacagcctga   1860
tgcaggacag ggatgctgcc tctgccaggg cctggcccaa gatgcacact gtgaatggct   1920
atgtgaacag gagcctgcct ggcctgattg gctgccacag gaagtctgtg tactggcatg   1980
tgattggcat gggcaccacc cctgaggtgc acagcatctt cctggagggc cacaccttcc   2040
tggtcaggaa ccacaggcag gccagcctgg agatcagccc catcaccttc ctgactgccc   2100
agaccctgct gatggacctg ggccagttcc tgctgttctg ccacatcagc agccaccagc   2160
atgatggcat ggaggcctat gtgaaggtgg acagctgccc tgaggagccc cagctgagga   2220
tgaagaacaa tgaggaggct gaggactatg atgatgacct gactgactct gagatggatg   2280
tggtgaggtt tgatgatgac aacagcccca gcttcatcca gatcaggtct gtggccaaga   2340
agcaccccaa gacctgggtg cactacattg ctgctgagga ggaggactgg gactatgccc   2400
ccctggtgct ggcccctgat gacaggagct acaagagcca gtacctgaac aatggccccc   2460
agaggattgg caggaagtac aagaaggtca ggttcatggc ctacactgat gaaaccttca   2520
agaccaggga ggccatccag catgagtctg gcatcctggg cccccctgctg tatggggagg   2580
tgggggacac cctgctgatc atcttcaaga accaggccag caggccctac aacatctacc   2640
cccatggcat cactgatgtg aggcccctgt acagcaggag gctgcccaag gggtgaagc   2700
acctgaagga cttccccatc ctgcctgggg agatcttcaa gtacaagtgg actgtgactg   2760
tggaggatgg ccccaccaag tctgacccca ggtgcctgac cagatactac agcagctttg   2820
tgaacatgga gagggacctg gcctctggcc tgattggccc cctgctgatc tgctacaagg   2880
agtctgtgga ccagaggggc aaccagatca tgtctgacaa gaggaatgtg atcctgttct   2940
ctgtgtttga tgagaacagg agctggtacc tgactgagaa catccagagg ttcctgccca   3000
accctgctgg ggtgcagctg gaggaccctg agttccaggc cagcaacatc atgcacagca   3060
tcaatggcta tgtgtttgac agcctgcagc tgtctgtgtg cctgcatgag gtggcctact   3120
ggtacatcct gagcattggg gcccagactg acttcctgtc tgtgttcttc tctggctaca   3180
ccttcaagca caagatggtg tatgaggaca ccctgaccct gttccccttc tctggggaga   3240
ctgtgttcat gagcatggag aaccctggcc tgtggattct gggctgccac aactctgact   3300
tcaggaacag gggcatgact gccctgctga aagtctccag ctgtgacaag aacactgggg   3360
actactatga ggacagctat gaggacatct ctgcctacct gctgagcaag aacaatgcca   3420
ttgagcccag gagcttcagc cagaaccccc cagtgctgaa gaggcaccag agggagatca   3480
```

```
ccaggaccac cctgcagtct gaccaggagg agattgacta tgatgacacc atctctgtgg   3540
agatgaagaa ggaggacttt gacatctacg acgaggacga gaaccagagc cccaggagct   3600
tccagaagaa gaccaggcac tacttcattg ctgctgtgga gaggctgtgg gactatggca   3660
tgagcagcag cccccatgtg ctgaggaaca gggcccagtc tggctctgtg ccccagttca   3720
agaaggtggt gttccaggag ttcactgatg gcagcttcac ccagcccctg tacagagggg   3780
agctgaatga gcacctgggc ctgctgggcc cctacatcag ggctgaggtg gaggacaaca   3840
tcatggtgac cttcaggaac caggccagca ggccctacag cttctacagc agcctgatca   3900
gctatgagga ggaccagagg caggggctg agcccaggaa gaactttgtg aagcccaatg   3960
aaaccaagac ctacttctgg aaggtgcagc accacatggc cccaccaag gatgagtttg   4020
actgcaaggc ctgggcctac ttctctgatg tggacctgga gaaggatgtg cactctggcc   4080
tgattggccc cctgctggtg tgccacacca acaccctgaa ccctgcccat ggcaggcagg   4140
tgactgtgca ggagtttgcc ctgttcttca ccatctttga tgaaaccaag agctggtact   4200
tcactgagaa catggagagg aactgcaggg cccccctgcaa catccagatg gaggacccca   4260
ccttcaagga gaactacagg ttccatgcca tcaatggcta catcatggac accctgcctg   4320
gcctggtgat ggcccaggac cagaggatca ggtggtacct gctgagcatg ggcagcaatg   4380
agaacatcca cagcatccac ttctctggcc atgtgttcac tgtgaggaag aaggaggagt   4440
acaagatggc cctgtacaac ctgtaccctg ggtgtttga gactgtggag atgctgccca   4500
gcaaggctgg catctggagg gtggagtgcc tgattgggga gcacctgcat gctggcatga   4560
gcaccctgtt cctggtgtac agcaacaagt gccagacccc cctgggcatg gcctctggcc   4620
acatcaggga cttccagatc actgcctctg gccagtatgg ccagtgggcc cccaagctgg   4680
ccaggctgca ctactctggc agcatcaatg cctggagcac caaggagccc ttcagctgga   4740
tcaaggtgga cctgctggcc cccatgatca tccatggcat caagacccag gggccaggc   4800
agaagttcag cagcctgtac atcagccagt tcatcatcat gtacagcctg gatggcaaga   4860
agtggcagac ctacaggggc aacagcactg gcaccctgat ggtgttcttt ggcaatgtgg   4920
acagctctgg catcaagcac aacatcttca acccccccat cattgccaga tacatcaggc   4980
tgcaccccac ccactacagc atcaggagca ccctgaggat ggagctgatg ggctgtgacc   5040
tgaacagctg cagcatgccc ctgggcatgg agagcaaggc catctctgat gcccagatca   5100
ctgccagcag ctacttcacc aacatgtttg ccacctggag ccccagcaag gccaggctgc   5160
acctgcaggg caggagcaat gcctggaggc cccaggtcaa caaccccaag gagtggctgc   5220
aggtggactt ccagaagacc atgaaggtga ctggggtgac cacccagggg gtgaagagcc   5280
tgctgaccag catgtatgtg aaggagttcc tgatcagcag cagccaggat ggccaccagt   5340
ggaccctgtt cttccagaat ggcaaggtga aggtgttcca gggcaaccag gacagcttca   5400
cccctgtggt gaacagcctg gaccccccc tgctgaccag atacctgagg attcaccccc   5460
agagctgggt gcaccagatt gccctgagga tggaggtgct gggctgtgag gcccaggacc   5520
tgtactgagc tcgagctgtg ccttctagtt gccagccatc tgttgtttgc ccctcccccg   5580
tgccttcctt gaccctggaa ggtgccactc ccactgtcct ttcctaataa aatgaggaaa   5640
ttgcatcgca ttgtctgagt aggtgtcatt ctattctggg gggtggggtg gggcaggaca   5700
gcaaggggga ggattgggaa gacaatagca ggcatgctgg ggatgcggtg ggctctatgg   5760
accggtgcgg ccgcaggaac ccctagtgat ggagttggcc actccctctc tgcgcgctcg   5820
```

ctcgctcact gaggccgggc gaccaaaggt cgcccgacgc ccgggctttg cccgggcggc 5880
ctcagtgagc gagcgagcgc gcagagaggg agtggccaa 5919

<210> SEQ ID NO 23
<211> LENGTH: 5306
<212> TYPE: DNA
<213> ORGANISM: Adeno-Associated Virus 2

<400> SEQUENCE: 23
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttaaacgt cgaccctaaa 180
atgggcaaac attgcaagca gcaaacagca aactgacctt ggagctgggg cagaggtcag 240
agacctctct gggcactcga ccccttggaa tttcggtgga gaggagcaga ggtacacagc 300
cctccctgcc tgccccatgc cacctccaac atctgtcctg gcgtggttta ggtagtgtga 360
gaggggaatg actcctttcg gtaagtgcag tggaagctgt acactgccca ggcaaagcgt 420
ccgggcagcg taggcgggcg actcagatcc cagccagtgg acttagcccc tgtttgctcc 480
tccgataact ggggtgacct tggttaatat tcaccagcag cctcccccgt tgcccctctg 540
gatccactgc ttaaatacgg acgaggacag ggccctgtct cctcagcttc aggcaccacc 600
actgacctgg gacagtgaat cgcgatcgca ctgcttaaat acggacgagg acagggccct 660
gtctcctcag cttcaggcac caccactgac ctgggacagt gaatcgcgat cgccaccatg 720
cagattgagc tgagcacctg cttcttcctg tgcctgctga ggttctgctt ctctgccacc 780
aggagatact acctgggggc tgtggagctg agctgggact acatgcagtc tgacctgggg 840
gagctgcctg tggatgccag gttccccccc agagtgccca agagcttccc cttcaacacc 900
tctgtggtgt acaagaagac cctgtttgtg gagttcactg accacctgtt caacattgcc 960
aagcccaggc ccccctggat gggcctgctg ggccccacca tccaggctga ggtgtatgac 1020
actgtggtga tcaccctgaa gaacatggcc agccaccctg tgagcctgca tgctgtgggg 1080
gtgagctact ggaaggcctc tgagggggct gagtatgatg accagaccag ccagagggag 1140
aaggaggatg acaaggtgtt ccctgggggc agccacacct atgtgtggca ggtgctgaag 1200
gagaatggcc ccatggcctc tgacccccctg tgcctgacct acagctacct gagccatgtg 1260
gacctggtga aggacctgaa ctctggcctg attggggccc tgctggtgtg cagggagggc 1320
agcctggcca aggagaagac ccagaccctg cacaagttca tcctgctgtt tgctgtgttt 1380
gatgagggca agagctggca ctctgaaacc aagaacagcc tgatgcagga cagggatgct 1440
gcctctgcca gggcctggcc caagatgcac actgtgaatg gctatgtgaa caggagcctg 1500
cctggcctga ttggctgcca caggaagtct gtgtactggc atgtgattgg catgggcacc 1560 accccctgagg tgcacagcat cttcctggag ggccacacct tcctggtcag gaaccacagg 1620
caggccagcc tggagatcag ccccatcacc ttcctgactg cccagaccct gctgatggac 1680
ctgggccagt tcctgctgtt ctgccacatc agcagccacc agcatgatgg catggaggcc 1740
tatgtgaagg tggacagctg ccctgaggag ccccagctga ggatgaagaa caatgaggag 1800
gctgaggact atgatgatga cctgactgac tctgagatgg atgtggtgag gtttgatgat 1860
gacaacagcc ccagcttcat ccagatcagg tctgtggcca agaagcaccc caagacctgg 1920
gtgcactaca ttgctgctga ggaggaggac tgggactatg ccccccctggt gctggcccct 1980 gatgacagga gctacaagag ccagtacctg aacaatggcc cccagaggat tggcaggaag 2040

```
tacaagaagg tcaggttcat ggcctacact gatgaaacct tcaagaccag ggaggccatc   2100
cagcatgagt ctggcatcct gggccccctg ctgtatgggg aggtggggga caccctgctg   2160
atcatcttca agaaccaggc cagcaggccc tacaacatct acccccatgg catcactgat   2220
gtgaggcccc tgtacagcag gaggctgccc aagggggtga agcacctgaa ggacttcccc   2280
atcctgcctg ggagatcttt caagtacaag tggactgtga ctgtggagga tggccccacc   2340
aagtctgacc ccaggtgcct gaccagatac tacagcagct ttgtgaacat ggagagggac   2400
ctggcctctg gcctgattgg cccccctgctg atctgctaca aggagtctgt ggaccagagg   2460
ggcaaccaga tcatgtctga caagaggaat gtgatcctgt tctctgtgtt tgatgagaac   2520
aggagctggt acctgactga gaacatccag aggttcctgc ccaaccctgc tggggtgcag   2580
ctggaggacc ctgagttcca ggccagcaac atcatgcaca gcatcaatgg ctatgtgttt   2640
gacagcctgc agctgtctgt gtgcctgcat gaggtggcct actggtacat cctgagcatt   2700
ggggcccaga ctgacttcct gtctgtgttc ttctctggct acaccttcaa gcacaagatg   2760
gtgtatgagg acaccctgac cctgttcccc ttctctgggg agactgtgtt catgagcatg   2820
gagaaccctg gcctgtggat tctgggctgc cacaactctg acttcaggaa caggggcatg   2880
actgccctgc tgaaagtctc cagctgtgac aagaacactg ggactacta tgaggacagc   2940
tatgaggaca tctctgccta cctgctgagc aagaacaatg ccattgagcc caggagcttc   3000
agccagaacc ccccagtgct gaagaggcac cagagggaga tcaccaggac caccctgcag   3060
tctgaccagg aggagattga ctatgatgac accatctctg tggagatgaa gaaggaggac   3120
tttgacatct acgacgagga cgagaaccag agccccagga gcttccagaa gaagaccagg   3180
cactacttca ttgctgctgt ggagaggctg tgggactatg gcatgagcag cagcccccat   3240
gtgctgagga acagggccca gtctggctct gtgccccagt tcaagaaggt ggtgttccag   3300
gagttcactg atggcagctt cacccagccc ctgtacagag gggagctgaa tgagcacctg   3360
ggcctgctgg gcccctacat cagggctgag gtggaggaca acatcatggt gaccttcagg   3420
aaccaggcca gcaggcccta cagcttctac agcagcctga tcagctatga ggaggaccag   3480
aggcaggggg ctgagcccag gaagaacttt gtgaagccca atgaaaccaa gacctacttc   3540
tggaaggtgc agcaccacat ggcccccacc aaggatgagt ttgactgcaa ggcctgggcc   3600
tacttctctg atgtggacct ggagaaggat gtgcactctg gcctgattgg cccccctgctg   3660
gtgtgccaca ccaacaccct gaaccctgcc catggcaggc aggtgactgt gcaggagttt   3720
gccctgttct tcaccatctt tgatgaaacc aagagctggt acttcactga gaacatggag   3780
aggaactgca gggcccccctg caacatccag atggaggacc ccaccttcaa ggagaactac   3840
aggttccatg ccatcaatgg ctacatcatg gacaccctgc ctggcctggt gatggcccag   3900
gaccagagga tcaggtggta cctgctgagc atgggcagca atgagaacat ccacagcatc   3960
cacttctctg gccatgtgtt cactgtgagg aagaaggagg agtacaagat ggccctgtac   4020
aacctgtacc ctggggtgtt tgagactgtg gagatgctgc ccagcaaggc tggcatctgg   4080
agggtggagt gcctgattgg ggagcacctg catgctggca tgagcaccct gttcctggtg   4140
tacagcaaca agtgccagac cccccctgggc atggcctctg gccacatcag ggacttccag   4200
atcactgcct ctggccagta tggccagtgg gcccccaagc tggccaggct gcactactct   4260
ggcagcatca atgcctggag caccaaggag cccttcagct ggatcaaggt ggacctgctg   4320
gcccccatga tcatccatgg catcaagacc caggggggcca ggcagaagtt cagcagcctg   4380
```

```
tacatcagcc agttcatcat catgtacagc ctggatggca agaagtggca gacctacagg   4440

ggcaacagca ctggcaccct gatggtgttc tttggcaatg tggacagctc tggcatcaag   4500

cacaacatct tcaacccccc catcattgcc agatacatca ggctgcaccc caccccactac   4560

agcatcagga gcaccctgag gatggagctg atgggctgtg acctgaacag ctgcagcatg   4620

cccctgggca tggagagcaa ggccatctct gatgcccaga tcactgccag cagctacttc   4680

accaacatgt ttgccacctg gagccccagc aaggccaggc tgcacctgca gggcaggagc   4740

aatgcctgga ggccccaggt caacaacccc aaggagtggc tgcaggtgga cttccagaag   4800

accatgaagg tgactggggt gaccacccag gggtgaaga gcctgctgac cagcatgtat   4860

gtgaaggagt tcctgatcag cagcagccag gatggccacc agtggaccct gttcttccag   4920

aatggcaagg tgaaggtgtt ccagggcaac caggacagct tcacccctgt ggtgaacagc   4980

ctggaccccc ccctgctgac cagatacctg aggattcacc cccagagctg ggtgcaccag   5040

attgccctga ggatggaggt gctgggctgt gaggcccagg acctgtactg acctcgagga   5100

ataaaggaaa tttattttca ttgcaatagt gtgttggttt tttgtgtcac gtggcggccg   5160

caggaacccc tagtgatgga gttggccact ccctctctgc gcgctcgctc gctcactgag   5220

gccgggcgac caaaggtcgc ccgacgcccg ggctttgccc gggcggcctc agtgagcgag   5280

cgagcgcgca gagagggagt ggccaa                                         5306
```

```
<210> SEQ ID NO 24
<211> LENGTH: 5461
<212> TYPE: DNA
<213> ORGANISM: Adeno-Associated Virus 2

<400> SEQUENCE: 24

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactt tatttgccac    180

aaaaacccta tcagatgggc gtctttatca tttccattgt acagatgggg aaacaggctt    240

cggggtcggg gcatagccac ttactgacga ctccccaccc agcaagtggt tttgaacccg    300

gaccctctca cactacctaa accacgccag gacaacctct gctcctctcc accgaaattc    360

caaggggtcg agtggatgtt ggaggtggca tgggcccaga gaggtctctg acctctgccc    420

cagctccaag gtcagcaggc agggagggct gtgtgtttgc tgtttgctgc ttgcaatgtt    480

tgcccatttt agggacatga gtaggctgaa gtttgttcag tgtggacttc agaggcagca    540

cacaaacagc tgctggagga tgggaactga ggggttggaa gggggcaggg tgagcccaga    600

aactcctgtg tgcctctgag cctgcagacg cgaaacgtcg actggacaca ggacgctgtg    660

gtttctgagc caggggggcga ctcagatccc agccagtgga cttagcccct gtttgctcct    720

ccgataactg gggtgacctt ggttaatatt caccagcagc ctcccccgtt gcccctctgg    780

atccactgct taaatacgga cgaggacagg gccctgtctc ctcagcttca ggcaccacca    840

ctgacctggg acagtgaatc gcgatcgcca ccatgcagat tgagctgagc acctgcttct    900

tcctgtgcct gctgaggttc tgcttctctg ccaccaggag atactacctg gggctgtgg     960

agctgagctg ggactacatg cagtctgacc tgggggagct gcctgtggat gccaggttcc   1020

cccccagagt gcccaagagc ttccccttca acacctctgt ggtgtacaag aagaccctgt   1080

ttgtggagtt cactgaccac ctgttcaaca ttgccaagcc caggcccccc tggatgggcc   1140

tgctgggccc caccatccag gctgaggtgt atgacactgt ggtgatcacc ctgaagaaca   1200
```

-continued

```
tggccagcca ccctgtgagc ctgcatgctg tgggggtgag ctactggaag gcctctgagg   1260

gggctgagta tgatgaccag accagccaga gggagaagga ggatgacaag gtgttccctg   1320

ggggcagcca cacctatgtg tggcaggtgc tgaaggagaa tggccccatg gcctctgacc   1380

ccctgtgcct gacctacagc tacctgagcc atgtggacct ggtgaaggac ctgaactctg   1440

gcctgattgg ggccctgctg gtgtgcaggg agggcagcct ggccaaggag aagacccaga   1500

ccctgcacaa gttcatcctg ctgtttgctg tgtttgatga gggcaagagc tggcactctg   1560

aaaccaagaa cagcctgatg caggacaggg atgctgcctc tgccagggcc tggcccaaga   1620

tgcacactgt gaatggctat gtgaacagga gcctgcctgg cctgattggc tgccacagga   1680

agtctgtgta ctggcatgtg attggcatgg gcaccacccc tgaggtgcac agcatcttcc   1740

tggagggcca caccttcctg gtcaggaacc acaggcaggc cagcctggag atcagcccca   1800

tcaccttcct gactgcccag accctgctga tggacctggg ccagttcctg ctgttctgcc   1860

acatcagcag ccaccagcat gatggcatgg aggcctatgt gaaggtggac agctgccctg   1920

aggagcccca gctgaggatg aagaacaatg aggaggctga ggactatgat gatgacctga   1980

ctgactctga gatggatgtg gtgaggtttg atgatgacaa cagccccagc ttcatccaga   2040

tcaggtctgt ggccaagaag caccccaaga cctgggtgca ctacattgct gctgaggagg   2100

aggactggga ctatgccccc ctggtgctgg cccctgatga caggagctac aagagccagt   2160

acctgaacaa tggcccccag aggattggca ggaagtacaa gaaggtcagg ttcatggcct   2220

acactgatga aaccttcaag accagggagg ccatccagca tgagtctggc atcctgggcc   2280

ccctgctgta tggggaggtg gggacaccc tgctgatcat cttcaagaac caggccagca    2340

ggccctacaa catctacccc catggcatca ctgatgtgag gcccctgtac agcaggaggc   2400

tgcccaaggg ggtgaagcac ctgaaggact tccccatcct gcctggggag atcttcaagt   2460

acaagtggac tgtgactgtg gaggatggcc ccaccaagtc tgaccccagg tgcctgacca   2520

gatactacag cagctttgtg aacatggaga gggacctggc ctctggcctg attggccccc   2580

tgctgatctg ctacaaggag tctgtggacc agaggggcaa ccagatcatg tctgacaaga   2640

ggaatgtgat cctgttctct gtgtttgatg agaacaggag ctggtacctg actgagaaca   2700

tccagaggtt cctgcccaac cctgctgggg tgcagctgga ggaccctgag ttccaggcca   2760

gcaacatcat gcacagcatc aatggctatg tgtttgacag cctgcagctg tctgtgtgcc   2820

tgcatgaggt ggcctactgg tacatcctga gcattggggc ccagactgac ttcctgtctg   2880

tgttcttctc tggctacacc ttcaagcaca agatggtgta tgaggacacc ctgaccctgt   2940

tccccttctc tggggagact gtgttcatga gcatggagaa ccctggcctg tggattctgg   3000

gctgccacaa ctctgacttc aggaacaggg gcatgactgc cctgctgaaa gtctccagct   3060

gtgacaagaa cactggggac tactatgagg acagctatga ggacatctct gcctacctgc   3120

tgagcaagaa caatgccatt gagcccagga gcttcagcca gaaccccccca gtgctgaaga  3180

ggcaccagag ggagatcacc aggaccaccc tgcagtctga ccaggaggag attgactatg   3240

atgacaccat ctctgtggag atgaagaagg aggactttga catctacgac gaggacgaga   3300

accagagccc caggagcttc cagaagaaga ccaggcacta cttcattgct gctgtggaga   3360

ggctgtggga ctatggcatg agcagcagcc cccatgtgct gaggaacagg gcccagtctg   3420

gctctgtgcc ccagttcaag aaggtggtgt tccaggagtt cactgatggc agcttcaccc   3480

agcccctgta cagaggggag ctgaatgagc acctgggcct gctgggcccc tacatcaggg   3540
```

```
ctgaggtgga ggacaacatc atggtgacct tcaggaacca ggccagcagg ccctacagct   3600
tctacagcag cctgatcagc tatgaggagg accagaggca gggggctgag cccaggaaga   3660
actttgtgaa gcccaatgaa accaagacct acttctggaa ggtgcagcac cacatggccc   3720
ccaccaagga tgagtttgac tgcaaggcct gggcctactt ctctgatgtg gacctggaga   3780
aggatgtgca ctctggcctg attggccccc tgctggtgtg ccacaccaac accctgaacc   3840
ctgcccatgg caggcaggtg actgtgcagg agtttgccct gttcttcacc atctttgatg   3900
aaaccaagag ctggtacttc actgagaaca tggagaggaa ctgcagggcc ccctgcaaca   3960
tccagatgga ggacccccacc ttcaaggaga actacaggtt ccatgccatc aatggctaca   4020
tcatggacac cctgcctggc ctggtgatgg cccaggacca gaggatcagg tggtacctgc   4080
tgagcatggg cagcaatgag aacatccaca gcatccactt ctctggccat gtgttcactg   4140
tgaggaagaa ggaggagtac aagatggccc tgtacaacct gtaccctggg gtgtttgaga   4200
ctgtggagat gctgcccagc aaggctggca tctggagggt ggagtgcctg attggggagc   4260
acctgcatgc tggcatgagc accctgttcc tggtgtacag caacaagtgc cagacccccc   4320
tgggcatggc ctctggccac atcagggact tccagatcac tgcctctggc cagtatggcc   4380
agtgggcccc caagctggcc aggctgcact actctggcag catcaatgcc tggagcacca   4440
aggagccctt cagctggatc aaggtggacc tgctggcccc catgatcatc catggcatca   4500
agacccaggg ggccaggcag aagttcagca gcctgtacat cagccagttc atcatcatgt   4560
acagcctgga tggcaagaag tggcagacct acaggggcaa cagcactggc accctgatgg   4620
tgttctttgg caatgtggac agctctggca tcaagcacaa catcttcaac ccccccatca   4680
ttgccagata catcaggctg caccccaccc actacagcat caggagcacc ctgaggatgg   4740
agctgatggg ctgtgacctg aacagctgca gcatgcccct gggcatggag agcaaggcca   4800
tctctgatgc ccagatcact gccagcagct acttcaccaa catgtttgcc acctggagcc   4860
ccagcaaggc caggctgcac ctgcagggca ggagcaatgc ctggaggccc caggtcaaca   4920
accccaagga gtggctgcag gtggacttcc agaagaccat gaaggtgact ggggtgacca   4980
cccagggggt gaagagcctg ctgaccagca tgtatgtgaa ggagttcctg atcagcagca   5040
gccaggatgg ccaccagtgg accctgttct tccagaatgg caaggtgaag gtgttccagg   5100
gcaaccagga cagcttcacc cctgtggtga acagcctgga cccccccctg ctgaccagat   5160
acctgaggat tcacccccag agctgggtgc accagattgc cctgaggatg gaggtgctgg   5220
gctgtgaggc ccaggacctg tactgacctc gaggaataaa ggaaatttat tttcattgca   5280
atagtgtgtt ggttttttgt gtcacgtggc ggccgcagga acccctagtg atggagttgg   5340
ccactccctc tctgcgcgct cgctcgctca ctgaggccgg gcgaccaaag gtcgcccgac   5400
gcccgggctt tgcccgggcg gcctcagtga gcgagcgagc gcgcagagag ggagtggcca   5460
a                                                                   5461
```

<210> SEQ ID NO 25
<211> LENGTH: 5327
<212> TYPE: DNA
<213> ORGANISM: Adeno-Associated Virus 2

<400> SEQUENCE: 25

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
```

```
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccccctgga tgggcctgct gggccccacc   1020
atccaggctg aggtgtatga cactgtggtg atcaccctga agaacatggc cagccaccct   1080
gtgagcctgc atgctgtggg ggtgagctac tggaaggcct ctgagggggc tgagtatgat   1140
gaccagacca gccagaggga gaaggaggat gacaaggtgt tccctggggg cagccacacc   1200
tatgtgtggc aggtgctgaa ggagaatggc cccatggcct ctgacccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gccccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggccccct gctgtatggg   2160
gaggtggggg acaccctgct gatcatcttc aagaaccagg ccagcaggcc ctacaacatc   2220
taccccccatg gcatcactga tgtgaggccc ctgtacagca ggaggctgcc caagggggtg   2280
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gcccccctgct gatctgctac   2460
aaggagtctg tggaccagag gggcaaccag atcatgtctg acaagaggaa tgtgatcctg   2520
```

```
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
tacaccttca agcacaagat ggtgtatgag gacaccctga ccctgttccc cttctctggg   2820
gagactgtgt tcatgagcat ggagaaccct ggcctgtgga ttctgggctg ccacaactct   2880
gacttcagga acaggggcat gactgccctg ctgaaagtct ccagctgtga caagaacact   2940
ggggactact atgaggacag ctatgaggac atctctgcct acctgctgag caagaacaat   3000
gccattgagc ccaggagctt cagccagaac ccccccagtgc tgaagaggca ccagagggag   3060
atcaccagga ccaccctgca gtctgaccag gaggagattg actatgatga caccatctct   3120
gtggagatga agaaggagga ctttgacatc tacgacgagg acgagaacca gagccccagg   3180
agcttccaga agaagaccag gcactacttc attgctgctg tggagaggct gtgggactat   3240
ggcatgagca gcagccccca tgtgctgagg aacagggccc agtctggctc tgtgccccag   3300
ttcaagaagg tggtgttcca ggagttcact gatggcagct tcacccagcc cctgtacaga   3360
ggggagctga atgagcacct gggcctgctg ggcccctaca tcagggctga ggtggaggac   3420
aacatcatgg tgaccttcag gaaccaggcc agcaggccct acagcttcta cagcagcctg   3480
atcagctatg aggaggacca gaggcagggg gctgagccca ggaagaactt tgtgaagccc   3540
aatgaaacca agacctactt ctggaaggtg cagcaccaca tggcccccac caaggatgag   3600
tttgactgca aggcctgggc ctacttctct gatgtggacc tggagaagga tgtgcactct   3660
ggcctgattg gccccctgct ggtgtgccac accaacaccc tgaaccctgc ccatggcagg   3720
caggtgactg tgcaggagtt tgccctgttc ttcaccatct ttgatgaaac caagagctgg   3780
tacttcactg agaacatgga gaggaactgc agggcccccct gcaacatcca gatggaggac   3840
cccaccttca aggagaacta caggttccat gccatcaatg gctacatcat ggacaccctg   3900
cctggcctgg tgatggccca ggaccagagg atcaggtggt acctgctgag catgggcagc   3960
aatgagaaca tccacagcat ccacttctct ggccatgtgt tcactgtgag gaagaaggag   4020
gagtacaaga tggccctgta caacctgtac cctggggtgt ttgagactgt ggagatgctg   4080
cccagcaagg ctggcatctg gagggtggag tgcctgattg gggagcacct gcatgctggc   4140
atgagcaccc tgttcctggt gtacagcaac aagtgccaga cccccctgggg catggcctct   4200
ggccacatca gggacttcca gatcactgcc tctggccagt atggccagtg ggcccccaag   4260
ctggccaggc tgcactactc tggcagcatc aatgcctgga gcaccaagga gcccttcagc   4320
tggatcaagg tggacctgct ggcccccatg atcatccatg gcatcaagac ccaggggggcc   4380
aggcagaagt tcagcagcct gtacatcagc cagttcatca tcatgtacag cctggatggc   4440
aagaagtggc agacctacag gggcaacagc actggcaccc tgatggtgtt ctttggcaat   4500
gtggacagct ctggcatcaa gcacaacatc ttcaaccccc ccatcattgc cagatacatc   4560
aggctgcacc ccacccacta cagcatcagg agcaccctga ggatggagct gatgggctgt   4620
gacctgaaca gctgcagcat gcccctgggc atggagagca aggccatctc tgatgcccag   4680
atcactgcca gcagctactt caccaacatg tttgccacct ggagccccag caaggccagg   4740
ctgcacctgc agggcaggag caatgcctgg aggccccagg tcaacaaccc caaggagtgg   4800
ctgcaggtgg acttccagaa gaccatgaag gtgactgggg tgaccaccca gggggtgaag   4860
agcctgctga ccagcatgta tgtgaaggag ttcctgatca gcagcagcca ggatggccac   4920
```

```
cagtggaccc tgttcttcca gaatggcaag gtgaaggtgt tccagggcaa ccaggacagc   4980

ttcacccctg tggtgaacag cctggacccc cccctgctga ccagatacct gaggattcac   5040

ccccagagct gggtgcacca gattgccctg aggatggagg tgctgggctg tgaggcccag   5100

gacctgtact gacctcgagg aataaaggaa atttattttc attgcaatag tgtgttggtt   5160

ttttgtgtca cgtggcggcc gcaggaaccc ctagtgatgg agttggccac tccctctctg   5220

cgcgctcgct cgctcactga ggccgggcga ccaaaggtcg cccgacgccc gggctttgcc   5280

cgggcggcct cagtgagcga gcgagcgcgc agagagggag tggccaa                 5327
```

```
<210> SEQ ID NO 26
<211> LENGTH: 5309
<212> TYPE: DNA
<213> ORGANISM: Adeno-Associated Virus 2

<400> SEQUENCE: 26

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtc tgcaggctca gaggcacaca    180

ggagtttctg ggctcaccct gccccettcc aacccctcag ttcccatcct ccagcagctg    240

tttgtgtgct gcctctgaag tccacactga acaaacttca gcctactcat gtccctaaaa    300

tgggcaaaca ttgcaagcag caaacagcaa acacacagcc ctccctgcct gctgaccttg    360

gagctggggc agaggtcaga gacctctctg ggcccatgcc acctccaaca tccactcgac    420

cccttggaat ttcggtggag aggagcagag gttgtcctgg cgtggtttag gtagtgtgag    480

aggggtcgac tggacacagg acgctgtggt ttctgagcca gggggcgact cagatcccag    540

ccagtggact tagcccctgt ttgctcctcc gataactggg gtgaccttgg ttaatattca    600

ccagcagcct cccccgttgc cctctggat ccactgctta aatacggacg aggacagggc     660

cctgtctcct cagcttcagg caccaccact gacctgggac agtgaatcgc gatcgccacc    720

atgcagattg agctgagcac ctgcttcttc ctgtgcctgc tgaggttctg cttctctgcc    780

accaggagat actacctggg ggctgtggag ctgagctggg actacatgca gtctgacctg    840

ggggagctgc ctgtggatgc caggttcccc cccagagtgc ccaagagctt ccccttcaac    900

acctctgtgg tgtacaagaa gaccctgttt gtggagttca ctgaccacct gttcaacatt    960

gccaagccca ggccccctg gatgggcctg ctgggcccca ccatccaggc tgaggtgtat    1020

gacactgtgg tgatcaccct gaagaacatg gccagccacc ctgtgagcct gcatgctgtg   1080

ggggtgagct actggaaggc ctctgagggg gctgagtatg atgaccagac cagccagagg   1140

gagaaggagg atgacaaggt gttccctggg ggcagccaca cctatgtgtg gcaggtgctg   1200

aaggagaatg gccccatggc ctctgacccc ctgtgcctga cctacagcta cctgagccat   1260

gtggacctgg tgaaggacct gaactctggc ctgattgggg ccctgctggt gtgcagggag   1320

ggcagcctgg ccaaggagaa gacccagacc ctgcacaagt tcatcctgct gtttgctgtg   1380

tttgatgagg gcaagagctg gcactctgaa accaagaaca gcctgatgca ggacagggat   1440

gctgcctctg ccagggcctg gcccaagatg cacactgtga atggctatgt gaacaggagc   1500

ctgcctggcc tgattggctg ccacaggaag tctgtgtact ggcatgtgat tggcatgggc   1560

accacccctg aggtgcacag catcttcctg gagggccaca ccttcctggt caggaaccac   1620

aggcaggcca gcctggagat cagccccatc accttcctga ctgcccagac cctgctgatg   1680
```

```
gacctgggcc agttcctgct gttctgccac atcagcagcc accagcatga tggcatggag   1740
gcctatgtga aggtggacag ctgccctgag gagccccagc tgaggatgaa gaacaatgag   1800
gaggctgagg actatgatga tgacctgact gactctgaga tggatgtggt gaggtttgat   1860
gatgacaaca gccccagctt catccagatc aggtctgtgg ccaagaagca ccccaagacc   1920
tgggtgcact acattgctgc tgaggaggag gactgggact atgcccccct ggtgctggcc   1980
cctgatgaca ggagctacaa gagccagtac ctgaacaatg gcccccagag gattggcagg   2040
aagtacaaga aggtcaggtt catggcctac actgatgaaa ccttcaagac cagggaggcc   2100
atccagcatg agtctggcat cctgggcccc ctgctgtatg gggaggtggg ggacaccctg   2160
ctgatcatct tcaagaacca ggccagcagg ccctacaaca tctaccccca tggcatcact   2220
gatgtgaggc ccctgtacag caggaggctg cccaaggggg tgaagcacct gaaggacttc   2280
cccatcctgc ctggggagat cttcaagtac aagtggactg tgactgtgga ggatggcccc   2340
accaagtctg accccaggtg cctgaccaga tactacagca gctttgtgaa catggagagg   2400
gacctggcct ctggcctgat tggccccctg ctgatctgct acaaggagtc tgtggaccag   2460
aggggcaacc agatcatgtc tgacaagagg aatgtgatcc tgttctctgt gtttgatgag   2520
aacaggagct ggtacctgac tgagaacatc cagaggttcc tgcccaaccc tgctggggtg   2580
cagctggagg accctgagtt ccaggccagc aacatcatgc acagcatcaa tggctatgtg   2640
tttgacagcc tgcagctgtc tgtgtgcctg catgaggtgg cctactggta catcctgagc   2700
attggggccc agactgactt cctgtctgtg ttcttctctg gctacacctt caagcacaag   2760
atggtgtatg aggacaccct gaccctgttc cccttctctg ggagactgt gttcatgagc   2820
atggagaacc ctggcctgtg gattctgggc tgccacaact ctgacttcag gaacaggggc   2880
atgactgccc tgctgaaagt ctccagctgt gacaagaaca ctggggacta ctatgaggac   2940
agctatgagg acatctctgc ctacctgctg agcaagaaca atgccattga gcccaggagc   3000
ttcagccaga accccccagt gctgaagagg caccagaggg agatcaccag gaccaccctg   3060
cagtctgacc aggaggagat tgactatgat gacaccatct ctgtggagat gaagaaggag   3120
gactttgaca tctacgacga ggacgagaac cagagcccca ggagcttcca gaagaagacc   3180
aggcactact tcattgctgc tgtggagagg ctgtgggact atggcatgag cagcagcccc   3240
catgtgctga ggaacagggc ccagtctggc tctgtgcccc agttcaagaa ggtggtgttc   3300
caggagttca ctgatggcag cttcacccag cccctgtaca gaggggagct gaatgagcac   3360
ctgggcctgc tgggccccta catcagggct gaggtggagg acaacatcat ggtgaccttc   3420
aggaaccagg ccagcaggcc ctacagcttc tacagcagcc tgatcagcta tgaggaggac   3480
cagaggcagg gggctgagcc caggaagaac tttgtgaagc ccaatgaaac caagacctac   3540
ttctggaagg tgcagcacca catggccccc accaaggatg agtttgactg caaggcctgg   3600
gcctacttct ctgatgtgga cctggagaag gatgtgcact ctggcctgat tggccccctg   3660
ctggtgtgcc acaccaacac cctgaaccct gcccatggca ggcaggtgac tgtgcaggag   3720
tttgccctgt tcttcaccat ctttgatgaa accaagagct ggtacttcac tgagaacatg   3780
gagaggaact gcagggcccc ctgcaacatc cagatggagg accccacctt caaggagaac   3840
tacaggttcc atgccatcaa tggctacatc atggacaccc tgcctggcct ggtgatggcc   3900
caggaccaga ggatcaggtg gtacctgctg agcatgggca gcaatgagaa catccacagc   3960
atccacttct ctggccatgt gttcactgtg aggaagaagg aggagtacaa gatggccctg   4020
tacaacctgt accctggggt gtttgagact gtggagatgc tgcccagcaa ggctggcatc   4080
```

```
tggagggtgg agtgcctgat tggggagcac ctgcatgctg gcatgagcac cctgttcctg   4140

gtgtacagca acaagtgcca gaccccccctg ggcatggcct ctggccacat cagggacttc   4200

cagatcactg cctctggcca gtatggccag tgggcccccca agctggccag gctgcactac   4260

tctggcagca tcaatgcctg gagcaccaag gagcccttca gctggatcaa ggtggacctg   4320

ctggccccca tgatcatcca tggcatcaag acccaggggg ccaggcagaa gttcagcagc   4380

ctgtacatca gccagttcat catcatgtac agcctggatg gcaagaagtg gcagacctac   4440

aggggcaaca gcactggcac cctgatggtg ttctttggca atgtggacag ctctggcatc   4500

aagcacaaca tcttcaaccc ccccatcatt gccagataca tcaggctgca ccccacccac   4560

tacagcatca ggagcaccct gaggatggag ctgatgggct gtgacctgaa cagctgcagc   4620

atgcccctgg gcatggagag caaggccatc tctgatgccc agatcactgc cagcagctac   4680

ttcaccaaca tgtttgccac ctggagcccc agcaaggcca ggctgcacct gcagggcagg   4740

agcaatgcct ggaggcccca ggtcaacaac cccaaggagt ggctgcaggt ggacttccag   4800

aagaccatga aggtgactgg ggtgaccacc caggggggtga agagcctgct gaccagcatg   4860

tatgtgaagg agttcctgat cagcagcagc caggatggcc accagtggac cctgttcttc   4920

cagaatggca aggtgaaggt gttccagggc aaccaggaca gcttcacccc tgtggtgaac   4980

agcctggacc ccccccctgct gaccagatac ctgaggattc acccccagag ctgggtgcac   5040

cagattgccc tgaggatgga ggtgctgggc tgtgaggccc aggacctgta ctgacctcga   5100

ggaataaagg aaatttattt tcattgcaat agtgtgttgg ttttttgtgt cacgtggcgg   5160

ccgcaggaac ccctagtgat ggagttggcc actccctctc tgcgcgctcg ctcgctcact   5220

gaggccgggc gaccaaaggt cgcccgacgc ccgggctttg cccgggcggc ctcagtgagc   5280

gagcgagcgc gcagagaggg agtggccaa                                    5309


<210> SEQ ID NO 27
<211> LENGTH: 5532
<212> TYPE: DNA
<213> ORGANISM: Adeno-Associated Virus 2

<400> SEQUENCE: 27

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg    240

gatgttggag gtggcatggg cccagagagg tctctgacct ctgccccagc tccaaggtca    300

gcaggcaggg agggctgtgt gtttgctgtt tgctgcttgc aatgtttgcc cattttaggg    360

acatgagtag gctgaagttt gttcagtgtg gacttcagag gcagcacaca aacagctgct    420

ggaggatggg aactgagggg ttggaagggg gcagggtgag cccagaaact cctgtgtgcc    480

tctgagcctg cagacgcgaa acgtcgactg gacacaggac gctgtggttt ctgagccagg    540

gggcgactca gatcccagcc agtggactta gcccctgttt gctcctccga taactggggt    600

gaccttggtt aatattcacc agcagcctcc cccgttgccc ctctggatcc actgcttaaa    660

tacggacgag gacagggccc tgtctcctca gcttcaggca ccaccactga cctgggacag    720

tgaatcgtaa gtatgccttt cactgcgaga ggttctggag aggcttctga gctccccatg    780

gcccaggcag gcagcaggtc tggggcagga ggggggttgt ggagtgcctt gactcggggc    840
```

```
ctggcccccc catctctgtc ttgcaggaca attgccgtct tctgtctcgt ggggcatcct    900
cctgctggca ggcctgtgct gcctggtccc tgcgatcgcc accatgcaga ttgagctgag    960
cacctgcttc ttcctgtgcc tgctgaggtt ctgcttctct gccaccagga gatactacct   1020
gggggctgtg gagctgagct gggactacat gcagtctgac ctgggggagc tgcctgtgga   1080
tgccaggttc ccccccagag tgcccaagag cttccccttc aacacctctg tggtgtacaa   1140
gaagaccctg tttgtggagt tcactgacca cctgttcaac attgccaagc ccaggccccc   1200
ctggatgggc ctgctgggcc ccaccatcca ggctgaggtg tatgacactg tggtgatcac   1260
cctgaagaac atggccagcc accctgtgag cctgcatgct gtgggggtga gctactggaa   1320
ggcctctgag gggggctgagt atgatgacca gaccagccag agggagaagg aggatgacaa   1380
ggtgttccct gggggcagcc acacctatgt gtggcaggtg ctgaaggaga atggccccat   1440
ggcctctgac cccctgtgcc tgacctacag ctacctgagc catgtggacc tggtgaagga   1500
cctgaactct ggcctgattg gggccctgct ggtgtgcagg gagggcagcc tggccaagga   1560
gaagacccag accctgcaca agttcatcct gctgtttgct gtgtttgatg agggcaagag   1620
ctggcactct gaaaccaaga acagcctgat gcaggacagg gatgctgcct ctgccagggc   1680
ctggcccaag atgcacactg tgaatggcta tgtgaacagg agcctgcctg gcctgattgg   1740
ctgccacagg aagtctgtgt actggcatgt gattggcatg ggcaccaccc ctgaggtgca   1800
cagcatcttc ctggagggcc acaccttcct ggtcaggaac cacaggcagg ccagcctgga   1860
gatcagcccc atcaccttcc tgactgccca gaccctgctg atggacctgg gccagttcct   1920
gctgttctgc cacatcagca gccaccagca tgatggcatg gaggcctatg tgaaggtgga   1980
cagctgccct gaggagcccc agctgaggat gaagaacaat gaggaggctg aggactatga   2040
tgatgacctg actgactctg agatggatgt ggtgaggttt gatgatgaca acagccccag   2100
cttcatccag atcaggtctg tggccaagaa gcaccccaag acctgggtgc actacattgc   2160
tgctgaggag gaggactggg actatgcccc cctggtgctg gcccctgatg acaggagcta   2220
caagagccag tacctgaaca atggccccca gaggattggc aggaagtaca agaaggtcag   2280
gttcatggcc tacactgatg aaaccttcaa gaccagggag gccatccagc atgagtctgg   2340
catcctgggc cccctgctgt atggggaggt gggggacacc ctgctgatca tcttcaagaa   2400
ccaggccagc aggccctaca acatctaccc ccatggcatc actgatgtga ggcccctgta   2460
cagcaggagg ctgcccaagg gggtgaagca cctgaaggac ttccccatcc tgcctgggga   2520
gatcttcaag tacaagtgga ctgtgactgt ggaggatggc cccaccaagt ctgaccccag   2580
gtgcctgacc agatactaca gcagctttgt gaacatggag agggacctgg cctctggcct   2640
gattggcccc ctgctgatct gctacaagga gtctgtggac cagaggggca accagatcat   2700
gtctgacaag aggaatgtga tcctgttctc tgtgtttgat gagaacagga gctggtacct   2760
gactgagaac atccagaggt tcctgcccaa ccctgctggg gtgcagctgg aggaccctga   2820
gttccaggcc agcaacatca tgcacagcat caatggctat gtgtttgaca gcctgcagct   2880
gtctgtgtgc ctgcatgagg tggcctactg gtacatcctg agcattgggg cccagactga   2940
cttcctgtct gtgttcttct ctggctacac cttcaagcac aagatggtgt atgaggacac   3000
cctgaccctg ttccccttct ctggggagac tgtgttcatg agcatggaga accctggcct   3060
gtggattctg ggctgccaca actctgactt caggaacagg ggcatgactg ccctgctgaa   3120
agtctccagc tgtgacaaga acactgggga ctactatgag gacagctatg aggacatctc   3180
tgcctacctg ctgagcaaga acaatgccat tgagcccagg agcttcagcc agaacccccc   3240
```

```
agtgctgaag aggcaccaga gggagatcac caggaccacc ctgcagtctg accaggagga   3300
gattgactat gatgacacca tctctgtgga gatgaagaag gaggactttg acatctacga   3360
cgaggacgag aaccagagcc ccaggagctt ccagaagaag accaggcact acttcattgc   3420
tgctgtggag aggctgtggg actatggcat gagcagcagc ccccatgtgc tgaggaacag   3480
ggcccagtct ggctctgtgc cccagttcaa gaaggtggtg ttccaggagt tcactgatgg   3540
cagcttcacc cagcccctgt acagagggga gctgaatgag cacctgggcc tgctgggccc   3600
ctacatcagg gctgaggtgg aggacaacat catggtgacc ttcaggaacc aggccagcag   3660
gccctacagc ttctacagca gcctgatcag ctatgaggag gaccagaggc aggggggctga   3720
gcccaggaag aactttgtga agcccaatga aaccaagacc tacttctgga aggtgcagca   3780
ccacatggcc cccaccaagg atgagtttga ctgcaaggcc tgggcctact tctctgatgt   3840
ggacctggag aaggatgtgc actctggcct gattggcccc ctgctggtgt gccacaccaa   3900
caccctgaac cctgcccatg gcaggcaggt gactgtgcag gagtttgccc tgttcttcac   3960
catctttgat gaaaccaaga gctggtactt cactgagaac atggagagga actgcagggc   4020
cccctgcaac atccagatgg aggaccccac cttcaaggag aactacaggt tccatgccat   4080
caatggctac atcatggaca ccctgcctgg cctggtgatg gcccaggacc agaggatcag   4140
gtggtacctg ctgagcatgg gcagcaatga gaacatccac agcatccact tctctggcca   4200
tgtgttcact gtgaggaaga aggaggagta caagatggcc ctgtacaacc tgtaccctgg   4260
ggtgtttgag actgtggaga tgctgcccag caaggctggc atctggaggg tggagtgcct   4320
gattggggag cacctgcatg ctggcatgag caccctgttc ctggtgtaca gcaacaagtg   4380
ccagaccccc ctgggcatgg cctctggcca catcagggac ttccagatca ctgcctctgg   4440
ccagtatggc cagtgggccc ccaagctggc caggctgcac tactctggca gcatcaatgc   4500
ctggagcacc aaggagccct tcagctggat caaggtggac ctgctggccc ccatgatcat   4560
ccatggcatc aagacccagg gggccaggca gaagttcagc agcctgtaca tcagccagtt   4620
catcatcatg tacagcctgg atggcaagaa gtggcagacc tacaggggca acagcactgg   4680
caccctgatg gtgttctttg gcaatgtgga cagctctggc atcaagcaca acatcttcaa   4740
ccccccatc attgccagat acatcaggct gcaccccacc cactacagca tcaggagcac   4800
cctgaggatg gagctgatgg gctgtgacct gaacagctgc agcatgcccc tgggcatgga   4860
gagcaaggcc atctctgatg cccagatcac tgccagcagc tacttcacca acatgtttgc   4920
cacctggagc cccagcaagg ccaggctgca cctgcagggc aggagcaatg cctggaggcc   4980
ccaggtcaac aaccccaagg agtggctgca ggtggacttc cagaagacca tgaaggtgac   5040
tggggtgacc acccaggggg tgaagagcct gctgaccagc atgtatgtga aggagttcct   5100
gatcagcagc agccaggatg gccaccagtg gaccctgttc ttccagaatg gcaaggtgaa   5160
ggtgttccag ggcaaccagg acagcttcac ccctgtggtg aacagcctgg accccccct   5220
gctgaccaga tacctgagga ttcaccccca gagctgggtg caccagattg ccctgaggat   5280
ggaggtgctg ggctgtgagg cccaggacct gtactgacct cgaggaataa aggaaattta   5340
ttttcattgc aatagtgtgt tggtttttg tgtcacgtgg cggccgcagg aacccctagt   5400
gatggagttg gccactccct ctctgcgcgc tcgctcgctc actgaggccg ggcgaccaaa   5460
ggtcgcccga cgcccgggct ttgcccgggc ggcctcagtg agcgagcgag cgcgcagaga   5520
gggagtggcc aa                                                      5532
```

<210> SEQ ID NO 28
<211> LENGTH: 5877
<212> TYPE: DNA
<213> ORGANISM: Adeno-Associated Virus 2

<400> SEQUENCE: 28
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgaccc ctctcacact 180
acctaaacca cgccaggaca acctctgctc ctctccaccg aaattccaag ggtcgagtg 240 gatgttggag gtggcatggg cccagagagg tctctgacct ctgccccagc tccaaggtca 300
gcaggcaggg agggctgtgt gtttgctgtt tgctgcttgc aatgtttgcc cattttaggg 360
acatgagtag gctgaagttt gttcagtgtg gacttcagag gcagcacaca aacagctgct 420
ggaggatggg aactgagggg ttggaagggg gcagggtgag cccagaaact cctgtgtgcc 480
tctgagcctg cagacgcgaa acgtcgacag gttaattttt aaaaagcagt caaaagtcca 540
agtggccctt ggcagcattt actctctctg tttgctctgg ttaataatct caggagcaca 600
aacattcctg gaggcaggag aagaaatcaa catcctggac ttatcctctg ggcctctccc 660
cacccccagg agaggctcag gttaattttt aaaaagcagt caaaagtcca agtggccctt 720
ggcagcattt actctctctg tttgctctgg ttaataatct caggagcaca aacattcctg 780
gaggcaggag aagaaatcaa catcctggac ttatcctctg ggcctctccc cacccccagg 840
agaggctgtc gactggacac aggacgctgt ggtttctgag ccagggggcg actcagatcc 900
cagccagtgg acttagcccc tgtttgctcc tccgataact ggggtgacct tggttaatat 960
tcaccagcag cctcccccgt tgcccctctg gatccactgc ttaaatacgg acgaggacag 1020
ggccctgtct cctcagcttc aggcaccacc actgacctgg gacagtgaat cgtaagtatg 1080
cctttcactg cgagaggttc tggagaggct tctgagctcc ccatggccca ggcaggcagc 1140
aggtctgggg caggaggggg gttgtggagt gccttgactc ggggcctggc ccccccatct 1200
ctgtcttgca ggacaattgc cgtcttctgt ctcgtggggc atcctcctgc tggcaggcct 1260
gtgctgcctg gtccctgcga tcgccaccat gcagattgag ctgagcacct gcttcttcct 1320
gtgcctgctg aggttctgct tctctgccac caggagatac tacctggggg ctgtggagct 1380
gagctgggac tacatgcagt ctgacctggg ggagctgcct gtggatgcca ggttcccccc 1440
cagagtgccc aagagcttcc ccttcaacac ctctgtggtg tacaagaaga ccctgtttgt 1500
ggagttcact gaccacctgt tcaacattgc caagcccagg ccccccctgga tgggcctgct 1560 gggccccacc atccaggctg aggtgtatga cactgtggtg atcaccctga agaacatggc 1620
cagccaccct gtgagcctgc atgctgtggg ggtgagctac tggaaggcct ctgagggggc 1680
tgagtatgat gaccagacca gccagaggga gaaggaggat gacaaggtgt tccctggggg 1740
cagccacacc tatgtgtggc aggtgctgaa ggagaatggc cccatggcct ctgacccccct 1800 gtgcctgacc tacagctacc tgagccatgt ggacctggtg aaggacctga actctggcct 1860
gattggggcc ctgctggtgt gcagggaggg cagcctggcc aaggagaaga cccagaccct 1920
gcacaagttc atcctgctgt ttgctgtgtt tgatgagggc aagagctggc actctgaaac 1980
caagaacagc ctgatgcagg acagggatgc tgcctctgcc agggcctggc ccaagatgca 2040
cactgtgaat ggctatgtga acaggagcct gcctggcctg attggctgcc acaggaagtc 2100
tgtgtactgg catgtgattg gcatgggcac cacccctgag gtgcacagca tcttcctgga 2160

-continued

```
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggccccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gccccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac cccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
tgtgcactct ggcctgattg gccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggccccct gcaacatcca   4380
gatggaggac cccaccttca aggagaacta caggttccat gccatcaatg gctacatcat   4440
ggacaccctg cctggcctgg tgatggccca ggaccagagg atcaggtggt acctgctgag   4500
```

```
catgggcagc aatgagaaca tccacagcat ccacttctct ggccatgtgt tcactgtgag   4560
gaagaaggag gagtacaaga tggccctgta caacctgtac cctggggtgt ttgagactgt   4620
ggagatgctg cccagcaagg ctggcatctg gagggtggag tgcctgattg gggagcacct   4680
gcatgctggc atgagcaccc tgttcctggt gtacagcaac aagtgccaga ccccccctggg   4740
catggcctct ggccacatca gggacttcca gatcactgcc tctggccagt atggccagtg   4800
ggcccccaag ctggccaggc tgcactactc tggcagcatc aatgcctgga gcaccaagga   4860
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggacccc cccctgctga ccagatacct   5580
gaggattcac ccccagagct gggtgcacca gattgccctg aggatggagg tgctgggctg   5640
tgaggcccag gacctgtact gacctcgagg aataaaggaa atttattttc attgcaatag   5700
tgtgttggtt ttttgtgtca cgtggcggcc gcaggaaccc ctagtgatgg agttggccac   5760
tccctctctg cgcgctcgct cgctcactga ggccgggcga ccaaaggtcg cccgacgccc   5820
gggctttgcc cgggcggcct cagtgagcga gcgagcgcgc agagagggag tggccaa      5877
```

<210> SEQ ID NO 29
<211> LENGTH: 6054
<212> TYPE: DNA
<213> ORGANISM: Adeno-Associated Virus 2

<400> SEQUENCE: 29

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg     240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540
agtggccctt ggcagcattt actctctctg tttgctctgg ttaataatct caggagcaca    600
aacattcctg gaggcaggag aagaaatcaa catcctggac ttatcctctg ggcctctccc    660
cacccccagg agaggctcag gttaattttt aaaaagcagt caaaagtcca agtggccctt    720
ggcagcattt actctctctg tttgctctgg ttaataatct caggagcaca aacattcctg    780
```

```
gaggcaggag aagaaatcaa catcctggac ttatcctctg ggcctctccc cacccccagg    840
agaggctgtc gactggacac aggacgctgt ggtttctgag ccagggggcg actcagatcc    900
cagccagtgg acttagcccc tgtttgctcc tccgataact ggggtgacct tggttaatat    960
tcaccagcag cctcccccgt tgcccctctg gatccactgc ttaaatacgg acgaggacag   1020
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc ccccccatct   1200
ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccccctgga tgggcctgct   1560
gggccccacc atccaggctg aggtgtatga cactgtggtg atcaccctga agaacatggc   1620
cagccaccct gtgagcctgc atgctgtggg ggtgagctac tggaaggcct ctgagggggc   1680
tgagtatgat gaccagacca gccagaggga gaaggaggat gacaaggtgt tccctggggg   1740
cagccacacc tatgtgtggc aggtgctgaa ggagaatggc cccatggcct ctgacccccct   1800
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac cacccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggcccccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gcccccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
```

```
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac cccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
tgtgcactct ggcctgattg gccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggccccct gcaacatcca   4380
gatggaggac cccaccttca aggagaacta caggttccat gccatcaatg gctacatcat   4440
ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggccctgta caacctgtac cctggggtgt ttgagactgt   4620
ggagatgctg cccagcaagg ctggcatctg gagggtggag tgcctgattg gggagcacct   4680
gcatgctggc atgagcaccc tgttcctggt gtacagcaac aagtgccaga ccccccctggg   4740
catggcctct ggccacatca gggacttcca gatcactgcc tctggccagt atggccagtg   4800
ggcccccaag ctggccaggc tgcactactc tggcagcatc aatgcctgga gcaccaagga   4860
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
```

```
ccaggacagc ttcacccctg tggtgaacag cctggacccc cccctgctga ccagatacct   5580
gaggattcac ccccagagct gggtgcacca gattgccctg aggatggagg tgctgggctg   5640
tgaggcccag gacctgtact gacctcgagg tgtgccttct agttgccagc catctgttgt   5700
ttgcccctcc cccgtgcctt ccttgaccct ggaaggtgcc actcccactg tcctttccta   5760
ataaaatgag gaaattgcat cgcattgtct gagtaggtgt cattctattc tggggggtgg   5820
ggtggggcag gacagcaagg gggaggattg ggaagacaat agcaggcatg ctggggatgc   5880
ggtgggctct atgggcacgt ggcggccgca ggaaccccta gtgatggagt tggccactcc   5940
ctctctgcgc gctcgctcgc tcactgaggc cgggcgacca aaggtcgccc gacgcccggg   6000
ctttgcccgg gcggcctcag tgagcgagcg agcgcgcaga gagggagtgg ccaa         6054
```

<210> SEQ ID NO 30
<211> LENGTH: 6054
<212> TYPE: DNA
<213> ORGANISM: Adeno-Associated Virus 2

<400> SEQUENCE: 30

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg     240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgaagc ctctcctggg ggtggggaga ggcccagagg    540
ataagtccag gatgttgatt tcttctcctg cctccaggaa tgtttgtgct cctgagatta    600
ttaaccagag caaacagaga gagtaaatgc tgccaagggc cacttggact tttgactgct    660
ttttaaaaat taacctgagc ctctcctggg ggtggggaga ggcccagagg ataagtccag    720
gatgttgatt tcttctcctg cctccaggaa tgtttgtgct cctgagatta ttaaccagag    780
caaacagaga gagtaaatgc tgccaagggc cacttggact tttgactgct ttttaaaaat    840
taacctggtc gactggacac aggacgctgt ggtttctgag ccagggggcg actcagatcc    900
cagccagtgg acttagcccc tgtttgctcc tccgataact ggggtgacct tggttaatat    960
tcaccagcag cctcccccgt tgcccctctg gatccactgc ttaaatacgg acgaggacag   1020
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc ccccccatct   1200
ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccccctgga tgggcctgct  1560
```

```
gggccccacc atccaggctg aggtgtatga cactgtggtg atcaccctga agaacatggc   1620
cagccaccct gtgagcctgc atgctgtggg ggtgagctac tggaaggcct ctgagggggc   1680
tgagtatgat gaccagacca gccagaggga gaaggaggat gacaaggtgt tccctggggg   1740
cagccacacc tatgtgtggc aggtgctgaa ggagaatggc cccatggcct ctgacccccct  1800
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac caccccctgag gtgcacagca tcttcctgga  2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc ccccagcttca tccagatcag  2460
gtctgtggcc aagaagcacc ccaagacctg ggtgcactac attgctgctg aggaggagga   2520
ctgggactat gccccccctgg tgctggcccc tgatgacagg agctacaaga gccagtacct  2580
gaacaatggc ccccagagga ttggcaggaa gtacaagaag gtcaggttca tggcctacac   2640
tgatgaaacc ttcaagacca gggaggccat ccagcatgag tctggcatcc tgggcccccct  2700
gctgtatggg gaggtggggg acaccctgct gatcatcttc aagaaccagg ccagcaggcc   2760
ctacaacatc taccccccatg gcatcactga tgtgaggccc ctgtacagca ggaggctgcc  2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gcccccctgct  3000
gatctgctac aaggagtctg tggaccagag ggcaaccag atcatgtctg acaagaggaa    3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac cccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
```

```
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
tgtgcactct ggcctgattg gcccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggccccct gcaacatcca   4380
gatggaggac cccaccttca aggagaacta caggttccat gccatcaatg gctacatcat   4440
ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggccctgta caacctgtac cctggggtgt ttgagactgt   4620
ggagatgctg cccagcaagg ctggcatctg gagggtggag tgcctgattg gggagcacct   4680
gcatgctggc atgagcaccc tgttcctggt gtacagcaac aagtgccaga ccccccctggg   4740
catggcctct ggccacatca gggacttcca gatcactgcc tctggccagt atggccagtg   4800
ggcccccaag ctggccaggc tgcactactc tggcagcatc aatgcctgga gcaccaagga   4860
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggacccc cccctgctga ccagatacct   5580
gaggattcac ccccagagct gggtgcacca gattgccctg aggatggagg tgctgggctg   5640
tgaggcccag gacctgtact gacctcgagg tgtgccttct agttgccagc catctgttgt   5700
ttgcccctcc cccgtgcctt ccttgaccct ggaaggtgcc actcccactg tcctttccta   5760
ataaaatgag gaaattgcat cgcattgtct gagtaggtgt cattctattc tggggggtgg   5820
ggtggggcag gacagcaagg gggaggattg ggaagacaat agcaggcatg ctggggatgc   5880
ggtgggctct atgggcacgt ggcggccgca ggaaccccta gtgatggagt tggccactcc   5940
ctctctgcgc gctcgctcgc tcactgaggc cgggcgacca aaggtcgccc gacgcccggg   6000
ctttgcccgg gcggcctcag tgagcgagcg agcgcgcaga gagggagtgg ccaa         6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccccctgga tgggcctgct gggccccacc   1020
atccaggctg aggtgtatga cactgtggtg atcaccctga agaacatggc cagccaccct   1080
gtgagcctgc atgctgtggg ggtgagctac tggaaggcct ctgagggggc tgagtatgat   1140
gaccagacca gccagaggga gaaggaggat gacaaggtgt tccctggggg cagccacacc   1200
tatgtgtggc aggtgctgaa ggagaatggc cccatggcct ctgacccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggccccct gctgtatggg   2160
gaggtggggg acaccctgct gatcatcttc aagaaccagg ccagcaggcc ctacaacatc   2220
taccccatg gcatcactga tgtgaggccc ctgtacagca ggaggctgcc caagggggtg   2280
```

```
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gcccccctgct gatctgctac  2460
aaggagtctg tggaccagag ggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
tacaccttca agcacaagat ggtgtatgag gacaccctga ccctgttccc cttctctggg   2820
gagactgtgt tcatgagcat ggagaaccct ggcctgtgga ttctgggctg ccacaactct   2880
gacttcagga acaggggcat gactgccctg ctgaaagtct ccagctgtga caagaacact   2940
ggggactact atgaggacag ctatgaggac atctctgcct acctgctgag caagaacaat   3000
gccattgagc ccaggagctt cagccagaac cccccagtgc tgaagaggca ccagagggag   3060
atcaccagga ccaccctgca gtctgaccag gaggagattg actatgatga caccatctct   3120
gtggagatga agaaggagga ctttgacatc tacgacgagg acgagaacca gagccccagg   3180
agcttccaga agaagaccag gcactacttc attgctgctg tggagaggct gtgggactat   3240
ggcatgagca gcagccccca tgtgctgagg aacagggccc agtctggctc tgtgccccag   3300
ttcaagaagg tggtgttcca ggagttcact gatggcagct tcacccagcc cctgtacaga   3360
ggggagctga atgagcacct gggcctgctg ggcccctaca tcagggctga ggtggaggac   3420
aacatcatgg tgaccttcag gaaccaggcc agcaggccct acagcttcta cagcagcctg   3480
atcagctatg aggaggacca gaggcagggg gctgagccca ggaagaactt tgtgaagccc   3540
aatgaaacca agacctactt ctggaaggtg cagcaccaca tggcccccac caaggatgag   3600
tttgactgca aggcctgggc ctacttctct gatgtggacc tggagaagga tgtgcactct   3660
ggcctgattg gcccccctgct ggtgtgccac accaacaccc tgaaccctgc ccatggcagg  3720
caggtgactg tgcaggagtt tgccctgttc ttcaccatct ttgatgaaac caagagctgg   3780
tacttcactg agaacatgga gaggaactgc agggccccct gcaacatcca gatggaggac   3840
cccaccttca aggagaacta caggttccat gccatcaatg gctacatcat ggacaccctg   3900
cctggcctgg tgatggccca ggaccagagg atcaggtggt acctgctgag catgggcagc   3960
aatgagaaca tccacagcat ccacttctct ggccatgtgt tcactgtgag gaagaaggag   4020
gagtacaaga tggccctgta caacctgtac cctggggtgt ttgagactgt ggagatgctg   4080
cccagcaagg ctggcatctg gagggtggag tgcctgattg gggagcacct gcatgctggc   4140
atgagcaccc tgttcctggt gtacagcaac aagtgccaga cccccctggg catggcctct   4200
ggccacatca gggacttcca gatcactgcc tctggccagt atggccagtg ggcccccaag   4260
ctggccaggc tgcactactc tggcagcatc aatgcctgga gcaccaagga gcccttcagc   4320
tggatcaagg tggacctgct ggcccccatg atcatccatg gcatcaagac ccagggggcc   4380
aggcagaagt tcagcagcct gtacatcagc cagttcatca tcatgtacag cctggatggc   4440
aagaagtggc agacctacag gggcaacagc actggcaccc tgatggtgtt ctttggcaat   4500
gtggacagct ctggcatcaa gcacaacatc ttcaaccccc ccatcattgc cagatacatc   4560
aggctgcacc ccacccacta cagcatcagg agcaccctga ggatggagct gatgggctgt   4620
gacctgaaca gctgcagcat gcccctgggc atggagagca aggccatctc tgatgcccag   4680
```

atcactgcca gcagctactt caccaacatg tttgccacct ggagccccag caaggccagg 4740
ctgcacctgc agggcaggag caatgcctgg aggccccagg tcaacaaccc caaggagtgg 4800
ctgcaggtgg acttccagaa gaccatgaag gtgactgggg tgaccaccca gggggtgaag 4860
agcctgctga ccagcatgta tgtgaaggag ttcctgatca gcagcagcca ggatggccac 4920
cagtggaccc tgttcttcca gaatggcaag gtgaaggtgt tccagggcaa ccaggacagc 4980
ttcacccctg tggtgaacag cctggacccc cccctgctga ccagatacct gaggattcac 5040
ccccagagct gggtgcacca gattgccctg aggatggagg tgctgggctg tgaggcccag 5100
gacctgtact gacctcgagg tgtgccttct agttgccagc catctgttgt ttgcccctcc 5160
cccgtgcctt ccttgaccct ggaaggtgcc actcccactg tcctttccta ataaaatgag 5220
gaaattgcat cgcattgtct gagtaggtgt cattctattc tggggggtgg ggtggggcag 5280
gacagcaagg gggaggattg ggaagacaat agcaggcatg ctggggatgc ggtgggctct 5340
atgggcacgt ggcggccgca ggaacccta gtgatggagt tggccactcc ctctctgcgc 5400
gctcgctcgc tcactgaggc cgggcgacca aaggtcgccc gacgcccggg ctttgcccgg 5460
gcggcctcag tgagcgagcg agcgcgcaga gagggagtgg ccaa 5504

<210> SEQ ID NO 32
<211> LENGTH: 5507
<212> TYPE: DNA
<213> ORGANISM: Adeno-Associated Virus 2

<400> SEQUENCE: 32
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgaccc ctctcacact 180
acctaaacca cgccaggaca acctctgctc ctctccaccg aaattccaag ggtcgagtg 240 gatgttggag gtggcatggg cccagagagg tctctgacct ctgccccagc tccaaggtca 300
gcaggcaggg agggctgtgt gtttgctgtt tgctgcttgc aatgtttgcc cattttaggg 360
acatgagtag gctgaagttt gttcagtgtg gacttcagag gcagcacaca aacagctgct 420
ggaggatggg aactgagggg ttggaagggg gcagggtgag cccagaaact cctgtgtgcc 480
tctgagcctg cagacgcgaa acgtcgacga tcttgctacc agtggaacag ccactaagga 540
ttctgcagtg agagcagagg gccagctaag tggtactctc ccagagactg tctgactcac 600 gccacccct ccaccttgga cacaggacgc tgtggtttct gagccaggta caatgactcc 660
tttcggtaag tgcagtggaa gctgtacact gcccaggcaa agcgtccggg cagcgtaggc 720
gggcgactca gatcccagcc agtggactta gcccctgttt gctcctccga taactggggt 780
gaccttggtt aatattcacc agcagcctcc cccgttgccc ctctggatcc actgcttaaa 840
tacggacgag gacagggccc tgtctcctca gcttcaggca ccaccactga cctgggacag 900
tgaatcgcga tcgccaccat gcagattgag ctgagcacct gcttcttcct gtgcctgctg 960
aggttctgct tctctgccac caggagatac tacctggggg ctgtggagct gagctgggac 1020
tacatgcagt ctgacctggg ggagctgcct gtggatgcca ggttcccccc cagagtgccc 1080
aagagcttcc ccttcaacac ctctgtggtg tacaagaaga ccctgtttgt ggagttcact 1140
gaccacctgt tcaacattgc caagcccagg ccccccctgga tgggcctgct gggccccacc 1200
atccaggctg aggtgtatga cactgtggtg atcaccctga agaacatggc cagccaccct 1260

-continued

```
gtgagcctgc atgctgtggg ggtgagctac tggaaggcct ctgagggggc tgagtatgat   1320
gaccagacca gccagaggga gaaggaggat gacaaggtgt tccctggggg cagccacacc   1380
tatgtgtggc aggtgctgaa ggagaatggc cccatggcct ctgacccccct gtgcctgacc   1440
tacagctacc tgagccatgt ggacctggtg aaggacctga actctggcct gattggggcc   1500
ctgctggtgt gcagggaggg cagcctggcc aaggagaaga cccagaccct gcacaagttc   1560
atcctgctgt ttgctgtgtt tgatgagggc aagagctggc actctgaaac caagaacagc   1620
ctgatgcagg acagggatgc tgcctctgcc agggcctggc ccaagatgca cactgtgaat   1680
ggctatgtga acaggagcct gcctggcctg attggctgcc acaggaagtc tgtgtactgg   1740
catgtgattg gcatgggcac cacccctgag gtgcacagca tcttcctgga gggccacacc   1800
ttcctggtca ggaaccacag gcaggccagc ctggagatca gccccatcac cttcctgact   1860
gcccagaccc tgctgatgga cctgggccag ttcctgctgt tctgccacat cagcagccac   1920
cagcatgatg gcatggaggc ctatgtgaag gtggacagct gccctgagga gccccagctg   1980
aggatgaaga acaatgagga ggctgaggac tatgatgatg acctgactga ctctgagatg   2040
gatgtggtga ggtttgatga tgacaacagc cccagcttca tccagatcag gtctgtggcc   2100
aagaagcacc ccaagacctg ggtgcactac attgctgctg aggaggagga ctgggactat   2160
gcccccctgg tgctggcccc tgatgacagg agctacaaga gccagtacct gaacaatggc   2220
ccccagagga ttggcaggaa gtacaagaag gtcaggttca tggcctacac tgatgaaacc   2280
ttcaagacca gggaggccat ccagcatgag tctggcatcc tgggcccccct gctgtatggg   2340
gaggtggggg acaccctgct gatcatcttc aagaaccagg ccagcaggcc ctacaacatc   2400
tacccccatg gcatcactga tgtgaggccc ctgtacagca ggaggctgcc caagggggtg   2460
aagcacctga aggacttccc catcctgcct ggggagatct tcaagtacaa gtggactgtg   2520
actgtggagg atggccccac caagtctgac cccaggtgcc tgaccagata ctacagcagc   2580
tttgtgaaca tggagaggga cctggcctct ggcctgattg gcccccctgct gatctgctac   2640
aaggagtctg tggaccagag ggcaaccag atcatgtctg acaagaggaa tgtgatcctg   2700
ttctctgtgt ttgatgagaa caggagctgg tacctgactg agaacatcca gaggttcctg   2760
cccaaccctg ctggggtgca gctggaggac cctgagttcc aggccagcaa catcatgcac   2820
agcatcaatg gctatgtgtt tgacagcctg cagctgtctg tgtgcctgca tgaggtggcc   2880
tactggtaca tcctgagcat tggggcccag actgacttcc tgtctgtgtt cttctctggc   2940
tacaccttca agcacaagat ggtgtatgag gacaccctga ccctgttccc cttctctggg   3000
gagactgtgt tcatgagcat ggagaaccct ggcctgtgga ttctgggctg ccacaactct   3060
gacttcagga acaggggcat gactgccctg ctgaaagtct ccagctgtga caagaacact   3120
ggggactact atgaggacag ctatgaggac atctctgcct acctgctgag caagaacaat   3180
gccattgagc ccaggagctt cagccagaac cccccagtgc tgaagaggca ccagagggag   3240
atcaccagga ccaccctgca gtctgaccag gaggagattg actatgatga caccatctct   3300
gtggagatga agaaggagga ctttgacatc tacgacgagg acgagaacca gagccccagg   3360
agcttccaga agaagaccag gcactacttc attgctgctg tggagaggct gtgggactat   3420
ggcatgagca gcagcccccca tgtgctgagg aacagggccc agtctggctc tgtgccccag   3480
ttcaagaagg tggtgttcca ggagttcact gatggcagct tcacccagcc cctgtacaga   3540
ggggagctga atgagcacct gggcctgctg ggcccctaca tcagggctga ggtggaggac   3600
aacatcatgg tgaccttcag gaaccaggcc agcaggccct acagcttcta cagcagcctg   3660
```

```
atcagctatg aggaggacca gaggcagggg gctgagccca ggaagaactt tgtgaagccc   3720
aatgaaacca agacctactt ctggaaggtg cagcaccaca tggcccccac caaggatgag   3780
tttgactgca aggcctgggc ctacttctct gatgtggacc tggagaagga tgtgcactct   3840
ggcctgattg gcccctgct ggtgtgccac accaacaccc tgaaccctgc ccatggcagg   3900
caggtgactg tgcaggagtt tgccctgttc ttcaccatct ttgatgaaac caagagctgg   3960
tacttcactg agaacatgga gaggaactgc agggcccct gcaacatcca gatggaggac   4020
cccaccttca aggagaacta caggttccat gccatcaatg gctacatcat ggacaccctg   4080
cctggcctgg tgatggccca ggaccagagg atcaggtggt acctgctgag catgggcagc   4140
aatgagaaca tccacagcat ccacttctct ggccatgtgt tcactgtgag gaagaaggag   4200
gagtacaaga tggccctgta caacctgtac cctggggtgt ttgagactgt ggagatgctg   4260
cccagcaagg ctggcatctg gagggtggag tgcctgattg gggagcacct gcatgctggc   4320
atgagcaccc tgttcctggt gtacagcaac aagtgccaga cccccctggg catggcctct   4380
ggccacatca gggacttcca gatcactgcc tctggccagt atggccagtg ggcccccaag   4440
ctggccaggc tgcactactc tggcagcatc aatgcctgga gcaccaagga gcccttcagc   4500
tggatcaagg tggacctgct ggcccccatg atcatccatg gcatcaagac ccaggggggcc   4560
aggcagaagt tcagcagcct gtacatcagc cagttcatca tcatgtacag cctggatggc   4620
aagaagtggc agacctacag gggcaacagc actggcaccc tgatggtgtt ctttggcaat   4680
gtggacagct ctggcatcaa gcacaacatc ttcaaccccc ccatcattgc cagatacatc   4740
aggctgcacc ccacccacta cagcatcagg agcaccctga ggatggagct gatgggctgt   4800
gacctgaaca gctgcagcat gcccctgggc atggagagca aggccatctc tgatgcccag   4860
atcactgcca gcagctactt caccaacatg tttgccacct ggagccccag caaggccagg   4920
ctgcacctgc agggcaggag caatgcctgg aggccccagg tcaacaaccc caaggagtgg   4980
ctgcaggtgg acttccagaa gaccatgaag gtgactgggg tgaccaccca gggggtgaag   5040
agcctgctga ccagcatgta tgtgaaggag ttcctgatca gcagcagcca ggatggccac   5100
cagtggaccc tgttcttcca gaatggcaag gtgaaggtgt tccagggcaa ccaggacagc   5160
ttcacccctg tggtgaacag cctggacccc cccctgctga ccagatacct gaggattcac   5220
ccccagagct gggtgcacca gattgccctg aggatggagg tgctgggctg tgaggcccag   5280
gacctgtact gacctcgagg aataaaggaa atttattttc attgcaatag tgtgttggtt   5340
ttttgtgtca cgtggcggcc gcaggaaccc ctagtgatgg agttggccac tccctctctg   5400
cgcgctcgct cgctcactga ggccgggcga ccaaaggtcg cccgacgccc gggctttgcc   5460
cgggcggcct cagtgagcga gcgagcgcgc agagagggag tggccaa                   5507
```

<210> SEQ ID NO 33
<211> LENGTH: 5311
<212> TYPE: DNA
<213> ORGANISM: Adeno-Associated Virus 2

<400> SEQUENCE: 33

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacgc agagaggtct    180
ctgacctctg ccccagctcc aaggtcagca ggcagggagg gctgtgtgtt tgctgtttgc    240
```

-continued

```
tgcttgcaat gtttgcccat tttagggaca tgagtaggct gaagtttgtt cagtgtggac    300
ttcagaggca gcacacaaac agccagagag gtctctgacc tctgccccag ctccaaggtc    360
agcaggcagg gagggctgtg tgtttgctgt ttgctgcttg caatgtttgc ccattttagg    420
gacatgagta ggctgaagtt tgttcagtgt ggacttcaga ggcagcacac aaacagcacg    480
cgaaacgtcg actggacaca ggacgctgtg gtttctgagc caggggcga ctcagatccc    540
agccagtgga cttagcccct gtttgctcct ccgataactg ggtgaccttt ggttaatatt    600
caccagcagc ctcccccgtt gcccctctgg atccactgct taaatacgga cgaggacagg    660
gccctgtctc ctcagcttca ggcaccacca ctgacctggg acagtgaatc gcgatcgcca    720
ccatgcagat tgagctgagc acctgcttct tcctgtgcct gctgaggttc tgcttctctg    780
ccaccaggag atactacctg gggctgtgg agctgagctg ggactacatg cagtctgacc    840
tgggggagct gcctgtggat gccaggttcc cccccagagt gcccaagagc ttccccttca    900
acacctctgt ggtgtacaag aagaccctgt ttgtggagtt cactgaccac ctgttcaaca    960
ttgccaagcc caggcccccc tggatgggcc tgctgggccc caccatccag gctgaggtgt   1020
atgacactgt ggtgatcacc ctgaagaaca tggccagcca ccctgtgagc ctgcatgctg   1080
tgggggtgag ctactggaag gcctctgagg gggctgagta tgatgaccag accagccaga   1140
gggagaagga ggatgacaag gtgttccctg gggcagcca cacctatgtg tggcaggtgc   1200
tgaaggagaa tggccccatg gcctctgacc ccctgtgcct gacctacagc tacctgagcc   1260
atgtggacct ggtgaaggac ctgaactctg gcctgattgg ggccctgctg gtgtgcaggg   1320
agggcagcct ggccaaggag aagacccaga ccctgcacaa gttcatcctg ctgtttgctg   1380
tgtttgatga gggcaagagc tggcactctg aaaccaagaa cagcctgatg caggacaggg   1440
atgctgcctc tgccagggcc tggcccaaga tgcacactgt gaatggctat gtgaacagga   1500
gcctgcctgg cctgattggc tgccacagga agtctgtgta ctggcatgtg attggcatgg   1560
gcaccacccc tgaggtgcac agcatcttcc tggagggcca caccttcctg gtcaggaacc   1620
acaggcaggc cagcctggag atcagcccca tcaccttcct gactgcccag accctgctga   1680
tggacctggg ccagttcctg ctgttctgcc acatcagcag ccaccagcat gatggcatgg   1740
aggcctatgt gaaggtggac agctgccctg aggagcccca gctgaggatg aagaacaatg   1800
aggaggctga ggactatgat gatgacctga ctgactctga gatggatgtg gtgaggtttg   1860
atgatgacaa cagccccagc ttcatccaga tcaggtctgt ggccaagaag caccccaaga   1920
cctgggtgca ctacattgct gctgaggagg aggactggga ctatgccccc ctggtgctgg   1980
cccctgatga caggagctac aagagccagt acctgaacaa tggcccccag aggattggca   2040
ggaagtacaa gaaggtcagg ttcatggcct acactgatga aaccttcaag accagggagg   2100
ccatccagca tgagtctggc atcctgggcc ccctgctgta tggggaggtg ggggacaccc   2160
tgctgatcat cttcaagaac caggccagca ggccctacaa catctacccc catggcatca   2220
ctgatgtgag gcccctgtac agcaggaggc tgcccaaggg ggtgaagcac ctgaaggact   2280
tccccatcct gcctggggag atcttcaagt acaagtggac tgtgactgtg gaggatggcc   2340
ccaccaagtc tgaccccagg tgcctgacca gatactacag cagctttgtg aacatggaga   2400
gggacctggc ctctggcctg attggccccc tgctgatctg ctacaaggag tctgtggacc   2460
agaggggcaa ccagatcatg tctgacaaga ggaatgtgat cctgttctct gtgtttgatg   2520
agaacaggag ctggtacctg actgagaaca tccagaggtt cctgcccaac cctgctgggg   2580
tgcagctgga ggaccctgag ttccaggcca gcaacatcat gcacagcatc aatggctatg   2640
```

```
tgtttgacag cctgcagctg tctgtgtgcc tgcatgaggt ggcctactgg tacatcctga   2700
gcattggggc ccagactgac ttcctgtctg tgttcttctc tggctacacc ttcaagcaca   2760
agatggtgta tgaggacacc ctgaccctgt tccccttctc tggggagact gtgttcatga   2820
gcatggagaa ccctggcctg tggattctgg gctgccacaa ctctgacttc aggaacaggg   2880
gcatgactgc cctgctgaaa gtctccagct gtgacaagaa cactggggac tactatgagg   2940
acagctatga ggacatctct gcctacctgc tgagcaagaa caatgccatt gagcccagga   3000
gcttcagcca gaacccccca gtgctgaaga ggcaccagag ggagatcacc aggaccaccc   3060
tgcagtctga ccaggaggag attgactatg atgacaccat ctctgtggag atgaagaagg   3120
aggactttga catctacgac gaggacgaga accagagccc caggagcttc cagaagaaga   3180
ccaggcacta cttcattgct gctgtggaga ggctgtggga ctatggcatg agcagcagcc   3240
cccatgtgct gaggaacagg gcccagtctg gctctgtgcc ccagttcaag aaggtggtgt   3300
tccaggagtt cactgatggc agcttcaccc agcccctgta cagaggggag ctgaatgagc   3360
acctgggcct gctgggcccc tacatcaggg ctgaggtgga ggacaacatc atggtgacct   3420
tcaggaacca ggccagcagg ccctacagct tctacagcag cctgatcagc tatgaggagg   3480
accagaggca gggggctgag cccaggaaga actttgtgaa gcccaatgaa accaagacct   3540
acttctggaa ggtgcagcac cacatggccc ccaccaagga tgagtttgac tgcaaggcct   3600
gggcctactt ctctgatgtg gacctggaga aggatgtgca ctctggcctg attggccccc   3660
tgctggtgtg ccacaccaac accctgaacc ctgcccatgg caggcaggtg actgtgcagg   3720
agtttgccct gttcttcacc atctttgatg aaaccaagag ctggtacttc actgagaaca   3780
tggagaggaa ctgcagggcc ccctgcaaca tccagatgga ggaccccacc ttcaaggaga   3840
actacaggtt ccatgccatc aatggctaca tcatggacac cctgcctggc ctggtgatgg   3900
cccaggacca gaggatcagg tggtacctgc tgagcatggg cagcaatgag aacatccaca   3960
gcatccactt ctctggccat gtgttcactg tgaggaagaa ggaggagtac aagatggccc   4020
tgtacaacct gtaccctggg gtgtttgaga ctgtggagat gctgcccagc aaggctggca   4080
tctggagggt ggagtgcctg attggggagc acctgcatgc tggcatgagc accctgttcc   4140
tggtgtacag caacaagtgc cagacccccc tgggcatggc ctctggccac atcagggact   4200
tccagatcac tgcctctggc cagtatggcc agtgggcccc caagctggcc aggctgcact   4260
actctggcag catcaatgcc tggagcacca aggagccctt cagctggatc aaggtggacc   4320
tgctggcccc catgatcatc catggcatca agacccaggg ggccaggcag aagttcagca   4380
gcctgtacat cagccagttc atcatcatgt acagcctgga tggcaagaag tggcagacct   4440
acaggggcaa cagcactggc accctgatgg tgttctttgg caatgtggac agctctggca   4500
tcaagcacaa catcttcaac ccccccatca ttgccagata catcaggctg caccccaccc   4560
actacagcat caggagcacc ctgaggatgg agctgatggg ctgtgacctg aacagctgca   4620
gcatgcccct gggcatggag agcaaggcca tctctgatgc ccagatcact gccagcagct   4680
acttcaccaa catgtttgcc acctggagcc ccagcaaggc caggctgcac ctgcagggca   4740
ggagcaatgc ctggaggccc caggtcaaca accccaagga gtggctgcag gtggacttcc   4800
agaagaccat gaaggtgact ggggtgacca cccagggggt gaagagcctg ctgaccagca   4860
tgtatgtgaa ggagttcctg atcagcagca gccaggatgg ccaccagtgg accctgttct   4920
tccagaatgg caaggtgaag gtgttccagg gcaaccagga cagcttcacc cctgtggtga   4980
```

```
acagcctgga cccccccctg ctgaccagat acctgaggat tcacccccag agctgggtgc   5040

accagattgc cctgaggatg gaggtgctgg gctgtgaggc ccaggacctg tactgacctc   5100

gaggaataaa ggaaatttat tttcattgca atagtgtgtt ggtttttttgt gtcacgtggc   5160

ggccgcagga acccctagtg atggagttgg ccactccctc tctgcgcgct cgctcgctca   5220

ctgaggccgg gcgaccaaag gtcgcccgac gcccgggctt tgcccgggcg gcctcagtga   5280

gcgagcgagc gcgcagagag ggagtggcca a                                  5311
```

<210> SEQ ID NO 34
<211> LENGTH: 5156
<212> TYPE: DNA
<213> ORGANISM: Adeno-Associated Virus 2

<400> SEQUENCE: 34

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgacca gagaggtctc    180

tgacctctgc ccagctccca aggtcagcag gcagggaggg ctgtgtgttt gctgtttgct    240

gcttgcaatg tttgcccatt ttagggacat gagtaggctg aagtttgttc agtgtggact    300

tcagaggcag cacacaaaca gcacgcgaaa cgtcgactgg acacaggacg ctgtggtttc    360

tgagccaggg ggcgactcag atcccagcca gtggacttag cccctgtttg ctcctccgat    420

aactggggtg accttggtta atattcacca gcagcctccc ccgttgcccc tctggatcca    480

ctgcttaaat acggacgagg acagggccct gtctcctcag cttcaggcac caccactgac    540

ctgggacagt gaatcgcgat cgccaccatg cagattgagc tgagcacctg cttcttcctg    600

tgcctgctga ggttctgctt ctctgccacc aggagatact acctgggggc tgtggagctg    660

agctgggact acatgcagtc tgacctgggg gagctgcctg tggatgccag gttccccccc    720

agagtgccca agagcttccc cttcaacacc tctgtggtgt acaagaagac cctgtttgtg    780

gagttcactg accacctgtt caacattgcc aagcccaggc ccccctggat gggcctgctg    840

ggccccacca tccaggctga ggtgtatgac actgtggtga tcaccctgaa gaacatggcc    900

agccaccctg tgagcctgca tgctgtgggg gtgagctact ggaaggcctc tgagggggct    960

gagtatgatg accagaccag ccagagggag aaggaggatg acaaggtgtt ccctgggggc   1020

agccacacct atgtgtggca ggtgctgaag gagaatggcc ccatggcctc tgacccccctg   1080

tgcctgacct acagctacct gagccatgtg gacctggtga aggacctgaa ctctggcctg   1140

attggggccc tgctggtgtg cagggagggc agcctggcca aggagaagac ccagaccctg   1200

cacaagttca tcctgctgtt tgctgtgttt gatgagggca agagctggca ctctgaaacc   1260

aagaacagcc tgatgcagga cagggatgct gcctctgcca gggcctggcc caagatgcac   1320

actgtgaatg gctatgtgaa caggagcctg cctggcctga ttggctgcca caggaagtct   1380

gtgtactggc atgtgattgg catgggcacc acccctgagg tgcacagcat cttcctggag   1440

ggccacacct tcctggtcag gaaccacagg caggccagcc tggagatcag ccccatcacc   1500

ttcctgactg cccagaccct gctgatggac ctgggccagt tcctgctgtt ctgccacatc   1560

agcagccacc agcatgatgg catggaggcc tatgtgaagg tggacagctg ccctgaggag   1620

ccccagctga ggatgaagaa caatgaggag gctgaggact atgatgatga cctgactgac   1680

tctgagatgg atgtggtgag gtttgatgat gacaacagcc ccagcttcat ccagatcagg   1740

tctgtggcca agaagcaccc caagacctgg gtgcactaca ttgctgctga ggaggaggac   1800
```

```
tgggactatg ccccccctggt gctggcccct gatgacagga gctacaagag ccagtacctg   1860
aacaatggcc cccagaggat tggcaggaag tacaagaagg tcaggttcat ggcctacact   1920
gatgaaacct tcaagaccag ggaggccatc cagcatgagt ctggcatcct gggccccctg   1980
ctgtatgggg aggtggggga caccctgctg atcatcttca agaaccaggc cagcaggccc   2040
tacaacatct acccccatgg catcactgat gtgaggcccc tgtacagcag gaggctgccc   2100
aagggggtga agcacctgaa ggacttcccc atcctgcctg gggagatctt caagtacaag   2160
tggactgtga ctgtggagga tggccccacc aagtctgacc ccaggtgcct gaccagatac   2220
tacagcagct ttgtgaacat ggagagggac ctggcctctg gcctgattgg cccccctgctg   2280
atctgctaca aggagtctgt ggaccagagg ggcaaccaga tcatgtctga caagaggaat   2340
gtgatcctgt tctctgtgtt tgatgagaac aggagctggt acctgactga gaacatccag   2400
aggttcctgc ccaaccctgc tggggtgcag ctggaggacc ctgagttcca ggccagcaac   2460
atcatgcaca gcatcaatgg ctatgtgttt gacagcctgc agctgtctgt gtgcctgcat   2520
gaggtggcct actggtacat cctgagcatt ggggcccaga ctgacttcct gtctgtgttc   2580
ttctctggct acaccttcaa gcacaagatg gtgtatgagg acaccctgac cctgttcccc   2640
ttctctgggg agactgtgtt catgagcatg gagaaccctg gcctgtggat tctgggctgc   2700
cacaactctg acttcaggaa caggggcatg actgccctgc tgaaagtctc cagctgtgac   2760
aagaacactg ggactacta tgaggacagc tatgaggaca tctctgccta cctgctgagc    2820
aagaacaatg ccattgagcc caggagcttc agccagaacc ccccagtgct gaagaggcac   2880
cagagggaga tcaccaggac caccctgcag tctgaccagg aggagattga ctatgatgac   2940
accatctctg tggagatgaa gaaggaggac tttgacatct acgacgagga cgagaaccag   3000
agccccagga gcttccagaa gaagaccagg cactacttca ttgctgctgt ggagaggctg   3060
tgggactatg gcatgagcag cagcccccat gtgctgagga acagggccca gtctggctct   3120
gtgccccagt tcaagaaggt ggtgttccag gagttcactg atggcagctt cacccagccc   3180
ctgtacagag gggagctgaa tgagcacctg ggcctgctgg gcccctacat cagggctgag   3240
gtggaggaca acatcatggt gaccttcagg aaccaggcca gcaggcccta cagcttctac   3300
agcagcctga tcagctatga ggaggaccag aggcaggggg ctgagcccag gaagaacttt   3360
gtgaagccca atgaaaccaa gacctacttc tggaaggtgc agcaccacat ggccccccacc   3420
aaggatgagt ttgactgcaa ggcctgggcc tacttctctg atgtggacct ggagaaggat   3480
gtgcactctg gcctgattgg cccccctgctg gtgtgccaca ccaacaccct gaaccctgcc   3540
catggcaggc aggtgactgt gcaggagttt gccctgttct tcaccatctt tgatgaaacc   3600
aagagctggt acttcactga gaacatggag aggaactgca gggccccctg caacatccag   3660
atggaggacc ccaccttcaa ggagaactac aggttccatg ccatcaatgg ctacatcatg   3720
gacaccctgc ctggcctggt gatggcccag gaccagagga tcaggtggta cctgctgagc   3780
atgggcagca atgagaacat ccacagcatc cacttctctg gccatgtgtt cactgtgagg   3840
aagaaggagg agtacaagat ggccctgtac aacctgtacc ctggggtgtt tgagactgtg   3900
gagatgctgc ccagcaaggc tggcatctgg agggtggagt gcctgattgg ggagcacctg   3960
catgctggca tgagcaccct gttcctggtg tacagcaaca agtgccagac ccccctgggc   4020
atggcctctg gccacatcag ggacttccag atcactgcct ctggccagta tggccagtgg   4080
gcccccaagc tggccaggct gcactactct ggcagcatca atgcctggag caccaaggag   4140
```

```
cccttcagct ggatcaaggt ggacctgctg gcccccatga tcatccatgg catcaagacc   4200
caggggcca ggcagaagtt cagcagcctg tacatcagcc agttcatcat catgtacagc   4260
ctggatggca agaagtggca gacctacagg ggcaacagca ctggcaccct gatggtgttc   4320
tttggcaatg tggacagctc tggcatcaag cacaacatct tcaacccccc catcattgcc   4380
agatacatca ggctgcaccc cacccactac agcatcagga gcaccctgag gatggagctg   4440
atgggctgtg acctgaacag ctgcagcatg cccctgggca tggagagcaa ggccatctct   4500
gatgcccaga tcactgccag cagctacttc accaacatgt ttgccacctg gagccccagc   4560
aaggccaggc tgcacctgca gggcaggagc aatgcctgga ggccccaggt caacaacccc   4620
aaggagtggc tgcaggtgga cttccagaag accatgaagg tgactggggt gaccacccag   4680
ggggtgaaga gcctgctgac cagcatgtat gtgaaggagt tcctgatcag cagcagccag   4740
gatggccacc agtggaccct gttcttccag aatggcaagg tgaaggtgtt ccagggcaac   4800
caggacagct tcacccctgt ggtgaacagc ctggaccccc ccctgctgac cagatacctg   4860
aggattcacc cccagagctg ggtgcaccag attgccctga ggatggaggt gctgggctgt   4920
gaggcccagg acctgtactg acctcgagga ataaaggaaa tttattttca ttgcaatagt   4980
gtgttggttt tttgtgtcac gtggcggccg caggaacccc tagtgatgga gttggccact   5040
ccctctctgc gcgctcgctc gctcactgag gccgggcgac caaaggtcgc ccgacgcccg   5100
ggctttgccc gggcggcctc agtgagcgag cgagcgcgca gagagggagt ggccaa       5156
```

```
<210> SEQ ID NO 35
<211> LENGTH: 5178
<212> TYPE: DNA
<213> ORGANISM: Adeno-Associated Virus 2

<400> SEQUENCE: 35
```

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg gacaacgcga aacgtcgact    360
ggacacagga cgctgtggtt tctgagccag gggcgactc agatcccagc cagtggactt     420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgcg atcgccacca tgcagattga    600
gctgagcacc tgcttcttcc tgtgcctgct gaggttctgc ttctctgcca ccaggagata    660
ctacctgggg gctgtggagc tgagctggga ctacatgcag tctgacctgg gggagctgcc    720
tgtggatgcc aggttccccc ccagagtgcc caagagcttc cccttcaaca cctctgtggt    780
gtacaagaag accctgtttg tggagttcac tgaccacctg ttcaacattg ccaagcccag    840
gcccccctgg atgggcctgc tgggccccac catccaggct gaggtgtatg acactgtggt    900
gatcaccctg aagaacatgg ccagccaccc tgtgagcctg catgctgtgg gggtgagcta    960
ctggaaggcc tctgaggggg ctgagtatga tgaccagacc agccagaggg agaaggagga   1020
tgacaaggtg ttccctgggg gcagccacac ctatgtgtgg caggtgctga aggagaatgg   1080
ccccatggcc tctgaccccc tgtgcctgac ctacagctac ctgagccatg tggacctggt   1140
```

```
gaaggacctg aactctggcc tgattggggc cctgctggtg tgcagggagg gcagcctggc   1200
caaggagaag acccagaccc tgcacaagtt catcctgctg tttgctgtgt ttgatgaggg   1260
caagagctgg cactctgaaa ccaagaacag cctgatgcag gacagggatg ctgcctctgc   1320
cagggcctgg cccaagatgc acactgtgaa tggctatgtg aacaggagcc tgcctggcct   1380
gattggctgc cacaggaagt ctgtgtactg gcatgtgatt ggcatgggca ccacccctga   1440
ggtgcacagc atcttcctgg agggccacac cttcctggtc aggaaccaca ggcaggccag   1500
cctggagatc agccccatca ccttcctgac tgcccagacc ctgctgatgg acctgggcca   1560
gttcctgctg ttctgccaca tcagcagcca ccagcatgat ggcatggagg cctatgtgaa   1620
ggtggacagc tgccctgagg agccccagct gaggatgaag aacaatgagg aggctgagga   1680
ctatgatgat gacctgactg actctgagat ggatgtggtg aggtttgatg atgacaacag   1740
ccccagcttc atccagatca ggtctgtggc caagaagcac cccaagacct gggtgcacta   1800
cattgctgct gaggaggagg actgggacta tgccccccctg gtgctggccc ctgatgacag   1860
gagctacaag agccagtacc tgaacaatgg cccccagagg attggcagga agtacaagaa   1920
ggtcaggttc atggcctaca ctgatgaaac cttcaagacc agggaggcca tccagcatga   1980
gtctggcatc ctgggccccc tgctgtatgg ggaggtgggg gacaccctgc tgatcatctt   2040
caagaaccag gccagcaggc cctacaacat ctacccccat ggcatcactg atgtgaggcc   2100
cctgtacagc aggaggctgc ccaagggggt gaagcacctg aaggacttcc ccatcctgcc   2160
tggggagatc ttcaagtaca agtggactgt gactgtggag gatggcccca ccaagtctga   2220
ccccaggtgc ctgaccagat actacagcag ctttgtgaac atggagaggg acctggcctc   2280
tggcctgatt ggcccccctgc tgatctgcta caaggagtct gtggaccaga ggggcaacca   2340
gatcatgtct gacaagagga atgtgatcct gttctctgtg tttgatgaga acaggagctg   2400
gtacctgact gagaacatcc agaggttcct gcccaaccct gctggggtgc agctggagga   2460
ccctgagttc caggccagca acatcatgca cagcatcaat ggctatgtgt ttgacagcct   2520
gcagctgtct gtgtgcctgc atgaggtggc ctactggtac atcctgagca ttggggccca   2580
gactgacttc ctgtctgtgt tcttctctgg ctacaccttc aagcacaaga tggtgtatga   2640
ggacaccctg accctgttcc ccttctctgg ggagactgtg ttcatgagca tggagaaccc   2700
tggcctgtgg attctgggct gccacaactc tgacttcagg aacaggggca tgactgccct   2760
gctgaaagtc tccagctgtg acaagaacac tggggactac tatgaggaca gctatgagga   2820
catctctgcc tacctgctga gcaagaacaa tgccattgag cccaggagct tcagccagaa   2880
ccccccagtg ctgaagaggc accagaggga gatcaccagg accaccctgc agtctgacca   2940
ggaggagatt gactatgatg acaccatctc tgtggagatg aagaaggagg actttgacat   3000
ctacgacgag gacgagaacc agagccccag gagcttccag aagaagacca ggcactactt   3060
cattgctgct gtggagaggc tgtgggacta tggcatgagc agcagccccc atgtgctgag   3120
gaacagggcc cagtctggct ctgtgcccca gttcaagaag gtggtgttcc aggagttcac   3180
tgatggcagc ttcacccagc ccctgtacag aggggagctg aatgagcacc tgggcctgct   3240
gggcccctac atcagggctg aggtggagga caacatcatg gtgaccttca ggaaccaggc   3300
cagcaggccc tacagcttct acagcagcct gatcagctat gaggaggacc agaggcaggg   3360
ggctgagccc aggaagaact ttgtgaagcc caatgaaacc aagacctact tctggaaggt   3420
gcagcaccac atggccccca ccaaggatga gtttgactgc aaggcctggg cctacttctc   3480
```

```
tgatgtggac ctggagaagg atgtgcactc tggcctgatt ggcccccctgc tggtgtgcca   3540
caccaacacc ctgaaccctg cccatggcag gcaggtgact gtgcaggagt ttgccctgtt   3600
cttcaccatc tttgatgaaa ccaagagctg gtacttcact gagaacatgg agaggaactg   3660
cagggccccc tgcaacatcc agatggagga ccccaccttc aaggagaact acaggttcca   3720
tgccatcaat ggctacatca tggacaccct gcctggcctg gtgatggccc aggaccagag   3780
gatcaggtgg tacctgctga gcatgggcag caatgagaac atccacagca tccacttctc   3840
tggccatgtg ttcactgtga ggaagaagga ggagtacaag atggccctgt acaacctgta   3900
ccctggggtg tttgagactg tggagatgct gcccagcaag gctggcatct ggagggtgga   3960
gtgcctgatt ggggagcacc tgcatgctgg catgagcacc ctgttcctgg tgtacagcaa   4020
caagtgccag accccccctgg gcatggcctc tggccacatc agggacttcc agatcactgc   4080
ctctggccag tatggccagt gggcccccaa gctggccagg ctgcactact ctggcagcat   4140
caatgcctgg agcaccaagg agcccttcag ctggatcaag gtggacctgc tggcccccat   4200
gatcatccat ggcatcaaga cccagggggc caggcagaag ttcagcagcc tgtacatcag   4260
ccagttcatc atcatgtaca gcctggatgg caagaagtgg cagacctaca ggggcaacag   4320
cactggcacc ctgatggtgt tctttggcaa tgtggacagc tctggcatca agcacaacat   4380
cttcaacccc cccatcattg ccagatacat caggctgcac cccacccact acagcatcag   4440
gagcaccctg aggatggagc tgatgggctg tgacctgaac agctgcagca tgcccctggg   4500
catggagagc aaggccatct ctgatgccca gatcactgcc agcagctact tcaccaacat   4560
gtttgccacc tggagcccca gcaaggccag gctgcacctg cagggcagga gcaatgcctg   4620
gaggccccag gtcaacaacc ccaaggagtg gctgcaggtg gacttccaga agaccatgaa   4680
ggtgactggg gtgaccaccc agggggtgaa gagcctgctg accagcatgt atgtgaagga   4740
gttcctgatc agcagcagcc aggatggcca ccagtggacc ctgttcttcc agaatggcaa   4800
ggtgaaggtg ttccagggca accaggacag cttcacccct gtggtgaaca gcctggaccc   4860
ccccctgctg accagatacc tgaggattca cccccagagc tgggtgcacc agattgccct   4920
gaggatggag gtgctgggct gtgaggccca ggacctgtac tgacctcgag gaataaagga   4980
aatttatttt cattgcaata gtgtgttggt tttttgtgtc acgtggcggc cgcaggaacc   5040
cctagtgatg gagttggcca ctccctctct gcgcgctcgc tcgctcactg aggccgggcg   5100
accaaaggtc gcccgacgcc cgggctttgc ccgggcggcc tcagtgagcg agcgagcgcg   5160
cagagaggga gtggccaa                                                 5178
```

<210> SEQ ID NO 36
<211> LENGTH: 5160
<212> TYPE: DNA
<213> ORGANISM: Adeno-Associated Virus 2

<400> SEQUENCE: 36

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtt gtccctaaaa tgggcaaaca    180
ttgcaagcag caaacagcaa acatgtccct aaaatgggca aacattgcaa gcagcaaaca    240
gcaaacatgt ccctaaaatg ggcaaacatt gcaagcagca aacagcaaac atgtccctaa    300
aatgggcaaa cattgcaagc agcaaacagc aaacagtcga ctggacacag gacgctgtgg    360
tttctgagcc agggggcgac tcagatccca gccagtggac ttagcccctg tttgctcctc    420
```

-continued

```
cgataactgg ggtgaccttg gttaatattc accagcagcc tcccccgttg cccctctgga    480
tccactgctt aaatacggac gaggacaggg ccctgtctcc tcagcttcag gcaccaccac    540
tgacctggga cagtgaatcg cgatcgccac catgcagatt gagctgagca cctgcttctt    600
cctgtgcctg ctgaggttct gcttctctgc caccaggaga tactacctgg gggctgtgga    660
gctgagctgg gactacatgc agtctgacct gggggagctg cctgtggatg ccaggttccc    720
ccccagagtg cccaagagct tccccttcaa cacctctgtg gtgtacaaga agaccctgtt    780
tgtggagttc actgaccacc tgttcaacat tgccaagccc aggccccccct ggatgggcct    840
gctgggcccc accatccagg ctgaggtgta tgacactgtg gtgatcaccc tgaagaacat    900
ggccagccac cctgtgagcc tgcatgctgt gggggtgagc tactggaagg cctctgaggg    960
ggctgagtat gatgaccaga ccagccagag ggagaaggag gatgacaagg tgttccctgg   1020
gggcagccac acctatgtgt ggcaggtgct gaaggagaat ggccccatgg cctctgaccc   1080
cctgtgcctg acctacagct acctgagcca tgtggacctg gtgaaggacc tgaactctgg   1140
cctgattggg gccctgctgg tgtgcaggga gggcagcctg gccaaggaga agacccagac   1200
cctgcacaag ttcatcctgc tgtttgctgt gtttgatgag ggcaagagct ggcactctga   1260
aaccaagaac agcctgatgc aggacaggga tgctgcctct gccagggcct ggcccaagat   1320
gcacactgtg aatggctatg tgaacaggag cctgcctggc ctgattggct gccacaggaa   1380
gtctgtgtac tggcatgtga ttggcatggg caccacccct gaggtgcaca gcatcttcct   1440
ggagggccac accttcctgg tcaggaacca caggcaggcc agcctggaga tcagccccat   1500
caccttcctg actgcccaga ccctgctgat ggacctgggc cagttcctgc tgttctgcca   1560
catcagcagc caccagcatg atggcatgga ggcctatgtg aaggtggaca gctgccctga   1620
ggagccccag ctgaggatga agaacaatga ggaggctgag gactatgatg atgacctgac   1680
tgactctgag atggatgtgg tgaggtttga tgatgacaac agccccagct tcatccagat   1740
caggtctgtg gccaagaagc accccaagac ctgggtgcac tacattgctg ctgaggagga   1800
ggactgggac tatgcccccc tggtgctggc ccctgatgac aggagctaca agagccagta   1860
cctgaacaat ggcccccaga ggattggcag gaagtacaag aaggtcaggt tcatggccta   1920
cactgatgaa accttcaaga ccagggaggc catccagcat gagtctggca tcctgggccc   1980
cctgctgtat ggggaggtgg gggacaccct gctgatcatc ttcaagaacc aggccagcag   2040
gccctacaac atctaccccc atggcatcac tgatgtgagg cccctgtaca gcaggaggct   2100
gcccaagggg gtgaagcacc tgaaggactt ccccatcctg cctggggaga tcttcaagta   2160
caagtggact gtgactgtgg aggatggccc caccaagtct gaccccaggt gcctgaccag   2220
atactacagc agctttgtga acatggagag ggacctggcc tctggcctga ttggcccccct   2280
gctgatctgc tacaaggagt ctgtggacca gaggggcaac cagatcatgt ctgacaagag   2340
gaatgtgatc ctgttctctg tgtttgatga gaacaggagc tggtacctga ctgagaacat   2400
ccagaggttc ctgcccaacc ctgctggggt gcagctggag gaccctgagt tccaggccag   2460
caacatcatg cacagcatca atggctatgt gtttgacagc ctgcagctgt ctgtgtgcct   2520
gcatgaggtg gcctactggt acatcctgag cattggggcc cagactgact tcctgtctgt   2580
gttcttctct ggctacacct tcaagcacaa gatggtgtat gaggacaccc tgaccctgtt   2640
ccccttctct ggggagactg tgttcatgag catggagaac cctggcctgt ggattctggg   2700
ctgccacaac tctgacttca ggaacagggg catgactgcc ctgctgaaag tctccagctg   2760
```

-continued

```
tgacaagaac actggggact actatgagga cagctatgag gacatctctg cctacctgct   2820
gagcaagaac aatgccattg agcccaggag cttcagccag aaccccccag tgctgaagag   2880
gcaccagagg gagatcacca ggaccaccct gcagtctgac caggaggaga ttgactatga   2940
tgacaccatc tctgtggaga tgaagaagga ggactttgac atctacgacg aggacgagaa   3000
ccagagcccc aggagcttcc agaagaagac caggcactac ttcattgctg ctgtggagag   3060
gctgtgggac tatggcatga gcagcagccc ccatgtgctg aggaacaggg cccagtctgg   3120
ctctgtgccc cagttcaaga aggtggtgtt ccaggagttc actgatggca gcttcaccca   3180
gcccctgtac agaggggagc tgaatgagca cctgggcctg ctgggcccct acatcagggc   3240
tgaggtggag gacaacatca tggtgacctt caggaaccag gccagcaggc cctacagctt   3300
ctacagcagc ctgatcagct atgaggagga ccagaggcag gggctgagc ccaggaagaa   3360
ctttgtgaag cccaatgaaa ccaagaccta cttctggaag gtgcagcacc acatggcccc   3420
caccaaggat gagtttgact gcaaggcctg ggcctacttc tctgatgtgg acctggagaa   3480
ggatgtgcac tctggcctga ttggcccct gctggtgtgc cacaccaaca ccctgaaccc   3540
tgcccatggc aggcaggtga ctgtgcagga gtttgccctg ttcttcacca tctttgatga   3600
aaccaagagc tggtacttca ctgagaacat ggagaggaac tgcagggccc cctgcaacat   3660
ccagatggag gaccccacct tcaaggagaa ctacaggttc catgccatca atggctacat   3720
catggacacc ctgcctggcc tggtgatggc ccaggaccag aggatcaggt ggtacctgct   3780
gagcatgggc agcaatgaga acatccacag catccacttc tctggccatg tgttcactgt   3840
gaggaagaag gaggagtaca agatggccct gtacaacctg taccctgggg tgtttgagac   3900
tgtggagatg ctgcccagca aggctggcat ctggagggtg gagtgcctga ttggggagca   3960
cctgcatgct ggcatgagca ccctgttcct ggtgtacagc aacaagtgcc agacccccct   4020
gggcatggcc tctggccaca tcagggactt ccagatcact gcctctggcc agtatggcca   4080
gtgggccccc aagctggcca ggctgcacta ctctggcagc atcaatgcct ggagcaccaa   4140
ggagcccttc agctggatca aggtggacct gctggccccc atgatcatcc atggcatcaa   4200
gacccagggg gccaggcaga agttcagcag cctgtacatc agccagttca tcatcatgta   4260
cagcctggat ggcaagaagt ggcagaccta caggggcaac agcactggca ccctgatggt   4320
gttctttggc aatgtggaca gctctggcat caagcacaac atcttcaacc cccccatcat   4380
tgccagatac atcaggctgc accccaccca ctacagcatc aggagcaccc tgaggatgga   4440
gctgatgggc tgtgacctga acagctgcag catgcccctg ggcatggaga gcaaggccat   4500
ctctgatgcc cagatcactg ccagcagcta cttcaccaac atgtttgcca cctggagccc   4560
cagcaaggcc aggctgcacc tgcagggcag gagcaatgcc tggaggcccc aggtcaacaa   4620
ccccaaggag tggctgcagg tggacttcca gaagaccatg aaggtgactg gggtgaccac   4680
ccagggggtg aagagcctgc tgaccagcat gtatgtgaag gagttcctga tcagcagcag   4740
ccaggatggc caccagtgga ccctgttctt ccagaatggc aaggtgaagg tgttccaggg   4800
caaccaggac agcttcaccc ctgtggtgaa cagcctggac ccccccctgc tgaccagata   4860
cctgaggatt cacccccaga gctgggtgca ccagattgcc ctgaggatgg aggtgctggg   4920
ctgtgaggcc caggacctgt actgacctcg aggaataaag gaaatttatt ttcattgcaa   4980
tagtgtgttg gtttttgtg tcacgtggcg gccgcaggaa cccctagtga tggagttggc   5040
cactccctct ctgcgcgctc gctcgctcac tgaggccggg cgaccaaagg tcgcccgacg   5100
cccgggcttt gcccgggcgg cctcagtgag cgagcgagcg cgcagagagg gagtggccaa   5160
```

<210> SEQ ID NO 37
<211> LENGTH: 5383
<212> TYPE: DNA
<213> ORGANISM: Adeno-Associated Virus 2

<400> SEQUENCE: 37
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgactg tttgctgttt 180
gctgcttgca atgtttgccc attttaggga catgtttgct gtttgctgct tgcaatgttt 240
gcccatttta gggacatgtt tgctgtttgc tgcttgcaat gtttgcccat tttagggaca 300
tgtttgctgt ttgctgcttg caatgtttgc ccattttagg gacaacgcga aacgtcgact 360
ggacacagga cgctgtggtt tctgagccag ggggcgactc agatcccagc cagtggactt 420
agcccctgtt tgctcctccg ataactgggg tgaccttggt taatattcac cagcagcctc 480
ccccgttgcc cctctggatc cactgcttaa atacggacga ggacagggcc ctgtctcctc 540
agcttcaggc accaccactg acctgggaca gtgaatcgta agtatgcctt tcactgcgag 600
aggttctgga gaggcttctg agctccccat ggcccaggca ggcagcaggt ctggggcagg 660 agggggggttg tggagtgcct tgactcgggg cctggccccc ccatctctgt cttgcaggac 720
aattgccgtc ttctgtctcg tggggcatcc tcctgctggc aggcctgtgc tgcctggtcc 780
ctgcgatcgc caccatgcag attgagctga gcacctgctt cttcctgtgc ctgctgaggt 840
tctgcttctc tgccaccagg agatactacc tgggggctgt ggagctgagc tgggactaca 900
tgcagtctga cctgggggag ctgcctgtgg atgccaggtt cccccccaga gtgcccaaga 960
gcttcccctt caacacctct gtggtgtaca agaagaccct gtttgtggag ttcactgacc 1020
acctgttcaa cattgccaag cccaggcccc cctggatggg cctgctgggc cccaccatcc 1080
aggctgaggt gtatgacact gtggtgatca ccctgaagaa catggccagc caccctgtga 1140
gcctgcatgc tgtgggggtg agctactgga aggcctctga gggggctgag tatgatgacc 1200
agaccagcca gagggagaag gaggatgaca aggtgttccc tgggggcagc cacacctatg 1260
tgtggcaggt gctgaaggag aatggcccca tggcctctga ccccctgtgc ctgacctaca 1320
gctacctgag ccatgtggac ctggtgaagg acctgaactc tggcctgatt ggggccctgc 1380
tggtgtgcag ggagggcagc ctggccaagg agaagaccca gaccctgcac aagttcatcc 1440
tgctgtttgc tgtgtttgat gagggcaaga gctggcactc tgaaaccaag aacagcctga 1500
tgcaggacag ggatgctgcc tctgccaggg cctggcccaa gatgcacact gtgaatggct 1560
atgtgaacag gagcctgcct ggcctgattg gctgccacag gaagtctgtg tactggcatg 1620
tgattggcat gggcaccacc cctgaggtgc acagcatctt cctggagggc cacaccttcc 1680
tggtcaggaa ccacaggcag gccagcctgg agatcagccc catcaccttc ctgactgccc 1740
agaccctgct gatggacctg ggccagttcc tgctgttctg ccacatcagc agccaccagc 1800
atgatggcat ggaggcctat gtgaaggtgg acagctgccc tgaggagccc cagctgagga 1860
tgaagaacaa tgaggaggct gaggactatg atgatgacct gactgactct gagatggatg 1920
tggtgaggtt tgatgatgac aacagcccca gcttcatcca gatcaggtct gtggccaaga 1980
agcaccccaa gacctgggtg cactacattg ctgctgagga ggaggactgg gactatgccc 2040
ccctggtgct ggcccctgat gacaggagct acaagagcca gtacctgaac aatggccccc 2100

```
agaggattgg caggaagtac aagaaggtca ggttcatggc ctacactgat gaaaccttca   2160
agaccaggga ggccatccag catgagtctg gcatcctggg ccccctgctg tatggggagg   2220
tgggggacac cctgctgatc atcttcaaga accaggccag caggccctac aacatctacc   2280
cccatggcat cactgatgtg aggcccctgt acagcaggag gctgcccaag gggtgaagc   2340
acctgaagga cttccccatc ctgcctgggg agatcttcaa gtacaagtgg actgtgactg   2400
tggaggatgg ccccaccaag tctgacccca ggtgcctgac cagatactac agcagctttg   2460
tgaacatgga gagggacctg gcctctggcc tgattggccc cctgctgatc tgctacaagg   2520
agtctgtgga ccagaggggc aaccagatca tgtctgacaa gaggaatgtg atcctgttct   2580
ctgtgtttga tgagaacagg agctggtacc tgactgagaa catccagagg ttcctgccca   2640
accctgctgg ggtgcagctg gaggaccctg agttccaggc cagcaacatc atgcacagca   2700
tcaatggcta tgtgtttgac agcctgcagc tgtctgtgtg cctgcatgag gtggcctact   2760
ggtacatcct gagcattggg gcccagactg acttcctgtc tgtgttcttc tctggctaca   2820
ccttcaagca caagatggtg tatgaggaca ccctgaccct gttccccttc tctggggaga   2880
ctgtgttcat gagcatggag aaccctggcc tgtggattct gggctgccac aactctgact   2940
tcaggaacag gggcatgact gccctgctga aagtctccag ctgtgacaag aacactgggg   3000
actactatga ggacagctat gaggacatct ctgcctacct gctgagcaag aacaatgcca   3060
ttgagcccag gagcttcagc cagaaccccc cagtgctgaa gaggcaccag agggagatca   3120
ccaggaccac cctgcagtct gaccaggagg agattgacta tgatgacacc atctctgtgg   3180
agatgaagaa ggaggacttt gacatctacg acgaggacga gaaccagagc cccaggagct   3240
tccagaagaa gaccaggcac tacttcattg ctgctgtgga gaggctgtgg gactatggca   3300
tgagcagcag cccccatgtg ctgaggaaca gggcccagtc tggctctgtg ccccagttca   3360
agaaggtggt gttccaggag ttcactgatg gcagcttcac ccagcccctg tacagagggg   3420
agctgaatga gcacctgggc ctgctgggcc cctacatcag ggctgaggtg gaggacaaca   3480
tcatggtgac cttcaggaac caggccagca ggccctacag cttctacagc agcctgatca   3540
gctatgagga ggaccagagg caggggctg agcccaggaa gaactttgtg aagcccaatg   3600
aaaccaagac ctacttctgg aaggtgcagc accacatggc cccaccaag gatgagtttg   3660
actgcaaggc ctgggcctac ttctctgatg tggacctgga gaaggatgtg cactctggcc   3720
tgattggccc cctgctggtg tgccacacca acaccctgaa ccctgcccat ggcaggcagg   3780
tgactgtgca ggagtttgcc ctgttcttca ccatctttga tgaaaccaag agctggtact   3840
tcactgagaa catggagagg aactgcaggg ccccctgcaa catccagatg gaggacccca   3900
ccttcaagga gaactacagg ttccatgcca tcaatggcta catcatggac accctgcctg   3960
gcctggtgat ggcccaggac cagaggatca ggtggtacct gctgagcatg ggcagcaatg   4020
agaacatcca cagcatccac ttctctggcc atgtgttcac tgtgaggaag aaggaggagt   4080
acaagatggc cctgtacaac ctgtaccctg ggtgtttga gactgtggag atgctgccca   4140
gcaaggctgg catctggagg gtggagtgcc tgattgggga gcacctgcat gctggcatga   4200
gcaccctgtt cctggtgtac agcaacaagt gccagacccc cctgggcatg gcctctggcc   4260
acatcaggga cttccagatc actgcctctg gccagtatgg ccagtgggcc cccaagctgg   4320
ccaggctgca ctactctggc agcatcaatg cctggagcac caaggagccc ttcagctgga   4380
tcaaggtgga cctgctggcc cccatgatca tccatggcat caagacccag ggggccaggc   4440
agaagttcag cagcctgtac atcagccagt tcatcatcat gtacagcctg gatggcaaga   4500
```

```
agtggcagac ctacaggggc aacagcactg gcaccctgat ggtgttcttt ggcaatgtgg   4560
acagctctgg catcaagcac aacatcttca acccccccat cattgccaga tacatcaggc   4620
tgcaccccac ccactacagc atcaggagca ccctgaggat ggagctgatg ggctgtgacc   4680
tgaacagctg cagcatgccc ctgggcatgg agagcaaggc catctctgat gcccagatca   4740
ctgccagcag ctacttcacc aacatgtttg ccacctggag ccccagcaag gccaggctgc   4800
acctgcaggg caggagcaat gcctggaggc cccaggtcaa caaccccaag gagtggctgc   4860
aggtggactt ccagaagacc atgaaggtga ctggggtgac cacccagggg gtgaagagcc   4920
tgctgaccag catgtatgtg aaggagttcc tgatcagcag cagccaggat ggccaccagt   4980
ggaccctgtt cttccagaat ggcaaggtga aggtgttcca gggcaaccag gacagcttca   5040
cccctgtggt gaacagcctg gacccccccc tgctgaccag atacctgagg attcaccccc   5100
agagctgggt gcaccagatt gccctgagga tggaggtgct gggctgtgag gcccaggacc   5160
tgtactgacc tcgaggaata aaggaaattt attttcattg caatagtgtg ttggtttttt   5220
gtgtcacgtg gcggccgcag gaacccctag tgatggagtt ggccactccc tctctgcgcg   5280
ctcgctcgct cactgaggcc gggcgaccaa aggtcgcccg acgcccgggc tttgcccggg   5340
cggcctcagt gagcgagcga gcgcgcagag agggagtggc caa                     5383
```

<210> SEQ ID NO 38
<211> LENGTH: 5728
<212> TYPE: DNA
<213> ORGANISM: Adeno-Associated Virus 2

<400> SEQUENCE: 38

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg gacaacgcga aacgtcgaca    360
ggttaatttt taaaaagcag tcaaaagtcc aagtggccct tggcagcatt tactctctct    420
gtttgctctg gttaataatc tcaggagcac aaacattcct ggaggcagga gaagaaatca    480
acatcctgga cttatcctct gggcctctcc ccacccccag gagaggctca ggttaatttt    540
taaaaagcag tcaaaagtcc aagtggccct tggcagcatt tactctctct gtttgctctg    600
gttaataatc tcaggagcac aaacattcct ggaggcagga gaagaaatca acatcctgga    660
cttatcctct gggcctctcc ccacccccag gagaggctgt cgactggaca caggacgctg    720
tggtttctga gccagggggc gactcagatc ccagccagtg gacttagccc ctgtttgctc    780
ctccgataac tggggtgacc ttggttaata ttcaccagca gcctcccccg ttgcccctct    840
ggatccactg cttaaatacg gacgaggaca gggccctgtc tcctcagctt caggcaccac    900
cactgacctg ggacagtgaa tcgtaagtat gcctttcact gcgagaggtt ctggagaggc    960
ttctgagctc cccatggccc aggcaggcag caggtctggg gcaggagggg ggttgtggag   1020
tgccttgact cggggcctgg cccccccatc tctgtcttgc aggacaattg ccgtcttctg   1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
```

```
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttg tggagttcac tgaccacctg ttcaacattg   1380
ccaagcccag gccccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg gcagccacac ctatgtgtgg caggtgctga   1620
aggagaatgg ccccatggcc tctgaccccc tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccacccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgccccccctg gtgctggccc   2400
ctgatgacag gagctacaag agccagtacc tgaacaatgg cccccagagg attggcagga   2460
agtacaagaa ggtcaggttc atggcctaca ctgatgaaac cttcaagacc agggaggcca   2520
tccagcatga gtctggcatc ctgggccccc tgctgtatgg ggaggtgggg gacaccctgc   2580
tgatcatctt caagaaccag gccagcaggc cctacaacat ctaccccccat ggcatcactg   2640
atgtgaggcc cctgtacagc aggaggctgc ccaagggggt gaagcacctg aaggacttcc   2700
ccatcctgcc tggggagatc ttcaagtaca agtggactgt gactgtggag gatggcccca   2760
ccaagtctga ccccaggtgc ctgaccagat actacagcag ctttgtgaac atggagaggg   2820
acctggcctc tggcctgatt ggccccctgc tgatctgcta caaggagtct gtggaccaga   2880
ggggcaacca gatcatgtct gacaagagga atgtgatcct gttctctgtg tttgatgaga   2940
acaggagctg gtacctgact gagaacatcc agaggttcct gcccaaccct gctggggtgc   3000
agctggagga ccctgagttc caggccagca acatcatgca cagcatcaat ggctatgtgt   3060
ttgacagcct gcagctgtct gtgtgcctgc atgaggtggc ctactggtac atcctgagca   3120
ttggggccca gactgacttc ctgtctgtgt tcttctctgg ctacaccttc aagcacaaga   3180
tggtgtatga ggacaccctg accctgttcc ccttctctgg ggagactgtg ttcatgagca   3240
tggagaaccc tggcctgtgg attctgggct gccacaactc tgacttcagg aacaggggca   3300
tgactgccct gctgaaagtc tccagctgtg acaagaacac tggggactac tatgaggaca   3360
gctatgagga catctctgcc tacctgctga gcaagaacaa tgccattgag cccaggagct   3420
tcagccagaa ccccccagtg ctgaagaggc accagaggga gatcaccagg accaccctgc   3480
agtctgacca ggaggagatt gactatgatg acaccatctc tgtggagatg aagaaggagg   3540
actttgacat ctacgacgag gacgagaacc agagccccag gagcttccag aagaagacca   3600
```

```
ggcactactt cattgctgct gtggagaggc tgtgggacta tggcatgagc agcagccccc   3660
atgtgctgag gaacagggcc cagtctggct ctgtgcccca gttcaagaag gtggtgttcc   3720
aggagttcac tgatggcagc ttcacccagc ccctgtacag aggggagctg aatgagcacc   3780
tgggcctgct gggcccctac atcagggctg aggtggagga caacatcatg gtgaccttca   3840
ggaaccaggc cagcaggccc tacagcttct acagcagcct gatcagctat gaggaggacc   3900
agaggcaggg ggctgagccc aggaagaact ttgtgaagcc caatgaaacc aagacctact   3960
tctggaaggt gcagcaccac atggccccca ccaaggatga gtttgactgc aaggcctggg   4020
cctacttctc tgatgtggac ctggagaagg atgtgcactc tggcctgatt ggcccccctgc  4080
tggtgtgcca caccaacacc ctgaaccctg cccatggcag gcaggtgact gtgcaggagt   4140
ttgccctgtt cttcaccatc tttgatgaaa ccaagagctg gtacttcact gagaacatgg   4200
agaggaactg cagggccccc tgcaacatcc agatggagga ccccaccttc aaggagaact   4260
acaggttcca tgccatcaat ggctacatca tggacaccct gcctggcctg gtgatggccc   4320
aggaccagag gatcaggtgg tacctgctga gcatgggcag caatgagaac atccacagca   4380
tccacttctc tggccatgtg ttcactgtga ggaagaagga ggagtacaag atggccctgt   4440
acaacctgta ccctggggtg tttgagactg tggagatgct gcccagcaag gctggcatct   4500
ggagggtgga gtgcctgatt ggggagcacc tgcatgctgg catgagcacc ctgttcctgg   4560
tgtacagcaa caagtgccag accccccctgg gcatggcctc tggccacatc agggacttcc  4620
agatcactgc ctctggccag tatggccagt gggcccccaa gctggccagg ctgcactact   4680
ctggcagcat caatgcctgg agcaccaagg agcccttcag ctggatcaag gtggacctgc   4740
tggcccccat gatcatccat ggcatcaaga cccagggggc caggcagaag ttcagcagcc   4800
tgtacatcag ccagttcatc atcatgtaca gcctggatgg caagaagtgg cagacctaca   4860
ggggcaacag cactggcacc ctgatggtgt tctttggcaa tgtggacagc tctggcatca   4920
agcacaacat cttcaacccc cccatcattg ccagatacat caggctgcac cccacccact   4980
acagcatcag gagcaccctg aggatggagc tgatgggctg tgacctgaac agctgcagca   5040
tgcccctggg catggagagc aaggccatct ctgatgccca gatcactgcc agcagctact   5100
tcaccaacat gtttgccacc tggagcccca gcaaggccag gctgcacctg cagggcagga   5160
gcaatgcctg gaggccccag gtcaacaacc ccaaggagtg gctgcaggtg gacttccaga   5220
agaccatgaa ggtgactggg gtgaccaccc agggggtgaa gagcctgctg accagcatgt   5280
atgtgaagga gttcctgatc agcagcagcc aggatggcca ccagtggacc ctgttcttcc   5340
agaatggcaa ggtgaaggtg ttccagggca accaggacag cttcacccct gtggtgaaca   5400
gcctggaccc cccccctgctg accagatacc tgaggattca cccccagagc tgggtgcacc  5460
agattgccct gaggatggag gtgctgggct gtgaggccca ggacctgtac tgacctcgag   5520
gaataaagga aatttatttt cattgcaata gtgtgttggt tttttgtgtc acgtggcggc   5580
cgcaggaacc cctagtgatg gagttggcca ctccctctct gcgcgctcgc tcgctcactg   5640
aggccgggcg accaaaggtc gcccgacgcc cgggctttgc ccgggcggcc tcagtgagcg   5700
agcgagcgcg cagagaggga gtggccaa                                      5728
```

<210> SEQ ID NO 39
<211> LENGTH: 5905
<212> TYPE: DNA
<213> ORGANISM: Adeno-Associated Virus 2

<400> SEQUENCE: 39

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg gacaacgcga aacgtcgaca    360
ggttaatttt taaaaagcag tcaaaagtcc aagtggccct tggcagcatt tactctctct    420
gtttgctctg gttaataatc tcaggagcac aaacattcct ggaggcagga gaagaaatca    480
acatcctgga cttatcctct gggcctctcc ccacccccag gagaggctca ggttaatttt    540
taaaaagcag tcaaaagtcc aagtggccct tggcagcatt tactctctct gtttgctctg    600
gttaataatc tcaggagcac aaacattcct ggaggcagga gaagaaatca acatcctgga    660
cttatcctct gggcctctcc ccacccccag gagaggctgt cgactggaca caggacgctg    720
tggtttctga gccagggggc gactcagatc ccagccagtg gacttagccc ctgtttgctc    780
ctccgataac tggggtgacc ttggttaata ttcaccagca gcctcccccg ttgcccctct    840
ggatccactg cttaaatacg gacgaggaca gggccctgtc tcctcagctt caggcaccac    900
cactgacctg ggacagtgaa tcgtaagtat gcctttcact gcgagaggtt ctggagaggc    960
ttctgagctc ccatggccc aggcaggcag caggtctggg gcaggagggg ggttgtggag    1020
tgccttgact cggggcctgg cccccccatc tctgtcttgc aggacaattg ccgtcttctg   1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttg tggagttcac tgaccacctg ttcaacattg   1380
ccaagcccag gccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg gcagccacac ctatgtgtgg caggtgctga   1620
aggagaatgg ccccatggcc tctgaccccc tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccacccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
```

```
gggtgcacta cattgctgct gaggaggagg actgggacta tgccccccctg gtgctggccc   2400
ctgatgacag gagctacaag agccagtacc tgaacaatgg cccccagagg attggcagga   2460
agtacaagaa ggtcaggttc atggcctaca ctgatgaaac cttcaagacc agggaggcca   2520
tccagcatga gtctggcatc ctgggccccc tgctgtatgg ggaggtgggg gacaccctgc   2580
tgatcatctt caagaaccag gccagcaggc cctacaacat ctacccccat ggcatcactg   2640
atgtgaggcc cctgtacagc aggaggctgc ccaagggggt gaagcacctg aaggacttcc   2700
ccatcctgcc tggggagatc ttcaagtaca agtggactgt gactgtggag gatggcccca   2760
ccaagtctga ccccaggtgc ctgaccagat actacagcag ctttgtgaac atggagaggg   2820
acctggcctc tggcctgatt ggcccccctgc tgatctgcta caaggagtct gtggaccaga   2880
ggggcaacca gatcatgtct gacaagagga atgtgatcct gttctctgtg tttgatgaga   2940
acaggagctg gtacctgact gagaacatcc agaggttcct gcccaaccct gctggggtgc   3000
agctggagga ccctgagttc caggccagca acatcatgca cagcatcaat ggctatgtgt   3060
ttgacagcct gcagctgtct gtgtgcctgc atgaggtggc ctactggtac atcctgagca   3120
ttggggccca gactgacttc ctgtctgtgt tcttctctgg ctacaccttc aagcacaaga   3180
tggtgtatga ggacaccctg accctgttcc ccttctctgg ggagactgtg ttcatgagca   3240
tggagaaccc tggcctgtgg attctgggct gccacaactc tgacttcagg aacaggggca   3300
tgactgccct gctgaaagtc tccagctgtg acaagaacac tggggactac tatgaggaca   3360
gctatgagga catctctgcc tacctgctga gcaagaacaa tgccattgag cccaggagct   3420
tcagccagaa cccccccagtg ctgaagaggc accagaggga gatcaccagg accaccctgc   3480
agtctgacca ggaggagatt gactatgatg acaccatctc tgtggagatg aagaaggagg   3540
actttgacat ctacgacgag gacgagaacc agagccccag gagcttccag aagaagacca   3600
ggcactactt cattgctgct gtggagaggc tgtgggacta tggcatgagc agcagccccc   3660
atgtgctgag gaacagggcc cagtctggct ctgtgcccca gttcaagaag gtggtgttcc   3720
aggagttcac tgatggcagc ttcacccagc ccctgtacag aggggagctg aatgagcacc   3780
tgggcctgct gggcccctac atcagggctg aggtggagga caacatcatg gtgaccttca   3840
ggaaccaggc cagcaggccc tacagcttct acagcagcct gatcagctat gaggaggacc   3900
agaggcaggg ggctgagccc aggaagaact ttgtgaagcc caatgaaacc aagacctact   3960
tctggaaggt gcagcaccac atggccccca ccaaggatga gtttgactgc aaggcctggg   4020
cctacttctc tgatgtggac ctggagaagg atgtgcactc tggcctgatt ggccccctgc   4080
tggtgtgcca caccaacacc ctgaaccctg cccatggcag gcaggtgact gtgcaggagt   4140
ttgccctgtt cttcaccatc tttgatgaaa ccaagagctg gtacttcact gagaacatgg   4200
agaggaactg cagggccccc tgcaacatcc agatggagga ccccaccttc aaggagaact   4260
acaggttcca tgccatcaat ggctacatca tggacaccct gcctggcctg gtgatggccc   4320
aggaccagag gatcaggtgg tacctgctga gcatgggcag caatgagaac atccacagca   4380
tccacttctc tggccatgtg ttcactgtga ggaagaagga ggagtacaag atggccctgt   4440
acaacctgta ccctggggtg tttgagactg tggagatgct gcccagcaag gctggcatct   4500
ggagggtgga gtgcctgatt ggggagcacc tgcatgctgg catgagcacc ctgttcctgg   4560
tgtacagcaa caagtgccag accccccctgg gcatggcctc tggccacatc agggacttcc   4620
agatcactgc ctctggccag tatggccagt gggcccccaa gctggccagg ctgcactact   4680
```

```
ctggcagcat caatgcctgg agcaccaagg agcccttcag ctggatcaag gtggacctgc   4740

tggcccccat gatcatccat ggcatcaaga cccagggggc caggcagaag ttcagcagcc   4800

tgtacatcag ccagttcatc atcatgtaca gcctggatgg caagaagtgg cagacctaca   4860

ggggcaacag cactggcacc ctgatggtgt tctttggcaa tgtggacagc tctggcatca   4920

agcacaacat cttcaacccc cccatcattg ccagatacat caggctgcac cccacccact   4980

acagcatcag gagcaccctg aggatggagc tgatgggctg tgacctgaac agctgcagca   5040

tgcccctggg catggagagc aaggccatct ctgatgccca gatcactgcc agcagctact   5100

tcaccaacat gtttgccacc tggagcccca gcaaggccag gctgcacctg cagggcagga   5160

gcaatgcctg gaggccccag gtcaacaacc ccaaggagtg gctgcaggtg gacttccaga   5220

agaccatgaa ggtgactggg gtgaccaccc agggggtgaa gagcctgctg accagcatgt   5280

atgtgaagga gttcctgatc agcagcagcc aggatggcca ccagtggacc ctgttcttcc   5340

agaatggcaa ggtgaaggtg ttccagggca accaggacag cttcacccct gtggtgaaca   5400

gcctggaccc ccccctgctg accagatacc tgaggattca cccccagagc tgggtgcacc   5460

agattgccct gaggatggag gtgctgggct gtgaggccca ggacctgtac tgacctcgag   5520

gtgtgccttc tagttgccag ccatctgttg tttgcccctc ccccgtgcct tccttgaccc   5580

tggaaggtgc cactcccact gtcctttcct aataaaatga ggaaattgca tcgcattgtc   5640

tgagtaggtg tcattctatt ctggggggtg gggtggggca ggacagcaag ggggaggatt   5700

gggaagacaa tagcaggcat gctggggatg cggtgggctc tatgggcacg tggcggccgc   5760

aggaacccct agtgatggag ttggccactc cctctctgcg cgctcgctcg ctcactgagg   5820

ccgggcgacc aaaggtcgcc cgacgcccgg gctttgcccg ggcggcctca gtgagcgagc   5880

gagcgcgcag agagggagtg gccaa                                         5905
```

<210> SEQ ID NO 40
<211> LENGTH: 5355
<212> TYPE: DNA
<213> ORGANISM: Adeno-Associated Virus 2

<400> SEQUENCE: 40

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactg tttgctgttt    180

gctgcttgca atgtttgccc attttaggga catgtttgct gtttgctgct tgcaatgttt    240

gcccatttta gggacatgtt tgctgtttgc tgcttgcaat gtttgcccat tttagggaca    300

tgtttgctgt ttgctgcttg caatgtttgc ccattttagg gacaacgcga aacgtcgact    360

ggacacagga cgctgtggtt tctgagccag gggcgactc agatcccagc cagtggactt     420

agcccctgtt tgctcctccg ataactgggg tgaccttggt taatattcac cagcagcctc    480

ccccgttgcc cctctggatc cactgcttaa atacggacga ggacagggcc ctgtctcctc    540

agcttcaggc accaccactg acctgggaca gtgaatcgcg atcgccacca tgcagattga    600

gctgagcacc tgcttcttcc tgtgcctgct gaggttctgc ttctctgcca ccaggagata    660

ctacctgggg gctgtggagc tgagctggga ctacatgcag tctgacctgg gggagctgcc    720

tgtggatgcc aggttccccc ccagagtgcc caagagcttc cccttcaaca cctctgtggt    780

gtacaagaag accctgtttg tggagttcac tgaccacctg ttcaacattg ccaagcccag    840

gccccccctgg atgggcctgc tgggccccac catccaggct gaggtgtatg acactgtggt    900
```

```
gatcaccctg aagaacatgg ccagccaccc tgtgagcctg catgctgtgg gggtgagcta    960
ctggaaggcc tctgaggggg ctgagtatga tgaccagacc agccagaggg agaaggagga   1020
tgacaaggtg ttccctgggg gcagccacac ctatgtgtgg caggtgctga aggagaatgg   1080
ccccatggcc tctgaccccc tgtgcctgac ctacagctac ctgagccatg tggacctggt   1140
gaaggacctg aactctggcc tgattggggc cctgctggtg tgcagggagg gcagcctggc   1200
caaggagaag acccagaccc tgcacaagtt catcctgctg tttgctgtgt ttgatgaggg   1260
caagagctgg cactctgaaa ccaagaacag cctgatgcag gacagggatg ctgcctctgc   1320
cagggcctgg cccaagatgc acactgtgaa tggctatgtg aacaggagcc tgcctggcct   1380
gattggctgc cacaggaagt ctgtgtactg gcatgtgatt ggcatgggca ccacccctga   1440
ggtgcacagc atcttcctgg agggccacac cttcctggtc aggaaccaca ggcaggccag   1500
cctggagatc agccccatca ccttcctgac tgcccagacc ctgctgatgg acctgggcca   1560
gttcctgctg ttctgccaca tcagcagcca ccagcatgat ggcatggagg cctatgtgaa   1620
ggtggacagc tgccctgagg agccccagct gaggatgaag aacaatgagg aggctgagga   1680
ctatgatgat gacctgactg actctgagat ggatgtggtg aggtttgatg atgacaacag   1740
ccccagcttc atccagatca ggtctgtggc caagaagcac cccaagacct gggtgcacta   1800
cattgctgct gaggaggagg actgggacta tgcccccctg gtgctggccc ctgatgacag   1860
gagctacaag agccagtacc tgaacaatgg cccccagagg attggcagga agtacaagaa   1920
ggtcaggttc atggcctaca ctgatgaaac cttcaagacc agggaggcca tccagcatga   1980
gtctggcatc ctgggccccc tgctgtatgg ggaggtgggg gacaccctgc tgatcatctt   2040
caagaaccag gccagcaggc cctacaacat ctacccccat ggcatcactg atgtgaggcc   2100
cctgtacagc aggaggctgc ccaagggggt gaagcacctg aaggacttcc ccatcctgcc   2160
tggggagatc ttcaagtaca agtggactgt gactgtggag gatggcccca ccaagtctga   2220
ccccaggtgc ctgaccagat actacagcag ctttgtgaac atggagaggg acctggcctc   2280
tggcctgatt ggcccccctgc tgatctgcta caaggagtct gtggaccaga ggggcaacca   2340
gatcatgtct gacaagagga atgtgatcct gttctctgtg tttgatgaga acaggagctg   2400
gtacctgact gagaacatcc agaggttcct gcccaaccct gctggggtgc agctggagga   2460
ccctgagttc caggccagca acatcatgca cagcatcaat ggctatgtgt ttgacagcct   2520
gcagctgtct gtgtgcctgc atgaggtggc ctactggtac atcctgagca ttggggccca   2580
gactgacttc ctgtctgtgt tcttctctgg ctacaccttc aagcacaaga tggtgtatga   2640
ggacaccctg accctgttcc ccttctctgg ggagactgtg ttcatgagca tggagaaccc   2700
tggcctgtgg attctgggct gccacaactc tgacttcagg aacaggggca tgactgccct   2760
gctgaaagtc tccagctgtg acaagaacac tggggactac tatgaggaca gctatgagga   2820
catctctgcc tacctgctga gcaagaacaa tgccattgag cccaggagct tcagccagaa   2880
ccccccagtg ctgaagaggc accagaggga gatcaccagg accaccctgc agtctgacca   2940
ggaggagatt gactatgatg acaccatctc tgtggagatg aagaaggagg actttgacat   3000
ctacgacgag gacgagaacc agagccccag gagcttccag aagaagacca ggcactactt   3060
cattgctgct gtggagaggc tgtgggacta tggcatgagc agcagccccc atgtgctgag   3120
gaacagggcc cagtctggct ctgtgcccca gttcaagaag gtggtgttcc aggagttcac   3180
tgatggcagc ttcacccagc ccctgtacag aggggagctg aatgagcacc tgggcctgct   3240
```

```
gggcccctac atcagggctg aggtggagga caacatcatg gtgaccttca ggaaccaggc   3300
cagcaggccc tacagcttct acagcagcct gatcagctat gaggaggacc agaggcaggg   3360
ggctgagccc aggaagaact ttgtgaagcc caatgaaacc aagacctact tctggaaggt   3420
gcagcaccac atggccccca ccaaggatga gtttgactgc aaggcctggg cctacttctc   3480
tgatgtggac ctggagaagg atgtgcactc tggcctgatt ggccccctgc tggtgtgcca   3540
caccaacacc ctgaaccctg cccatggcag gcaggtgact gtgcaggagt ttgccctgtt   3600
cttcaccatc tttgatgaaa ccaagagctg gtacttcact gagaacatgg agaggaactg   3660
cagggccccc tgcaacatcc agatggagga ccccaccttc aaggagaact acaggttcca   3720
tgccatcaat ggctacatca tggacaccct gcctggcctg gtgatggccc aggaccagag   3780
gatcaggtgg tacctgctga gcatgggcag caatgagaac atccacagca tccacttctc   3840
tggccatgtg ttcactgtga ggaagaagga ggagtacaag atggccctgt acaacctgta   3900
ccctggggtg tttgagactg tggagatgct gcccagcaag gctggcatct ggagggtgga   3960
gtgcctgatt ggggagcacc tgcatgctgg catgagcacc ctgttcctgg tgtacagcaa   4020
caagtgccag acccccctgg gcatggcctc tggccacatc agggacttcc agatcactgc   4080
ctctggccag tatggccagt gggcccccaa gctggccagg ctgcactact ctggcagcat   4140
caatgcctgg agcaccaagg agcccttcag ctggatcaag gtggacctgc tggcccccat   4200
gatcatccat ggcatcaaga cccagggggc caggcagaag ttcagcagcc tgtacatcag   4260
ccagttcatc atcatgtaca gcctggatgg caagaagtgg cagacctaca ggggcaacag   4320
cactggcacc ctgatggtgt tctttggcaa tgtggacagc tctggcatca agcacaacat   4380
cttcaacccc cccatcattg ccagatacat caggctgcac ccccacccact acagcatcag   4440
gagcaccctg aggatggagc tgatgggctg tgacctgaac agctgcagca tgcccctggg   4500
catggagagc aaggccatct ctgatgccca gatcactgcc agcagctact tcaccaacat   4560
gtttgccacc tggagcccca gcaaggccag gctgcacctg cagggcagga gcaatgcctg   4620
gaggccccag gtcaacaacc ccaaggagtg gctgcaggtg gacttccaga agaccatgaa   4680
ggtgactggg gtgaccaccc agggggtgaa gagcctgctg accagcatgt atgtgaagga   4740
gttcctgatc agcagcagcc aggatggcca ccagtggacc ctgttcttcc agaatggcaa   4800
ggtgaaggtg ttccagggca accaggacag cttcacccct gtggtgaaca gcctggaccc   4860
cccccctgctg accagatacc tgaggattca cccccagagc tgggtgcacc agattgccct   4920
gaggatggag gtgctgggct gtgaggccca ggacctgtac tgacctcgag gtgtgccttc   4980
tagttgccag ccatctgttg tttgcccctc ccccgtgcct tccttgaccc tggaaggtgc   5040
cactcccact gtcctttcct aataaaatga ggaaattgca tcgcattgtc tgagtaggtg   5100
tcattctatt ctggggggtg gggtggggca ggacagcaag ggggaggatt gggaagacaa   5160
tagcaggcat gctggggatg cggtgggctc tatgggcacg tggcggccgc aggaacccct   5220
agtgatggag ttggccactc cctctctgcg cgctcgctcg ctcactgagg ccgggcgacc   5280
aaaggtcgcc cgacgcccgg gctttgcccg ggcggcctca gtgagcgagc gagcgcgcag   5340
agagggagtg gccaa                                                    5355
```

<210> SEQ ID NO 41
<211> LENGTH: 5618
<212> TYPE: DNA
<213> ORGANISM: Adeno-Associated Virus 2

<400> SEQUENCE: 41

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacca gagaggtctc    180
tgacctctgc cccagctcca aggtcagcag gcagggaggg ctgtgtgttt gctgtttgct    240
gcttgcaatg tttgcccatt ttagggacat gagtaggctg aagtttgttc agtgtggact    300
tcagaggcag cacacaaaca gccagagagg tctctgacct ctgccccagc tccaaggtca    360
gcaggcaggg agggctgtgt gtttgctgtt tgctgcttgc aatgtttgcc cattttaggg    420
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gccccagctc    660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga aacgtcgact ggacacagga cgctgtggtt tctgagccag ggggcgactc    840
agatcccagc cagtggactt agcccctgtt tgctcctccg ataactgggg tgaccttggt    900
taatattcac cagcagcctc ccccgttgcc cctctggatc cactgcttaa atacggacga    960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gccccccctgg atgggcctgc tgggccccac catccaggct   1320
gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg gcagcctggc caaggagaag acccagaccc tgcacaagtt catcctgctg   1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccacccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agccccagct gaggatgaag   2100
aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgcccccctg   2280
```

```
gtgctggccc ctgatgacag gagctacaag agccagtacc tgaacaatgg cccccagagg   2340
attggcagga agtacaagaa ggtcaggttc atggcctaca ctgatgaaac cttcaagacc   2400
agggaggcca tccagcatga gtctggcatc ctgggccccc tgctgtatgg ggaggtgggg   2460
gacaccctgc tgatcatctt caagaaccag gccagcaggc cctacaacat ctacccccat   2520
ggcatcactg atgtgaggcc cctgtacagc aggaggctgc ccaagggggt gaagcacctg   2580
aaggacttcc ccatcctgcc tggggagatc ttcaagtaca agtggactgt gactgtggag   2640
gatggcccca ccaagtctga ccccaggtgc ctgaccagat actacagcag ctttgtgaac   2700
atggagaggg acctggcctc tggcctgatt ggcccccctgc tgatctgcta caaggagtct   2760
gtggaccaga ggggcaacca gatcatgtct gacaagagga atgtgatcct gttctctgtg   2820
tttgatgaga acaggagctg gtacctgact gagaacatcc agaggttcct gcccaaccct   2880
gctggggtgc agctggagga ccctgagttc caggccagca acatcatgca cagcatcaat   2940
ggctatgtgt ttgacagcct gcagctgtct gtgtgcctgc atgaggtggc ctactggtac   3000
atcctgagca ttggggccca gactgacttc ctgtctgtgt tcttctctgg ctacaccttc   3060
aagcacaaga tggtgtatga ggacaccctg accctgttcc ccttctctgg ggagactgtg   3120
ttcatgagca tggagaaccc tggcctgtgg attctgggct gccacaactc tgacttcagg   3180
aacaggggca tgactgccct gctgaaagtc tccagctgtg acaagaacac tggggactac   3240
tatgaggaca gctatgagga catctctgcc tacctgctga gcaagaacaa tgccattgag   3300
cccaggagct tcagccagaa ccccccagtg ctgaagaggc accagaggga gatcaccagg   3360
accaccctgc agtctgacca ggaggagatt gactatgatg acaccatctc tgtggagatg   3420
aagaaggagg actttgacat ctacgacgag gacgagaacc agagccccag gagcttccag   3480
aagaagacca ggcactactt cattgctgct gtggagaggc tgtgggacta tggcatgagc   3540
agcagccccc atgtgctgag gaacagggcc cagtctggct ctgtgcccca gttcaagaag   3600
gtggtgttcc aggagttcac tgatggcagc ttcacccagc ccctgtacag aggggagctg   3660
aatgagcacc tgggcctgct gggcccctac atcagggctg aggtggagga caacatcatg   3720
gtgaccttca ggaaccaggc cagcaggccc tacagcttct acagcagcct gatcagctat   3780
gaggaggacc agaggcaggg ggctgagccc aggaagaact ttgtgaagcc caatgaaacc   3840
aagacctact tctggaaggt gcagcaccac atggccccca ccaaggatga gtttgactgc   3900
aaggcctggg cctacttctc tgatgtggac ctggagaagg atgtgcactc tggcctgatt   3960
ggcccccctgc tggtgtgcca caccaacacc ctgaaccctg cccatggcag gcaggtgact   4020
gtgcaggagt ttgccctgtt cttcaccatc tttgatgaaa ccaagagctg gtacttcact   4080
gagaacatgg agaggaactg cagggccccc tgcaacatcc agatggagga ccccaccttc   4140
aaggagaact acaggttcca tgccatcaat ggctacatca tggacaccct gcctggcctg   4200
gtgatggccc aggaccagag gatcaggtgg tacctgctga gcatgggcag caatgagaac   4260
atccacagca tccacttctc tggccatgtg ttcactgtga ggaagaagga ggagtacaag   4320
atggccctgt acaacctgta ccctggggtg tttgagactg tggagatgct gcccagcaag   4380
gctggcatct ggagggtgga gtgcctgatt ggggagcacc tgcatgctgg catgagcacc   4440
ctgttcctgg tgtacagcaa caagtgccag accccccctgg gcatggcctc tggccacatc   4500
agggacttcc agatcactgc ctctggccag tatggccagt gggcccccaa gctggccagg   4560
ctgcactact ctggcagcat caatgcctgg agcaccaagg agcccttcag ctggatcaag   4620
gtggacctgc tggcccccat gatcatccat ggcatcaaga cccagggggc caggcagaag   4680
```

```
ttcagcagcc tgtacatcag ccagttcatc atcatgtaca gcctggatgg caagaagtgg   4740
cagacctaca ggggcaacag cactggcacc ctgatggtgt tctttggcaa tgtggacagc   4800
tctggcatca agcacaacat cttcaacccc cccatcattg ccagatacat caggctgcac   4860
cccacccact acagcatcag gagcaccctg aggatggagc tgatgggctg tgacctgaac   4920
agctgcagca tgcccctggg catggagagc aaggccatct ctgatgccca gatcactgcc   4980
agcagctact tcaccaacat gtttgccacc tggagcccca gcaaggccag gctgcacctg   5040
cagggcagga gcaatgcctg gaggccccag gtcaacaacc ccaaggagtg gctgcaggtg   5100
gacttccaga agaccatgaa ggtgactggg gtgaccaccc agggggtgaa gagcctgctg   5160
accagcatgt atgtgaagga gttcctgatc agcagcagcc aggatggcca ccagtggacc   5220
ctgttcttcc agaatggcaa ggtgaaggtg ttccagggca accaggacag cttcacccct   5280
gtggtgaaca gcctggaccc ccccctgctg accagatacc tgaggattca cccccagagc   5340
tgggtgcacc agattgccct gaggatggag gtgctgggct gtgaggccca ggacctgtac   5400
tgacctcgag gaataaagga aatttatttt cattgcaata gtgtgttggt tttttgtgtc   5460
acgtggcggc cgcaggaacc cctagtgatg gagttggcca ctccctctct gcgcgctcgc   5520
tcgctcactg aggccgggcg accaaaggtc gcccgacgcc cgggctttgc ccgggcggcc   5580
tcagtgagcg agcgagcgcg cagagaggga gtggccaa                           5618
```

<210> SEQ ID NO 42
<211> LENGTH: 5993
<212> TYPE: DNA
<213> ORGANISM: Adeno-Associated Virus 2

<400> SEQUENCE: 42

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttcccccc    900
cagagtgccc aagagcttcc ccttcaacac ctctgtggtg tacaagaaga ccctgtttgt    960
ggagttcact gaccacctgt tcaacattgc caagcccagg ccccccctgga tgggcctgct   1020
gggccccacc atccaggctg aggtgtatga cactgtggtg atcaccctga agaacatggc   1080
cagccaccct gtgagcctgc atgctgtggg ggtgagctac tggaaggcct ctgaggggggc   1140
```

```
tgagtatgat gaccagacca gccagaggga gaaggaggat gacaaggtgt tccctggggg   1200
cagccacacc tatgtgtggc aggtgctgaa ggagaatggc cccatggcct ctgacccccct   1260
gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc ccaagatgca   1500
cactgtgaat ggctatgtga acaggagcct gcctggcctg attggctgcc acaggaagtc   1560
tgtgtactgg catgtgattg gcatgggcac cacccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga acaatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagga   1980
ctgggactat gcccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggcccccct   2160
gctgtatggg gaggtggggg acaccctgct gatcatcttc aagaaccagg ccagcaggcc   2220
ctacaacatc taccccccatg gcatcactga tgtgaggccc ctgtacagca ggaggctgcc   2280
caagggggtg aagcacctga aggacttccc catcctgcct ggggagatct tcaagtacaa   2340
gtggactgtg actgtggagg atggccccac caagtctgac cccaggtgcc tgaccagata   2400
ctacagcagc tttgtgaaca tggagaggga cctggcctct ggcctgattg gcccccctgct   2460
gatctgctac aaggagtctg tggaccagag gggcaaccag atcatgtctg acaagaggaa   2520
tgtgatcctg ttctctgtgt ttgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca agcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga ctttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg ggcccctaca tcagggctga   3420
ggtggaggac aacatcatgg tgaccttcag gaaccaggcc agcaggccct acagcttcta   3480
cagcagcctg atcagctatg aggaggacca gaggcagggg gctgagccca ggaagaactt   3540
```

```
tgtgaagccc aatgaaacca agacctactt ctggaaggtg cagcaccaca tggcccccac   3600
caaggatgag tttgactgca aggcctgggc ctacttctct gatgtggacc tggagaagga   3660
tgtgcactct ggcctgattg gcccccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggccccct gcaacatcca   3840
gatggaggac cccaccttca aggagaacta caggttccat gccatcaatg gctacatcat   3900
ggacaccctg cctggcctgg tgatggccca ggaccagagg atcaggtggt acctgctgag   3960
catgggcagc aatgagaaca tccacagcat ccacttctct ggccatgtgt tcactgtgag   4020
gaagaaggag gagtacaaga tggccctgta caacctgtac cctggggtgt ttgagactgt   4080
ggagatgctg cccagcaagg ctggcatctg gagggtggag tgcctgattg ggagcacct   4140
gcatgctggc atgagcaccc tgttcctggt gtacagcaac aagtgccaga ccccccctggg   4200
catggcctct ggccacatca gggacttcca gatcactgcc tctggccagt atggccagtg   4260
ggcccccaag ctggccaggc tgcactactc tggcagcatc aatgcctgga gcaccaagga   4320
gcccttcagc tggatcaagg tggacctgct ggcccccatg atcatccatg gcatcaagac   4380
ccaggggggcc aggcagaagt tcagcagcct gtacatcagc cagttcatca tcatgtacag   4440
cctggatggc aagaagtggc agacctacag gggcaacagc actggcaccc tgatggtgtt   4500
ctttggcaat gtggacagct ctggcatcaa gcacaacatc ttcaaccccc ccatcattgc   4560
cagatacatc aggctgcacc ccacccacta cagcatcagg agcaccctga ggatggagct   4620
gatgggctgt gacctgaaca gctgcagcat gcccctgggc atggagagca aggccatctc   4680
tgatgcccag atcactgcca gcagctactt caccaacatg tttgccacct ggagccccag   4740
caaggccagg ctgcacctgc agggcaggag caatgcctgg aggccccagg tcaacaaccc   4800
caaggagtgg ctgcaggtgg acttccagaa gaccatgaag gtgactgggg tgaccaccca   4860
gggggtgaag agcctgctga ccagcatgta tgtgaaggag ttcctgatca gcagcagcca   4920
ggatggccac cagtggaccc tgttcttcca gaatggcaag gtgaaggtgt tccagggcaa   4980
ccaggacagc ttcacccctg tggtgaacag cctggacccc cccctgctga ccagatacct   5040
gaggattcac ccccagagct gggtgcacca gattgccctg aggatggagg tgctgggctg   5100
tgaggcccag gacctgtact gacctcgagg aataaaggaa atttattttc attgcaatag   5160
tgtgttggtt ttttgtgtca cgtgccctct cacactacct aaaccacgcc aggacaacct   5220
ctgctcctct ccaccgaaat tccaaggggt cgagtggatg ttggaggtgg catgggccca   5280
gagaggtctc tgacctctgc cccagctcca aggtcagcag gcagggaggg ctgtgtgttt   5340
gctgtttgct gcttgcaatg tttgcccatt ttagggacat gagtaggctg aagtttgttc   5400
agtgtggact tcagaggcag cacacaaaca gctgctggag gatgggaact gaggggttgg   5460
aagggggcag ggtgagccca gaaactcctg tgtgcctctg agcctgcagc cctctcacac   5520
tacctaaacc acgccaggac aacctctgct cctctccacc gaaattccaa ggggtcgagt   5580
ggatgttgga ggtggcatgg gcccagagag gtctctgacc tctgccccag ctccaaggtc   5640
agcaggcagg gagggctgtg tgtttgctgt ttgctgcttg caatgtttgc ccattttagg   5700
gacatgagta ggctgaagtt tgttcagtgt ggacttcaga ggcagcacac aaacagctgc   5760
tggaggatgg gaactgaggg gttggaaggg ggcagggtga gcccagaaac tcctgtgtgc   5820
ctctgagcct gcagcacgtg gcggccgcag gaacccctag tgatggagtt ggccactccc   5880
```

```
tctctgcgcg ctcgctcgct cactgaggcc gggcgaccaa aggtcgcccg acgcccgggc   5940

tttgcccggg cggcctcagt gagcgagcga gcgcgcagag agggagtggc caa          5993
```

<210> SEQ ID NO 43
<211> LENGTH: 5337
<212> TYPE: DNA
<213> ORGANISM: Adeno-Associated Virus 2

<400> SEQUENCE: 43

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg tttaaacgtc gacaggttaa    180

tttttaaaaa gcagtcaaaa gtccaagtgg cccttggcag catttactct ctctgtttgc    240

tctggttaat aatctcagga gcacaaacat tcctggaggc aggagaagaa atcaacatcc    300

tggacttatc ctctgggcct ctccccaccc ccaggagagg ctcaggttaa tttttaaaaa    360

gcagtcaaaa gtccaagtgg cccttggcag catttactct ctctgtttgc tctggttaat    420

aatctcagga gcacaaacat tcctggaggc aggagaagaa atcaacatcc tggacttatc    480

ctctgggcct ctccccaccc ccaggagagg ctgtcgactg gacacaggac gctgtggttt    540

ctgagccagg gggcgactca gatcccagcc agtggactta gcccctgttt gctcctccga    600

taactggggt gaccttggtt aatattcacc agcagcctcc cccgttgccc ctctggatcc    660

actgcttaaa tacggacgag gacagggccc tgtctcctca gcttcaggca ccaccactga    720

cctgggacag tgaatcgcga tcgccaccat gcagattgag ctgagcacct gcttcttcct    780

gtgcctgctg aggttctgct tctctgccac caggagatac tacctggggg ctgtggagct    840

gagctgggac tacatgcagt ctgacctggg ggagctgcct gtggatgcca ggttcccccc    900

cagagtgccc aagagcttcc ccttcaacac ctctgtggtg tacaagaaga ccctgtttgt    960

ggagttcact gaccacctgt tcaacattgc caagcccagg ccccccctgga tgggcctgct   1020

gggccccacc atccaggctg aggtgtatga cactgtggtg atcaccctga agaacatggc   1080

cagccaccct gtgagcctgc atgctgtggg ggtgagctac tggaaggcct ctgagggggc   1140

tgagtatgat gaccagacca gccagaggga gaaggaggat gacaaggtgt tccctggggg   1200

cagccacacc tatgtgtggc aggtgctgaa ggagaatggc cccatggcct ctgacccccct   1260

gtgcctgacc tacagctacc tgagccatgt ggacctggtg aaggacctga actctggcct   1320

gattggggcc ctgctggtgt gcagggaggg cagcctggcc aaggagaaga cccagaccct   1380

gcacaagttc atcctgctgt ttgctgtgtt tgatgagggc aagagctggc actctgaaac   1440

caagaacagc ctgatgcagg acagggatgc tgcctctgcc agggcctggc ccaagatgca   1500

cactgtgaat ggctatgtga acaggagcct gcctggcctg attggctgcc acaggaagtc   1560

tgtgtactgg catgtgattg gcatgggcac cacccctgag gtgcacagca tcttcctgga   1620

gggccacacc ttcctggtca ggaaccacag gcaggccagc ctggagatca gccccatcac   1680

cttcctgact gcccagaccc tgctgatgga cctgggccag ttcctgctgt tctgccacat   1740

cagcagccac cagcatgatg gcatggaggc ctatgtgaag gtggacagct gccctgagga   1800

gccccagctg aggatgaaga acaatgagga ggctgaggac tatgatgatg acctgactga   1860

ctctgagatg gatgtggtga ggtttgatga tgacaacagc cccagcttca tccagatcag   1920

gtctgtggcc aagaagcacc ccaagacctg ggtgcactac attgctgctg aggaggagga   1980

ctgggactat gcccccctgg tgctggcccc tgatgacagg agctacaaga gccagtacct   2040
```

```
gaacaatggc ccccagagga ttggcaggaa gtacaagaag gtcaggttca tggcctacac   2100
tgatgaaacc ttcaagacca gggaggccat ccagcatgag tctggcatcc tgggcccccct   2160
gctgtatggg gaggtggggg acaccctgct gatcatcttc aagaaccagg ccagcaggcc   2220
ctacaacatc tacccccatg gcatcactga tgtgaggccc ctgtacagca ggaggctgcc   2280
caagggggtg aagcacctga aggacttccc catcctgcct ggggagatct tcaagtacaa   2340
gtggactgtg actgtggagg atggccccac caagtctgac cccaggtgcc tgaccagata   2400
ctacagcagc tttgtgaaca tggagaggga cctggcctct ggcctgattg gcccccctgct   2460
gatctgctac aaggagtctg tggaccagag gggcaaccag atcatgtctg acaagaggaa   2520
tgtgatcctg ttctctgtgt ttgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca agcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga ctttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg ggcccctaca tcagggctga   3420
ggtggaggac aacatcatgg tgaccttcag gaaccaggcc agcaggccct acagcttcta   3480
cagcagcctg atcagctatg aggaggacca gaggcagggg gctgagccca ggaagaactt   3540
tgtgaagccc aatgaaacca agacctactt ctggaaggtg cagcaccaca tggcccccac   3600
caaggatgag tttgactgca aggcctgggc ctacttctct gatgtggacc tggagaagga   3660
tgtgcactct ggcctgattg gcccccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggcccccct gcaacatcca   3840
gatggaggac cccaccttca aggagaacta caggttccat gccatcaatg gctacatcat   3900
ggacaccctg cctggcctgg tgatggccca ggaccagagg atcaggtggt acctgctgag   3960
catgggcagc aatgagaaca tccacagcat ccacttctct ggccatgtgt tcactgtgag   4020
gaagaaggag gagtacaaga tggccctgta caacctgtac cctggggtgt ttgagactgt   4080
ggagatgctg cccagcaagg ctggcatctg gagggtggag tgcctgattg gggagcacct   4140
gcatgctggc atgagcaccc tgttcctggt gtacagcaac aagtgccaga cccccctggg   4200
catggcctct ggccacatca gggacttcca gatcactgcc tctggccagt atggccagtg   4260
ggcccccaag ctggccaggc tgcactactc tggcagcatc aatgcctgga gcaccaagga   4320
gcccttcagc tggatcaagg tggacctgct ggcccccatg atcatccatg gcatcaagac   4380
```

```
ccagggggcc aggcagaagt tcagcagcct gtacatcagc cagttcatca tcatgtacag   4440

cctggatggc aagaagtggc agacctacag gggcaacagc actggcaccc tgatggtgtt   4500

ctttggcaat gtggacagct ctggcatcaa gcacaacatc ttcaaccccc ccatcattgc   4560

cagatacatc aggctgcacc ccacccacta cagcatcagg agcaccctga ggatggagct   4620

gatgggctgt gacctgaaca gctgcagcat gcccctgggc atggagagca aggccatctc   4680

tgatgcccag atcactgcca gcagctactt caccaacatg tttgccacct ggagccccag   4740

caaggccagg ctgcacctgc agggcaggag caatgcctgg aggccccagg tcaacaaccc   4800

caaggagtgg ctgcaggtgg acttccagaa gaccatgaag gtgactgggg tgaccaccca   4860

gggggtgaag agcctgctga ccagcatgta tgtgaaggag ttcctgatca gcagcagcca   4920

ggatggccac cagtggaccc tgttcttcca gaatggcaag gtgaaggtgt tccagggcaa   4980

ccaggacagc ttcacccctg tggtgaacag cctggacccc cccctgctga ccagatacct   5040

gaggattcac ccccagagct gggtgcacca gattgccctg aggatggagg tgctgggctg   5100

tgaggcccag gacctgtact gacctcgagg aataaaggaa atttattttc attgcaatag   5160

tgtgttggtt ttttgtgtca cgtggcggcc gcaggaaccc ctagtgatgg agttggccac   5220

tccctctctg cgcgctcgct cgctcactga ggccgggcga ccaaaggtcg cccgacgccc   5280

gggctttgcc cgggcggcct cagtgagcga gcgagcgcgc agagagggag tggccaa      5337
```

<210> SEQ ID NO 44
<211> LENGTH: 5542
<212> TYPE: DNA
<213> ORGANISM: Adeno-Associated Virus 2

<400> SEQUENCE: 44

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg tttaaacgtc gacaggttaa    180

tttttaaaaa gcagtcaaaa gtccaagtgg cccttggcag catttactct ctctgtttgc    240

tctggttaat aatctcagga gcacaaacat tcctggaggc aggagaagaa atcaacatcc    300

tggacttatc ctctgggcct ctccccaccc ccaggagagg ctcaggttaa tttttaaaaa    360

gcagtcaaaa gtccaagtgg cccttggcag catttactct ctctgtttgc tctggttaat    420

aatctcagga gcacaaacat tcctggaggc aggagaagaa atcaacatcc tggacttatc    480

ctctgggcct ctccccaccc ccaggagagg ctgtcgactg gacacaggac gctgtggttt    540

ctgagccagg gggcgactca gatcccagcc agtggactta gcccctgttt gctcctccga    600

taactggggt gaccttggtt aatattcacc agcagcctcc cccgttgccc ctctggatcc    660

actgcttaaa tacggacgag gacagggccc tgtctcctca gcttcaggca ccaccactga    720

cctgggacag tgaatcgtaa gtatgccttt cactgcgaga ggttctggag aggcttctga    780

gctccccatg gcccaggcag gcagcaggtc tggggcagga ggggggttgt ggagtgcctt    840

gactcggggc ctggcccccc catctctgtc ttgcaggaca attgccgtct tctgtctcgt    900

ggggcatcct cctgctggca ggcctgtgct gcctggtccc tgcgatcgcc accatgcaga    960

ttgagctgag cacctgcttc ttcctgtgcc tgctgaggtt ctgcttctct gccaccagga   1020

gatactacct gggggctgtg gagctgagct gggactacat gcagtctgac ctgggggagc   1080

tgcctgtgga tgccaggttc ccccccagag tgcccaagag cttccccttc aacacctctg   1140

tggtgtacaa gaagaccctg tttgtggagt tcactgacca cctgttcaac attgccaagc   1200
```

```
ccaggccccc ctggatgggc ctgctgggcc ccaccatcca ggctgaggtg tatgacactg   1260
tggtgatcac cctgaagaac atggccagcc accctgtgag cctgcatgct gtgggggtga   1320
gctactggaa ggcctctgag gggcctgagt atgatgacca gaccagccag agggagaagg   1380
aggatgacaa ggtgttccct gggggcagcc acacctatgt gtggcaggtg ctgaaggaga   1440
atggccccat ggcctctgac cccctgtgcc tgacctacag ctacctgagc catgtggacc   1500
tggtgaagga cctgaactct ggcctgattg gggccctgct ggtgtgcagg gagggcagcc   1560
tggccaagga gaagacccag accctgcaca agttcatcct gctgtttgct gtgtttgatg   1620
agggcaagag ctggcactct gaaaccaaga acagcctgat gcaggacagg gatgctgcct   1680
ctgccagggc ctggcccaag atgcacactg tgaatggcta tgtgaacagg agcctgcctg   1740
gcctgattgg ctgccacagg aagtctgtgt actggcatgt gattggcatg ggcaccaccc   1800
ctgaggtgca cagcatcttc ctggagggcc acaccttcct ggtcaggaac cacaggcagg   1860
ccagcctgga gatcagcccc atcaccttcc tgactgccca gaccctgctg atggacctgg   1920
gccagttcct gctgttctgc cacatcagca gccaccagca tgatggcatg gaggcctatg   1980
tgaaggtgga cagctgccct gaggagcccc agctgaggat gaagaacaat gaggaggctg   2040
aggactatga tgatgacctg actgactctg agatggatgt ggtgaggttt gatgatgaca   2100
acagccccag cttcatccag atcaggtctg tggccaagaa gcaccccaag acctgggtgc   2160
actacattgc tgctgaggag gaggactggg actatgcccc cctggtgctg gcccctgatg   2220
acaggagcta caagagccag tacctgaaca atggccccca gaggattggc aggaagtaca   2280
agaaggtcag gttcatggcc tacactgatg aaaccttcaa gaccagggag gccatccagc   2340
atgagtctgg catcctgggc cccctgctgt atggggaggt gggggacacc ctgctgatca   2400
tcttcaagaa ccaggccagc aggccctaca acatctaccc ccatggcatc actgatgtga   2460
ggcccctgta cagcaggagg ctgcccaagg gggtgaagca cctgaaggac ttccccatcc   2520
tgcctgggga gatcttcaag tacaagtgga ctgtgactgt ggaggatggc cccaccaagt   2580
ctgaccccag gtgcctgacc agatactaca gcagctttgt gaacatggag agggacctgg   2640
cctctggcct gattggcccc ctgctgatct gctacaagga gtctgtggac cagaggggca   2700
accagatcat gtctgacaag aggaatgtga tcctgttctc tgtgtttgat gagaacagga   2760
gctggtacct gactgagaac atccagaggt tcctgcccaa ccctgctggg gtgcagctgg   2820
aggaccctga gttccaggcc agcaacatca tgcacagcat caatggctat gtgtttgaca   2880
gcctgcagct gtctgtgtgc ctgcatgagg tggcctactg gtacatcctg agcattgggg   2940
cccagactga cttcctgtct gtgttcttct ctggctacac cttcaagcac aagatggtgt   3000
atgaggacac cctgaccctg ttccccttct ctggggagac tgtgttcatg agcatggaga   3060
accctggcct gtggattctg ggctgccaca actctgactt caggaacagg ggcatgactg   3120
ccctgctgaa agtctccagc tgtgacaaga acactgggga ctactatgag gacagctatg   3180
aggacatctc tgcctacctg ctgagcaaga acaatgccat tgagcccagg agcttcagcc   3240
agaacccccc agtgctgaag aggcaccaga gggagatcac caggaccacc ctgcagtctg   3300
accaggagga gattgactat gatgacacca tctctgtgga gatgaagaag gaggactttg   3360
acatctacga cgaggacgag aaccagagcc ccaggagctt ccagaagaag accaggcact   3420
acttcattgc tgctgtggag aggctgtggg actatggcat gagcagcagc ccccatgtgc   3480
```

```
tgaggaacag ggcccagtct ggctctgtgc cccagttcaa gaaggtggtg ttccaggagt   3540
tcactgatgg cagcttcacc cagcccctgt acagagggga gctgaatgag cacctgggcc   3600
tgctgggccc ctacatcagg gctgaggtgg aggacaacat catggtgacc ttcaggaacc   3660
aggccagcag gccctacagc ttctacagca gcctgatcag ctatgaggag gaccagaggc   3720
agggggctga gcccaggaag aactttgtga agcccaatga aaccaagacc tacttctgga   3780
aggtgcagca ccacatggcc cccaccaagg atgagtttga ctgcaaggcc tgggcctact   3840
tctctgatgt ggacctggag aaggatgtgc actctggcct gattggcccc ctgctggtgt   3900
gccacaccaa caccctgaac cctgcccatg gcaggcaggt gactgtgcag gagtttgccc   3960
tgttcttcac catctttgat gaaaccaaga gctggtactt cactgagaac atggagagga   4020
actgcagggc cccctgcaac atccagatgg aggaccccac cttcaaggag aactacaggt   4080
tccatgccat caatggctac atcatggaca ccctgcctgg cctggtgatg gcccaggacc   4140
agaggatcag gtggtacctg ctgagcatgg gcagcaatga gaacatccac agcatccact   4200
tctctggcca tgtgttcact gtgaggaaga aggaggagta caagatggcc ctgtacaacc   4260
tgtaccctgg ggtgtttgag actgtggaga tgctgcccag caaggctggc atctggaggg   4320
tggagtgcct gattggggag cacctgcatg ctggcatgag caccctgttc ctggtgtaca   4380
gcaacaagtg ccagaccccc ctgggcatgg cctctggcca catcagggac ttccagatca   4440
ctgcctctgg ccagtatggc cagtgggccc ccaagctggc caggctgcac tactctggca   4500
gcatcaatgc ctggagcacc aaggagccct tcagctggat caaggtggac ctgctggccc   4560
ccatgatcat ccatggcatc aagacccagg gggccaggca gaagttcagc agcctgtaca   4620
tcagccagtt catcatcatg tacagcctgg atggcaagaa gtggcagacc tacaggggca   4680
acagcactgg caccctgatg gtgttctttg gcaatgtgga cagctctggc atcaagcaca   4740
acatcttcaa cccccccatc attgccagat acatcaggct gcaccccacc cactacagca   4800
tcaggagcac cctgaggatg gagctgatgg gctgtgacct gaacagctgc agcatgcccc   4860
tgggcatgga gagcaaggcc atctctgatg cccagatcac tgccagcagc tacttcacca   4920
acatgtttgc cacctggagc cccagcaagg ccaggctgca cctgcagggc aggagcaatg   4980
cctggaggcc ccaggtcaac aaccccaagg agtggctgca ggtggacttc cagaagacca   5040
tgaaggtgac tggggtgacc acccaggggg tgaagagcct gctgaccagc atgtatgtga   5100
aggagttcct gatcagcagc agccaggatg gccaccagtg gaccctgttc ttccagaatg   5160
gcaaggtgaa ggtgttccag ggcaaccagg acagcttcac ccctgtggtg aacagcctgg   5220
acccccccct gctgaccaga tacctgagga ttcaccccca gagctgggtg caccagattg   5280
ccctgaggat ggaggtgctg ggctgtgagg cccaggacct gtactgacct cgaggaataa   5340
aggaaattta ttttcattgc aatagtgtgt tggttttttg tgtcacgtgg cggccgcagg   5400
aacccctagt gatggagttg gccactccct ctctgcgcgc tcgctcgctc actgaggccg   5460
ggcgaccaaa ggtcgcccga cgcccgggct ttgcccgggc ggcctcagtg agcgagcgag   5520
cgcgcagaga gggagtggcc aa                                            5542
```